United States Patent
Belema et al.

(10) Patent No.: US 9,855,230 B2
(45) Date of Patent: Jan. 2, 2018

(54) INHIBITORS OF HUMAN IMMUNODEFICIENCY VIRUS REPLICATION

(71) Applicant: ViiV Healthcare UK (No. 5) Limited, Brentford, Middlesex (GB)

(72) Inventors: Makonen Belema, Wallingford, CT (US); John A. Bender, Wallingford, CT (US); Brett Beno, Wallingford, CT (US); Robert G. Gentles, Wallingford, CT (US); Guo Li, Wallingford, CT (US); Nicholas A. Meanwell, Wallingford, CT (US); Annapurna Pendri, Wallingford, CT (US); Zhong Yang, Wallingford, CT (US); Shirong Zhu, Wallingford, CT (US)

(73) Assignee: ViiV HEALTHCARE UK (NO.5) LIMITED, Brentford, Middlesex (GB)

( * ) Notice: Subject to any disclaimer, the term of this patent is extended or adjusted under 35 U.S.C. 154(b) by 0 days.

(21) Appl. No.: 15/507,855

(22) PCT Filed: Sep. 3, 2015

(86) PCT No.: PCT/US2015/048271
§ 371 (c)(1),
(2) Date: Mar. 1, 2017

(87) PCT Pub. No.: WO2016/040084
PCT Pub. Date: Mar. 17, 2016

(65) Prior Publication Data
US 2017/0304239 A1    Oct. 26, 2017

Related U.S. Application Data

(60) Provisional application No. 62/048,017, filed on Sep. 9, 2014.

(51) Int. Cl.
| | | |
|---|---|---|
| *A61K 31/18* | (2006.01) | |
| *A01N 41/06* | (2006.01) | |
| *C07C 311/29* | (2006.01) | |
| *C07D 213/40* | (2006.01) | |
| *C07D 249/06* | (2006.01) | |
| *C07D 401/10* | (2006.01) | |
| *C07D 417/04* | (2006.01) | |
| *C07D 403/10* | (2006.01) | |
| *C07D 213/61* | (2006.01) | |
| *C07D 233/64* | (2006.01) | |

(52) U.S. Cl.
CPC ............ *A61K 31/18* (2013.01); *C07D 213/40* (2013.01); *C07D 213/61* (2013.01); *C07D 233/64* (2013.01); *C07D 249/06* (2013.01); *C07D 401/10* (2013.01); *C07D 403/10* (2013.01); *C07D 417/04* (2013.01)

(58) Field of Classification Search
CPC ....... A61K 31/18; A01N 41/06; C07C 311/29
See application file for complete search history.

(56) References Cited

FOREIGN PATENT DOCUMENTS

| WO | WO 94/10133 A1 | 5/1994 |
|---|---|---|
| WO | WO 2014/110298 A1 | 7/2014 |
| WO | WO 2014/134566 A2 | 9/2014 |

OTHER PUBLICATIONS

RN1216449-47-6, 2010.*
RN1216414-19-5, 2010.*
RN1215835-06-5, 2010.*
Pendri et al., 2016, caplus an 2016:427742.*
Database Registry [Online] Chemical Abstracts Service, Columbus, Ohio, US; Apr. 4, 2010. XP002746371, Database Accession No. 1216449-47-6, Abstract.
Database Registry [Online] Chemical Abstracts Service, Columbus, Ohio, US; Apr. 4, 2010. XP002746372, Database Accession No. 1216414-19-5, Abstract.
Database Registry [Online] Chemical Abstracts Service, Columbus, Ohio, US; Apr. 2, 2010. XP002746373, Database Accession No. 1215835-06-5, Abstract.

* cited by examiner

*Primary Examiner* — Sun Jae Yoo
(74) *Attorney, Agent, or Firm* — Robert H. Brink; Edward R. Gimmi; William R. Majarian

(57) ABSTRACT

Compounds of Formula I, including pharmaceutically acceptable salts thereof, and compositions and methods for treating human immunodeficiency virus (HIV) infection are set forth:

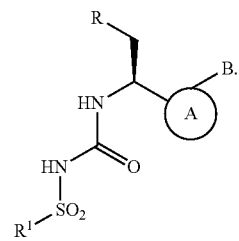

I

18 Claims, No Drawings

INHIBITORS OF HUMAN IMMUNODEFICIENCY VIRUS REPLICATION

CROSS REFERENCE TO RELATED APPLICATION

This application is a §371 of International Application No. PCT/US2015/048271, filed 3 Sep. 2015, which claims the benefit of U.S. Provisional Application No. 62/048,017, filed 9 Sep. 2014, which are incorporated herein in their entireties.

This non-provisional application claims the benefit of U.S. Provisional Application Ser. No. 62/048,017 filed Sep. 9, 2014 which is herein incorporated by reference in its entirety.

FIELD OF THE INVENTION

The invention relates to compounds, compositions, and methods for the treatment of human immunodeficiency virus (HIV) infection. More particularly, the invention provides novel inhibitors of HIV, pharmaceutical compositions containing such compounds, and methods for using these compounds in the treatment of HIV infection. The invention also relates to methods for making the compounds hereinafter described.

BACKGROUND OF THE INVENTION

Acquired immunodeficiency syndrome (AIDS) is the result of infection by HIV. It remains a major medical problem, with an estimated 34 million people infected worldwide at the end of 2011, 3.3 million of them under the age of 15. In 2011, there were 2.5 million new infections, and 1.7 million deaths from complications due to HIV/AIDS.

Current therapy for HIV-infected individuals consists of a combination of approved anti-retroviral agents. Over two dozen drugs are currently approved for HIV infection, either as single agents or as fixed dose combinations or single tablet regimens, the latter two containing 2-4 approved agents. These agents belong to a number of different classes, targeting either a viral enzyme or the function of a viral protein during the virus life cycle. Thus, agents are classified as either nucleotide reverse transcriptase inhibitors (NRTIs), non-nucleotide reverse transcriptase inhibitors (NNRTIs), protease inhibitors (PIs), integrase inhibitors (INIs), or entry inhibitors (one, maraviroc, targets the host CCR5 protein, while the other, enfuvirtide, is a peptide that targets the gp41 region of the viral gp160 protein). In addition, a pharmacokinetic enhancer with no antiviral activity (cobicistat) has recently been approved for use in combinations with antiretroviral agents (ARVs) that require boosting.

Despite the armamentarium of agents and drug combinations, there remains a medical need for new anti-retroviral agents, due in part to the need for chronic dosing to combat infection. Significant problems related to long-term toxicities are documented, creating a need to address and prevent these co-morbidities (e.g. CNS, CV/metabolic, renal disease). Also, increasing failure rates on current therapies continue to be a problem, due either to the presence or emergence of resistant strains or to non-compliance attributed to drug holidays or adverse side effects. For example, despite therapy, it has been estimated that 63% of subjects receiving combination therapy remained viremic, as they had viral loads >500 copies/ml (Oette, M, Kaiser, R, Däumer, M, et al. Primary HIV Drug Resistance and Efficacy of First-Line Antiretroviral Therapy Guided by Resistance Testing. J Acq Imm Def Synd 2006; 41(5):573-581). Among these patients, 76% had viruses that were resistant to one or more classes of antiretroviral agents. As a result, new drugs are needed that are easier to take, have high genetic barriers to the development of resistance and have improved safety over current agents. In this panoply of choices, novel MOAs that can be used as part of the preferred HAART regimen can still have a major role to play since they should be effective against viruses resistant to current agents.

Certain therapeutic compounds have now been set forth in WO 2013/006738, WO 2014/110298, and WO 2014/134566.

What is now needed in the art are additional compounds which are novel and useful in the treatment of HIV. Additionally, these compounds should provide advantages for pharmaceutical uses, for example, with regard to one or more of their mechanisms of action, binding, inhibition efficacy, target selectivity, solubility, safety profiles, or bioavailability. Also needed are new formulations and methods of treatment which utilize these compounds.

SUMMARY OF THE INVENTION

The invention encompasses compounds of Formula I, including pharmaceutically acceptable salts thereof, as well as pharmaceutical compositions, and their use in inhibiting HIV and treating those infected with HIV or AIDS.

One aspect of the invention is a compound of Formula I, including pharmaceutically acceptable salts thereof:

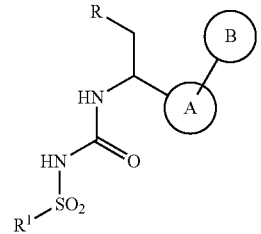

wherein:
R is selected from the group of alkyl, alkenyl, alkoxy, alkylthioxy, $C_5$-$C_8$ bicycloalkyl, $C_3$-$C_7$ cycloalkyl, aryl, and 5-6 member heteroaryl; and is substituted with 0-3 substituents selected from the group of alkyl, alkenyloxy, alkoxycarbonyl, alkylcarbonylamino, aminocarbonyl, aryl, benzyloxy, cyano, cycloalkoxy, cycloalkyl, halo, haloalkyl, haloalkoxy, hydroxy and (heteroaryl)sulfonyl;

$R^1$ is selected from the group of alkyl, cycloalkyl, (cycloalkyl)alkyl, aryl, and 5-6 member heteroaryl; and is substituted with 0-3 substituents selected from the group of alkyl, alkoxy, alkoxycarbonyl, aryl, cyano, cycloalkyl, halo, haloalkoxy, haloalkyl, 5-6 member heteroaryl, nitro, and —$NR^2R^3$, where $R^2$ and $R^3$ are each independently selected from H, alkyl, and cycloalkyl, or $R^2$ and $R^3$ together form heterocycles comprised of 1-3 rings;

A is a five or six-member heteroaryl ring optionally substituted with alkyl, alkenyl, alkynyl, alkoxy, cycloalkoxy, cycloalkyl, halo and haloalkyl; and B is selected from the group of alkyl, aryl, arylalkyl, $C_3$-$C_9$ cycloalkyl, and 5-6 member heteroaryl, and is substituted with 0-3 substituents selected from the group of alkyl, alkylsulphonyl, alkoxy, alkylaryl, allyloxy, arylalkoxy, cycloalkoxy, cycloalkyl, halo, haloalkoxy, heteroarylcycloalkyl amido, hydroxymethyl, nitro, —CN, —COOR², —NR²R³, —N(R²)COOR³, —NR²SO₂R³, —CONR²R³, —NH—CO-alkyl, and morpholinyl.

The invention also relates to pharmaceutical compositions comprising a compound of Formula I, including pharmaceutically acceptable salts thereof, and a pharmaceutically acceptable carrier, excipient, and/or diluent.

In addition, the invention provides one or more methods of treating HIV infection comprising administering a therapeutically effective amount of a compound of Formula I to a patient.

Also provided as part of the invention are one or more methods for making the compounds of Formula I.

The present invention is directed to these, as well as other important ends, hereinafter described.

DETAILED DESCRIPTION OF THE EMBODIMENTS

The singular forms "a", "an", and "the" include plural reference unless the context dictates otherwise.

Unless otherwise specifically set forth elsewhere in the application, the following terms shall have the following meanings:

"Alkenyl" means an optionally substituted straight or branched alkyl group comprised of 2 to 10 carbons with at least one double bond.

"Alkenyloxy" means an alkenyl group attached to the parent structure through oxygen atom.

"Alkoxy" means alkyl group attached to the parent structure by oxygen atom.

"Alkoxycarbonyl" means an alkoxy group attached to the parent structure by a carbonyl moiety.

"Alkoxycarbonylamino" means alkoxycarbonyl group attached to the parent structure by nitrogen where the nitrogen is optionally substituted with an alkyl group.

"Alkyl" means a straight or branched saturated hydrocarbon comprised of 1 to 10 carbons, and preferably 1 to 6 carbons.

"Alkylsulphonyl" means an alkyl group attached to the parent structure through a —SO₂— moiety.

"Alkylthioxy" means an alkyl group attached to the parent structure through a sulfur atom.

"Alkynyl" means an optionally substituted straight or branched alkyl group comprised of 2 to 10 carbons and containing at least one triple bond.

"Aminocarbonyl" means an amine group attached to the parent structure through a carbonyl moiety where the amine is optionally substituted with at least one or two alkyl, aryl, heteroaryl, heterocycle or any combination thereof.

"Aryl" mean a carbocyclic group comprised of 1-3 rings that are fused and/or bonded and at least one or a combination of which is aromatic. The non-aromatic carbocyclic portion, where present, will be comprised of C₃ to C₇ alkyl group. Examples of an aromatic group include phenyl, biphenyl, naphthalene, and tetrahydronaphthalene. The aryl group can be attached to the parent structure through any substitutable carbon atom in the group.

"Benzyloxy" means a benzyl group attached to the parent structure through an oxygen atom. The phenyl group of the benzyl moiety could be optionally substituted by 1-3 moieties independently selected from the group of alkyl, alkoxy, halo, haloalkyl, haloalkoxy and cyano.

"C₅-C₁₀ bicycloalkyl" means a bicyclic ring system comprised of 5 to 10 carbons. Examples include bicyclo[2.2.2]octane and octahydropentalene.

"C₃-C₇ cycloalkyl" means a monocyclic ring system comprised of 3 to 7 carbons.

"Cyano" refers to —CN.

"Halo" or "halogen" refers to —F, —Cl, —Br, or —I.

"Haloalkyl" means an alkyl group substituted by any combination of one to six halogen atoms.

"Haloalkoxy" means a haloalkyl group attached to the parent molecular moiety through an oxygen atom.

"Hydroxy" refers to —OH.

"Heteroaryl" is a subset of heterocyclic group as defined below and is comprised of 1-3 rings where at least one or a combination of which is aromatic and that the aromatic group contains at least one atom chosen from a group of oxygen, nitrogen and sulfur.

"Heterocyclic" means a cyclic group of 1-3 rings comprised of carbon and at least one other atom selected independently from the group of oxygen, nitrogen and sulfur. The rings could be fused and or bonded, through a direct or spiro attachment, with the option to have one or a combination thereof be aromatic. Examples include, but are not limited to, azaindole, azaindoline, benzimidazole, 2,3-dihydrobenzofuran, furan, imidazole, imidazo[1,2-a]pyridine, indazole, indole, indoline, morpholine, oxazole, 6-oxaspiro[2.5]octane, phenylquinoline, phenylpyrazole, piperidine, pyrazole, pyrazine, pyridine, pyrimidine, pyrrole, pyrrolidine, quinoline, 1,2,3,4-tetrahydroquinoline, 5,6,7,8-tetrahydroquinoline, thiazole, and thiophene. The heterocyclic group can be attached to the parent structure through any substitutable atom in the group that results in stable compound.

"—NR^xR^y" (as in the case of "—NR²R³") refers to two groups, R^x and R^y, which are attached to the parent structure through nitrogen atom and with an option to form heterocycles comprised of 1-3 rings.

Substituents which are illustrated by chemical drawing to bond at variable positions on a multiple ring system (for example a bicyclic ring system) are intended to bond to the ring where they are drawn to append.

Parenthetic and multiparenthetic terms are intended to clarify bonding relationships to those skilled in the art. For example, a term such as ((R)alkyl) means an alkyl substituent further substituted with the substituent R.

Those terms not specifically set forth herein shall have the meaning which is commonly understood and accepted in the art.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

As set forth above, the invention is directed to a compound of Formula I, including pharmaceutically acceptable salts thereof:

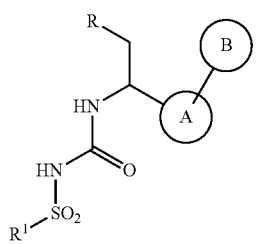

R is selected from the group of alkyl, alkenyl, alkoxy, alkylthioxy, $C_5$-$C_8$ bicycloalkyl, $C_3$-$C_7$ cycloalkyl, aryl, and 5-6 member heteroaryl; and is substituted with 0-3 substituents selected from the group of alkyl, alkenyloxy, alkoxycarbonyl, alkylcarbonylamino, aminocarbonyl, aryl, benzyloxy, cyano, cycloalkoxy, cycloalkyl, halo, haloalkyl, haloalkoxy, hydroxy and (heteroaryl)sulfonyl;

$R^1$ is selected from the group of alkyl, cycloalkyl, (cycloalkyl)alkyl, aryl, and 5-6 member heteroaryl; and is substituted with 0-3 substituents selected from the group of alkyl, alkoxy, alkoxycarbonyl, aryl, cyano, cycloalkyl, halo, haloalkoxy, haloalkyl, 5-6 member heteroaryl, nitro, and —NR$^2$R$^3$, where R$^2$ and R$^3$ are each independently selected from H, alkyl, and cycloalkyl, or R$^2$ and R$^3$ together form heterocycles comprised of 1-3 rings;

A is a five or six-member heteroaryl ring optionally substituted with alkyl, alkenyl, alkynyl, alkoxy, cycloalkoxy, cycloalkyl, halo and haloalkyl; and B is selected from the group of alkyl, aryl, arylalkyl, $C_3$-$C_9$ cycloalkyl, and 5-6 member heteroaryl, and is substituted with 0-3 substituents selected from the group of alkyl, alkylsulphonyl, alkoxy, alkylaryl, allyloxy, arylalkoxy, cycloalkoxy, cycloalkyl, halo, haloalkoxy, heteroarylcycloalkyl amido, hydroxymethyl, nitro, —CN, —COOR$^2$, —NR$^2$R$^3$, —N(R$^2$)COOR$^3$, —NR$^2$SO$_2$R$^3$, —CONR$^2$R$^3$, —NH—CO-alkyl, and morpholinyl.

For the compounds of Formula I, the scope of any instance of a variable substituent can be used independently with the scope of any other instance of a variable substituent. As such, the invention includes combinations of the different aspects.

Preferably, aryl is a monocyclic or bicyclic structure containing $C_6$-$C_{10}$ carbon atoms.

In certain embodiments of the compound of Formula I above, it is preferred that R is phenyl, which is optionally further substituted with one or more halo groups, preferably fluoro.

In another embodiment of the invention, it is preferred that R$^1$ is phenyl, and is optionally further substituted with one or more alkyl or halo groups.

It is also preferred that A is selected from the group of imidazole-2-yl, imidazole-3-yl, triazolyl, oxazolyl, pyridyl, pyrimidinyl, and pyrazinyl. In certain instances, the imidazole-2-yl, imidazole-3-yl, triazolyl, and pyridyl groups may be especially preferred.

Also preferred are the embodiments wherein B is phenyl. Further preferred are the embodiments wherein B is phenyl which is further substituted with at least one member selected from the group of halo, alkyl, alkoxy, haloalkoxy, and —N(R$^2$)COOR$^3$. Also preferred are the embodiments wherein B is a 5 to 10 membered aryl or heteroaryl group. More preferably, the aryl or heteroaryl group may be selected from the group of

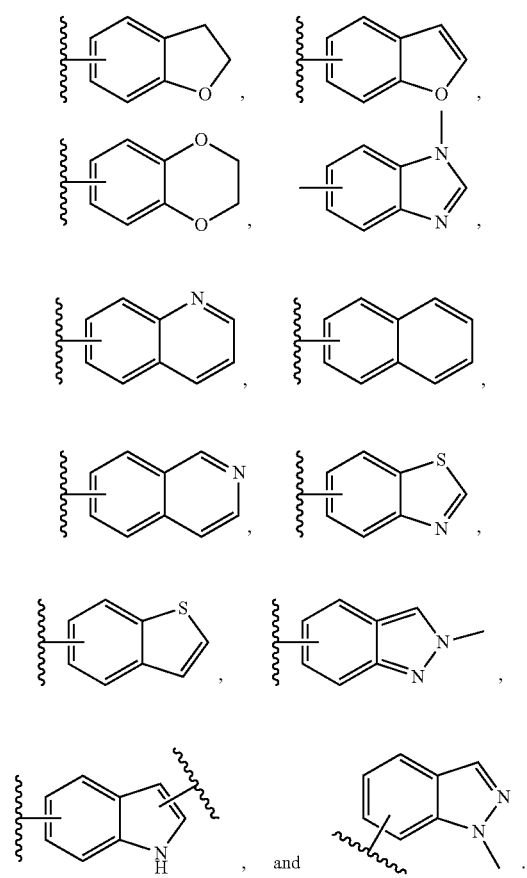

In certain embodiments, it is also preferred that A is selected from the group of imidazole-2-yl, imidazole-3-yl, triazolyl, and pyridyl groups, and further wherein each of B, R and R$^1$ are phenyl groups.

Preferred compounds of the invention, including pharmaceutically acceptable salts thereof, are selected from the group of:

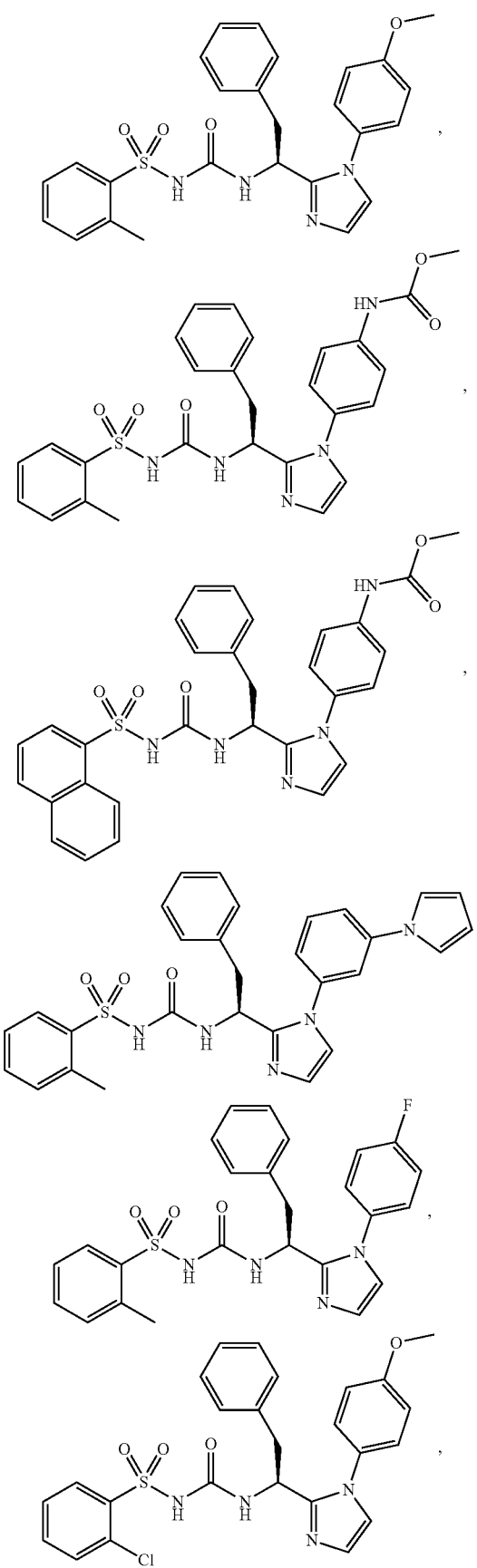
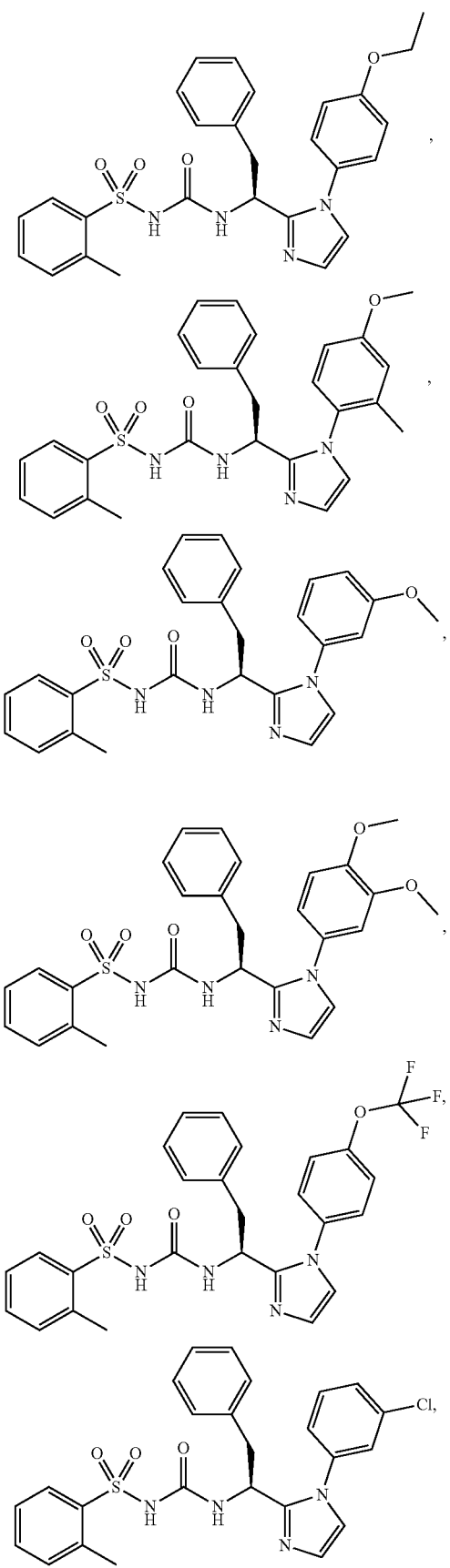

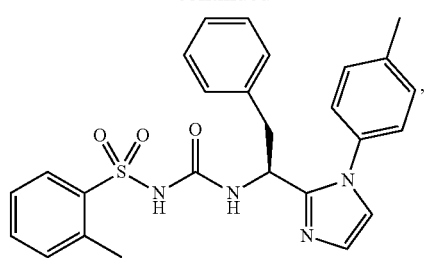
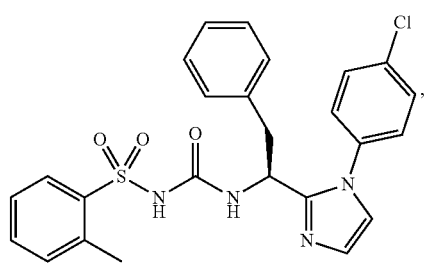
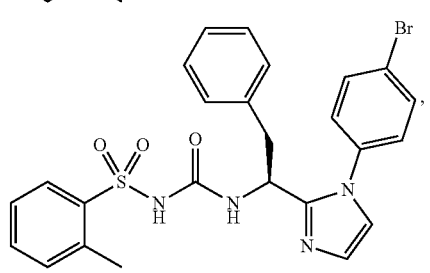
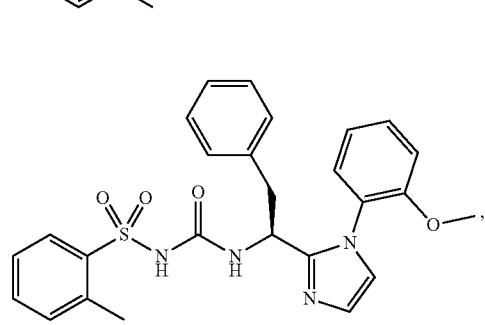
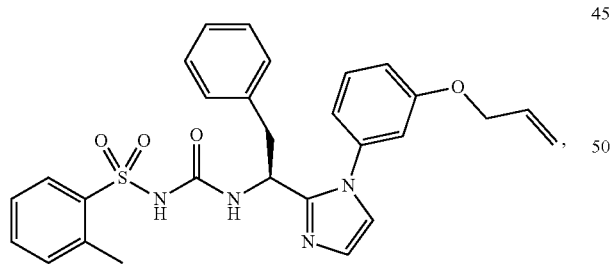
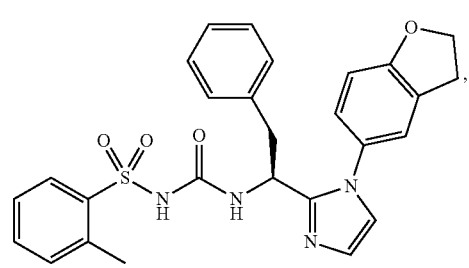
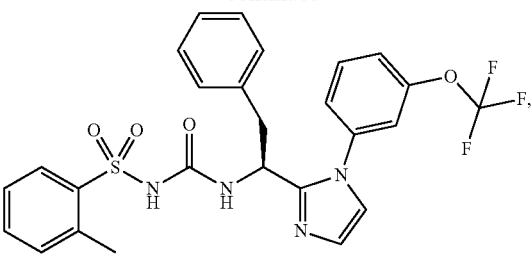
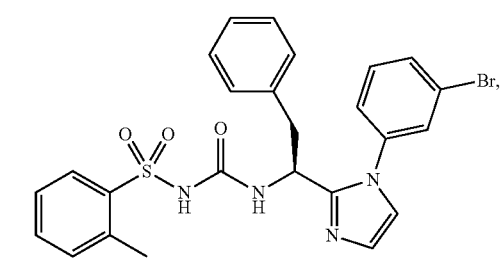
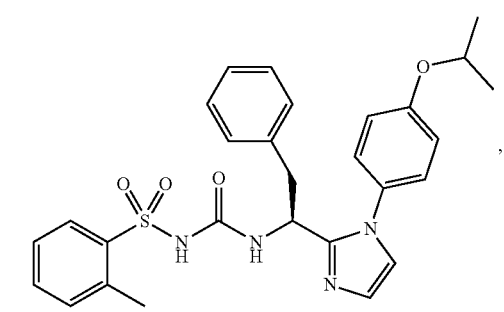
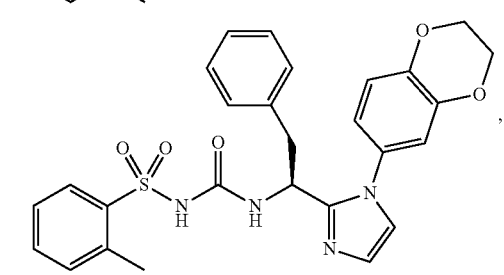
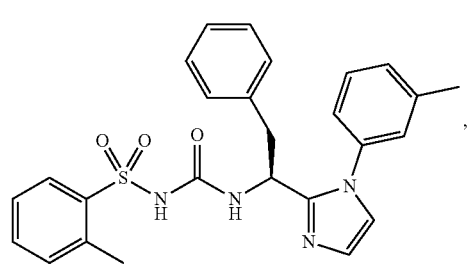
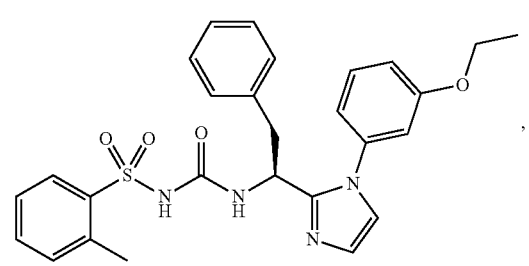

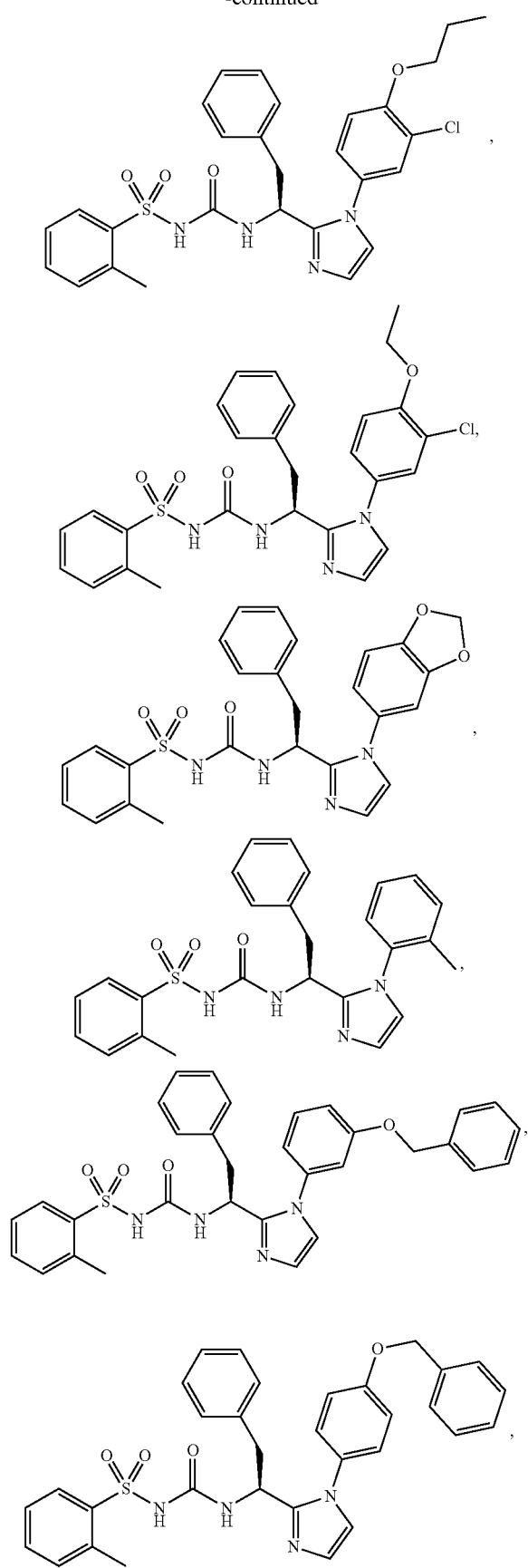
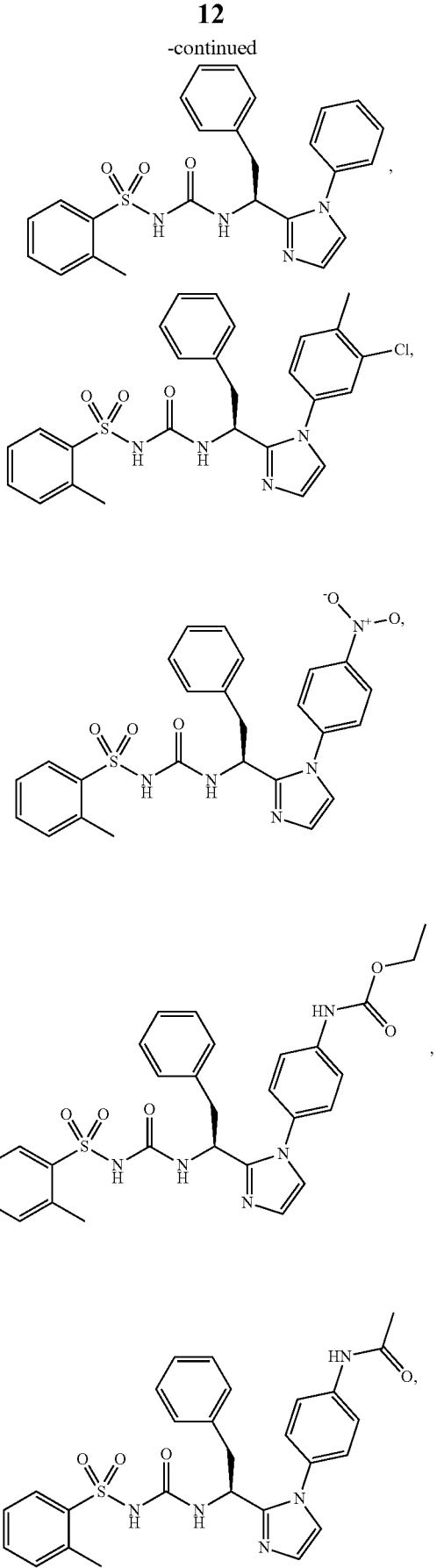

13
-continued
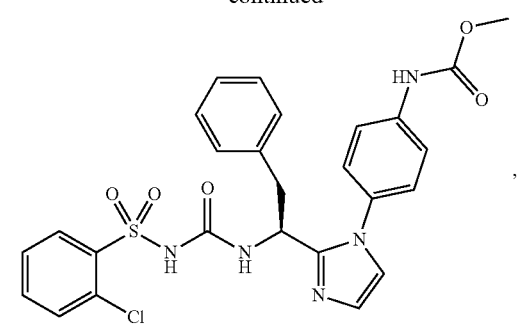
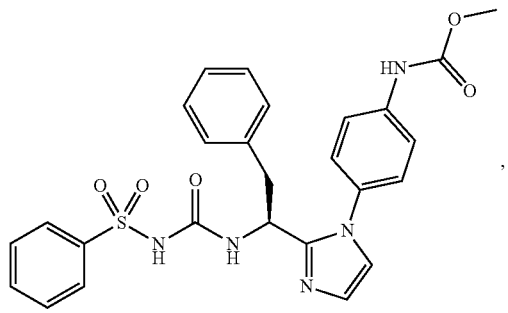
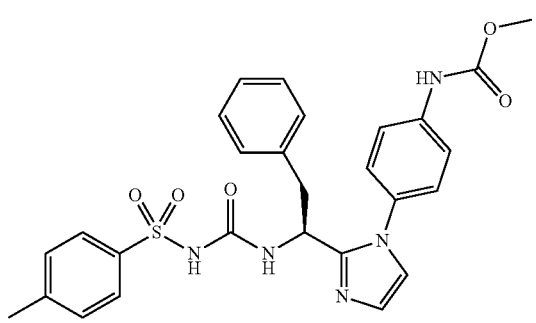
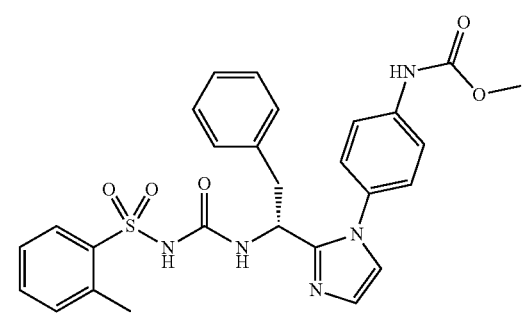
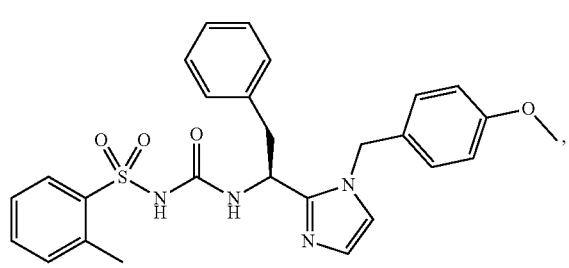
14
-continued
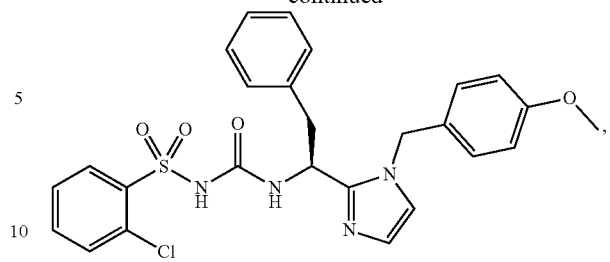
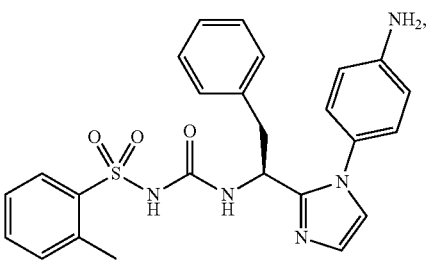
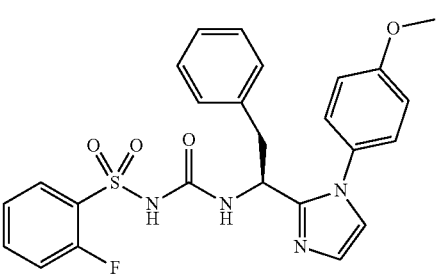
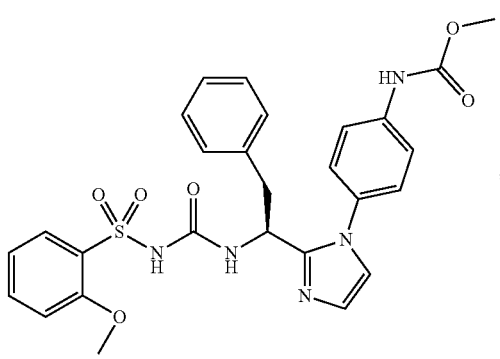
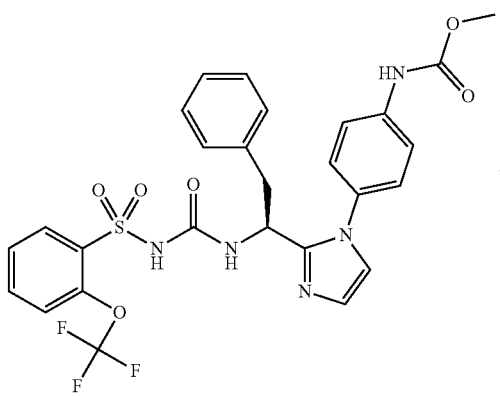

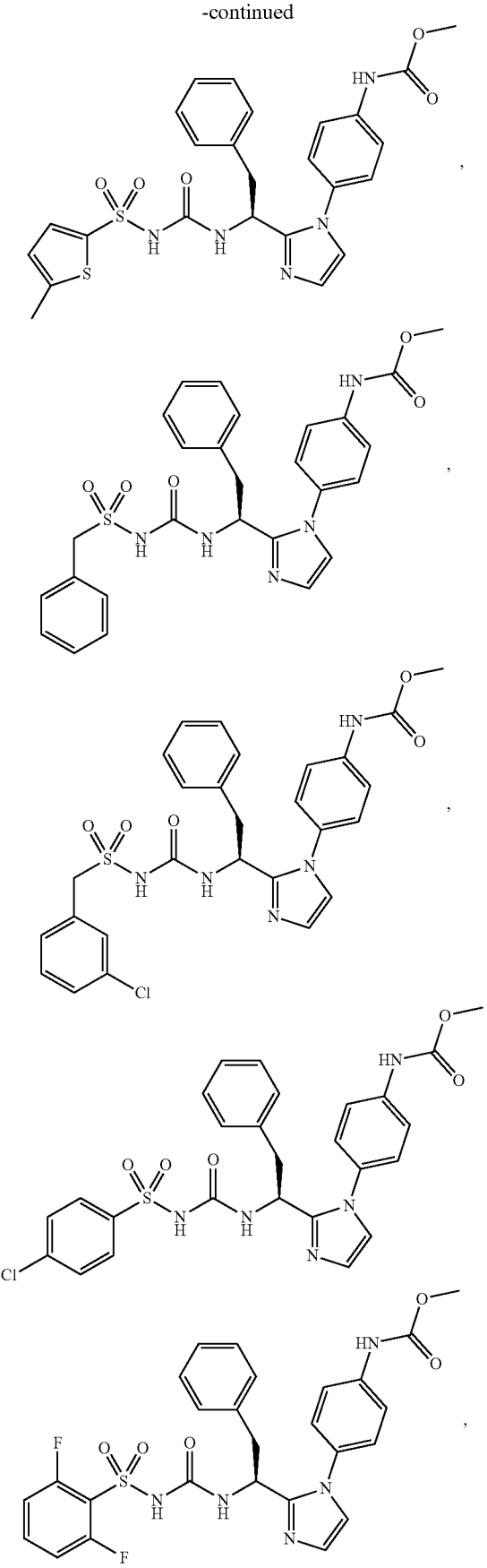
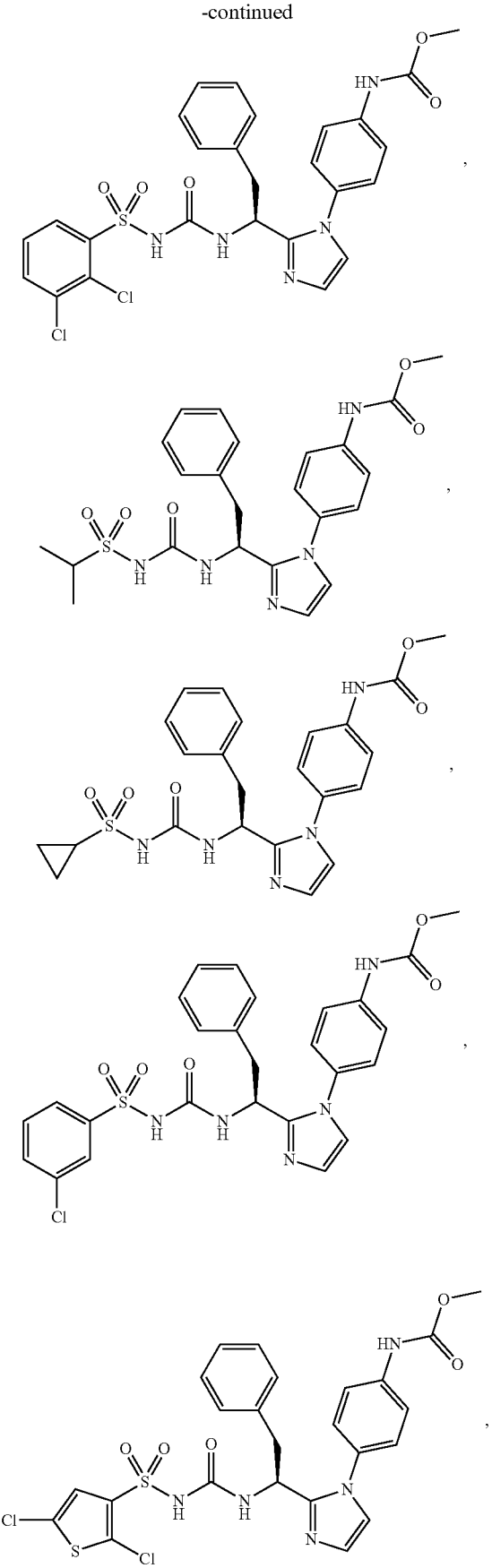

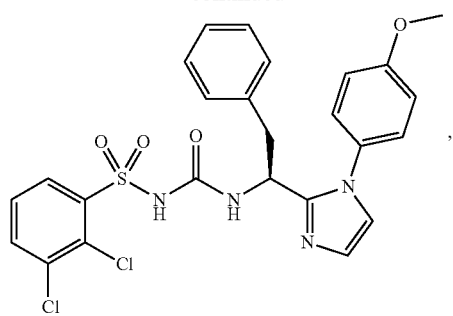
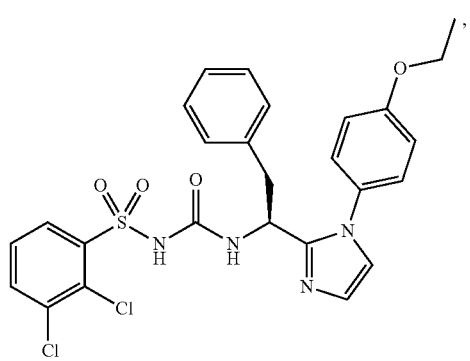
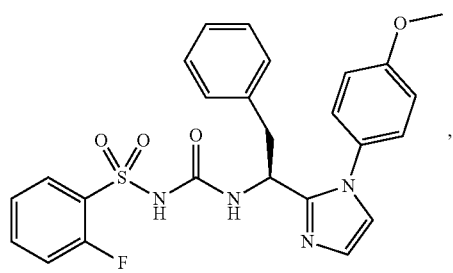
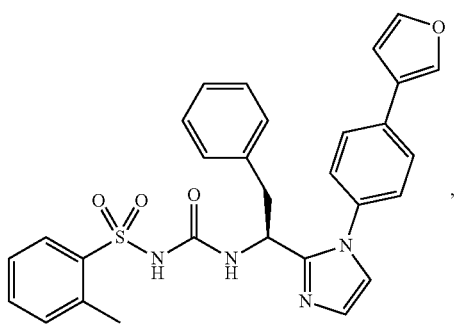
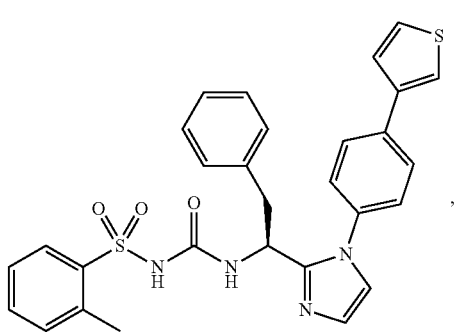
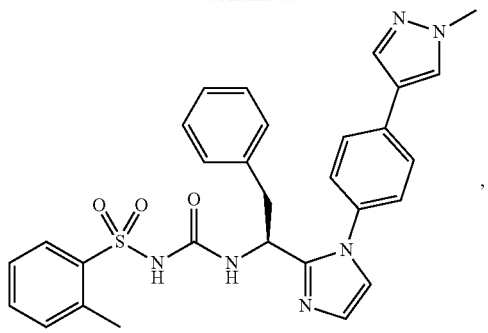
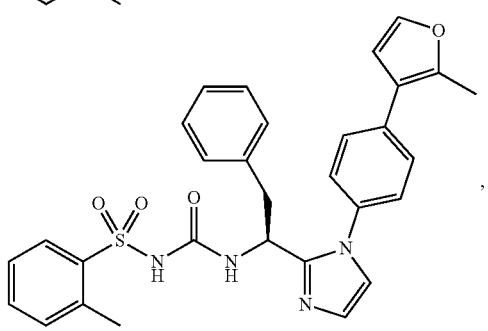
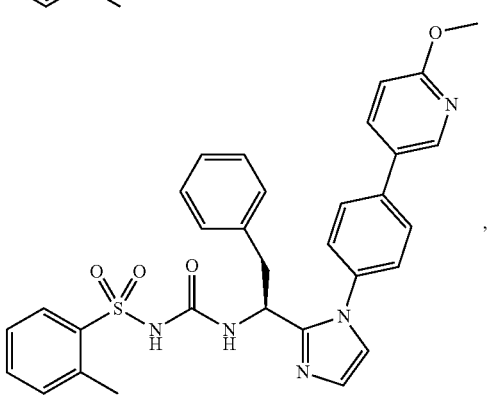
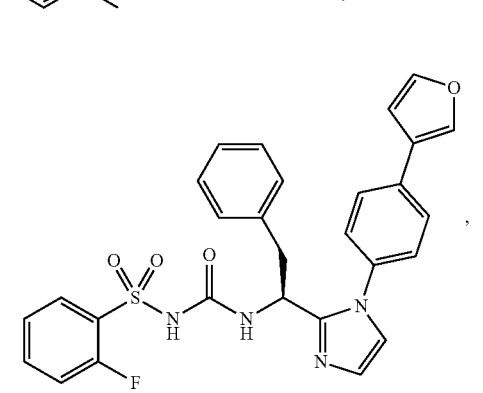
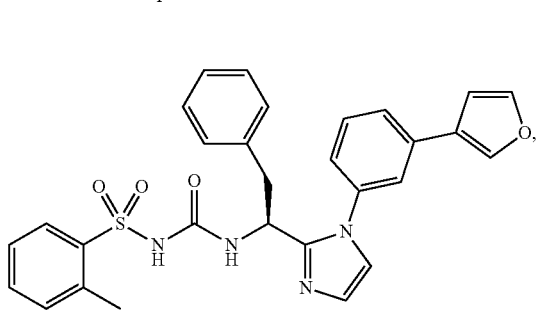

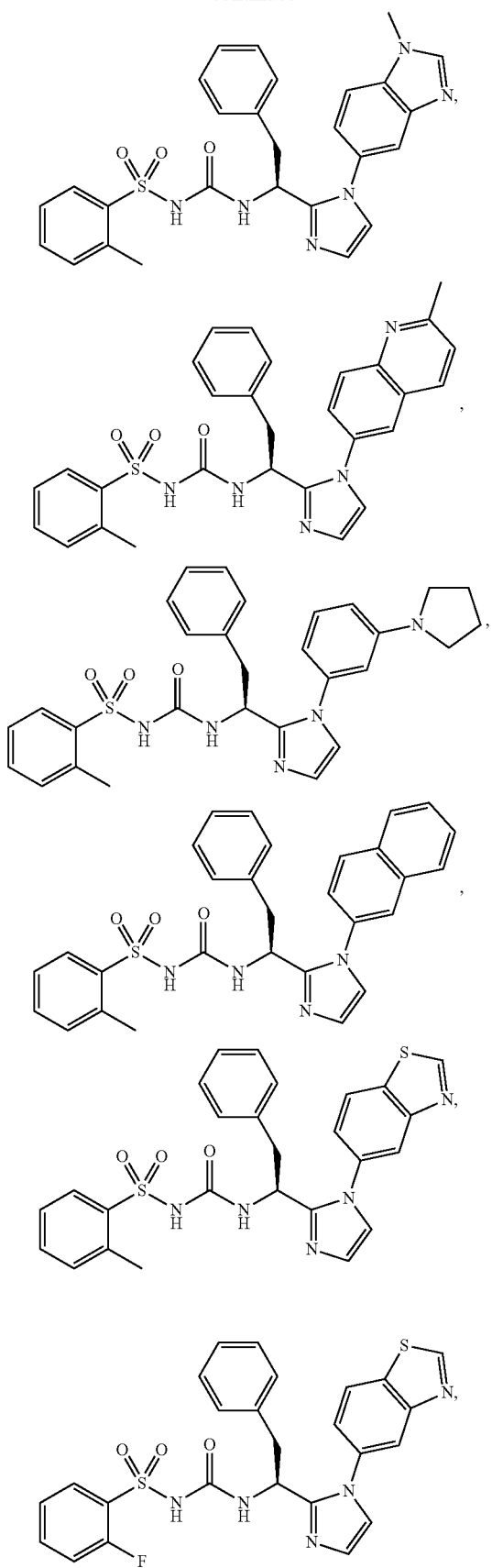
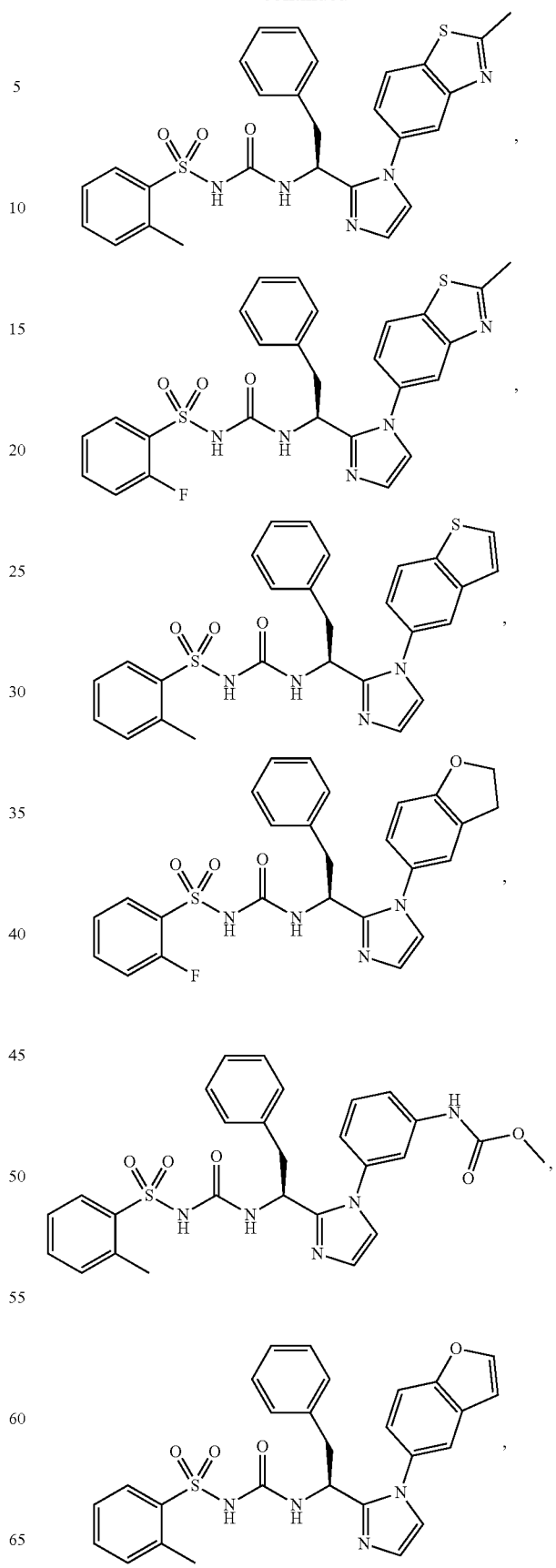

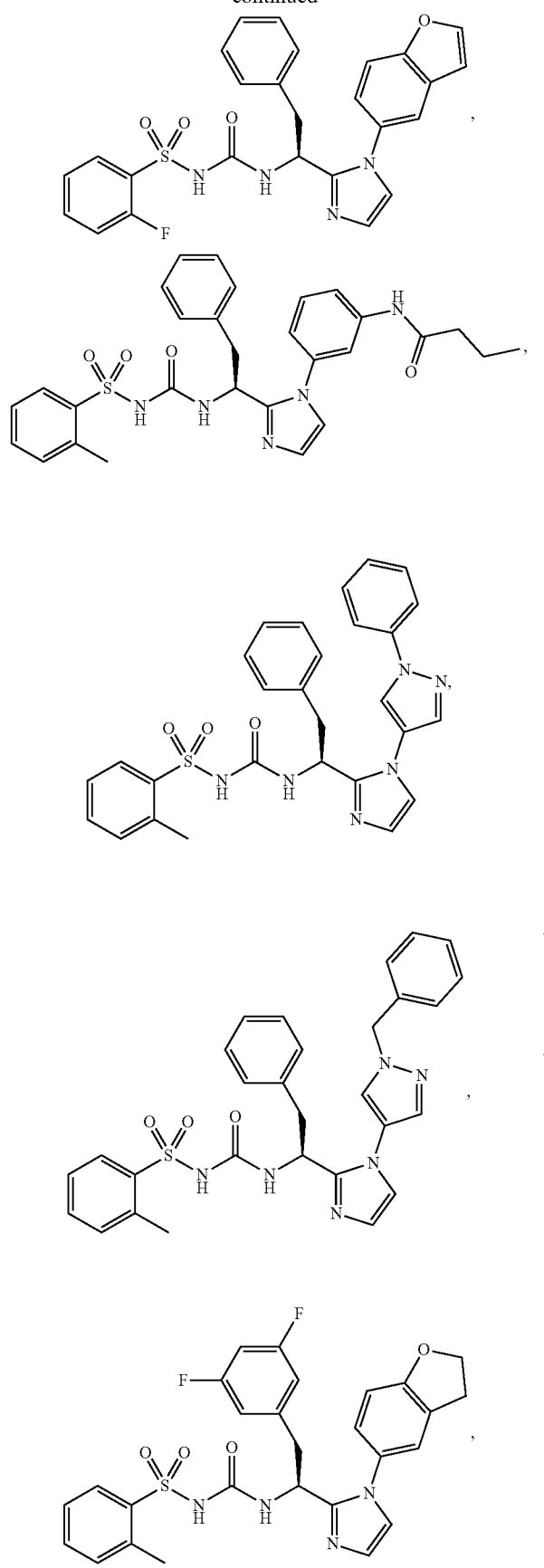
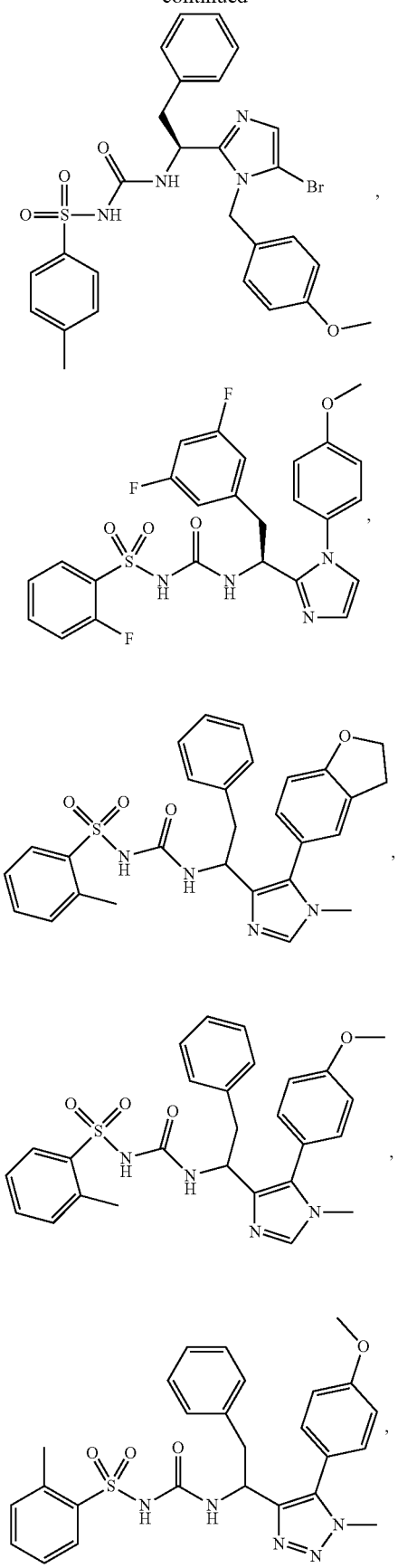

-continued
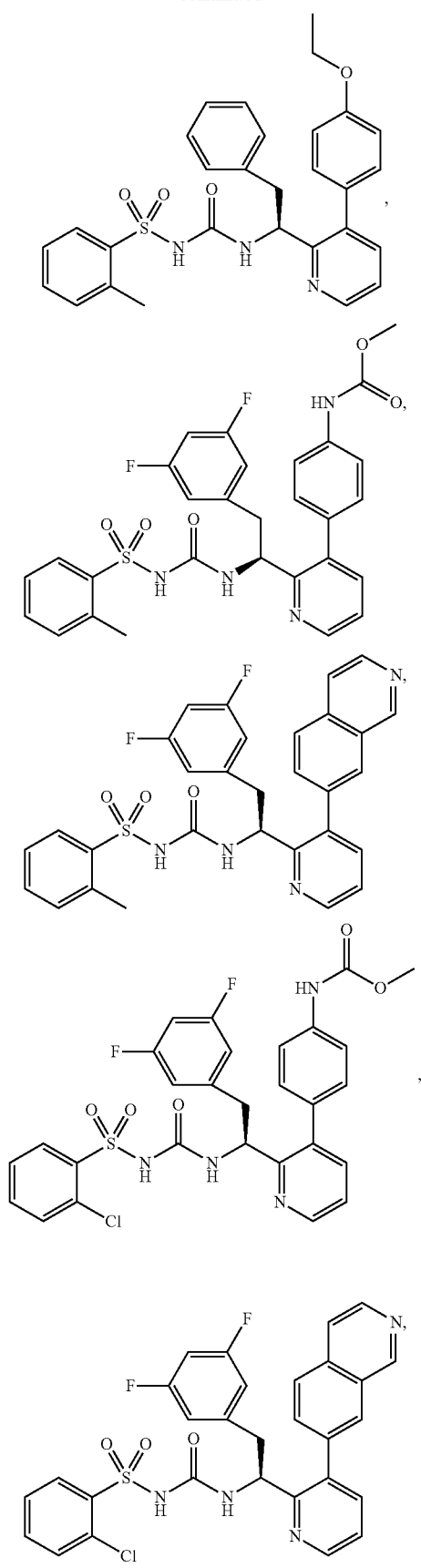
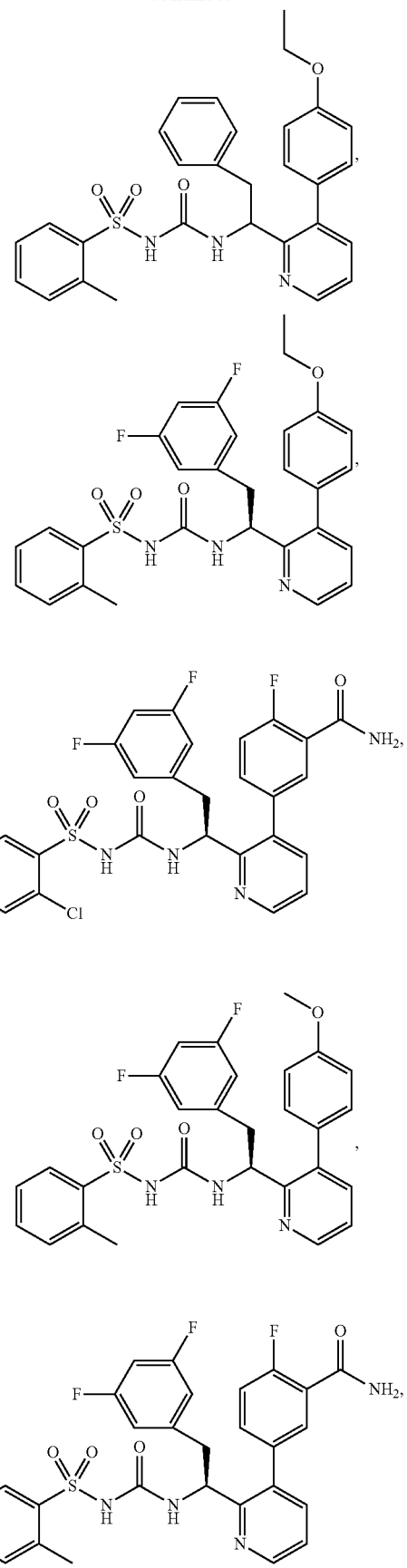

25
-continued
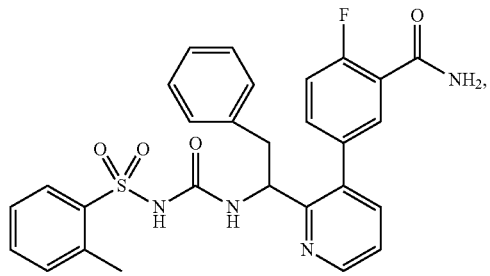
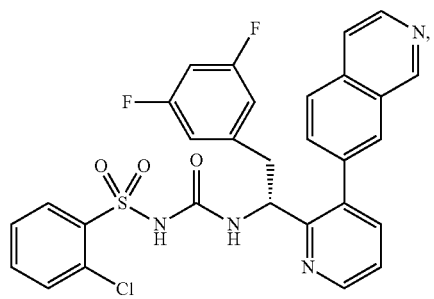
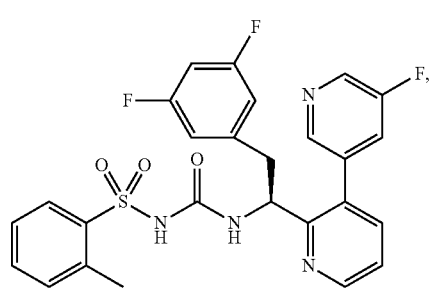
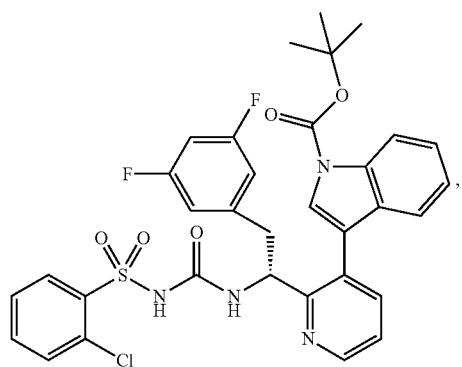
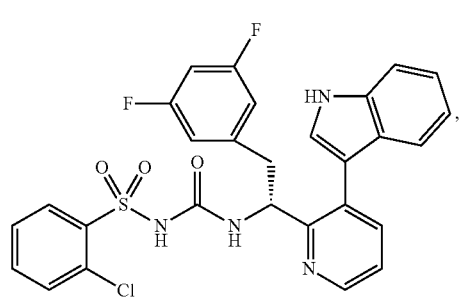
26
-continued
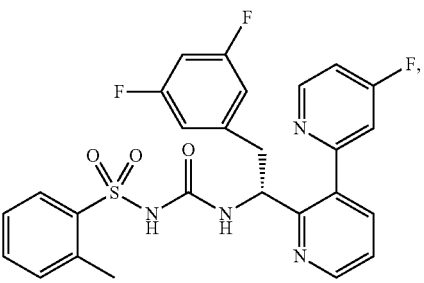
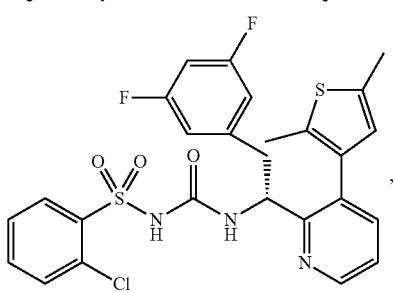
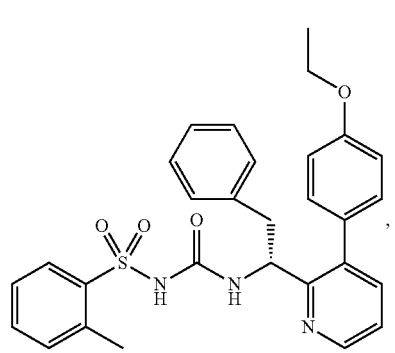
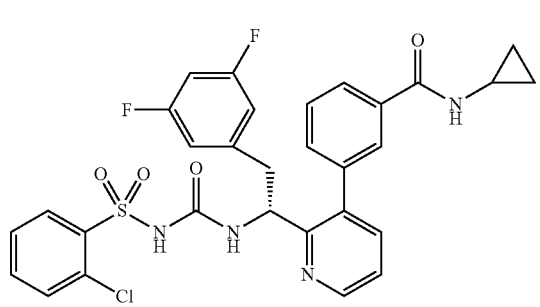
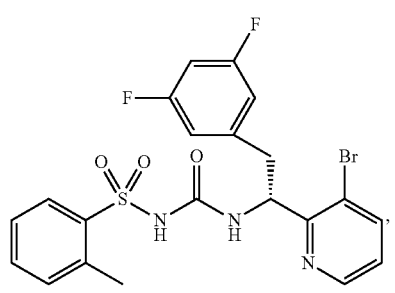

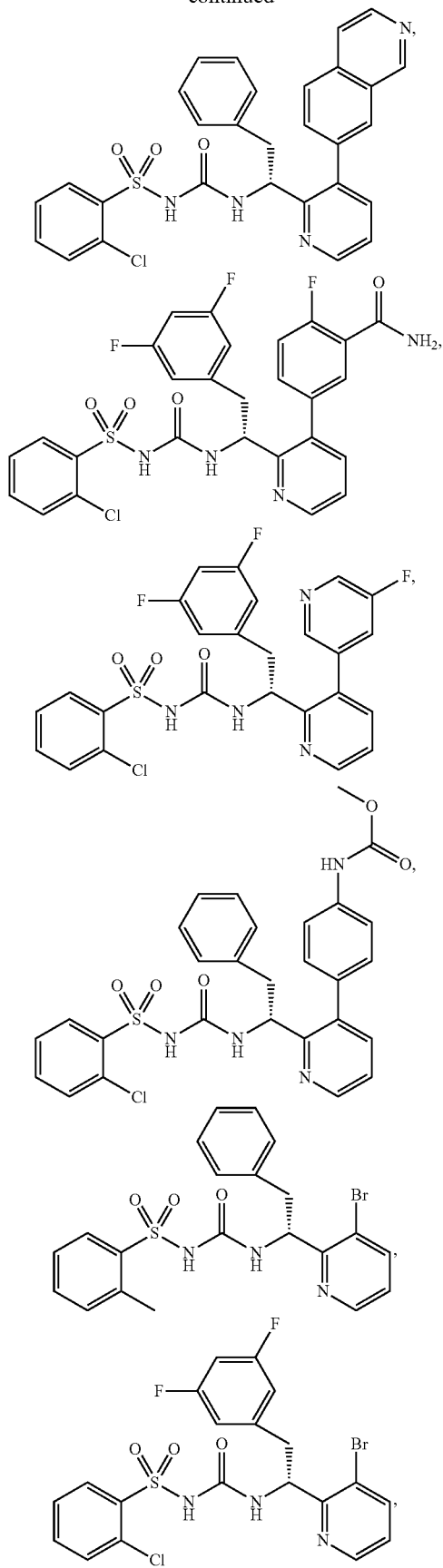
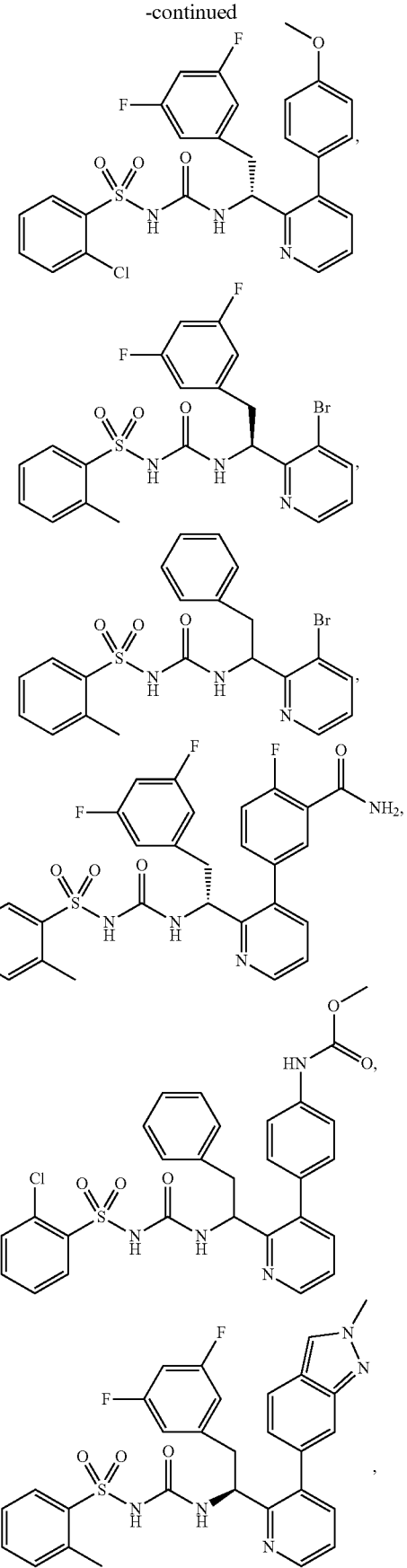

29
-continued
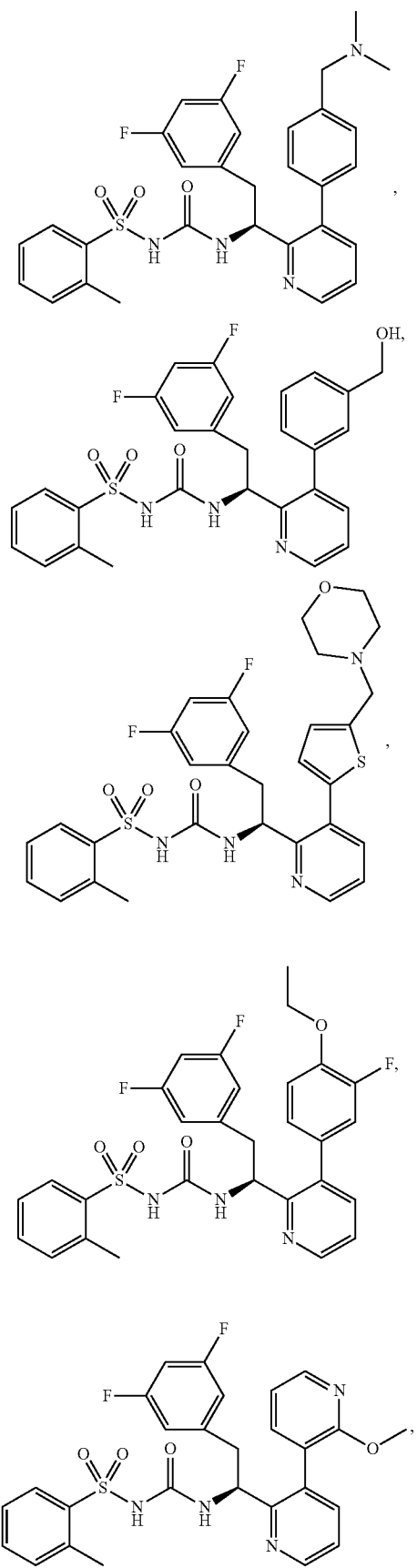
30
-continued
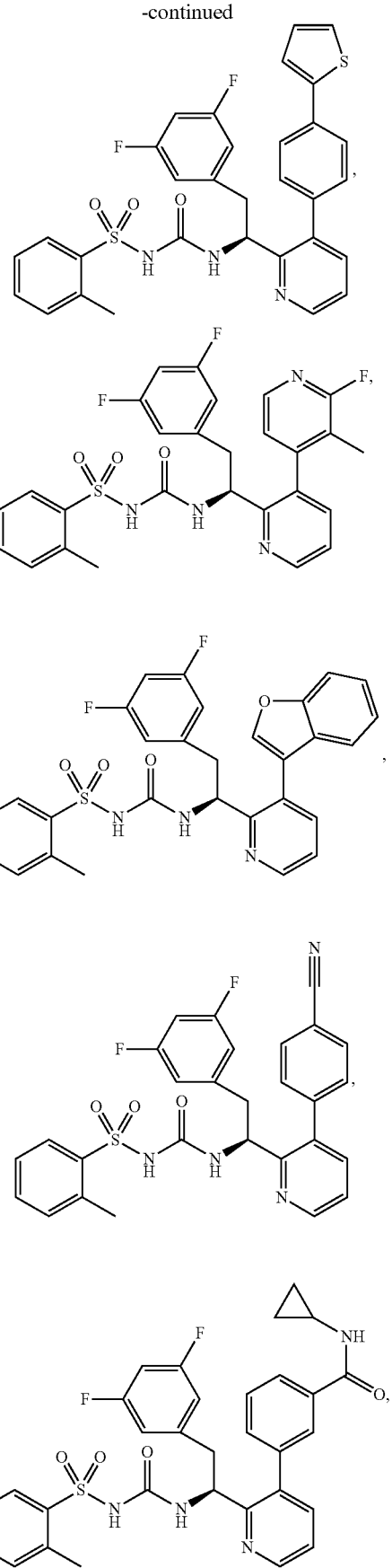

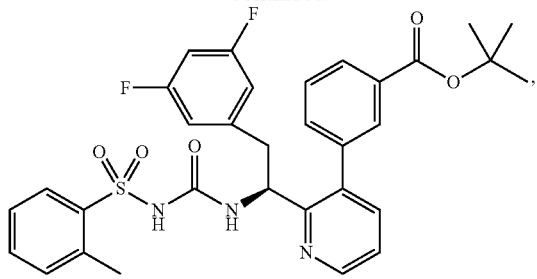
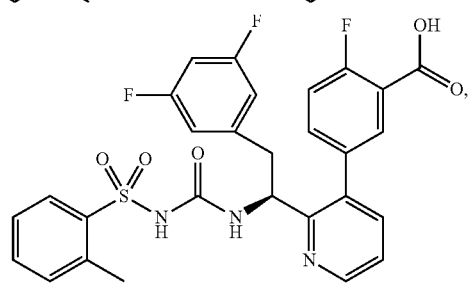
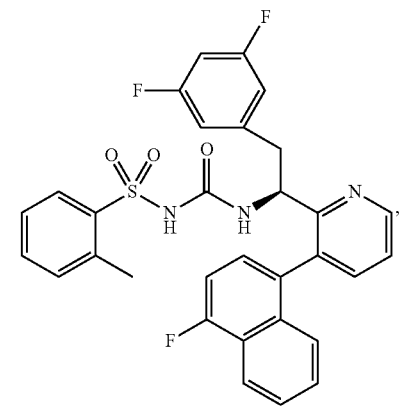
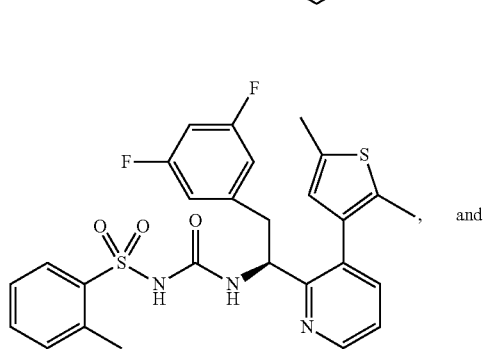
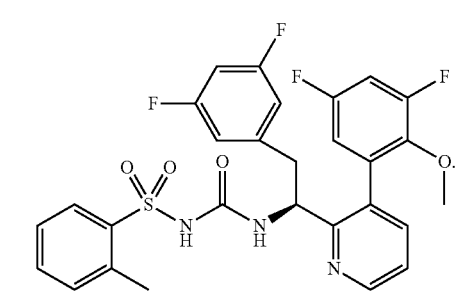
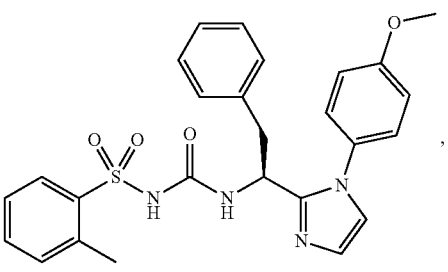
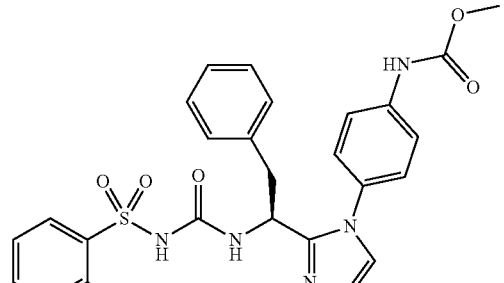
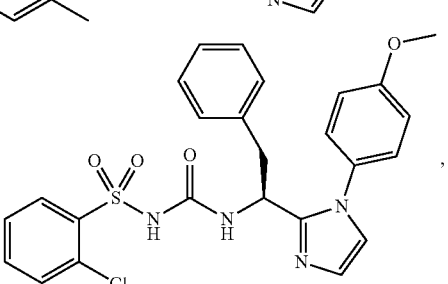
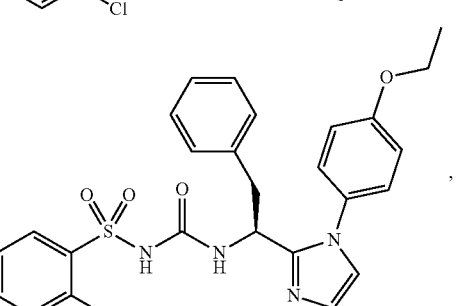
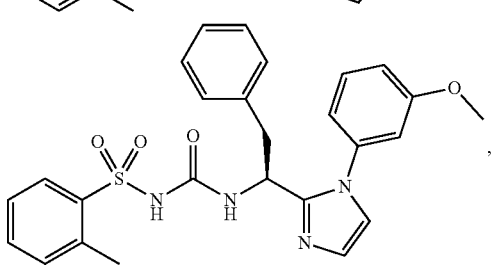
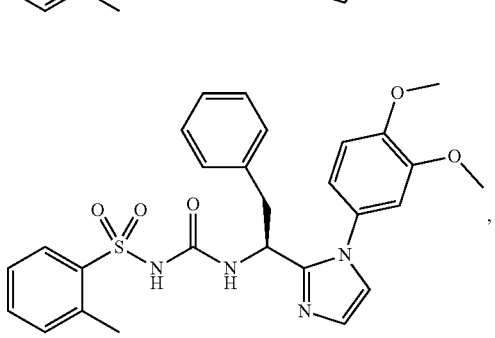
Other preferred compounds, including pharmaceutically acceptable salts thereof, are selected from the group of:

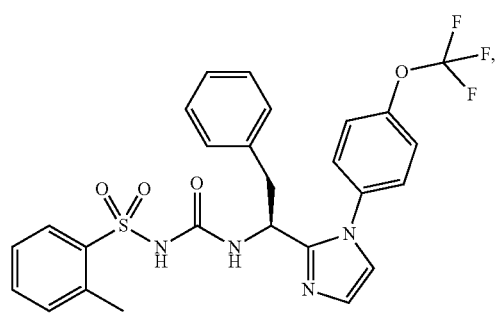
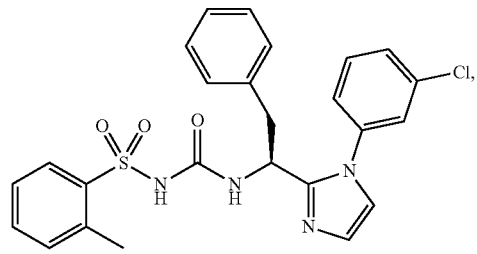
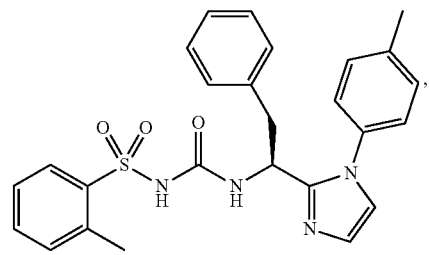
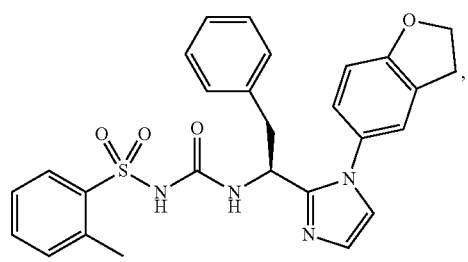
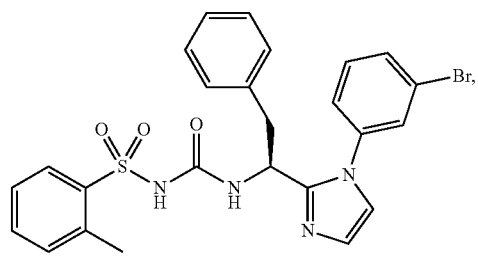
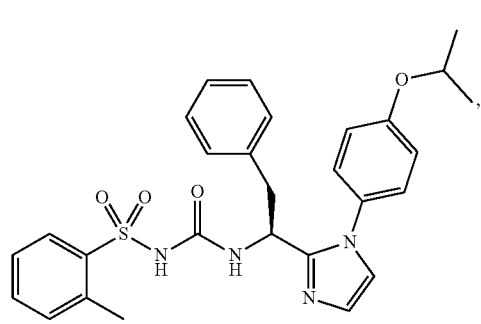
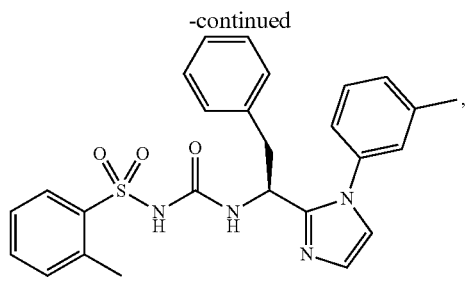
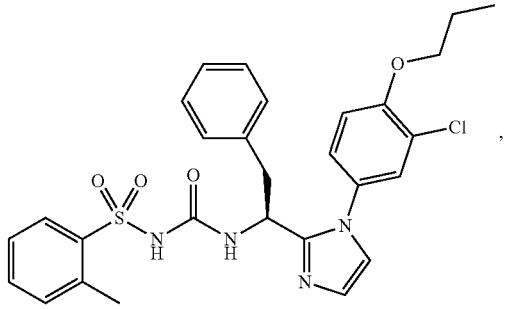
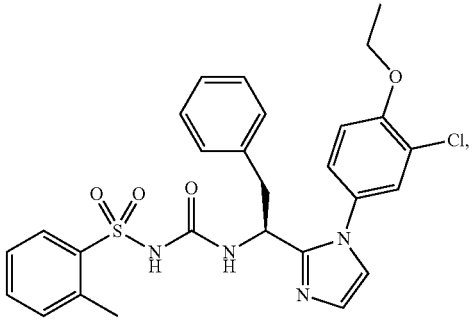
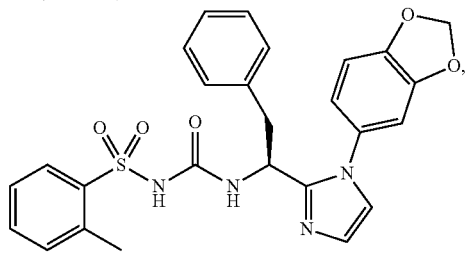
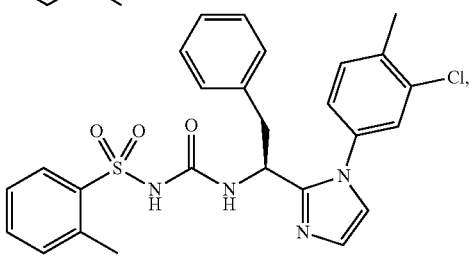
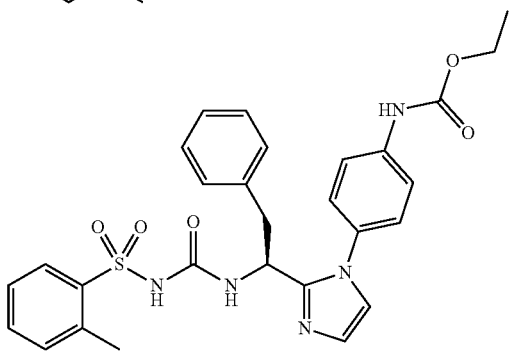

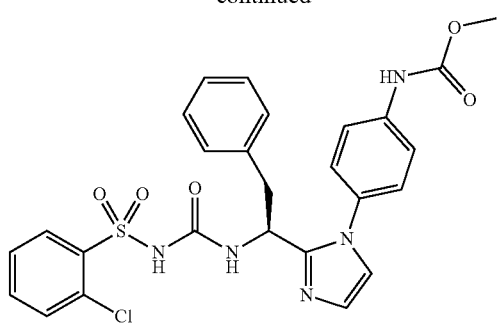
,
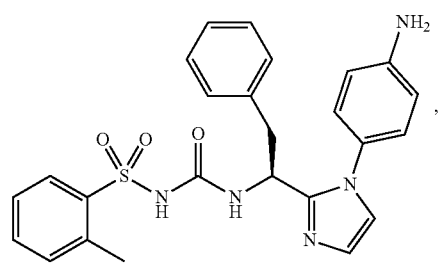
,
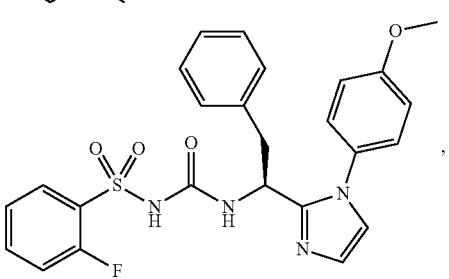
,
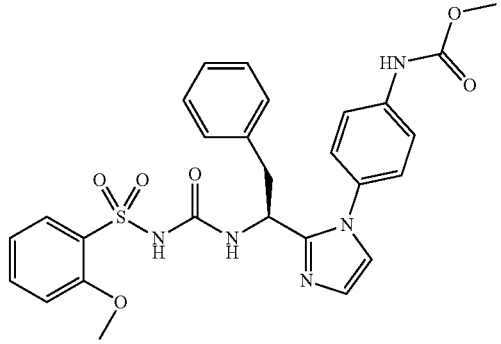
,
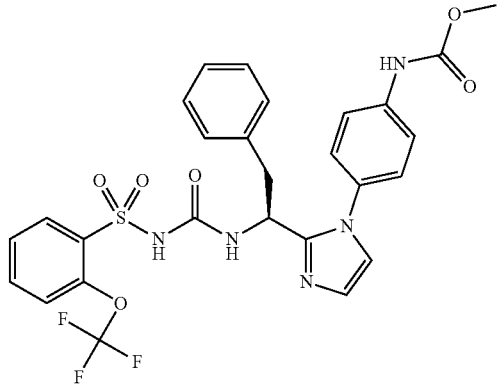
,
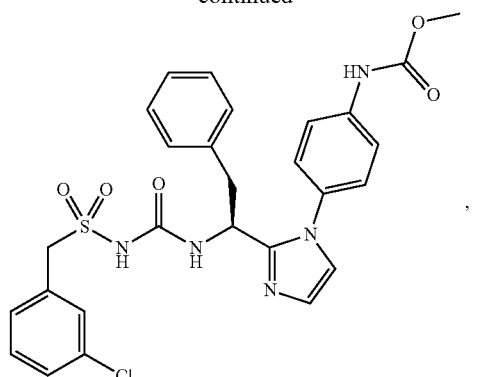
,
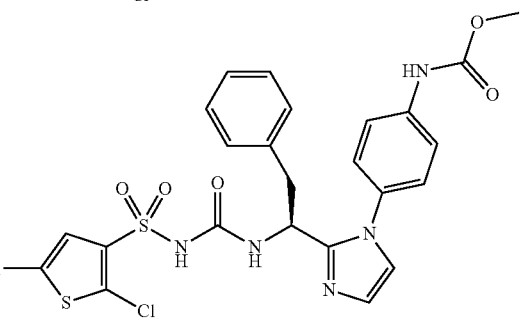
,
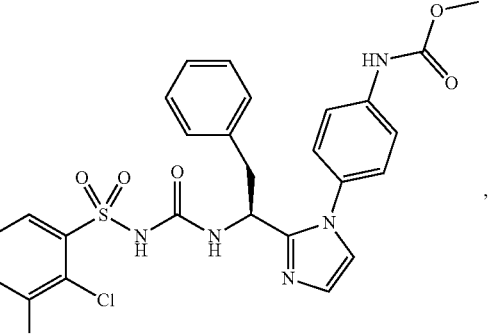
,
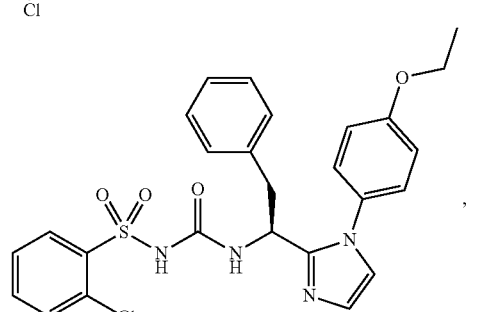
,
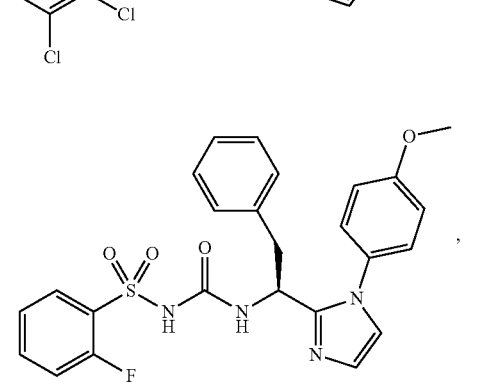
,

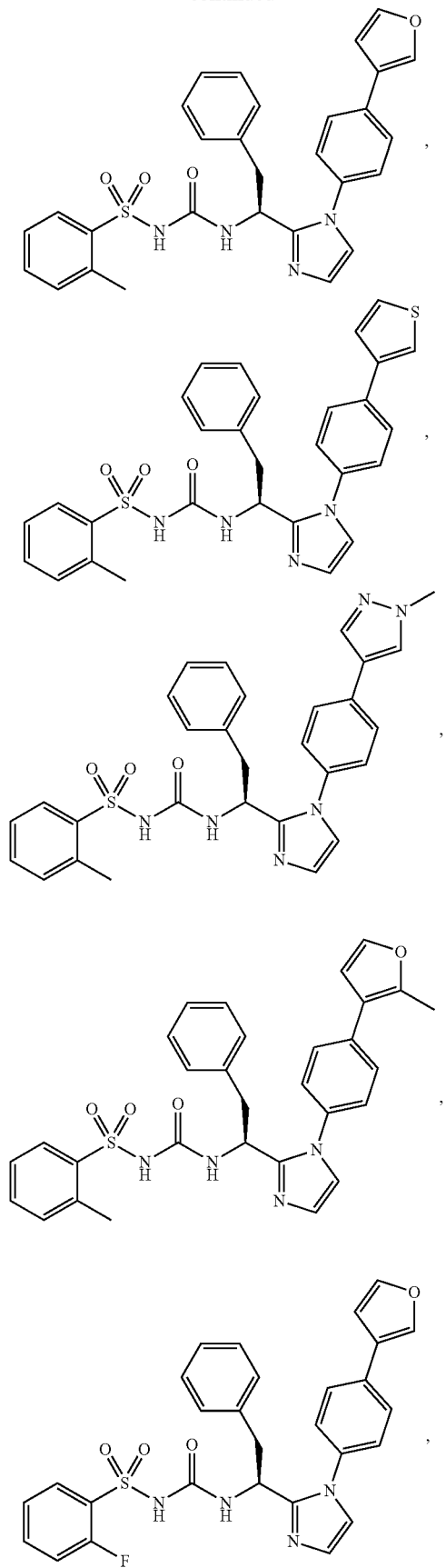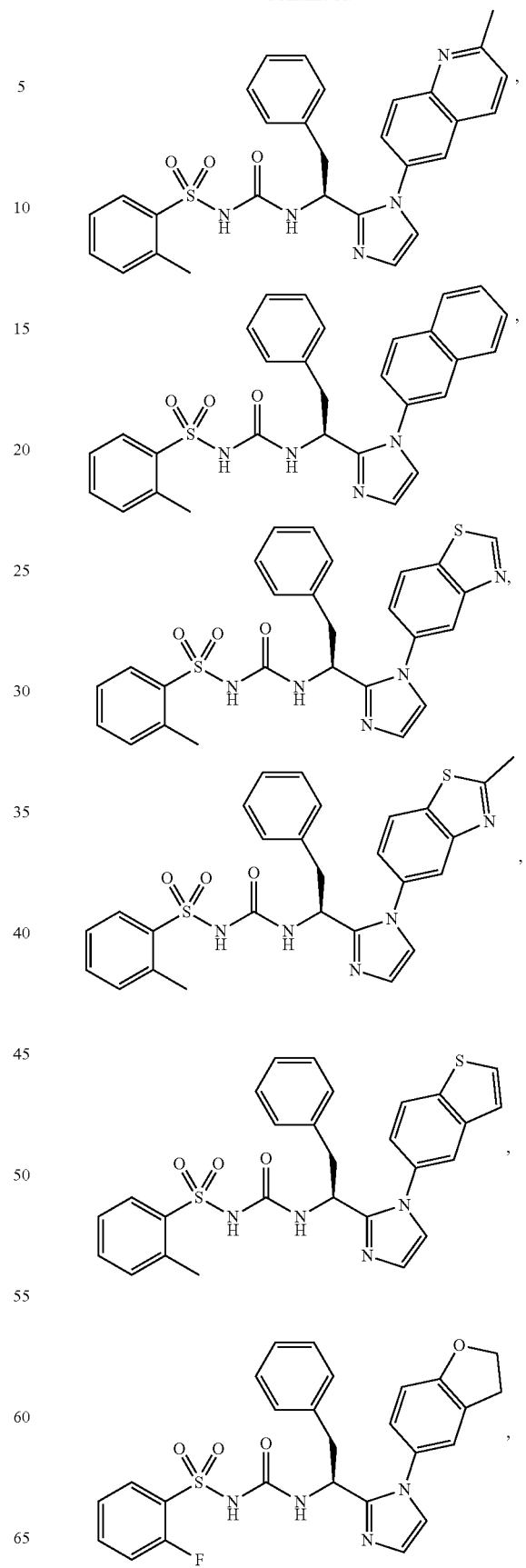

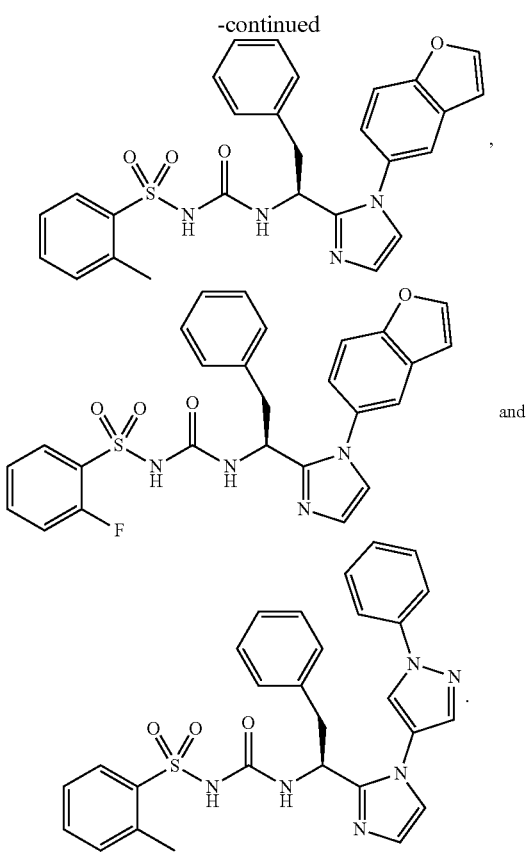

Pharmaceutical Compositions and Methods of Use

The compounds of the invention herein described and set forth are generally given as pharmaceutical compositions. These compositions are comprised of a therapeutically effective amount of a compound of Formula I or its pharmaceutically acceptable salt, and a pharmaceutically acceptable carrier and may contain conventional excipients and/or diluents. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, lozenges, and powders as well as liquid suspensions, syrups, elixirs, and solutions. Compositions are made using available formulation techniques, and conventional excipients (such as binding and wetting agents) and vehicles (such as water and alcohols) are generally used for compositions. See, for example, Remington's Pharmaceutical Sciences, 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regimen, however, will be determined by a physician using sound medical judgment.

The compounds of this invention have activity against HIV. Accordingly, another aspect of the invention is a method for treating HIV infection in a human patient comprising administering a therapeutically effective amount of a compound of Formula I, including a pharmaceutically acceptable salt thereof, with a pharmaceutically acceptable carrier, excipient and/or diluent.

The invention also encompasses methods where the compound is given in combination therapy. That is, the compound can be used in conjunction with, but separately from, other agents useful in treating AIDS and HIV infection. The compound can also be used in combination therapy wherein the compound and one or more of the other agents are physically together in a fixed-dose combination (FDC). Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regimen, however, will be determined by a physician using sound medical judgment.

"Combination," "coadministration," "concurrent" and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

Thus, as set forth above, contemplated herein are combinations of the compounds of Formula I, together with one or more agents useful in the treatment of AIDS. For example, the compounds of the invention may be effectively administered, whether at periods of pre-exposure and/or post-exposure, in combination with effective amounts of the AIDS antivirals, immunomodulators, anti-infectives, or vaccines, such as those in the following non-limiting table:

| Drug Name | Manufacturer | Indication |
|---|---|---|
| ANTIVIRALS | | |
| Rilpivirine | Tibotec | HIV infection, AIDS, ARC (non-nucleoside reverse transcriptase inhibitor) |

| Drug Name | Manufacturer | Indication |
| --- | --- | --- |
| COMPLERA® | Gilead | HIV infection, AIDS, ARC; combination with emtricitabine, rilpivirine, and tenofovir disoproxil fumarate |
| 097 | Hoechst/Bayer | HIV infection, AIDS, ARC (non-nucleoside reverse trans-criptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-234475 (CGP-61755) | Bristol-Myers Squibb/Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Darunavir | Tibotec-J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, SUSTIVA®) (-)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV Infections |
| Virazole Ribavirin | Viratek/ICN (Costa Mesa, CA) | asymptomatic HIV positive, LAS, ARC |

| Drug Name | Manufacturer | Indication |
|---|---|---|
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (VIREAD®) | Gilead | HIV infection, AIDS, (reverse transcriptase inhibitor) |
| EMTRIVA® (Emtricitabine) (FTC) | Gilead | HIV infection, AIDS, (reverse transcriptase inhibitor) |
| COMBIVIR® | GSK | HIV infection, AIDS, (reverse transcriptase inhibitor) |
| Abacavir succinate (or ZJAGEN®) | GSK | HIV infection, AIDS, (reverse transcriptase inhibitor) |
| REYATAZ® (or atazanavir) | Bristol-Myers Squibb | HIV infection AIDs, protease inhibitor |
| FUZEON® (Enfuvirtide or T-20) | Roche/Trimeris | HIV infection AIDs, viral Fusion inhibitor |
| LEXIVA® (or Fosamprenavir calcium) | GSK/Vertex | HIV infection AIDs, viral protease inhibitor |
| SELZENTRY ™ Maraviroc; (UK 427857) | Pfizer | HIV infection AIDs, (CCR5 antagonist, in development) |
| TRIZIVIR® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| TRUVADA® | Gilead | Combination of Tenofovir disoproxil fumarate salt (VIREAD®) and EMTRIVA® (Emtricitabine) |
| Integrase Inhibitor GS917/JTK-303 Elvitegravir | Gilead/Japan Tobacco | HIV Infection AIDs in development |
| Triple drug combination ATRIPLA® | Gilead/Bristol-Myers Squibb | Combination of Tenofovir disoproxil fumarate salt (VIREAD®), EMTRIVA® (Emtricitabine), and SUSTIVA® (Efavirenz) |
| FESTINAVIR® | Oncolys BioPharma | HIV infection AIDs in development |
| CMX-157 Lipid conjugate of nucleotide tenofovir | Chimerix | HIV infection AIDs |
| GSK1349572 Integrase inhibitor | GSK | HIV infection AIDs |

| Drug Name | Manufacturer | Indication |
|---|---|---|
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldesluken) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |

-continued

| Drug Name | Manufacturer | Indication |
|---|---|---|
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

"Therapeutically effective" means the amount of agent required to provide a meaningful patient benefit as understood by practitioners in the field of AIDS and HIV infection. In general, the goals of therapeutically effective treatment include suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

Methods of Synthesis

The compounds of the invention according to the various embodiments can be made by various methods available in the art, including those of the following schemes in the specific examples which follow. The structure numbering and variable numbering shown in the synthetic schemes may be distinct from, and should not be confused with, the structure or variable numbering in the claims or the rest of the specification. The variables in the schemes are meant only to illustrate how to make some of the compounds of the invention.

Abbreviations used in the schemes generally follow conventions used in the art. Some specific chemical abbreviations used in the examples are defined as follows: "DMF" for N,N-dimethylformamide; "MeOH" for methanol; "Ar" for aryl; "TFA" for trifluoroacetic acid; "BOC" for t-butoxycarbonate, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HATU" for (1-[Bis(dimethylamino)methylene]-1H-1,2,3-triazolo[4,5-b]pyridinium 3-oxid hexafluorophosphate) "DIEA" for diisopropylethylamine.

Certain other abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

EXAMPLES

The following examples are provided by way of illustration only, and should not be construed as limiting the scope of the invention.

Example 1

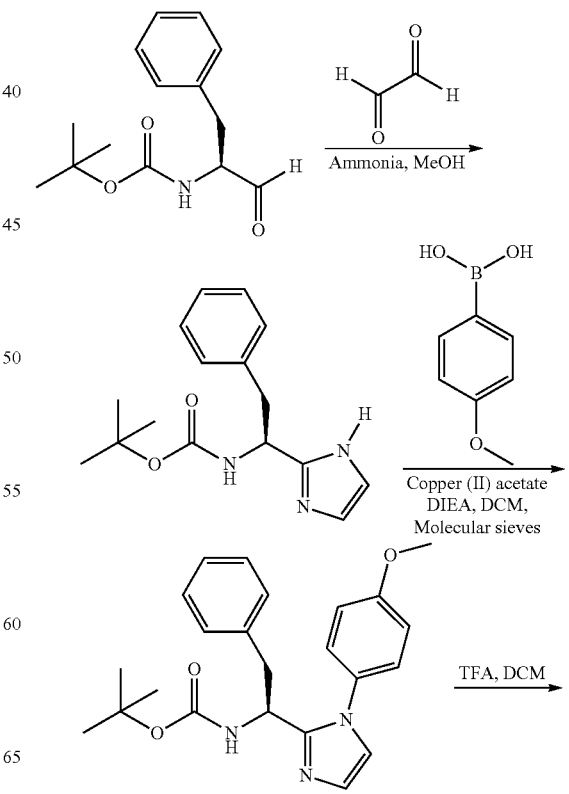

-continued

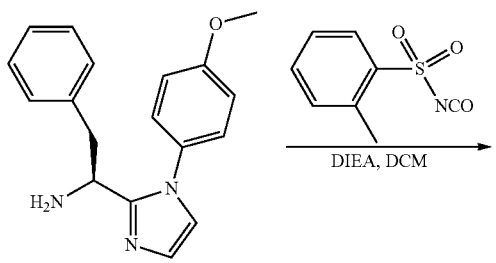

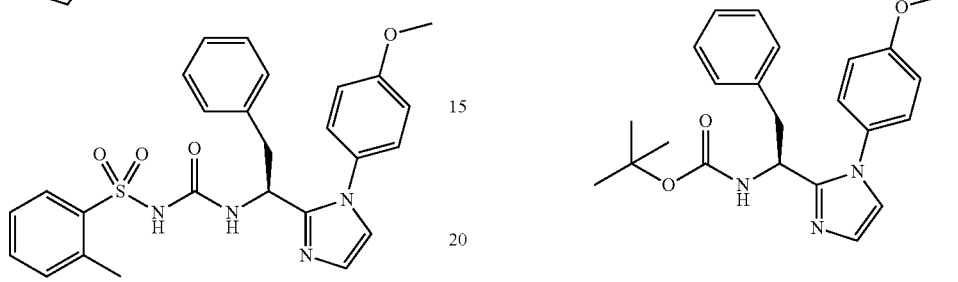

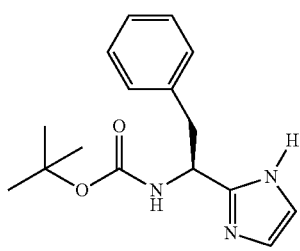 [SMILES: CC(C)(C)OC(=O)N[C@@H](Cc1ccccc1)c1ncc[nH]1]

(S)-tert-butyl (1-(1H-imidazol-2-yl)-2-phenylethyl)carbamate

To a mixture of (S)-tert-butyl (1-oxo-3-phenylpropan-2-yl)carbamate (4.4 g, 17.65 mmol) in MeOH (75 mL) at −10° C. was added 40% Glyoxal in water (2.024 mL, 17.65 mmol). At −10° C., ammonia gas was bubbled through the reaction mixture for 60 minutes. The reaction was warmed up to r.t. and stirred for 100 hrs. Most of the methanol was evaporated. Water was added to the reaction mixture and solid precipitated out. The solid was filtered and purified by silica gel chromatography to afford (1.7 g, 33.5%) of the title compound.

$^1$H NMR (400 MHz, DMSO-d$_6$) δ 11.74-11.59 (m, 1H), 7.24 (br. s., 2H), 7.20-7.13 (m, 3H), 7.10-7.02 (m, 1H), 7.01-6.94 (m, 1H), 6.80 (s, 1H), 4.89-4.74 (m, 1H), 3.23-3.14 (m, 1H), 3.03-2.90 (m, 1H), 1.31 (s, 9H).

| (S)-tert-butyl (1-(1H-imidazol-2-yl)-2-phenylethyl)carbamate | |
|---|---|
| MS (M + H)$^+$ Calcd. | 288 |
| MS (M + H)$^+$ Observ. | 288 |
| Retention Time | 1.022 min |
| | LC Condition |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 2 min |
| Flow Rate | 1 mL/min |
| Wavelength | 220 |
| Column | Phenomenex LUNA C18 30 × 2 mm, 3μ |

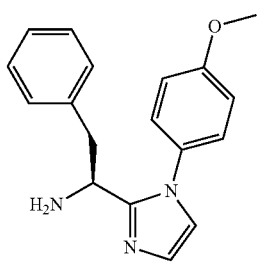 [SMILES: COc1ccc(-n2ccnc2[C@@H](N)Cc2ccccc2)cc1]

(S)-tert-butyl (1-(1-(4-methoxyphenyl)-1H-imidazol-2-yl)-2-phenylethyl)carbamate To a mixture of (S)-tert-butyl (1-(1H-imidazol-2-yl)-2-phenylethyl)carbamate (80 mg, 0.278 mmol), (4-methoxyphenyl)boronic acid (85 mg, 0.557 mmol), copper (II) acetate (50.6 mg, 0.278 mmol) was added dichloromethane (5 mL) followed by diisopropylethylamine (0.146 mL, 0.835 mmol) and molecular sieves. The reaction mixture was stirred at r.t. under an atmosphere of air for 4 days. The reaction mixture was filtered through a pad of silica gel and washed by 10% MeOH/DCM. The solvent was evaporated and the residue was purified by prep HPLC to afford (45 mg, 41%) of the title compound.

$^1$H NMR (400 MHz, METHANOL-d$_4$) δ 7.24-7.06 (m, 4H), 7.05-6.76 (m, 7H), 4.82-4.71 (m, 1H), 3.83 (s, 3H), 3.13-2.95 (m, 2H), 1.38 (s, 9H).

| (S)-tert-butyl (1-(1-(4-methoxyphenyl)-1H-imidazol-2-yl)-2-phenylethyl)carbamate | |
|---|---|
| MS (M + H)$^+$ Calcd. | 394 |
| MS (M + H)$^+$ Observ. | 394 |
| Retention Time | 1.39 min |
| | LC Condition |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 2 min |
| Flow Rate | 1 mL/min |
| Wavelength | 220 |
| Column | Phenomenex LUNA C18 30 × 2 mm, 3μ |

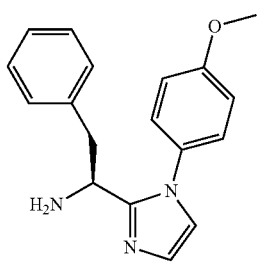 [SMILES: COc1ccc(-n2ccnc2[C@@H](N)Cc2ccccc2)cc1]

(S)-1-(1-(4-methoxyphenyl)-1H-imidazol-2-yl)-2-phenylethanamine, TFA Salt

To (S)-tert-butyl (1-(1-(4-methoxyphenyl)-1H-imidazol-2-yl)-2-phenylethyl)carbamate (20 mg, 0.051 mmol) was added 50% TFA in dichloromethane (1 ml). The reaction mixture was stirred at r.t. for 2 hrs. The solvent was evaporated to give (20 mg, 97%) of the title compound. It was used without further purification.

| (S)-1-(1-(4-methoxyphenyl)-1H-imidazol-2-yl)-2-phenylethanamine, TFA salt | |
|---|---|
| MS (M + H)+ Calcd. | 294 |
| MS (M + H)+ Observ. | 294 |
| Retention Time | 1.05 min |
| LC Condition | |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 2 min |
| Flow Rate | 1 mL/min |
| Wavelength | 220 |
| Column | Phenomenex LUNA C18 30 × 2 mm, 3μ |

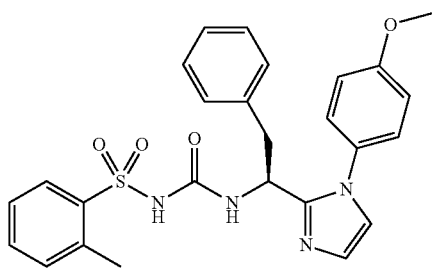 [SMILES: COc1ccc(-n2ccnc2[C@H](Cc2ccccc2)NC(=O)NS(=O)(=O)c2ccccc2C)cc1]

(S)-N-((1-(1-(4-methoxyphenyl)-1H-imidazol-2-yl)-2-phenylethyl)carbamoyl)-2-methylbenzene-sulfonamide To a solution of (S)-1-(1-(4-methoxyphenyl)-1H-imidazol-2-yl)-2-phenylethanamine, TFA (20 mg, 0.049 mmol) in dichloromethane (1 mL) was added diisopropylethylamine (0.026 mL, 0.147 mmol) followed by 2-methylbenzenesulfonyl isocyanate (14.5 mg, 0.074 mmol) in dichloromethane (1 mL). The reaction mixture was stirred at r.t. for 1 hr. The solvent was evaporated and the residue was purified by prepHPLC to afford (16.5 mg, 68.5%) of the title compound.

$^1$H NMR (500 MHz, DMSO-d$_6$) δ 7.84 (d, J=7.7 Hz, 1H), 7.61-7.52 (m, 1H), 7.45-7.32 (m, 2H), 7.18-7.08 (m, 4H), 7.03 (s, 1H), 6.96 (d, J=8.1 Hz, 1H), 6.91-6.79 (m, 4H), 6.70 (d, J=6.2 Hz, 2H), 4.69 (q, J=7.5 Hz, 1H), 3.77 (s, 3H), 3.02-2.71 (m, 2H), 2.53 (s, 3H).

| (S)-N-((1-(1-(4-methoxyphenyl)-1H-imidazol-2-yl)-2-phenylethyl)carbamoyl)-2-methylbenzenesulfonamide | |
|---|---|
| MS (M + H)+ Calcd. | 491 |
| MS (M + H)+ Observ. | 491 |
| Retention Time | 1.50 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

Example 2

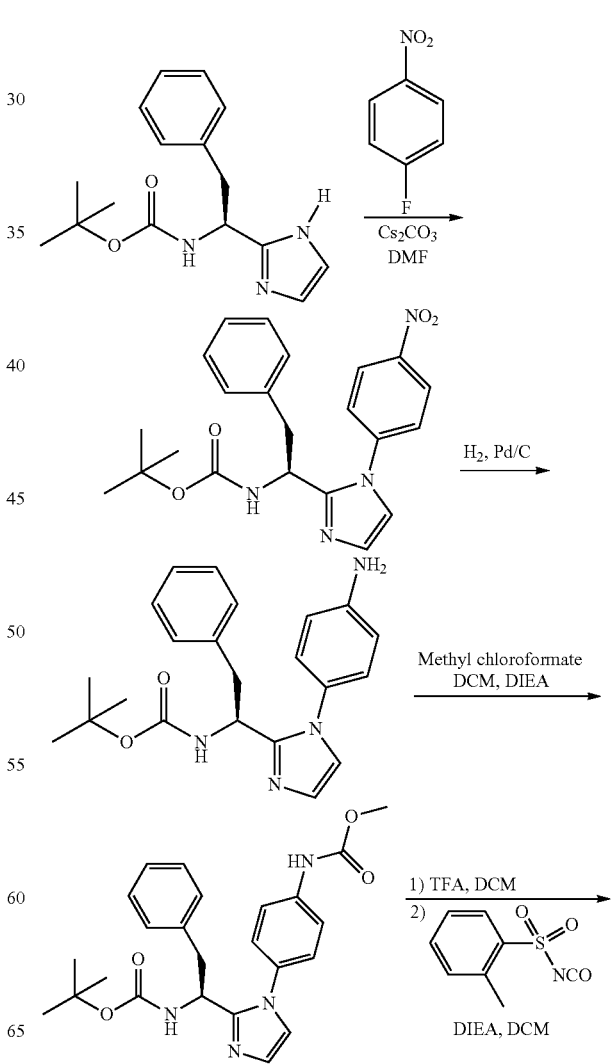

-continued

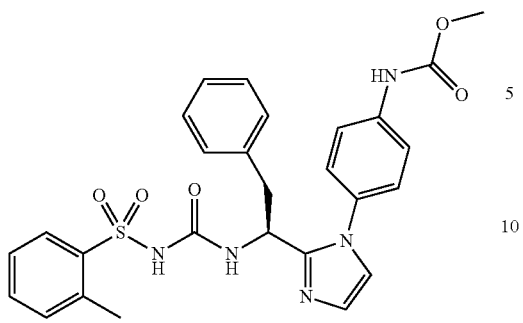

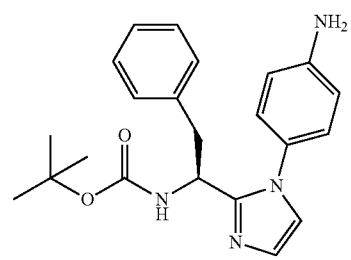 [SMILES: CC(C)(C)OC(=O)N[C@@H](Cc1ccccc1)c1nccn1-c1ccc(N)cc1]

(S)-tert-butyl (1-(1-(4-aminophenyl)-1H-imidazol-2-yl)-2-phenylethyl)carbamate

A mixture of 10% palladium on carbon (6 mg, 5.64 μmol) in methanol (1 mL) was stirred under H₂ balloon for 5 mins (S)-tert-butyl (1-(1-(4-nitrophenyl)-1H-imidazol-2-yl)-2-phenylethyl)carbamate (25 mg, 0.061 mmol) in methanol (1 mL) was added. The reaction mixture was stirred under H₂ balloon for 4 hrs. The palladium catalyst was filtered off and the solvent was evaporated to afford (20 mg, 86%) of the title compound.

$^1$H NMR (400 MHz, DMSO-d$_6$) δ 7.23 (d, J=8.5 Hz, 1H), 7.18-7.11 (m, 3H), 7.00 (s, 1H), 6.93 (s, 1H), 6.90-6.83 (m, 2H), 6.69 (d, J=8.3 Hz, 2H), 6.53 (d, J=8.3 Hz, 2H), 5.35 (s, 2H), 4.63 (d, J=7.8 Hz, 1H), 3.04-2.80 (m, 2H), 1.29 (s, 9H).

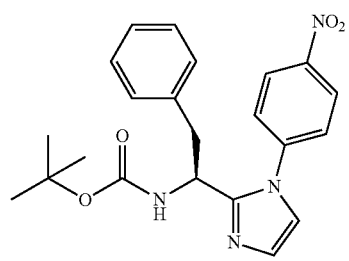

(S)-tert-butyl (1-(1-(4-nitrophenyl)-1H-imidazol-2-yl)-2-phenylethyl)carbamate

To (S)-tert-butyl (1-(1H-imidazol-2-yl)-2-phenylethyl)carbamate (200 mg, 0.696 mmol) in DMF (1 mL) was added cesium carbonate (454 mg, 1.392 mmol) followed by 1-fluoro-4-nitrobenzene (196 mg, 1.392 mmol). The reaction mixture was stirred at 60° C. for 4 hrs. The reaction mixture was cooled down and filtered. Purification by prepHPLC afforded (135 mg, 47.5%) of the title compound.

$^1$H NMR (400 MHz, DMSO-d$_6$) δ 8.25 (d, J=8.8 Hz, 2H), 7.47 (d, J=8.0 Hz, 1H), 7.41 (d, J=8.8 Hz, 2H), 7.29 (s, 1H), 7.15-7.05 (m, 4H), 6.94-6.86 (m, 2H), 4.81 (d, J=7.8 Hz, 1H), 3.15-2.90 (m, 2H), 1.22 (s, 9H).

| (S)-tert-butyl (1-(1-(4-nitrophenyl)-1H-imidazol-2-yl)-2-phenylethyl)carbamate | |
|---|---|
| MS (M + H)⁺ Calcd. | 409 |
| MS (M + H)⁺ Observ. | 409 |
| Retention Time | 1.32 min |
| LC Condition | |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 2 min |
| Flow Rate | 1 mL/min |
| Wavelength | 220 |
| Column | Phenomenex Luna 30 × 2.0 MM 3u |

| (S)-tert-butyl (1-(1-(4-aminophenyl)-1H-imidazol-2-yl)-2-phenylethyl)carbamate | |
|---|---|
| MS (M + H)⁺ Calcd. | 379 |
| MS (M + H)⁺ Observ. | 379 |
| Retention Time | 1.11 min |
| LC Condition | |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 2 min |
| Flow Rate | 1 mL/min |
| Wavelength | 220 |
| Column | Phenomenex Luna 30 × 2.0 MM 3u |

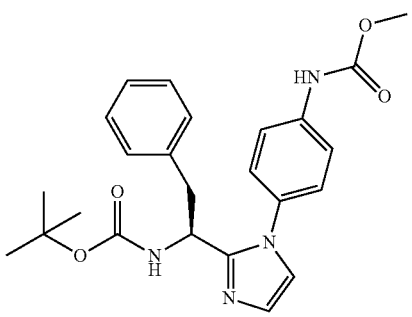 [SMILES: COC(=O)Nc1ccc(-n2ccnc2[C@H](Cc2ccccc2)NC(=O)OC(C)(C)C)cc1]

(S)-methyl (4-(2-(1-tert-butoxycarbonylamido-2-phenylethyl)-1H-imidazol-1-yl)phenyl)carbamate To a solution of (S)-tert-butyl (1-(1-(4-aminophenyl)-1H-imidazol-2-yl)-2-phenylethyl)carbamate (24 mg, 0.063 mmol) in dichloromethane (1 mL) was added diisopropylethylamine (0.033 mL, 0.190 mmol) followed by methylchloroformate (7.2 mg, 0.076 mmol) in dichloromethane (1 mL). The reaction mixture was stirred at r.t. for 1 hr. The solvent was evaporated and the residue was purified by prepHPLC to afford (20 mg, 72.3%) of the title compound.

| (S)-methyl (4-(2-(1-tert-butoxycarbonylamido-2-phenylethyl)-1H-imidazol-1-yl)phenyl)carbamate | |
|---|---|
| MS (M + H)⁺ Calcd. | 437 |
| MS (M + H)⁺ Observ. | 437 |
| Retention Time | 1.23 min |
| LC Condition | |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 2 min |
| Flow Rate | 1 mL/min |
| Wavelength | 220 |
| Column | Phenomenex Luna 30 × 2.0 MM 3u |

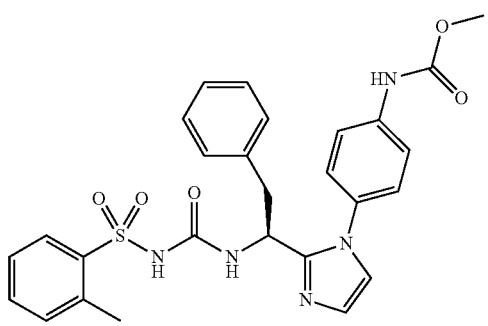 [SMILES: COC(=O)Nc1ccc(-n2ccnc2[C@H](Cc2ccccc2)NC(=O)NS(=O)(=O)c2ccccc2C)cc1]

(S)-methyl (4-(2-(2-phenyl-1-(3-(o-tolylsulfonyl)ureido)ethyl)-1H-imidazol-1-yl)phenyl)carbamate To (S)-methyl (4-(2-(1-tert-butoxycarbonylamido-2-phenylethyl)-1H-imidazol-1-yl)phenyl)carbamate (20 mg, 0.046 mmol) was added 50% TFA in dichloromethane (1 ml). The reaction mixture was stirred at r.t. for 1 hr. The solvent was evaporated to afford (S)-methyl (4-(2-(1-amino-2-phenylethyl)-1H-imidazol-1-yl)phenyl)carbamate, TFA salt. It was used for next step without further purification. To a solution of (S)-methyl (4-(2-(1-amino-2-phenylethyl)-1H-imidazol-1-yl)phenyl)carbamate, TFA salt in dichloromethane (1 mL) was added diisopropylethylamine (0.024 mL, 0.137 mmol) followed by 2-methylbenzenesulfonyl isocyanate (13.6 mg, 0.069 mmol) in dichloromethane (1 mL). The reaction mixture was stirred at r.t. for 1 hr. The solvent was evaporated and the residue was purified by prepHPLC to afford (11.6 mg, 47.4%) of the title compound.

¹H NMR (500 MHz, DMSO-d₆) δ 9.86 (s, 1H), 7.82 (d, J=7.3 Hz, 1H), 7.51 (d, J=7.0 Hz, 1H), 7.46-7.29 (m, 4H), 7.18-7.06 (m, 4H), 7.03 (s, 1H), 6.82 (d, J=8.1 Hz, 2H), 6.70 (d, J=6.6 Hz, 2H), 4.70 (d, J=6.2 Hz, 1H), 3.00-2.74 (m, 2H), 2.53 (s, 3H).

| (S)-methyl (4-(2-(2-phenyl-1-(3-(o-tolylsulfonyl)ureido)ethyl)-1H-imidazol-1-yl)phenyl)carbamate | |
|---|---|
| MS (M + H)⁺ Calcd. | 534 |
| MS (M + H)⁺ Observ. | 534 |
| Retention Time | 1.53 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

Example 3

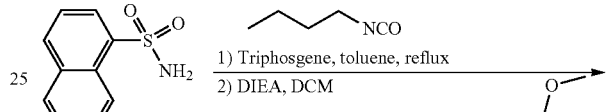

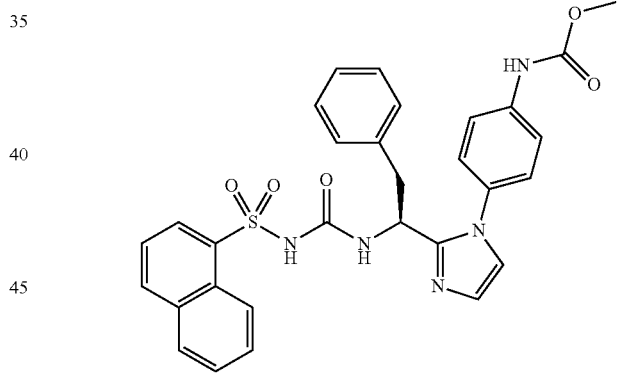

(S)-methyl (4-(2-(1-(3-(naphthalen-1-ylsulfonyl)ureido)-2-phenylethyl)-1H-imidazol-1-yl)phenyl)carbamate To a solution of naphthalene-1-sulfonamide (13.80 mg, 0.067 mmol) in toluene (1 mL) was added 1-isocyanatobutane (1.32 mg, 0.013 μmol) followed by triphosgene (6.59 mg, 0.022 mmol). The reaction mixture was stirred at 110° C. for 24 hrs. The reaction mixture was cooled down and the solvent was evaporated to afford naphthalene-1-sulfonyl isocyanate. It was used for next step without further purification. To a solution of (S)-methyl (4-(2-(1-amino-2-phenylethyl)-1H-imidazol-1-yl)phenyl)carbamate, TFA (20 mg, 0.044 mmol) in dichloromethane (0.5 mL) was added diisopropylethylamine (0.023 mL, 0.133 mmol) followed by naphthalene-1-sulfonyl isocyanate in dichloromethane (0.5 mL). The reaction mixture was stirred at r.t. for 1 hr. The solvent was evaporated and the residue was purified by prepHPLC to afford (13.1 mg, 51.8%) of the title compound.

¹H NMR (500 MHz, DMSO-d₆) δ 9.83 (br. s., 1H), 8.55 (d, J=8.1 Hz, 1H), 8.27 (d, J=8.4 Hz, 1H), 8.20-8.07 (m, 2H), 7.80-7.58 (m, 3H), 7.36 (d, J=8.1 Hz, 2H), 7.21-6.83 (m, 7H), 6.74 (d, J=8.4 Hz, 2H), 6.56 (d, J=7.3 Hz, 2H), 4.63 (d, J=6.6 Hz, 1H), 3.69 (s, 3H), 2.89-2.60 (m, 2H).

| (S)-methyl (4-(2-(1-(3-(naphthalen-1-ylsulfonyl)ureido)-2-phenylethyl)-1H-imidazol-1-yl)phenyl)carbamate | |
|---|---|
| MS (M + H)⁺ Calcd. | 570 |
| MS (M + H)⁺ Observ. | 570 |
| Retention Time | 1.34 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

Example 4

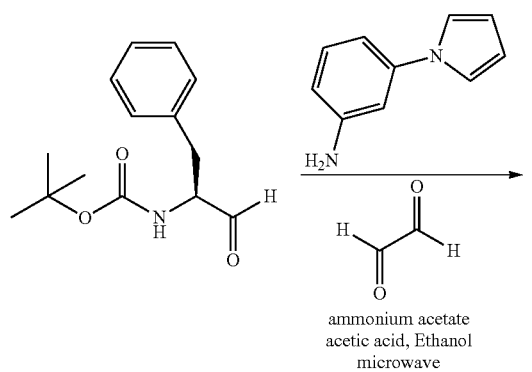

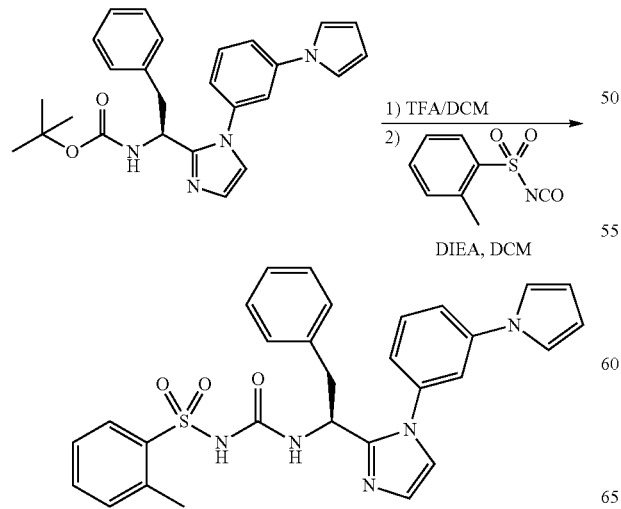

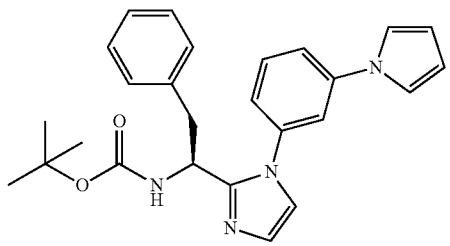 [SMILES: CC(C)(C)OC(=O)N[C@@H](Cc1ccccc1)c1nccn1-c1cccc(-n2cccc2)c1]

(S)-tert-butyl (1-(1-(3-(1H-pyrrol-1-yl)phenyl)-1H-imidazol-2-yl)-2-phenylethyl)carbamate To a 0.5-2 ml microwave tube was added (S)-tert-butyl (1-oxo-3-phenylpropan-2-yl)carbamate (150 mg, 0.602 mmol), 3-(1H-pyrrol-1-yl)aniline (95 mg, 0.602 mmol), ammonium acetate (46.4 mg, 0.602 mmol), 40% Glyoxal in water (87 mg, 0.602 mmol), acetic acid (0.172 mL, 3.01 mmol) and ethanol (3 mL). The reaction mixture was heated in a microwave reactor at 160° C. for 20 min. The reaction mixture was filtered and the filtrate was purified by PrepHPLC to afford (25 mg, 10%) of the title compound.

¹H NMR (500 MHz, METHANOL-d₄) δ 7.53 (br. s., 1H), 7.42 (s, 1H), 7.23 (t, J=2.0 Hz, 2H), 7.18-7.01 (m, 6H), 6.85-6.72 (m, 3H), 6.32 (t, J=2.0 Hz, 2H), 4.95-4.88 (m, 1H), 3.15-3.00 (m, 2H), 1.42 (s, 9H).

| (S)-tert-butyl (1-(1-(3-(1H-pyrrol-1-yl)phenyl)-1H-imidazol-2-yl)-2-phenylethyl)carbamate | |
|---|---|
| MS (M + H)⁺ Calcd. | 429 |
| MS (M + H)⁺ Observ. | 429 |
| Retention Time | 1.52 min |
| LC Condition | |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 2 min |
| Flow Rate | 1 mL/min |
| Wavelength | 220 |
| Column | Phenomenex Luna 30 × 2.0 MM 3 u |

(S)-N-((1-(1-(3-(1H-pyrrol-1-yl)phenyl)-1H-imidazol-2-yl)-2-phenylethyl)carbamoyl)-2-methyl-benzenesulfonamide To (S)-tert-butyl (1-(1-(3-(1H-pyrrol-1-yl)phenyl)-1H-imidazol-2-yl)-2-phenylethyl)carbamate (25 mg, 0.058 mmol) was added 50% TFA in dichloromethane (1 ml). The reaction mixture was stirred at r.t. for 1 hr. The solvent was evaporated to afford (S)-1-(1-(3-(1H-pyrrol-1-yl)phenyl)-1H-imidazol-2-yl)-2-phenylethanamine, TFA salt. It was used for next step without further purification. To a solution of (S)-1-(1-(3-(1H-pyrrol-1-yl)phenyl)-1H-imidazol-2-yl)-2-phenylethanamine, TFA salt in dichloromethane (1 mL) was added diisopropylethylamine (0.031 mL, 0.175 mmol) followed by 2-methylbenzenesulfonyl isocyanate (17.3 mg, 0.088 mmol) in dichloromethane (1 mL). The reaction mixture was stirred at r.t. for 1 hr. The solvent was evaporated and the residue was purified by prepHPLC to afford (16 mg, 52%) of the title compound.

$^1$H NMR (500 MHz, DMSO-$d_6$) δ 7.81 (d, J=7.3 Hz, 1H), 7.56 (d, J=8.1 Hz, 1H), 7.44-7.28 (m, 5H), 7.22 (br. s., 2H), 7.16 (s, 1H), 7.09-6.92 (m, 4H), 6.63 (br. s., 3H), 6.26 (s, 2H), 4.96-4.68 (m, 1H), 2.97-2.77 (m, 2H), 2.54 (s, 3H).

| (S)-N-((1-(1-(3-(1H-pyrrol-1-yl)phenyl)-1H-imidazol-2-yl)-2-phenylethyl)carbamoyl)-2-methylbenzenesulfonamide | |
|---|---|
| MS (M + H)$^+$ Calcd. | 526 |
| MS (M + H)$^+$ Observ. | 526 |
| Retention Time | 1.76 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

Examples 5-32 were synthesized using the procedure described above for Example 1.

Example 5

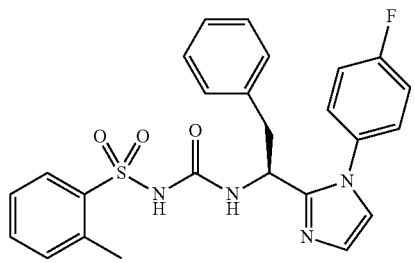

| (S)-N-((1-(1-(4-fluorophenyl)-1H-imidazol-2-yl)-2-phenylethyl)carbamoyl)-2-methylbenzenesulfonamide | |
|---|---|
| MS (M + H)$^+$ Calcd. | 479 |
| MS (M + H)$^+$ Observ. | 479 |
| Retention Time | 1.54 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 7.83 (d, J=7.7 Hz, 1H), 7.60-7.49 (m, 1H), 7.46-7.31 (m, 2H), 7.23-7.16 (m, 3H), 7.15-7.03 (m, 4H), 6.96 (br. s., 3H), 6.70 (d, J=6.6 Hz, 2H), 4.70 (d, J=7.0 Hz, 1H), 3.05-2.68 (m, 2H), 2.53 (s, 3H).

Example 6

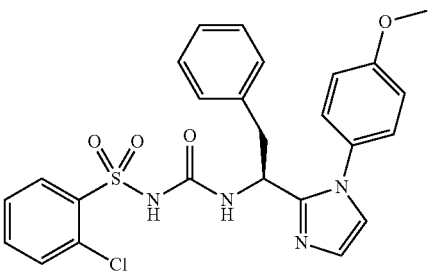 [SMILES: COc1ccc(-n2ccnc2[C@H](Cc2ccccc2)NC(=O)NS(=O)(=O)c2ccccc2Cl)cc1]

| (S)-2-chloro-N-((1-(1-(4-methoxyphenyl)-1H-imidazol-2-yl)-2-phenylethyl)carbamoyl)benzenesulfonamide | |
|---|---|
| MS (M + H)$^+$ Calcd. | 511 |
| MS (M + H)$^+$ Observ. | 511 |
| Retention Time | 1.42 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 7.99-7.87 (m, 1H), 7.66-7.39 (m, 3H), 7.11 (d, J=5.9 Hz, 4H), 7.02 (s, 1H), 6.92-6.78 (m, 4H), 6.76-6.68 (m, 2H), 4.67 (d, J=6.2 Hz, 1H), 3.76 (s, 3H), 3.01-2.75 (m, 2H).

Example 7

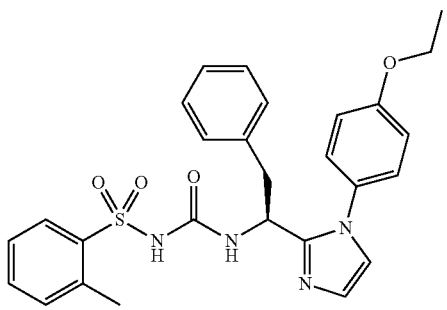 [SMILES: CCOc1ccc(-n2ccnc2[C@H](Cc2ccccc2)NC(=O)NS(=O)(=O)c2ccccc2C)cc1]

| (S)-N-((1-(1-(4-ethoxyphenyl)-1H-imidazol-2-yl)-2-phenylethyl)carbamoyl)-2-methylbenzenesulfonamide | |
|---|---|
| MS (M + H)+ Calcd. | 505 |
| MS (M + H)+ Observ. | 505 |
| Retention Time | 1.62 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 7.77 (d, J=8.1 Hz, 1H), 7.40 (br. s., 1H), 7.33-7.21 (m, 2H), 7.15-7.04 (m, 4H), 7.00 (s, 1H), 6.88-6.75 (m, 4H), 6.70 (d, J=6.2 Hz, 2H), 4.67 (br. s., 1H), 4.03 (q, J=6.4 Hz, 2H), 2.97-2.70 (m, 2H), 2.53 (s, 3H), 1.33 (t, J=6.8 Hz, 3H).

Example 8

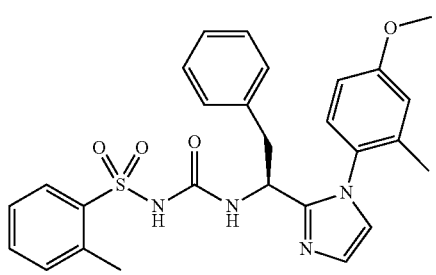 [SMILES: COc1ccc(-n2ccnc2[C@H](Cc2ccccc2)NC(=O)NS(=O)(=O)c2ccccc2C)c(C)c1]

| (S)-N-((1-(1-(4-methoxy-2-methylphenyl)-1H-imidazol-2-yl)-2-phenylethyl)carbamoyl)-2-methylbenzenesulfonamide | |
|---|---|
| MS (M + H)+ Calcd. | 505 |
| MS (M + H)+ Observ. | 505 |
| Retention Time | 1.65 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 7.73 (d, J=7.7 Hz, 1H), 7.46-7.20 (m, 3H), 7.19-6.98 (m, 5H), 6.92 (br. s., 1H), 6.85-6.66 (m, 3H), 6.55 (d, J=7.3 Hz, 1H), 4.37-4.24 (m, 1H), 3.74 (s, 3H), 3.03-2.79 (m, 2H), 2.55 (s, 3H), 2.50 (s, 3H).

Example 9

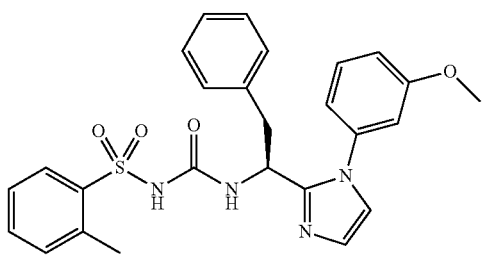 [SMILES: COc1cccc(-n2ccnc2[C@H](Cc2ccccc2)NC(=O)NS(=O)(=O)c2ccccc2C)c1]

| (S)-N-((1-(1-(3-methoxyphenyl)-1H-imidazol-2-yl)-2-phenylethyl)carbamoyl)-2-methylbenzenesulfonamide | |
|---|---|
| MS (M + H)+ Calcd. | 491 |
| MS (M + H)+ Observ. | 491 |
| Retention Time | 1.65 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 7.80 (d, J=7.3 Hz, 1H), 7.44 (br. s., 1H), 7.34-7.26 (m, 2H), 7.22 (t, J=8.1 Hz, 1H), 7.15 (br. s., 1H), 7.12-7.00 (m, 4H), 6.92 (d, J=8.4 Hz, 1H), 6.67 (d, J=7.0 Hz, 2H), 6.59 (br. s., 1H), 6.47 (d, J=7.0 Hz, 1H), 4.80 (br. s., 1H), 3.66 (s, 3H), 2.99-2.75 (m, 2H), 2.53 (s, 3H).

Example 10

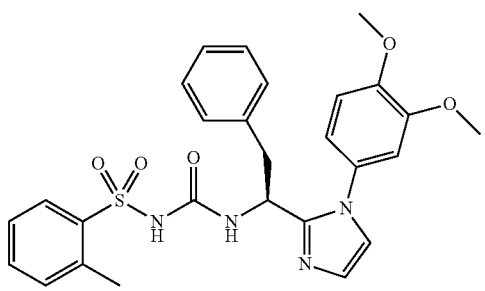 [SMILES: COc1ccc(-n2ccnc2[C@H](Cc2ccccc2)NC(=O)NS(=O)(=O)c2ccccc2C)cc1OC]

| (S)-N-((1-(1-(3,4-dimethoxyphenyl)-1H-imidazol-2-yl)-2-phenylethyl)carbamoyl)-2-methylbenzenesulfonamide | |
|---|---|
| MS (M + H)+ Calcd. | 521 |
| MS (M + H)+ Observ. | 521 |
| Retention Time | 1.49 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 7.78 (d, J=7.7 Hz, 1H), 7.39 (br. s., 1H), 7.30-7.20 (m, 2H), 7.13-7.04 (m, 4H), 7.01 (br. s., 1H), 6.83 (d, J=8.4 Hz, 1H), 6.73-6.55 (m, 3H), 6.35 (d, J=7.7 Hz, 1H), 4.81-4.68 (m, 1H), 3.75 (s, 6H), 3.02-2.76 (m, 2H), 2.52 (s, 3H).

Example 11

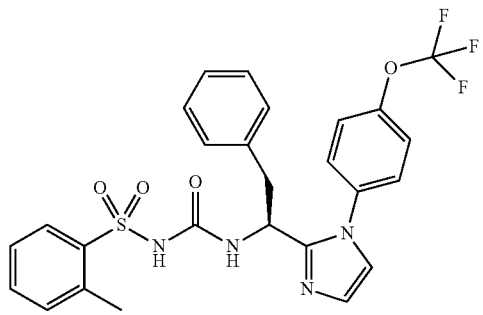 [SMILES: Cc1ccccc1S(=O)(=O)NC(=O)N[C@@H](Cc1ccccc1)c1nccn1-c1ccc(OC(F)(F)F)cc1]

| (S)-2-methyl-N-((2-phenyl-1-(1-(4-(trifluoromethoxy)phenyl)-1H-imidazol-2-yl)ethyl)carbamoyl)benzenesulfonamide | |
|---|---|
| MS (M + H)+ Calcd. | 545 |
| MS (M + H)+ Observ. | 545 |
| Retention Time | 1.83 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 7.83 (d, J=7.7 Hz, 1H), 7.57-7.47 (m, 1H), 7.42-7.30 (m, 4H), 7.23 (s, 1H), 7.16-6.86 (m, 7H), 6.67 (d, J=7.3 Hz, 2H), 4.74 (d, J=6.6 Hz, 1H), 2.95-2.77 (m, 3H), 2.54 (s, 3H).

Example 12

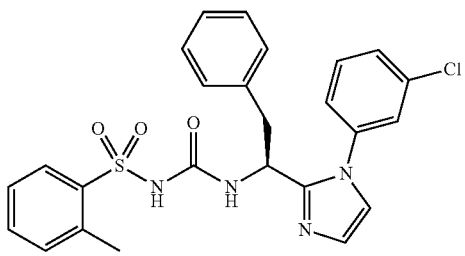 [SMILES: Cc1ccccc1S(=O)(=O)NC(=O)N[C@@H](Cc1ccccc1)c1nccn1-c1cccc(Cl)c1]

| (S)-N-((1-(1-(3-chlorophenyl)-1H-imidazol-2-yl)-2-phenylethyl)carbamoyl)-2-methylbenzenesulfonamide | |
|---|---|
| MS (M + H)+ Calcd. | 495 |
| MS (M + H)+ Observ. | 495 |
| Retention Time | 1.71 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 7.81 (d, J=7.0 Hz, 1H), 7.51-7.26 (m, 5H), 7.19 (br. s., 1H), 7.16-7.02 (m, 4H), 6.98 (d, J=6.6 Hz, 1H), 6.78 (s, 1H), 6.67 (d, J=6.6 Hz, 2H), 4.70 (br. s., 1H), 2.96-2.80 (m, 2H), 2.54 (s, 3H).

Example 13

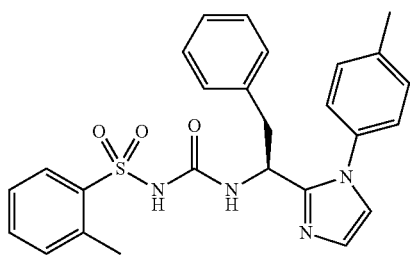

| (S)-2-methyl-N-((2-phenyl-1-(1-(p-tolyl)-1H-imidazol-2-yl)ethyl)carbamoyl)benzenesulfonamide | |
|---|---|
| MS (M + H)+ Calcd. | 475 |
| MS (M + H)+ Observ. | 475 |
| Retention Time | 1.73 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 7.80 (d, J=7.3 Hz, 1H), 7.49 (br. s., 1H), 7.40-7.27 (m, 2H), 7.19-7.07 (m, 6H), 7.03 (s, 1H), 6.79 (d, J=7.3 Hz, 3H), 6.70 (d, J=6.6 Hz, 2H), 4.70 (d, J=5.9 Hz, 1H), 3.00-2.74 (m, 2H), 2.52 (s, 3H), 2.31 (s, 3H).

Example 14

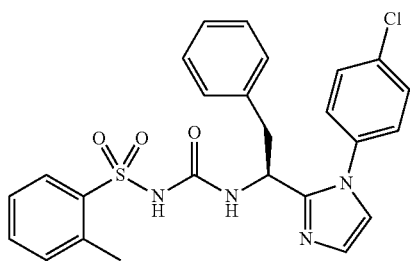

| (S)-N-((1-(1-(4-chlorophenyl)-1H-imidazol-2-yl)-2-phenylethyl)carbamoyl)-2-methylbenzenesulfonamide | |
|---|---|
| MS (M + H)+ Calcd. | 495 |
| MS (M + H)+ Observ. | 495 |
| Retention Time | 1.71 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 7.79 (d, J=7.3 Hz, 1H), 7.50-7.24 (m, 5H), 7.20-7.01 (m, 5H), 6.94 (d, J=8.4 Hz, 2H), 6.71 (d, J=7.0 Hz, 2H), 4.70 (d, J=6.2 Hz, 1H), 2.99-2.78 (m, 2H), 2.52 (s, 3H).

Example 15

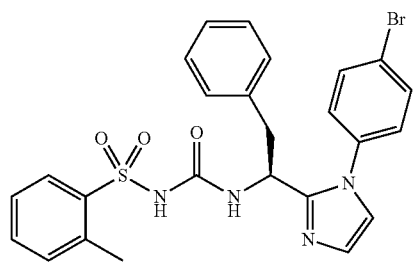 [SMILES: Cc1ccccc1S(=O)(=O)NC(=O)N[C@@H](Cc1ccccc1)c1nccn1-c1ccc(Br)cc1]

| (S)-N-((1-(1-(4-bromophenyl)-1H-imidazol-2-yl)-2-phenylethyl)carbamoyl)-2-methylbenzenesulfonamide | |
|---|---|
| MS (M + H)+ Calcd. | 539 |
| MS (M + H)+ Observ. | 539 |
| Retention Time | 1.82 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 7.75 (d, J=7.3 Hz, 1H), 7.48 (d, J=7.0 Hz, 2H), 7.35 (br. s., 1H), 7.24 (br. s., 2H), 7.14-6.98 (m, 5H), 6.88 (br. s., 2H), 6.71 (d, J=6.2 Hz, 2H), 4.70 (br. s., 1H), 2.99-2.77 (m, 2H), 2.53 (s, 3H).

Example 16

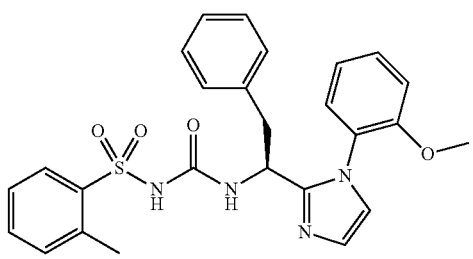 [SMILES: COc1ccccc1-n1ccnc1[C@H](Cc1ccccc1)NC(=O)NS(=O)(=O)c1ccccc1C]

| (S)-N-((1-(1-(2-methoxyphenyl)-1H-imidazol-2-yl)-2-phenylethyl)carbamoyl)-2-methylbenzenesulfonamide | |
|---|---|
| MS (M + H)+ Calcd. | 491 |
| MS (M + H)+ Observ. | 491 |
| Retention Time | 1.68 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 7.82 (d, J=6.2 Hz, 1H), 7.57-7.48 (m, 1H), 7.45-7.32 (m, 3H), 7.18-6.97 (m, 6H), 6.91-6.57 (m, 4H), 4.50 (br. s., 1H), 2.89-2.63 (m, 2H), 2.53 (s, 3H).

Example 17

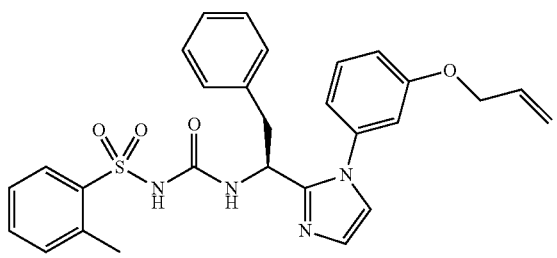 [SMILES: C=CCOc1cccc(-n2ccnc2[C@H](Cc2ccccc2)NC(=O)NS(=O)(=O)c2ccccc2C)c1]

| (S)-N-((1-(1-(3-(allyloxy)phenyl)-1H-imidazol-2-yl)-2-phenylethyl)carbamoyl)-2-methylbenzenesulfonamide | |
|---|---|
| MS (M + H)+ Calcd. | 517 |
| MS (M + H)+ Observ. | 517 |
| Retention Time | 2.04 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |

| (S)-N-((1-(1-(3-(allyloxy)phenyl)-1H-imidazol-2-yl)-2-phenylethyl)carbamoyl)-2-methylbenzenesulfonamide | |
|---|---|
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 7.82 (d, J=8.1 Hz, 1H), 7.56-7.45 (m, 1H), 7.41-7.29 (m, 2H), 7.28-7.20 (m, 1H), 7.17 (s, 1H), 7.13-7.02 (m, 4H), 6.96 (d, J=8.4 Hz, 1H), 6.67 (d, J=7.0 Hz, 2H), 6.62-6.57 (m, 1H), 6.47 (d, J=7.3 Hz, 1H), 6.09-5.91 (m, 1H), 5.43-5.20 (m, 2H), 4.81 (d, J=6.6 Hz, 1H), 4.50 (br. s., 2H), 3.00-2.76 (m, 2H), 2.53 (s, 3H).

Example 18

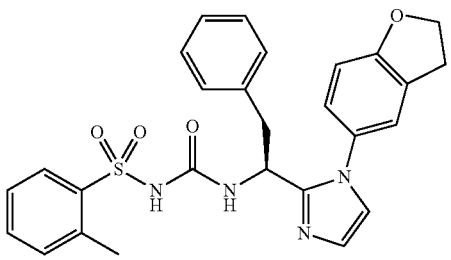 [SMILES: Cc1ccccc1S(=O)(=O)NC(=O)N[C@@H](Cc1ccccc1)c1nccn1-c1ccc2c(c1)CCO2]

| (S)-N-((1-(1-(2,3-dihydrobenzofuran-5-yl)-1H-imidazol-2-yl)-2-phenylethyl)carbamoyl)-2-methylbenzenesulfonamide | |
|---|---|
| MS (M + H)+ Calcd. | 503 |
| MS (M + H)+ Observ. | 503 |
| Retention Time | 1.84 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 7.81 (d, J=7.7 Hz, 1H), 7.49 (br. s., 1H), 7.40-7.25 (m, 2H), 7.20-7.08 (m, 3H), 7.06 (s, 1H), 7.01 (s, 1H), 6.71 (d, J=6.6 Hz, 2H), 6.68-6.59 (m, 2H), 6.47 (br. s., 1H), 4.70-4.51 (m, 3H), 3.14-2.77 (m, 4H), 2.53 (s, 3H).

Example 19

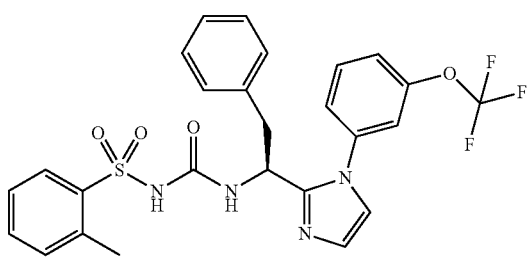 [SMILES: Cc1ccccc1S(=O)(=O)NC(=O)N[C@@H](Cc1ccccc1)c1nccn1-c1cccc(OC(F)(F)F)c1]

| (S)-2-methyl-N-((2-phenyl-1-(1-(3-(trifluoromethoxy)phenyl)-1H-imidazol-2-yl)ethyl)carbamoyl)benzenesulfonamide | |
|---|---|
| MS (M + H)+ Calcd. | 545 |
| MS (M + H)+ Observ. | 545 |
| Retention Time | 1.99 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 7.81 (d, J=7.0 Hz, 1H), 7.51-7.42 (m, 2H), 7.41-7.27 (m, 3H), 7.21 (s, 1H), 7.15-7.02 (m, 4H), 6.99 (d, J=7.0 Hz, 1H), 6.87 (br. s., 1H), 6.67 (d, J=7.0 Hz, 2H), 4.72 (d, J=7.3 Hz, 1H), 3.00-2.79 (m, 2H), 2.53 (s, 3H).

Example 20

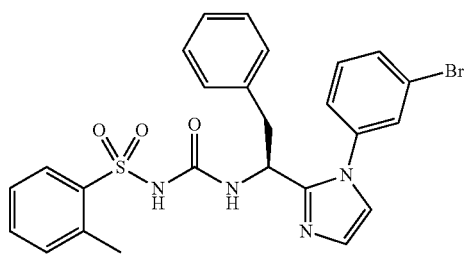 [SMILES: Cc1ccccc1S(=O)(=O)NC(=O)N[C@@H](Cc1ccccc1)c1nccn1-c1cccc(Br)c1]

| (S)-N-((1-(1-(3-bromophenyl)-1H-imidazol-2-yl)-2-phenylethyl)carbamoyl)-2-methylbenzenesulfonamide | |
|---|---|
| MS (M + H)+ Calcd. | 539 |
| MS (M + H)+ Observ. | 539 |
| Retention Time | 1.96 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 7.81 (d, J=8.1 Hz, 1H), 7.56 (d, J=7.7 Hz, 1H), 7.46 (d, J=7.0 Hz, 1H), 7.38-7.24 (m, 3H), 7.21-6.94 (m, 6H), 6.91-6.77 (m, 1H), 6.67 (d, J=7.3 Hz, 2H), 4.69 (br. s., 1H), 2.98-2.80 (m, 2H), 2.54 (s, 3H).

Example 21

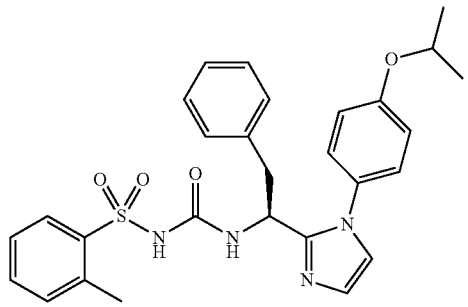 [SMILES: Cc1ccccc1S(=O)(=O)NC(=O)N[C@@H](Cc1ccccc1)c1nccn1-c1ccc(OC(C)C)cc1]

| (S)-N-((1-(1-(4-isopropoxyphenyl)-1H-imidazol-2-yl)-2-phenylethyl)carbamoyl)-2-methylbenzenesulfonamide | |
|---|---|
| MS (M + H)+ Calcd. | 519 |
| MS (M + H)+ Observ. | 519 |
| Retention Time | 1.85 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 7.80 (d, J=8.1 Hz, 1H), 7.47 (br. s., 1H), 7.39-7.26 (m, 2H), 7.17-7.05 (m, 4H), 7.01 (s, 1H), 6.88-6.75 (m, 4H), 6.69 (d, J=7.0 Hz, 2H), 4.76-4.54 (m, 2H), 2.98-2.71 (m, 2H), 2.53 (s, 3H), 1.27 (d, J=6.2 Hz, 6H).

Example 22

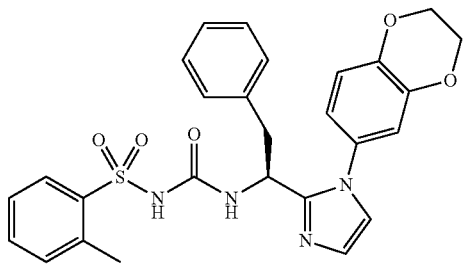 [SMILES: Cc1ccccc1S(=O)(=O)NC(=O)N[C@@H](Cc1ccccc1)c1nccn1-c1ccc2c(c1)OCCO2]

| (S)-N-((1-(1-(4-isopropoxyphenyl)-1H-imidazol-2-yl)-2-phenylethyl)carbamoyl)-2-methylbenzenesulfonamide | |
|---|---|
| MS (M + H)+ Calcd. | 519 |
| MS (M + H)+ Observ. | 519 |
| Retention Time | 1.71 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 7.82 (d, J=8.1 Hz, 1H), 7.51 (br. s., 1H), 7.35 (d, J=8.1 Hz, 2H), 7.11 (d, J=7.0 Hz, 4H), 7.00 (s, 1H), 6.79 (d, J=8.4 Hz, 1H), 6.69 (d, J=7.0 Hz, 2H), 6.47-6.33 (m, 2H), 4.73 (d, J=8.1 Hz, 1H), 4.26 (br. s., 4H), 2.99-2.75 (m, 2H), 2.53 (s, 3H).

Example 23

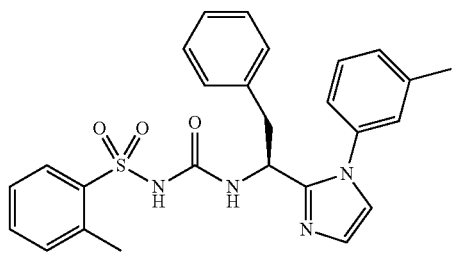 [SMILES: Cc1cccc(-n2ccnc2[C@H](Cc2ccccc2)NC(=O)NS(=O)(=O)c2ccccc2C)c1]

| (S)-2-methyl-N-((2-phenyl-1-(1-(m-tolyl)-1H-imidazol-2-yl)ethyl)carbamoyl)benzenesulfonamide | |
|---|---|
| MS (M + H)+ Calcd. | 475 |
| MS (M + H)+ Observ. | 475 |
| Retention Time | 1.90 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 7.77 (d, J=8.1 Hz, 1H), 7.39 (br. s., 1H), 7.31-7.15 (m, 5H), 7.15-7.06 (m, 5H), 7.03 (br. s., 1H), 6.69 (d, J=7.0 Hz, 2H), 6.49 (br. s., 1H), 4.70 (br. s., 1H), 2.99-2.77 (m, 2H), 2.53 (s, 3H), 2.20 (s, 3H).

Example 24

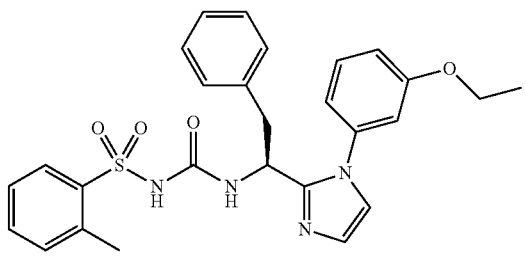 [SMILES: CCOc1cccc(-n2ccnc2[C@H](Cc2ccccc2)NC(=O)NS(=O)(=O)c2ccccc2C)c1]

| (S)-N-((1-(1-(3-ethoxyphenyl)-1H-imidazol-2-yl)-2-phenylethyl)carbamoyl)-2-methylbenzenesulfonamide | |
|---|---|
| MS (M + H)+ Calcd. | 505 |
| MS (M + H)+ Observ. | 505 |
| Retention Time | 2.00 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 7.75 (d, J=8.1 Hz, 1H), 7.38-7.29 (m, 1H), 7.27-7.15 (m, 3H), 7.13-6.97 (m, 5H), 6.89 (d, J=8.1 Hz, 1H), 6.74-6.36 (m, 4H), 4.89-4.69 (m, 1H), 3.93 (q, 2H), 2.92-2.79 (m, 2H), 2.51 (s, 3H), 1.29 (t, J=6.8 Hz, 3H).

Example 25

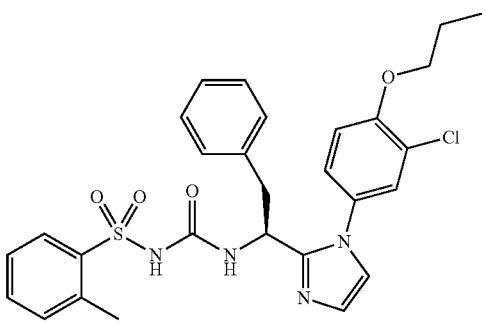 [SMILES: CCCOc1ccc(-n2ccnc2[C@H](Cc2ccccc2)NC(=O)NS(=O)(=O)c2ccccc2C)cc1Cl]

| (S)-N-((1-(1-(3-chloro-4-propoxyphenyl)-1H-imidazol-2-yl)-2-phenylethyl)carbamoyl)-2-methylbenzenesulfonamide | |
|---|---|
| MS (M + H)+ Calcd. | 553 |
| MS (M + H)+ Observ. | 553 |
| Retention Time | 2.07 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 7.81 (d, J=7.0 Hz, 1H), 7.46 (br. s., 1H), 7.32 (br. s., 2H), 7.19-6.97 (m, 6H), 6.89 (br. s., 1H), 6.70 (br. s., 3H), 4.64 (d, J=6.2 Hz, 1H), 4.03 (t, J=5.9 Hz, 2H), 2.99-2.77 (m, 2H), 2.54 (s, 3H), 1.81-1.69 (m, 2H), 1.01 (t, J=7.2 Hz, 3H).

Example 26

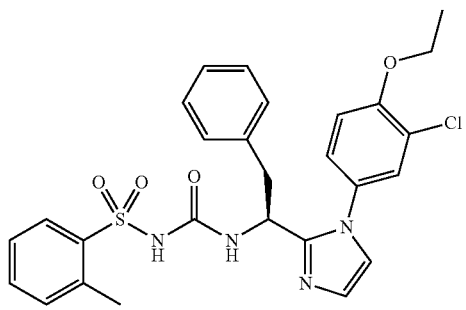 [SMILES: CCOc1ccc(-n2ccnc2[C@H](Cc2ccccc2)NC(=O)NS(=O)(=O)c2ccccc2C)cc1Cl]

| (S)-N-((1-(1-(3-chloro-4-ethoxyphenyl)-1H-imidazol-2-yl)-2-phenylethyl)carbamoyl)-2-methylbenzenesulfonamide | |
|---|---|
| MS (M + H)+ Calcd. | 539 |
| MS (M + H)+ Observ. | 539 |
| Retention Time | 1.67 min |

| (S)-N-((1-(1-(3-chloro-4-ethoxyphenyl)-1H-imidazol-2-yl)-2-phenylethyl)carbamoyl)-2-methylbenzenesulfonamide | |
|---|---|
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 7.81 (d, J=7.0 Hz, 1H), 7.48 (br. s., 1H), 7.34 (d, J=7.0 Hz, 2H), 7.19-6.97 (m, 6H), 6.88 (d, J=7.3 Hz, 1H), 6.75-6.62 (m, 3H), 4.64 (d, J=7.7 Hz, 1H), 4.12 (q, J=6.8 Hz, 2H), 3.01-2.79 (m, 2H), 2.54 (s, 3H), 1.36 (t, J=7.0 Hz, 3H).

Example 27

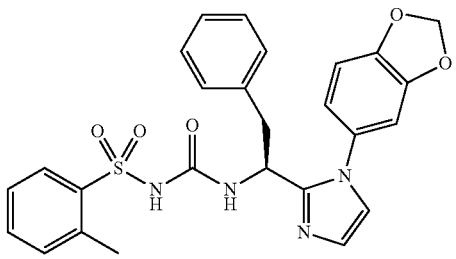

| (S)-N-((1-(1-(benzo[d][1,3]dioxol-5-yl)-1H-imidazol-2-yl)-2-phenylethyl)carbamoyl)-2-methylbenzenesulfonamide | |
|---|---|
| MS (M + H)+ Calcd. | 505 |
| MS (M + H)+ Observ. | 505 |
| Retention Time | 1.39 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 7.81 (d, J=7.7 Hz, 1H), 7.49 (br. s., 1H), 7.41-7.28 (m, 2H), 7.12 (d, J=7.0 Hz, 4H), 7.01 (br. s., 1H), 6.83 (d, J=8.1 Hz, 1H), 6.71 (d, J=6.2 Hz, 2H), 6.47-6.30 (m, 2H), 6.08 (d, J=2.2 Hz, 2H), 4.73 (br. s., 1H), 3.00-2.76 (m, 2H), 2.53 (s, 3H).

Example 28

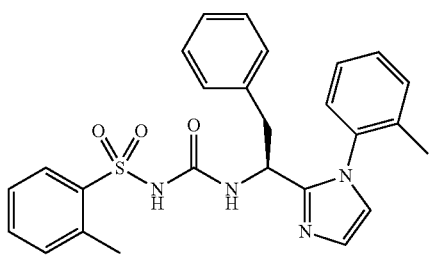 [SMILES: Cc1ccccc1-n1ccnc1[C@H](Cc1ccccc1)NC(=O)NS(=O)(=O)c1ccccc1C]

| (S)-2-methyl-N-((2-phenyl-1-(1-(o-tolyl)-1H-imidazol-2-yl)ethyl)carbamoyl)benzenesulfonamide | |
|---|---|
| MS (M + H)+ Calcd. | 475 |
| MS (M + H)+ Observ. | 475 |
| Retention Time | 1.52 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 7.73 (d, J=7.0 Hz, 1H), 7.39 (br. s., 1H), 7.34-7.19 (m, 4H), 7.18-6.87 (m, 6H), 6.82-6.67 (m, 2H), 6.61-6.40 (m, 1H), 4.57-4.22 (m, 1H), 3.01-2.76 (m, 2H), 2.54 (s, 3H), 2.51 (s, 3H).

Example 29

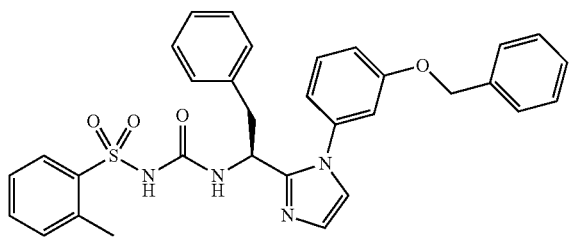 [SMILES: Cc1ccccc1S(=O)(=O)NC(=O)N[C@@H](Cc1ccccc1)c1nccn1-c1cccc(OCc2ccccc2)c1]

| (S)-N-((1-(1-(3-(benzyloxy)phenyl)-1H-imidazol-2-yl)-2-phenylethyl)carbamoyl)-2-methylbenzenesulfonamide | |
|---|---|
| MS (M + H)+ Calcd. | 567 |
| MS (M + H)+ Observ. | 567 |
| Retention Time | 2.14 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| (S)-N-((1-(1-(3-(benzyloxy)phenyl)-1H-imidazol-2-yl)-2-phenylethyl)carbamoyl)-2-methylbenzenesulfonamide | |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHz, DMSO-$d_6$) δ 7.77 (d, J=7.0 Hz, 1H), 7.51-7.31 (m, 6H), 7.28-7.14 (m, 3H), 7.13-6.94 (m, 6H), 6.74 (br. s., 1H), 6.65 (d, J=7.3 Hz, 3H), 6.46 (d, J=5.5 Hz, 1H), 5.15-4.93 (m, 2H), 4.82 (br. s., 1H), 2.99-2.76 (m, 2H), 2.53 (s, 3H).

Example 30

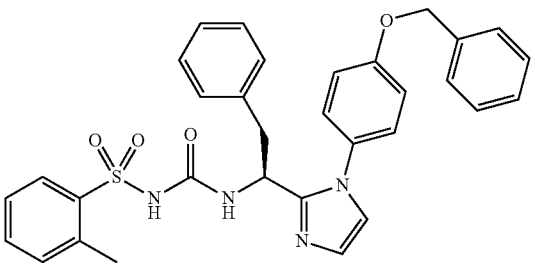 [SMILES: Cc1ccccc1S(=O)(=O)NC(=O)N[C@@H](Cc1ccccc1)c1nccn1-c1ccc(OCc2ccccc2)cc1]

| (S)-N-((1-(1-(4-(benzyloxy)phenyl)-1H-imidazol-2-yl)-2-phenylethyl)carbamoyl)-2-methylbenzenesulfonamide | |
|---|---|
| MS (M + H)+ Calcd. | 567 |
| MS (M + H)+ Observ. | 567 |
| Retention Time | 1.97 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHz, DMSO-$d_6$) δ 7.83 (d, J=7.9 Hz, 1H), 7.64 (br. s., 1H), 7.59-7.53 (m, 2H), 7.51-7.32 (m, 8H), 7.24-7.12 (m, 3H), 7.05 (d, J=8.9 Hz, 2H), 6.93 (d, J=8.9 Hz, 2H), 6.81 (d, J=7.3 Hz, 2H), 5.16 (s, 2H), 4.81-4.70 (m, 1H), 3.05 (d, J=7.3 Hz, 2H), 2.53 (s, 3H).

Example 31

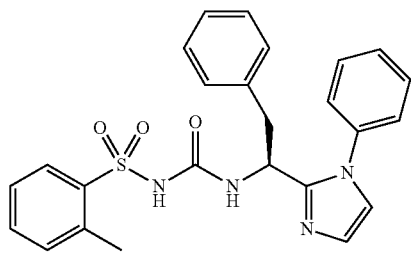 [SMILES: Cc1ccccc1S(=O)(=O)NC(=O)N[C@@H](Cc1ccccc1)c1nccn1-c1ccccc1]

(S)-2-methyl-N-((2-phenyl-1-(1-phenyl-1H-imidazol-2-yl)ethyl)carbamoyl)benzenesulfonamide

| | |
|---|---|
| MS (M + H)+ Calcd. | 461 |
| MS (M + H)+ Observ. | 461 |
| Retention Time | 1.76 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 7.77 (br. s., 1H), 7.47-7.20 (m, 6H), 7.19-6.99 (m, 5H), 6.94 (br. s., 2H), 6.68 (d, J=7.0 Hz, 2H), 6.60 (br. s., 1H), 4.75 (br. s., 1H), 2.99-2.75 (m, 2H), 2.53 (s, 3H).

Example 32

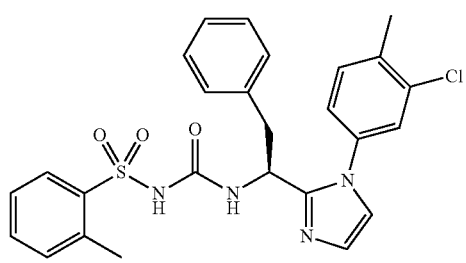 [SMILES: Cc1ccc(-n2ccnc2[C@H](Cc2ccccc2)NC(=O)NS(=O)(=O)c2ccccc2C)cc1Cl]

(S)-N-((1-(1-(3-chloro-4-methylphenyl)-1H-imidazol-2-yl)-2-phenylethyl)carbamoyl)-2-methylbenzenesulfonamide

| | |
|---|---|
| MS (M + H)+ Calcd. | 509 |
| MS (M + H)+ Observ. | 509 |
| Retention Time | 1.90 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 7.78 (d, J=5.9 Hz, 1H), 7.42 (br. s., 1H), 7.29 (d, J=7.0 Hz, 3H), 7.19-6.98 (m, 5H), 6.84 (d, J=5.5 Hz, 1H), 6.78-6.61 (m, 3H), 4.68 (br. s., 1H), 3.00-2.78 (m, 2H), 2.53 (s, 3H), 2.32 (s, 3H).

Examples 33-41 were synthesized using the procedure described above for Example 2.

Example 33

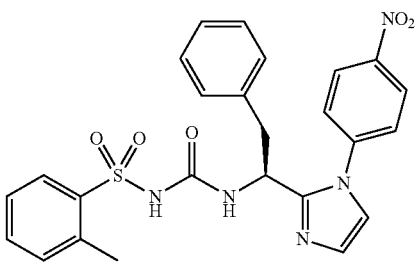

(S)-2-methyl-N-((1-(1-(4-nitrophenyl)-1H-imidazol-2-yl)-2-phenylethyl)carbamoyl)benzenesulfonamide

| | |
|---|---|
| MS (M + H)+ Calcd. | 506 |
| MS (M + H)+ Observ. | 506 |
| Retention Time | 1.53 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 8.18 (d, J=8.4 Hz, 2H), 7.80 (d, J=7.3 Hz, 1H), 7.54-7.46 (m, 1H), 7.40-7.22 (m, 5H), 7.17-7.01 (m, 4H), 6.92 (br. s., 1H), 6.74 (d, J=7.3 Hz, 2H), 4.84 (d, J=7.3 Hz, 1H), 3.04-2.82 (m, 2H), 2.51 (s, 3H).

Example 34

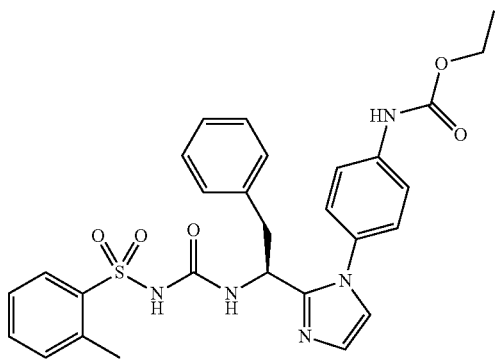 [SMILES: CCOC(=O)Nc1ccc(-n2ccnc2[C@H](Cc2ccccc2)NC(=O)NS(=O)(=O)c2ccccc2C)cc1]

| (S)-ethyl (4-(2-(2-phenyl-1-(3-(o-tolylsulfonyl)ureido)ethyl)-1H-imidazol-1-yl)phenyl)carbamate | |
|---|---|
| MS (M + H)+ Calcd. | 548 |
| MS (M + H)+ Observ. | 548 |
| Retention Time | 1.45 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 7.79 (d, J=7.3 Hz, 1H), 7.47 (br. s., 1H), 7.41 (d, J=8.8 Hz, 2H), 7.37-7.27 (m, 2H), 7.17-7.05 (m, 4H), 7.01 (s, 1H), 6.80 (d, J=8.1 Hz, 2H), 6.70 (d, J=6.6 Hz, 2H), 4.69 (d, J=7.0 Hz, 1H), 4.14 (q, J=7.2 Hz, 2H), 2.99-2.74 (m, 2H), 2.51 (s, 3H), 1.25 (t, J=7.0 Hz, 3H).

Example 35

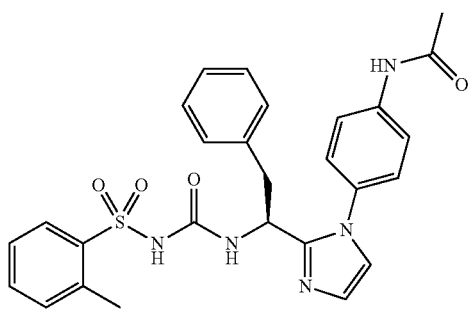

| (S)-N-(4-(2-(2-phenyl-1-(3-(o-tolylsulfonyl)ureido)ethyl)-1H-imidazol-1-yl)phenyl)acetamide | |
|---|---|
| MS (M + H)+ Calcd. | 518 |
| MS (M + H)+ Observ. | 518 |
| Retention Time | 1.23 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 7.78 (d, J=6.6 Hz, 1H), 7.53 (d, J=8.4 Hz, 2H), 7.45 (br. s., 1H), 7.31 (d, J=8.8 Hz, 2H), 7.17-7.05 (m, 4H), 7.02 (s, 1H), 6.81 (d, J=7.3 Hz, 2H), 6.69 (d, J=7.0 Hz, 3H), 4.70 (d, J=5.9 Hz, 1H), 2.99-2.74 (m, 2H), 2.51 (s, 3H), 2.06 (s, 3H).

Example 36

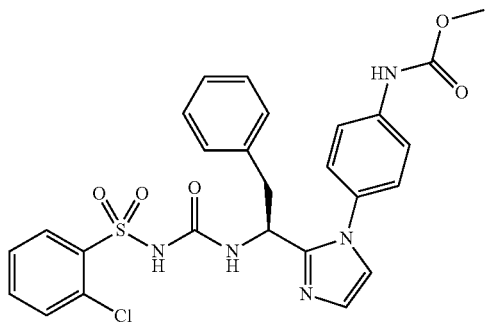 [SMILES: COC(=O)Nc1ccc(-n2ccnc2[C@H](Cc2ccccc2)NC(=O)NS(=O)(=O)c2ccccc2Cl)cc1]

| (S)-methyl (4-(2-(1-(3-((2-chlorophenyl)sulfonyl)ureido)-2-phenylethyl)-1H-imidazol-1-yl)phenyl)carbamate | |
|---|---|
| MS (M + H)+ Calcd. | 554 |
| MS (M + H)+ Observ. | 554 |
| Retention Time | 1.24 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 9.84 (br. s., 1H), 8.06-7.81 (m, 1H), 7.66-7.36 (m, 5H), 7.16-7.06 (m, 4H), 7.02 (s, 1H), 6.82 (d, J=7.7 Hz, 2H), 6.72 (d, J=6.6 Hz, 2H), 4.70 (br. s., 1H), 3.69 (s, 3H), 3.03-2.76 (m, 2H).

Example 37

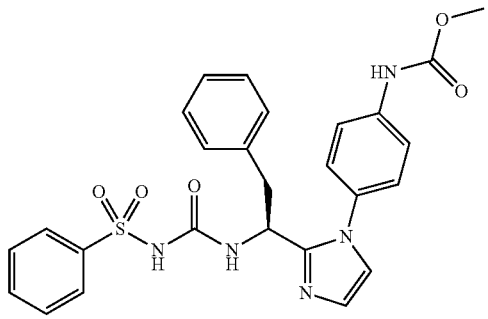 [SMILES: COC(=O)Nc1ccc(-n2ccnc2[C@H](Cc2ccccc2)NC(=O)NS(=O)(=O)c2ccccc2)cc1]

| (S)-methyl (4-(2-(2-phenyl-1-(3-(phenylsulfonyl)ureido)ethyl)-1H-imidazol-1-yl)phenyl)carbamate | |
|---|---|
| MS (M + H)⁺ Calcd. | 520 |
| MS (M + H)⁺ Observ. | 520 |
| Retention Time | 1.22 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 9.86 (s, 1H), 7.82 (d, J=7.3 Hz, 2H), 7.69-7.51 (m, 3H), 7.42 (d, J=8.4 Hz, 2H), 7.19-7.06 (m, 4H), 7.03 (s, 1H), 6.93 (br. s., 1H), 6.79 (d, J=8.1 Hz, 2H), 6.71 (d, J=7.0 Hz, 2H), 4.72 (d, J=7.3 Hz, 1H), 3.70 (s, 3H), 3.02-2.76 (m, 2H).

Example 38

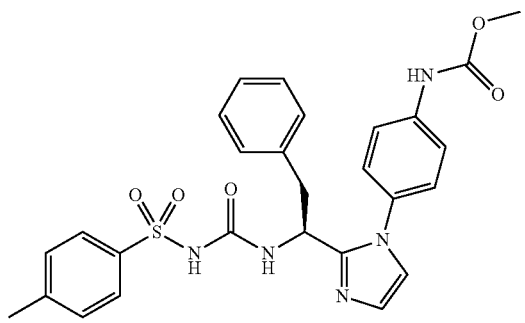

| (S)-methyl (4-(2-(2-phenyl-1-(3-tosylureido)ethyl)-1H-imidazol-1-yl)phenyl)carbamate | |
|---|---|
| MS (M + H)⁺ Calcd. | 534 |
| MS (M + H)⁺ Observ. | 534 |
| Retention Time | 1.36 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 9.86 (br. s., 1H), 7.68 (d, J=7.7 Hz, 2H), 7.42 (d, J=8.4 Hz, 2H), 7.34 (d, J=7.3 Hz, 2H), 7.18-7.06 (m, 4H), 7.02 (s, 1H), 6.79 (d, J=8.1 Hz, 3H), 6.71 (d, J=7.0 Hz, 2H), 4.71 (d, J=6.6 Hz, 1H), 3.69 (s, 3H), 3.03-2.76 (m, 2H), 2.37 (s, 3H).

Example 39

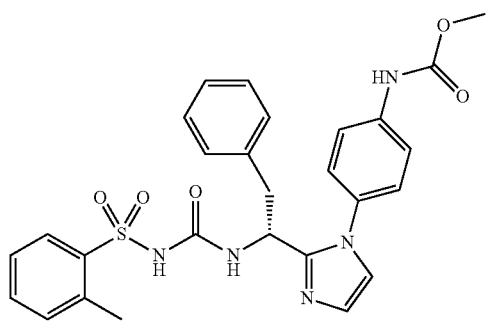 [SMILES: COC(=O)Nc1ccc(-n2ccnc2[C@@H](Cc2ccccc2)NC(=O)NS(=O)(=O)c2ccccc2C)cc1]

| | |
|---|---|
| MS (M + H)⁺ Calcd. | 534 |
| MS (M + H)⁺ Observ. | 534 |
| Retention Time | 1.56 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (400 MHz, METHANOL-$d_4$) δ 8.01-7.87 (m, 1H), 7.49-7.22 (m, 5H), 7.10 (s, 4H), 7.00-6.88 (m, 1H), 6.85-6.74 (m, 2H), 6.66-6.47 (m, 2H), 4.90-4.82 (m, 1H), 3.77 (s, 3H), 3.06-2.93 (m, 2H), 2.64 (s, 3H).

Example 40

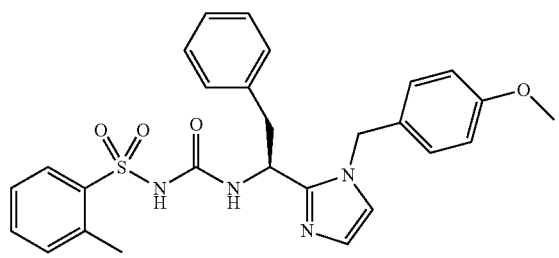 [SMILES: COc1ccc(Cn2ccnc2[C@H](Cc2ccccc2)NC(=O)NS(=O)(=O)c2ccccc2C)cc1]

| (S)-N-((1-(1-(4-methoxybenzyl)-1H-imidazol-2-yl)-2-phenylethyl)carbamoyl)-2-methylbenzenesulfonamide | |
|---|---|
| MS (M + H)$^+$ Calcd. | 505 |
| MS (M + H)$^+$ Observ. | 505 |
| Retention Time | 1.51 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (600 MHz, DMSO-d$_6$) δ 7.83 (d, J=8.1 Hz, 1H), 7.58-7.50 (m, 1H), 7.44-7.33 (m, 2H), 7.18-7.09 (m, 3H), 7.02 (s, 1H), 6.95-6.84 (m, 6H), 6.80 (d, J=8.4 Hz, 2H), 4.94 (q, J=7.3 Hz, 1H), 4.89-4.76 (m, 2H), 3.72 (s, 3H), 2.96-2.90 (m, 2H), 2.49 (s, 3H).

Example 41

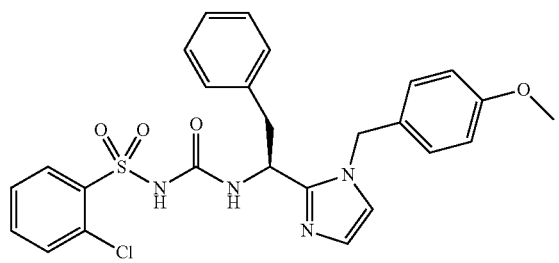 [SMILES: COc1ccc(Cn2ccnc2[C@H](Cc2ccccc2)NC(=O)NS(=O)(=O)c2ccccc2Cl)cc1]

| (S)-2-chloro-N-((1-(1-(4-methoxybenzyl)-1H-imidazol-2-yl)-2-phenylethyl)carbamoyl)benzenesulfonamide | |
|---|---|
| MS (M + H)$^+$ Calcd. | 525 |
| MS (M + H)$^+$ Observ. | 525 |
| Retention Time | 1.45 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (600 MHz, DMSO-d$_6$) δ 8.01-7.89 (m, 1H), 7.72-7.31 (m, 4H), 7.14 (br. s., 3H), 7.05-6.98 (m, 1H), 6.91 (br. s., 5H), 6.83-6.73 (m, 2H), 4.95 (d, J=7.7 Hz, 1H), 4.89-4.80 (m, 2H), 3.72 (s, 3H), 3.03-2.91 (m, 2H).

Example 42

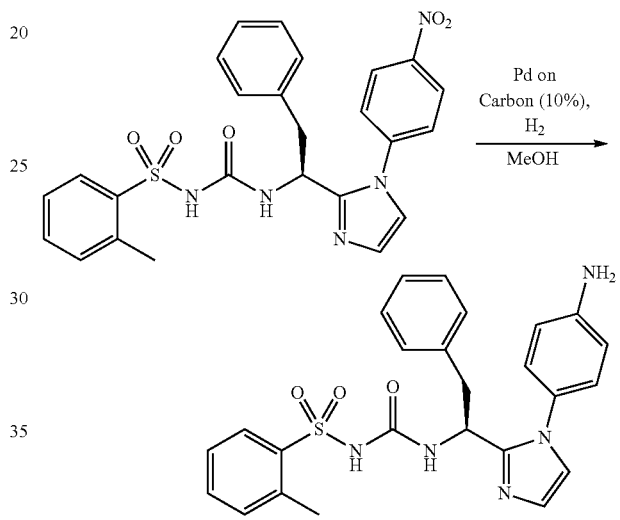

(S)-N-((1-(1-(4-aminophenyl)-1H-imidazol-2-yl)-2-phenylethyl)carbamoyl)-2-methylbenzenesulfonamide A mixture of 10% palladium on carbon (2 mg, 1.88 μmol) in methanol (1 mL) was stirred under H$_2$ balloon for 5 mins. (S)-2-methyl-N-((1-(1-(4-nitrophenyl)-1H-imidazol-2-yl)-2-phenylethyl)carbamoyl)benzenesulfonamide (14 mg, 0.028 mmol) in methanol (1 mL) was added. The reaction mixture was stirred under H$_2$ balloon for 4 hrs. The palladium catalyst was filtered off and the solvent was evaporated. The residue was purified by prepHPLC to afford (11.3 mg, 86%) of the title compound.

$^1$H NMR (500 MHz, DMSO-d$_6$) δ 7.83 (d, J=7.7 Hz, 1H), 7.60-7.50 (m, 1H), 7.45-7.34 (m, 2H), 7.19-7.08 (m, 3H), 7.06 (s, 1H), 6.98 (s, 1H), 6.89 (d, J=7.3 Hz, 1H), 6.69 (d, J=5.5 Hz, 2H), 6.59-6.51 (m, 2H), 6.50-6.39 (m, 2H), 4.68 (q, J=7.5 Hz, 1H), 2.98-2.65 (m, 2H), 2.53 (s, 3H).

| (S)-N-((1-(1-(4-aminophenyl)-1H-imidazol-2-yl)-2-phenylethyl)carbamoyl)-2-methylbenzenesulfonamide | |
|---|---|
| MS (M + H)$^+$ Calcd. | 476 |
| MS (M + H)$^+$ Observ. | 476 |
| Retention Time | 1.06 min |

-continued

| LC Condition | |
|---|---|
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

Examples 43-58 were synthesized using the procedure described above for Example 3.

Example 43

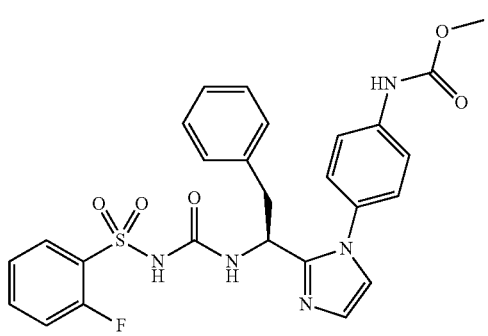

| (S)-methyl (4-(2-(1-(3-((2-fluorophenyl)sulfonyl)ureido)-2-phenylethyl)-1H-imidazol-1-yl)phenyl)carbamate | |
|---|---|
| MS (M + H)+ Calcd. | 538 |
| MS (M + H)+ Observ. | 538 |
| Retention Time | 1.21 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 9.82 (br. s., 1H), 7.67 (br. s., 1H), 7.52-7.31 (m, 3H), 7.27-7.02 (m, 6H), 6.99 (s, 1H), 6.81 (br. s., 2H), 6.72 (d, J=6.6 Hz, 2H), 4.71 (br. s., 1H), 3.69 (s, 3H), 3.00-2.77 (m, 2H).

Example 44

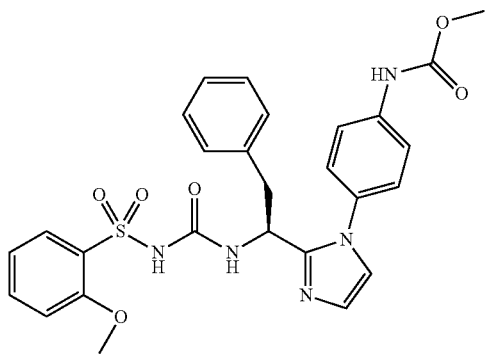 [SMILES: COC(=O)Nc1ccc(-n2ccnc2[C@H](Cc2ccccc2)NC(=O)NS(=O)(=O)c2ccccc2OC)cc1]

| (S)-methyl (4-(2-(1-(3-((2-methoxyphenyl)sulfonyl)ureido)-2-phenylethyl)-1H-imidazol-1-yl)phenyl)carbamate | |
|---|---|
| MS (M + H)+ Calcd. | 550 |
| MS (M + H)+ Observ. | 550 |
| Retention Time | 1.36 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 9.85 (s, 1H), 7.73 (d, J=7.3 Hz, 1H), 7.62 (t, J=7.7 Hz, 1H), 7.39 (d, J=8.4 Hz, 2H), 7.21 (d, J=8.4 Hz, 1H), 7.15-6.95 (m, 7H), 6.83-6.65 (m, 4H), 4.75-4.57 (m, 1H), 3.81 (s, 3H), 3.68 (s, 3H), 3.03-2.75 (m, 2H).

Example 45

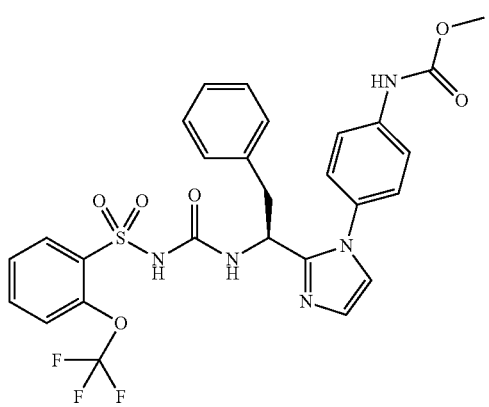 [SMILES: COC(=O)Nc1ccc(-n2ccnc2[C@H](Cc2ccccc2)NC(=O)NS(=O)(=O)c2ccccc2OC(F)(F)F)cc1]

| (S)-methyl (4-(2-(2-phenyl-1-(3-((2-(trifluoromethoxy)phenyl)sulfonyl)ureido)ethyl)-1H-imidazol-1-yl)phenyl)carbamate | |
|---|---|
| MS (M + H)+ Calcd. | 604 |
| MS (M + H)+ Observ. | 604 |
| Retention Time | 1.30 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^{1}$H NMR (500 MHz, DMSO-d$_{6}$) δ 9.82 (br. s., 1H), 7.83 (d, J=7.3 Hz, 1H), 7.56 (br. s., 1H), 7.39 (d, J=7.7 Hz, 4H), 7.19-7.03 (m, 4H), 7.00 (s, 1H), 6.78 (d, J=7.7 Hz, 2H), 6.71 (d, J=7.0 Hz, 2H), 4.69 (d, J=8.1 Hz, 1H), 3.68 (s, 3H), 3.01-2.77 (m, 2H).

Example 46

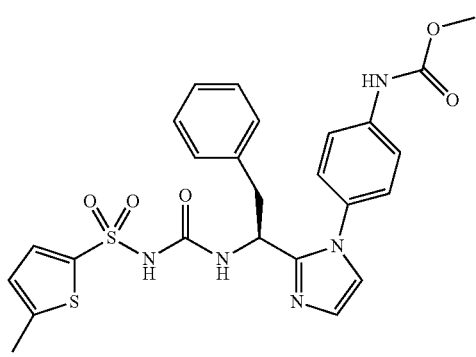 [SMILES: COC(=O)Nc1ccc(-n2ccnc2[C@H](Cc2ccccc2)NC(=O)NS(=O)(=O)c2ccc(C)s2)cc1]

| (S)-methyl (4-(2-(1-(3-((5-methylthiophen-2-yl)sulfonyl)ureido)-2-phenylethyl)-1H-imidazol-1-yl)phenyl)carbamate | |
|---|---|
| MS (M + H)+ Calcd. | 540 |
| MS (M + H)+ Observ. | 540 |
| Retention Time | 1.30 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^{1}$H NMR (500 MHz, DMSO-d$_{6}$) δ 9.87 (br. s., 1H), 7.45 (d, J=8.4 Hz, 1H), 7.37 (br. s., 1H), 7.22-7.07 (m, 4H), 7.03 (s, 1H), 6.88-6.63 (m, 5H), 4.76 (d, J=7.3 Hz, 1H), 3.70 (s, 3H), 3.04-2.78 (m, 2H), 2.48 (s, 3H).

Example 47

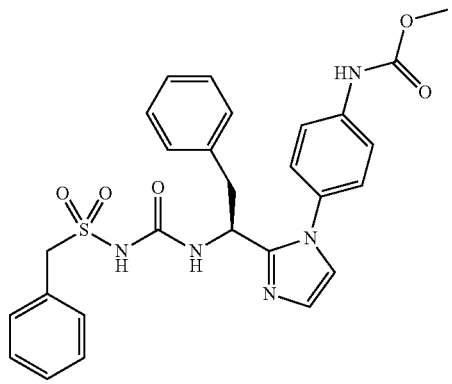 [SMILES: COC(=O)Nc1ccc(-n2ccnc2[C@H](Cc2ccccc2)NC(=O)NS(=O)(=O)Cc2ccccc2)cc1]

| (S)-methyl (4-(2-(1-(3-(benzylsulfonyl)ureido)-2-phenylethyl)-1H-imidazol-1-yl)phenyl)carbamate | |
|---|---|
| MS (M + H)+ Calcd. | 534 |
| MS (M + H)+ Observ. | 534 |
| Retention Time | 1.26 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^{1}$H NMR (500 MHz, DMSO-d$_{6}$) δ 9.90 (br. s., 1H), 7.51 (d, J=8.1 Hz, 1H), 7.33 (br. s., 3H), 7.23-7.12 (m, 6H), 7.07 (s, 1H), 6.93 (d, J=8.4 Hz, 2H), 6.84 (br. s., 2H), 4.88 (d, J=7.7 Hz, 1H), 4.49 (br. s., 2H), 3.69 (s, 3H), 3.09-2.90 (m, 2H).

Example 48

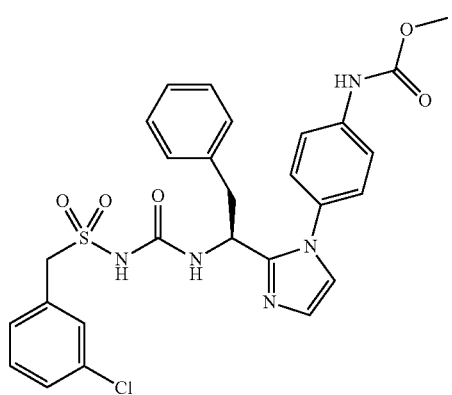 [SMILES: COC(=O)Nc1ccc(-n2ccnc2[C@H](Cc2ccccc2)NC(=O)NS(=O)(=O)Cc2cccc(Cl)c2)cc1]

| (S)-methyl (4-(2-(1-(3-((3-chlorobenzyl)sulfonyl)ureido)-2-phenylethyl)-1H-imidazol-1-yl)phenyl)carbamate | |
|---|---|
| MS (M + H)+ Calcd. | 568 |
| MS (M + H)+ Observ. | 568 |
| Retention Time | 1.33 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 9.90 (br. s., 1H), 7.50 (d, J=8.4 Hz, 2H), 7.46-7.41 (m, 1H), 7.41-7.31 (m, 2H), 7.23-7.11 (m, 5H), 7.07 (s, 1H), 6.88 (d, J=8.8 Hz, 2H), 6.83 (d, J=3.7 Hz, 3H), 4.92-4.80 (m, 1H), 4.62 (s, 2H), 3.69 (s, 3H), 3.09-2.91 (m, 2H).

Example 49

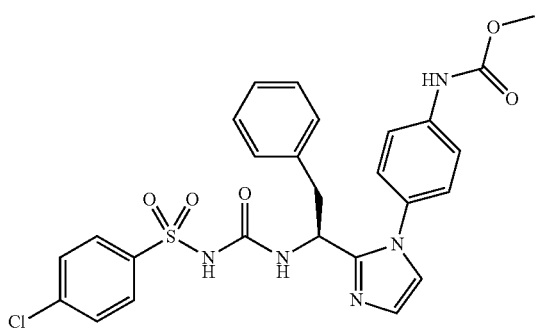 [SMILES: COC(=O)Nc1ccc(-n2ccnc2[C@H](Cc2ccccc2)NC(=O)NS(=O)(=O)c2ccc(Cl)cc2)cc1]

| (S)-methyl (4-(2-(1-(3-((4-chlorophenyl)sulfonyl)ureido)-2-phenylethyl)-1H-imidazol-1-yl)phenyl)carbamate | |
|---|---|
| MS (M + H)+ Calcd. | 554 |
| MS (M + H)+ Observ. | 554 |
| Retention Time | 1.29 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 9.88 (s, 1H), 7.83 (d, J=8.1 Hz, 2H), 7.66 (d, J=8.4 Hz, 2H), 7.45 (d, J=8.4 Hz, 2H), 7.21-6.94 (m, 6H), 6.84 (d, J=8.4 Hz, 2H), 6.72 (d, J=7.3 Hz, 2H), 4.72 (q, J=7.3 Hz, 1H), 3.70 (s, 3H), 3.05-2.75 (m, 2H).

Example 50

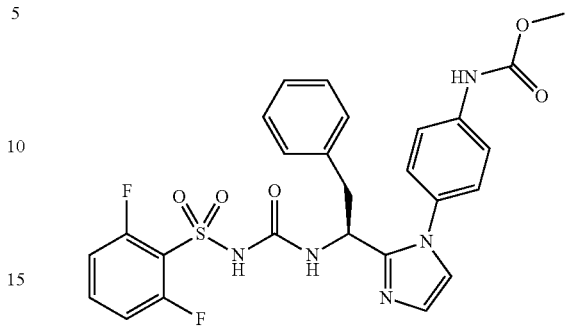

| (S)-methyl (4-(2-(1-(3-((2,6-difluorophenyl)sulfonyl)ureido)-2-phenylethyl)-1H-imidazol-1-yl)phenyl)carbamate | |
|---|---|
| MS (M + H)+ Calcd. | 556 |
| MS (M + H)+ Observ. | 556 |
| Retention Time | 1.15 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 9.87 (s, 1H), 7.73 (br. s., 1H), 7.43 (d, J=8.4 Hz, 2H), 7.28 (t, J=9.0 Hz, 2H), 7.21-7.01 (m, 5H), 6.95 (br. s., 1H), 6.84 (d, J=7.7 Hz, 2H), 6.73 (d, J=7.0 Hz, 2H), 4.73 (d, J=7.0 Hz, 1H), 3.69 (s, 3H), 3.06-2.76 (m, 2H).

Example 51

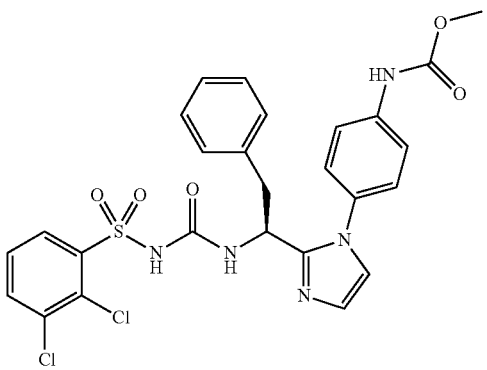 [SMILES: COC(=O)Nc1ccc(-n2ccnc2[C@H](Cc2ccccc2)NC(=O)NS(=O)(=O)c2cccc(Cl)c2Cl)cc1]

| (S)-methyl (4-(2-(1-(3-((2,3-dichlorophenyl)sulfonyl)ureido)-2-phenylethyl)-1H-imidazol-1-yl)phenyl)carbamate | |
|---|---|
| MS (M + H)+ Calcd. | 588 |
| MS (M + H)+ Observ. | 588 |
| Retention Time | 1.32 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 9.85 (s, 1H), 7.94-7.77 (m, 2H), 7.56-7.34 (m, 3H), 7.21-7.07 (m, 4H), 7.04 (br. s., 1H), 6.86 (d, J=8.1 Hz, 2H), 6.72 (d, J=7.0 Hz, 2H), 4.70 (d, J=5.9 Hz, 1H), 3.69 (s, 3H), 3.02-2.76 (m, 2H).

Example 52

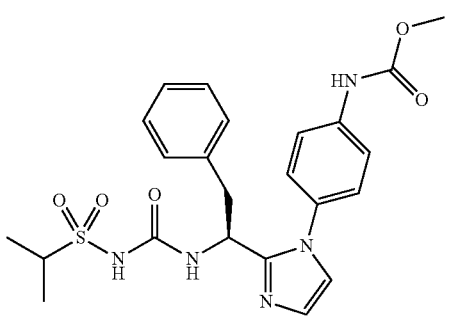 [SMILES: COC(=O)Nc1ccc(-n2ccnc2[C@H](Cc2ccccc2)NC(=O)NS(=O)(=O)C(C)C)cc1]

| (S)-methyl (4-(2-(1-(3-(isopropylsulfonyl)ureido)-2-phenylethyl)-1H-imidazol-1-yl)phenyl)carbamate | |
|---|---|
| MS (M + H)+ Calcd. | 486 |
| MS (M + H)+ Observ. | 486 |
| Retention Time | 1.16 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 9.88 (br. s., 1H), 7.48 (d, J=8.4 Hz, 2H), 7.16 (d, J=2.9 Hz, 4H), 7.04 (s, 1H), 6.96-6.68 (m, 5H), 4.92-4.73 (m, 1H), 3.70 (s, 3H), 3.50-3.39 (m, 1H), 3.09-2.83 (m, 2H), 1.26-1.08 (m, 6H).

Example 53

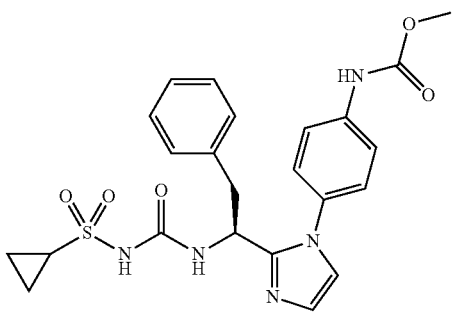 [SMILES: COC(=O)Nc1ccc(-n2ccnc2[C@H](Cc2ccccc2)NC(=O)NS(=O)(=O)C2CC2)cc1]

| (S)-methyl (4-(2-(1-(3-(cyclopropylsulfonyl)ureido)-2-phenylethyl)-1H-imidazol-1-yl)phenyl)carbamate | |
|---|---|
| MS (M + H)+ Calcd. | 484 |
| MS (M + H)+ Observ. | 484 |
| Retention Time | 1.12 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 9.87 (br. s., 1H), 7.46 (d, J=7.7 Hz, 2H), 7.25-7.07 (m, 4H), 7.03 (s, 1H), 6.93-6.65 (m, 4H), 4.91-4.73 (m, 1H), 3.69 (s, 3H), 3.01 (d, J=8.4 Hz, 1H), 2.95-2.62 (m, 2H), 0.91 (d, J=16.9 Hz, 4H).

Example 54

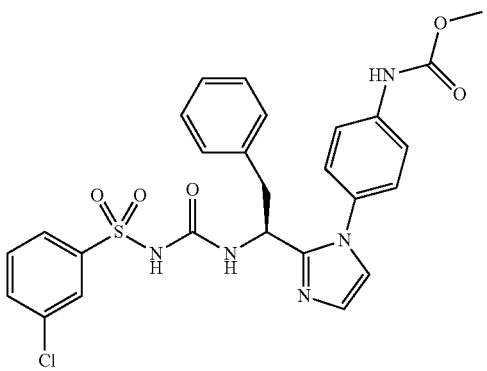 [SMILES: COC(=O)Nc1ccc(-n2ccnc2[C@H](Cc2ccccc2)NC(=O)NS(=O)(=O)c2cccc(Cl)c2)cc1]

| (S)-methyl (4-(2-(1-(3-((3-chlorophenyl)sulfonyl)ureido)-2-phenylethyl)-1H-imidazol-1-yl)phenyl)carbamate | |
|---|---|
| MS (M + H)+ Calcd. | 554 |
| MS (M + H)+ Observ. | 554 |
| Retention Time | 1.26 min |

-continued

| (S)-methyl (4-(2-(1-(3-((3-chlorophenyl)sulfonyl)ureido)-2-phenylethyl)-1H-imidazol-1-yl)phenyl)carbamate | |
|---|---|
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-µm particles |

$^1$H NMR (500 MHz, DMSO-$d_6$) δ 9.87 (s, 1H), 7.82 (br. s., 1H), 7.79-7.68 (m, 2H), 7.61 (t, J=7.9 Hz, 1H), 7.44 (d, J=8.4 Hz, 2H), 7.18-7.06 (m, 4H), 7.04 (s, 1H), 6.84 (d, J=8.1 Hz, 2H), 6.72 (d, J=7.0 Hz, 2H), 4.73 (d, J=6.6 Hz, 1H), 3.70 (s, 3H), 3.02-2.76 (m, 2H).

Example 55

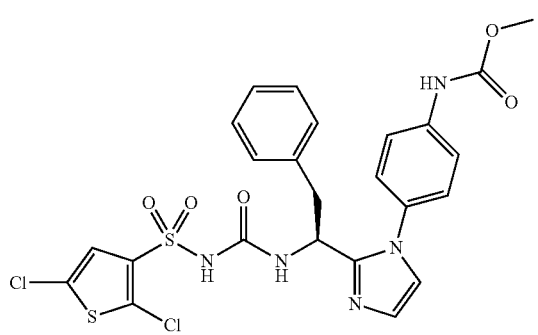 [SMILES: COC(=O)Nc1ccc(-n2ccnc2[C@H](Cc2ccccc2)NC(=O)NS(=O)(=O)c2cc(Cl)sc2Cl)cc1]

| (S)-methyl (4-(2-(1-(3-((2,5-dichlorothiophen-3-yl)sulfonyl)ureido)-2-phenylethyl)-1H-imidazol-1-yl)phenyl)carbamate | |
|---|---|
| MS (M + H)$^+$ Calcd. | 594 |
| MS (M + H)$^+$ Observ. | 594 |
| Retention Time | 1.28 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-µm particles |

$^1$H NMR (500 MHz, DMSO-$d_6$) δ 9.83 (br. s., 1H), 7.42 (d, J=8.4 Hz, 2H), 7.16-6.96 (m, 6H), 6.92-6.68 (m, 4H), 4.74 (br. s., 1H), 3.69 (s, 3H), 2.98-2.77 (m, 2H).

Example 56

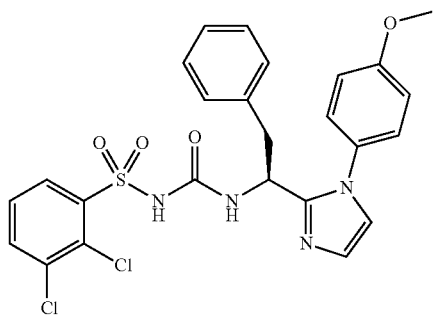 [SMILES: COc1ccc(-n2ccnc2[C@H](Cc2ccccc2)NC(=O)NS(=O)(=O)c2cccc(Cl)c2Cl)cc1]

| (S)-2,3-dichloro-N-((1-(1-(4-methoxyphenyl)-1H-imidazol-2-yl)-2-phenylethyl)carbamoyl)benzenesulfonamide | |
|---|---|
| MS (M + H)$^+$ Calcd. | 545 |
| MS (M + H)$^+$ Observ. | 545 |
| Retention Time | 1.67 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-µm particles |

$^1$H NMR (500 MHz, DMSO-$d_6$) δ 7.95-7.78 (m, 2H), 7.47 (br. s., 1H), 7.11 (br. s., 5H), 6.86 (br. s., 4H), 6.73 (br. s., 2H), 4.67 (br. s., 1H), 3.77 (s, 3H), 3.05-2.75 (m, 2H).

Example 57

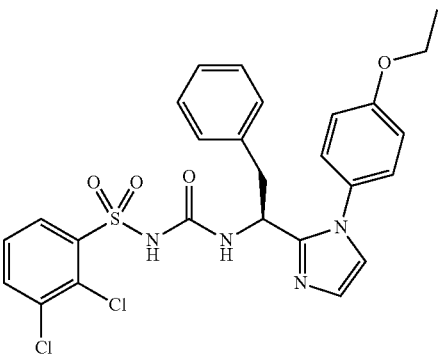 [SMILES: CCOc1ccc(-n2ccnc2[C@H](Cc2ccccc2)NC(=O)NS(=O)(=O)c2cccc(Cl)c2Cl)cc1]

| (S)-2,3-dichloro-N-((1-(1-(4-ethoxyphenyl)-1H-imidazol-2-yl)-2-phenylethyl)carbamoyl)benzenesulfonamide | |
|---|---|
| MS (M + H)$^+$ Calcd. | 559 |
| MS (M + H)$^+$ Observ. | 559 |
| Retention Time | 1.72 min |

-continued (S)-2,3-dichloro-N-((1-(1-(4-ethoxyphenyl)-1H-imidazol-2-yl)-2-phenylethyl)carbamoyl)benzenesulfonamide

| LC Condition | |
|---|---|
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 7.95-7.79 (m, 2H), 7.47 (br. s., 1H), 7.20-6.97 (m, 5H), 6.85 (br. s., 4H), 6.73 (br. s., 2H), 4.67 (br. s., 1H), 4.03 (d, J=7.0 Hz, 2H), 3.05-2.75 (m, 2H), 1.33 (t, J=7.0 Hz, 3H).

Example 58

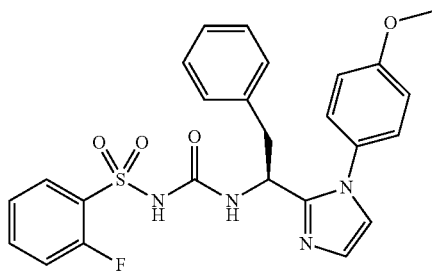

(S)-2-fluoro-N-((1-(1-(4-methoxyphenyl)-1H-imidazol-2-yl)-2-phenylethyl)carbamoyl)benzenesulfonamide

| MS (M + H)$^+$ Calcd. | 495 |
|---|---|
| MS (M + H)$^+$ Observ. | 495 |
| Retention Time | 1.24 min |
| LC Condition | |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 2 min |
| Flow Rate | 1 mL/min |
| Wavelength | 220 |
| Column | Phenomenex LUNA C18 30 × 2 mm, 3μ |

$^1$H NMR (400 MHz, METHANOL-d$_4$) δ 7.90 (t, J=7.3 Hz, 1H), 7.65 (br. s., 1H), 7.41-7.05 (m, 6H), 6.98 (br. s., 1H), 6.87-6.73 (m, 4H), 6.64 (d, J=7.0 Hz, 2H), 4.82 (br. s., 1H), 3.80 (s, 3H), 3.13-2.90 (m, 2H).

Example 59

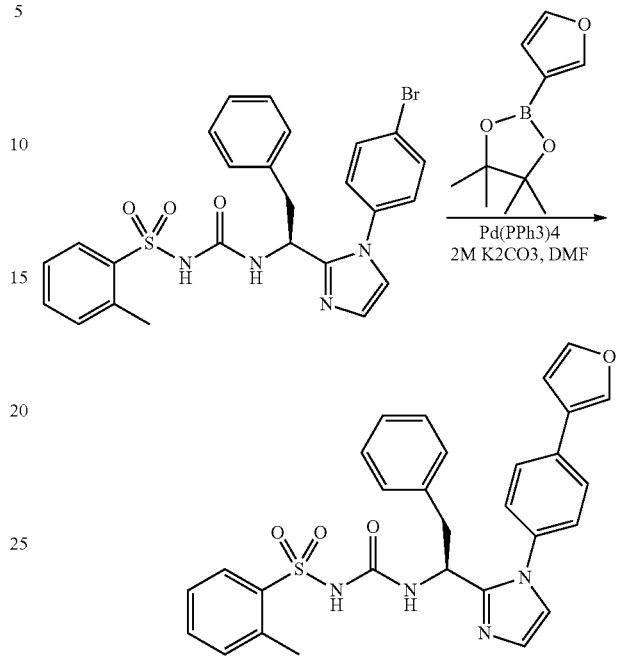

(S)-N-((1-(1-(4-(furan-3-yl)phenyl)-1H-imidazol-2-yl)-2-phenylethyl)carbamoyl)-2-methylbenzenesulfonamide To a 0.5-2 ml microwave tube was added (S)-N-((1-(1-(4-bromophenyl)-1H-imidazol-2-yl)-2-phenylethyl)carbamoyl)-2-methylbenzenesulfonamide (20 mg, 0.037 mmol), 2-(furan-3-yl)-4,4,5,5-tetramethyl-1,3,2-dioxaborolane (10.79 mg, 0.056 mmol), Tetrakis(triphenylphosphine)palladium(0) (4.28 mg, 3.71 μmol), followed by DMF (1 mL), 2M K$_2$CO$_3$ solution (50 μL, 0.100 mmol). The reaction mixture was heated in a microwave reactor at 125° C. for 15 mins. The reaction mixture was filtered and the filtrate was purified by PrepHPLC to afford (8.9 mg, 45.6%) of the title compound.

$^1$H NMR (500 MHz, DMSO-d$_6$) δ 8.25 (s, 1H), 7.85-7.74 (m, 2H), 7.57 (d, J=8.1 Hz, 2H), 7.45 (br. s., 1H), 7.37-7.26 (m, 2H), 7.22-7.04 (m, 5H), 7.00 (s, 1H), 6.94 (d, J=8.1 Hz, 2H), 6.71 (d, J=7.0 Hz, 2H), 4.78 (d, J=5.9 Hz, 1H), 3.02-2.77 (m, 2H), 2.53 (m, 3H).

| (S)-N-((1-(1-(4-(furan-3-yl)phenyl)-1H-imidazol-2-yl)-2-phenylethyl)carbamoyl)-2-methylbenzenesulfonamide | |
|---|---|
| MS (M + H)$^+$ Calcd. | 527 |
| MS (M + H)$^+$ Observ. | 527 |
| Retention Time | 1.60 min |
| LC Condition | |
| Solvent A | 5% acetonitrile:95% Water:10 mM Ammonium Acetate |
| Solvent B | 95% acetonitrile:5% Water:10 mM Ammonium Acetate |

-continued

| (S)-N-((1-(1-(4-(furan-3-yl)phenyl)-1H-imidazol-2-yl)-2-phenylethyl)carbamoyl)-2-methylbenzenesulfonamide | |
|---|---|
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-µm particles |

Examples 60-65 were synthesized using the procedure described above for Example 59.

Example 60

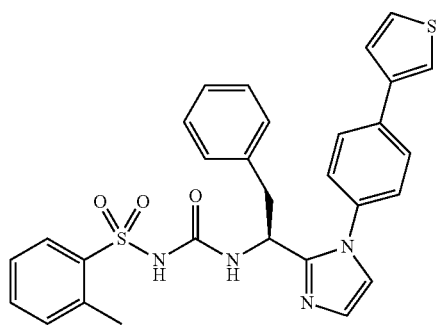 [SMILES: Cc1ccccc1S(=O)(=O)NC(=O)N[C@@H](Cc1ccccc1)c1nccn1-c1ccc(-c2ccsc2)cc1]

| (S)-2-methyl-N-((2-phenyl-1-(1-(4-(thiophen-3-yl)phenyl)-1H-imidazol-2-yl)ethyl)carbamoyl)benzenesulfonamide | |
|---|---|
| MS (M + H)$^+$ Calcd. | 543 |
| MS (M + H)$^+$ Observ. | 543 |
| Retention Time | 1.72 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-µm particles |

$^1$H NMR (400 MHz, METHANOL-d$_4$) δ 7.96 (dd, J=7.8, 1.0 Hz, 1H), 7.69 (dd, J=2.9, 1.5 Hz, 1H), 7.59-7.43 (m, 6H), 7.40-7.27 (m, 2H), 7.17-7.07 (m, 4H), 7.03 (d, J=1.2 Hz, 1H), 6.85-6.70 (m, 4H), 4.91 (d, 2H), 3.13-2.93 (m, 2H), 2.64 (s, 3H).

Example 61

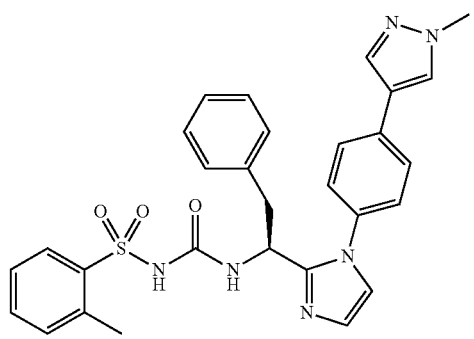 [SMILES: Cc1ccccc1S(=O)(=O)NC(=O)N[C@@H](Cc1ccccc1)c1nccn1-c1ccc(-c2cnn(C)c2)cc1]

| (S)-2-methyl-N-((1-(1-(4-(1-methyl-1H-pyrazol-4-yl)phenyl)-1H-imidazol-2-yl)-2-phenylethyl)carbamoyl)benzenesulfonamide | |
|---|---|
| MS (M + H)$^+$ Calcd. | 541 |
| MS (M + H)$^+$ Observ. | 541 |
| Retention Time | 1.36 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-µm particles |

$^1$H NMR (500 MHz, DMSO-d$_6$) δ 8.18 (s, 1H), 7.89 (s, 1H), 7.81-7.72 (m, 1H), 7.49 (d, J=8.1 Hz, 2H), 7.44-7.21 (m, 3H), 7.17-6.99 (m, 5H), 6.88 (d, J=7.0 Hz, 2H), 6.71 (d, J=6.6 Hz, 2H), 4.81-4.71 (m, 1H), 3.91 (s, 3H), 2.96-2.79 (m, 2H), 2.53 (s, 3H).

Example 62

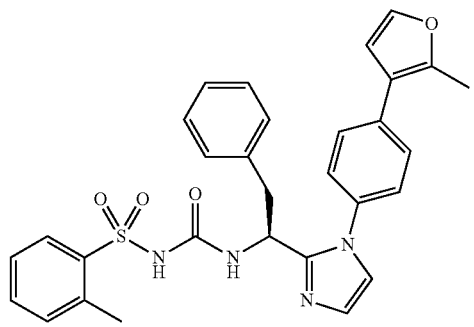 [SMILES: Cc1ccccc1S(=O)(=O)NC(=O)N[C@@H](Cc1ccccc1)c1nccn1-c1ccc(-c2ccoc2C)cc1]

| (S)-2-methyl-N-((1-(1-(4-(2-methylfuran-3-yl)phenyl)-1H-imidazol-2-yl)-2-phenylethyl)carbamoyl)benzenesulfonamide | |
|---|---|
| MS (M + H)+ Calcd. | 541 |
| MS (M + H)+ Observ. | 541 |
| Retention Time | 1.72 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 7.83 (d, J=7.7 Hz, 1H), 7.60 (s, 1H), 7.52 (br. s., 1H), 7.45-7.31 (m, 4H), 7.22 (s, 1H), 7.16-7.04 (m, 4H), 7.02-6.88 (m, 3H), 6.75 (s, 1H), 6.71 (d, J=7.0 Hz, 2H), 4.79 (d, J=7.0 Hz, 1H), 3.00-2.76 (m, 2H), 2.54 (s, 3H), 2.45 (s, 3H).

Example 63

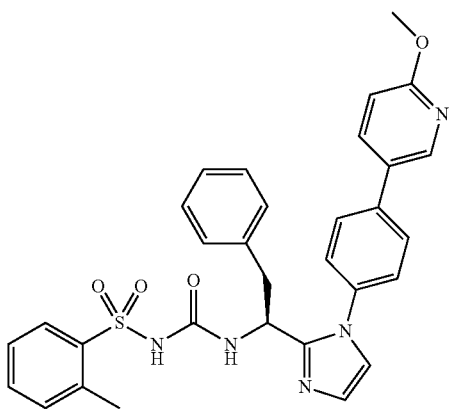 [SMILES: COc1ccc(-c2ccc(-n3ccnc3[C@H](Cc3ccccc3)NC(=O)NS(=O)(=O)c3ccccc3C)cc2)cn1]

| (S)-N-((1-(1-(4-(6-methoxypyridin-3-yl)phenyl)-1H-imidazol-2-yl)-2-phenylethyl)carbamoyl)-2-methylbenzenesulfonamide | |
|---|---|
| MS (M + H)+ Calcd. | 568 |
| MS (M + H)+ Observ. | 568 |
| Retention Time | 1.65 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 8.51 (s, 1H), 8.04 (d, J=8.4 Hz, 1H), 7.81 (d, J=7.3 Hz, 1H), 7.63 (d, J=8.4 Hz, 2H), 7.49 (br. s., 1H), 7.40-7.30 (m, 2H), 7.22 (br. s., 2H), 7.15-6.98 (m, 6H), 6.94 (d, J=8.8 Hz, 1H), 6.73 (d, J=7.0 Hz, 2H), 4.80 (d, J=5.5 Hz, 1H), 3.91 (s, 3H), 3.03-2.76 (m, 2H), 2.53 (s, 3H).

Example 64

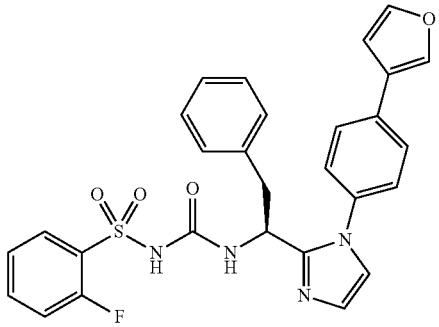 [SMILES: O=C(N[C@@H](Cc1ccccc1)c1nccn1-c1ccc(-c2ccoc2)cc1)NS(=O)(=O)c1ccccc1F]

| (S)-2-fluoro-N-((1-(1-(4-(furan-3-yl)phenyl)-1H-imidazol-2-yl)-2-phenylethyl)carbamoyl)benzenesulfonamide | |
|---|---|
| MS (M + H)+ Calcd. | 531 |
| MS (M + H)+ Observ. | 531 |
| Retention Time | 1.52 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 8.22 (s, 1H), 7.82-7.72 (m, 2H), 7.67 (br. s., 1H), 7.57 (d, J=8.1 Hz, 2H), 7.46-7.29 (m, 2H), 7.21-7.03 (m, 5H), 7.01-6.81 (m, 4H), 6.73 (d, J=6.6 Hz, 2H), 4.77 (d, J=7.0 Hz, 1H), 3.03-2.77 (m, 2H).

Example 65

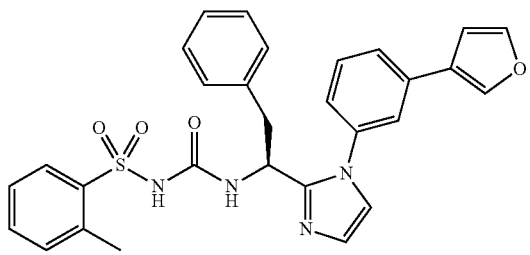 [SMILES: Cc1ccccc1S(=O)(=O)NC(=O)N[C@@H](Cc1ccccc1)c1nccn1-c1cccc(-c2ccoc2)c1]

| (S)-N-((1-(1-(3-(furan-3-yl)phenyl)-1H-imidazol-2-yl)-2-phenylethyl)carbamoyl)-2-methylbenzenesulfonamide | |
|---|---|
| MS (M + H)+ Calcd. | 527 |
| MS (M + H)+ Observ. | 527 |
| Retention Time | 1.64 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 8.17 (s, 1H), 7.85 (d, J=8.1 Hz, 1H), 7.76 (s, 1H), 7.62 (d, J=7.7 Hz, 1H), 7.50-7.26 (m, 5H), 7.19 (s, 1H), 7.10-6.98 (m, 4H), 6.92 (s, 1H), 6.74-6.61 (m, 3H), 4.84 (d, J=6.6 Hz, 1H), 3.00-2.78 (m, 2H), 2.54 (s, 3H).

Examples 66-82 were synthesized using the procedure described above for Example 4.

Example 66

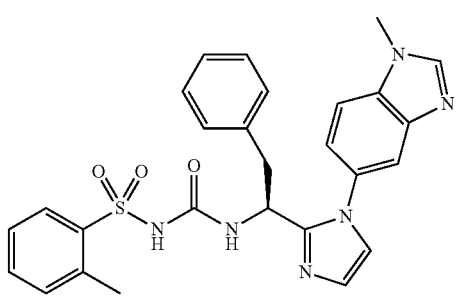 [SMILES: Cc1ccccc1S(=O)(=O)NC(=O)N[C@@H](Cc1ccccc1)c1nccn1-c1ccc2c(c1)ncn2C]

| (S)-2-methyl-N-((1-(1-(1-methyl-1H-benzo[d]imidazol-5-yl)-1H-imidazol-2-yl)-2-phenylethyl)carbamoyl)benzenesulfonamide | |
|---|---|
| MS (M + H)+ Calcd. | 515 |
| MS (M + H)+ Observ. | 515 |
| Retention Time | 1.43 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 8.28 (s, 1H), 7.76 (d, J=7.3 Hz, 1H), 7.48 (d, J=8.4 Hz, 1H), 7.40 (br. s., 1H), 7.33-7.21 (m, 2H), 7.20-6.99 (m, 6H), 6.77 (d, J=8.1 Hz, 1H), 6.68 (d, J=7.7 Hz, 2H), 4.74 (br. s., 1H), 3.86 (s, 3H), 2.99-2.74 (m, 2H), 2.51 (s, 3H).

Example 67

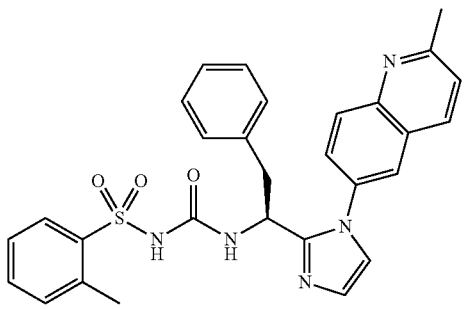 [SMILES: Cc1ccc2cc(-n3ccnc3[C@H](Cc3ccccc3)NC(=O)NS(=O)(=O)c3ccccc3C)ccc2n1]

| (S)-2-methyl-N-((1-(1-(2-methylquinolin-6-yl)-1H-imidazol-2-yl)-2-phenylethyl)carbamoyl)benzenesulfonamide | |
|---|---|
| MS (M + H)+ Calcd. | 526 |
| MS (M + H)+ Observ. | 526 |
| Retention Time | 1.64 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 7.96 (s, 1H), 7.76 (br. s., 2H), 7.46 (d, J=8.4 Hz, 1H), 7.38-6.89 (m, 10H), 6.68 (br. s., 2H), 4.86-4.65 (m, 1H), 3.05-2.78 (m, 2H), 2.68 (s, 3H), 2.53 (s, 3H).

Example 68

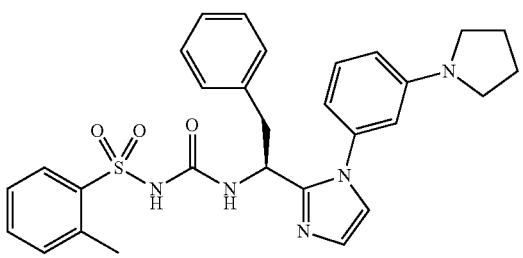 [SMILES: Cc1ccccc1S(=O)(=O)NC(=O)N[C@@H](Cc1ccccc1)c1nccn1-c1cccc(N2CCCC2)c1]

| (S)-2-methyl-N-((2-phenyl-1-(1-(3-(pyrrolidin-1-yl)phenyl)-1H-imidazol-2-yl)ethyl)carbamoyl)benzenesulfonamide | |
|---|---|
| MS (M + H)+ Calcd. | 530 |
| MS (M + H)+ Observ. | 530 |
| Retention Time | 1.90 min |
| | LC Condition |
| Solvent A | 5% acetonitrile: 95% Water: 10 mM Ammonium Acetate |

-continued (S)-2-methyl-N-((2-phenyl-1-(1-(3-(pyrrolidin-1-yl)phenyl)-1H-imidazol-2-yl)ethyl)carbamoyl)benzenesulfonamide

| Solvent B | 95% acetonitrile: 5% Water: 10 mM Ammonium Acetate |
| --- | --- |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^{1}$H NMR (400 MHz, METHANOL-d$_{4}$) δ 8.18-7.78 (m, 1H), 7.57-7.23 (m, 3H), 7.16-6.93 (m, 6H), 6.84-6.71 (m, 2H), 6.61-6.46 (m, 1H), 6.16-5.73 (m, 2H), 5.17-4.98 (m, 1H), 3.25-2.90 (m, 6H), 2.63 (s, 3H), 2.12-1.89 (m, 4H).

Example 69

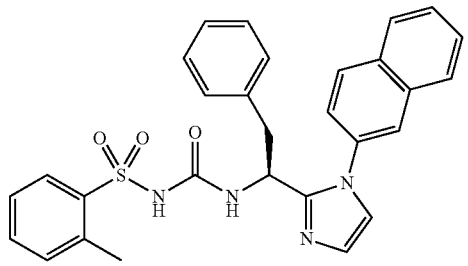 [SMILES: Cc1ccccc1S(=O)(=O)NC(=O)N[C@@H](Cc1ccccc1)c1nccn1-c1ccc2ccccc2c1]

(S)-2-methyl-N-((1-(1-(naphthalen-2-yl)-1H-imidazol-2-yl)-2-phenylethyl)carbamoyl)benzenesulfonamide

| MS (M + H)$^{+}$ Calcd. | 511 |
| --- | --- |
| MS (M + H)$^{+}$ Observ. | 511 |
| Retention Time | 1.98 min |
|  | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^{1}$H NMR (500 MHz, DMSO-d$_{6}$) δ 8.04-7.87 (m, 2H), 7.83 (d, J=8.1 Hz, 1H), 7.72 (br. s., 1H), 7.66-7.48 (m, 3H), 7.46-7.24 (m, 4H), 7.20-6.94 (m, 6H), 6.71 (d, J=7.3 Hz, 2H), 4.79 (d, J=5.5 Hz, 1H), 3.10-2.75 (m, 2H).

Example 70

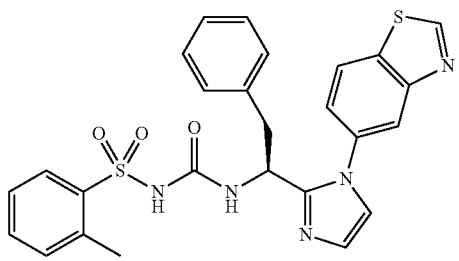 [SMILES: Cc1ccccc1S(=O)(=O)NC(=O)N[C@@H](Cc1ccccc1)c1nccn1-c1ccc2scnc2c1]

(S)-N-((1-(1-(benzo[d]thiazol-5-yl)-1H-imidazol-2-yl)-2-phenylethyl)carbamoyl)-2-methylbenzenesulfonamide

| MS (M + H)$^{+}$Calcd. | 518 |
| --- | --- |
| MS (M + H)$^{+}$Observ. | 518 |
| Retention Time | 1.32 min |
|  | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^{1}$H NMR (500 MHz, DMSO-d$_{6}$) δ 9.47 (s, 1H), 8.09 (d, J=8.5 Hz, 1H), 7.80-7.68 (m, 1H), 7.56 (br. s., 1H), 7.39-7.28 (m, 1H), 7.18 (s, 3H), 7.12-6.94 (m, 5H), 6.68 (d, J=7.3 Hz, 3H), 4.85-4.71 (m, 1H), 2.97-2.83 (m, 2H), 2.52 (s, 3H).

Example 71

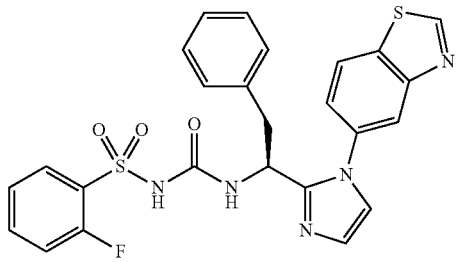 [SMILES: O=C(N[C@@H](Cc1ccccc1)c1nccn1-c1ccc2scnc2c1)NS(=O)(=O)c1ccccc1F]

(S)-N-((1-(1-(benzo[d]thiazol-5-yl)-1H-imidazol-2-yl)-2-phenylethyl)carbamoyl)-2-fluorobenzenesulfonamide

| MS (M + H)$^{+}$ Calcd. | 522 |
| --- | --- |
| MS (M + H)$^{+}$ Observ. | 522 |
| Retention Time | 1.20 min |
|  | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |

-continued

| (S)-N-((1-(1-(benzo[d]thiazol-5-yl)-1H-imidazol-2-yl)-2-phenylethyl)carbamoyl)-2-fluorobenzenesulfonamide | |
|---|---|
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 9.47 (s, 1H), 8.10 (d, J=8.4 Hz, 1H), 7.68 (br. s., 1H), 7.57 (br. s., 1H), 7.43 (br. s., 1H), 7.25-6.95 (m, 8H), 6.68 (d, J=7.3 Hz, 2H), 6.44 (d, J=6.6 Hz, 1H), 4.80 (br. s., 1H), 3.00-2.80 (m, 2H).

Example 72

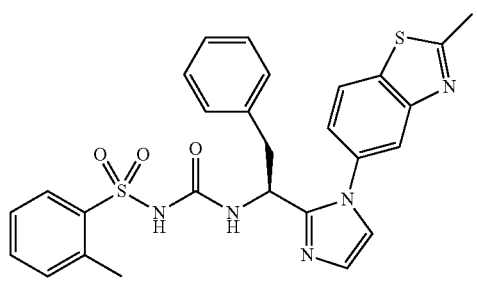 [SMILES: Cc1nc2cc(-n3ccnc3[C@H](Cc3ccccc3)NC(=O)NS(=O)(=O)c3ccccc3C)ccc2s1]

| (S)-2-methyl-N-((1-(1-(2-methylbenzo[d]thiazol-5-yl)-1H-imidazol-2-yl)-2-phenylethyl)carbamoyl)benzenesulfonamide | |
|---|---|
| MS (M + H)$^+$ Calcd. | 532 |
| MS (M + H)$^+$ Observ. | 532 |
| Retention Time | 1.44 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 7.96 (d, J=8.2 Hz, 1H), 7.79 (d, J=7.9 Hz, 1H), 7.50 (s, 1H), 7.41 (d, J=7.0 Hz, 1H), 7.33-7.24 (m, 2H), 7.21 (s, 1H), 7.15-7.00 (m, 4H), 6.91 (d, J=7.6 Hz, 1H), 6.80 (br. s., 1H), 6.69 (d, J=7.3 Hz, 2H), 4.81 (d, J=6.1 Hz, 1H), 3.01-2.78 (m, 5H), 2.54 (s, 3H).

Example 73

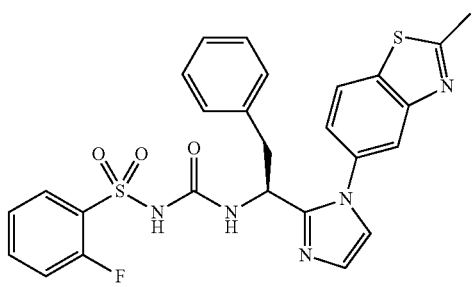 [SMILES: Cc1nc2cc(-n3ccnc3[C@H](Cc3ccccc3)NC(=O)NS(=O)(=O)c3ccccc3F)ccc2s1]

| (S)-2-fluoro-N-((1-(1-(2-methylbenzo[d]thiazol-5-yl)-1H-imidazol-2-yl)-2-phenylethyl)carbamoyl)benzenesulfonamide | |
|---|---|
| MS (M + H)$^+$ Calcd. | 536 |
| MS (M + H)$^+$ Observ. | 536 |
| Retention Time | 1.30 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 7.96 (d, J=8.4 Hz, 1H), 7.71 (br. s., 1H), 7.49 (br. s., 2H), 7.31-7.16 (m, 3H), 7.13-7.00 (m, 4H), 6.92 (d, J=8.1 Hz, 1H), 6.69 (d, J=7.3 Hz, 2H), 4.81 (d, J=5.9 Hz, 1H), 3.01-2.76 (m, 5H).

Example 74

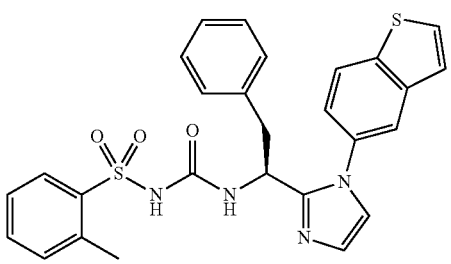

| (S)-N-((1-(1-(benzo[b]thiophen-5-yl)-1H-imidazol-2-yl)-2-phenylethyl)carbamoyl)-2-methylbenzenesulfonamide | |
|---|---|
| MS (M + H)$^+$ Calcd. | 517 |
| MS (M + H)$^+$ Observ. | 517 |
| Retention Time | 1.63 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |

-continued

| (S)-N-((1-(1-(benzo[b]thiophen-5-yl)-1H-imidazol-2-yl)-2-phenylethyl)carbamoyl)-2-methylbenzenesulfonamide | |
|---|---|
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 8.00-7.92 (m, 1H), 7.87 (d, J=5.2 Hz, 1H), 7.79 (d, J=7.9 Hz, 1H), 7.43 (d, J=6.1 Hz, 1H), 7.36-7.24 (m, 3H), 7.22-7.00 (m, 6H), 6.92 (d, J=7.6 Hz, 1H), 6.81 (br. s., 1H), 6.71 (d, J=7.0 Hz, 2H), 4.73 (d, J=4.9 Hz, 1H), 3.05-2.77 (m, 2H), 2.54 (s, 3H).

Example 75

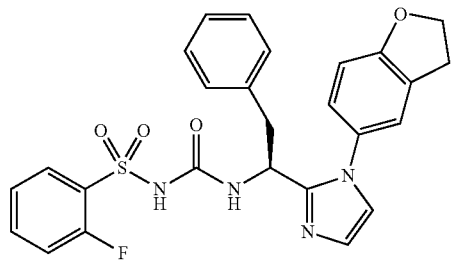 [SMILES: O=C(N[C@@H](Cc1ccccc1)c1nccn1-c1ccc2c(c1)CCO2)NS(=O)(=O)c1ccccc1F]

| (S)-N-((1-(1-(2,3-dihydrobenzofuran-5-yl)-1H-imidazol-2-yl)-2-phenylethyl)carbamoyl)-2-fluorobenzenesulfonamide | |
|---|---|
| MS (M + H)$^+$ Calcd. | 507 |
| MS (M + H)$^+$ Observ. | 507 |
| Retention Time | 1.31 min |
| LC Condition | |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 7.82 (t, J=7.3 Hz, 1H), 7.73 (d, J=5.5 Hz, 1H), 7.45 (t, J=9.3 Hz, 1H), 7.38 (t, J=7.5 Hz, 1H), 7.19-7.11 (m, 3H), 7.10 (s, 1H), 7.04 (s, 1H), 6.95 (d, J=7.9 Hz, 1H), 6.77-6.61 (m, 4H), 4.72-4.63 (m, 1H), 4.62-4.49 (m, 2H), 3.14-3.03 (m, 2H), 3.01-2.78 (m, 2H).

Example 76

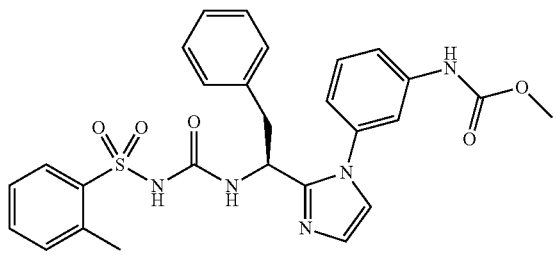 [SMILES: COC(=O)Nc1cccc(-n2ccnc2[C@H](Cc2ccccc2)NC(=O)NS(=O)(=O)c2ccccc2C)c1]

| (S)-methyl (3-(2-(2-phenyl-1-(3-(o-tolylsulfonyl)ureido)ethyl)-1H-imidazol-1-yl)phenyl)carbamate | |
|---|---|
| MS (M + H)$^+$ Calcd. | 534 |
| MS (M + H)$^+$ Observ. | 534 |
| Retention Time | 1.36 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 9.93-9.67 (m, 1H), 7.82-7.65 (m, 1H), 7.50-7.32 (m, 2H), 7.29-6.93 (m, 9H), 6.70 (br. s., 3H), 4.86-4.70 (m, 1H), 3.67 (s, 3H), 2.90-2.74 (m, 2H), 2.51 (s, 3H).

Example 77

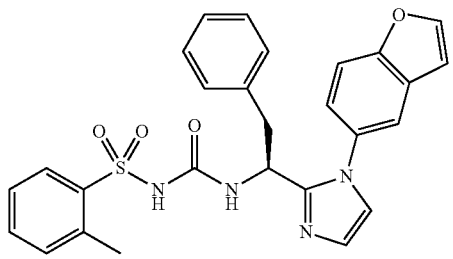 [SMILES: Cc1ccccc1S(=O)(=O)NC(=O)N[C@@H](Cc1ccccc1)c1nccn1-c1ccc2occc2c1]

| (S)-N-((1-(1-(benzofuran-5-yl)-1H-imidazol-2-yl)-2-phenylethyl)carbamoyl)-2-methylbenzenesulfonamide | |
|---|---|
| MS (M + H)$^+$ Calcd. | 501 |
| MS (M + H)$^+$ Observ. | 501 |
| Retention Time | 1.53 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |

-continued (S)-N-((1-(1-(benzofuran-5-yl)-1H-imidazol-2-yl)-2-phenylethyl)carbamoyl)-2-methylbenzenesulfonamide

| | |
|---|---|
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 8.09 (s, 1H), 7.79 (d, J=7.6 Hz, 1H), 7.53 (d, J=8.5 Hz, 1H), 7.42 (br. s., 1H), 7.35-7.23 (m, 2H), 7.19-6.97 (m, 6H), 6.94-6.62 (m, 5H), 4.70 (d, J=5.2 Hz, 1H), 3.01-2.77 (m, 2H), 2.54 (s, 3H).

Example 78

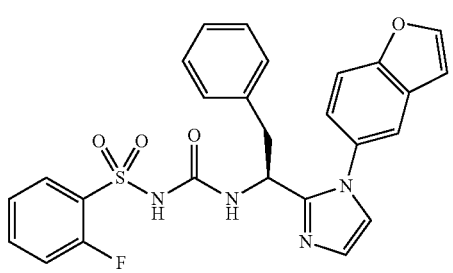 [SMILES: O=C(N[C@@H](Cc1ccccc1)c1nccn1-c1ccc2occc2c1)NS(=O)(=O)c1ccccc1F]

(S)-N-((1-(1-(benzofuran-5-yl)-1H-imidazol-2-yl)-2-phenylethyl)carbamoyl)-2-fluorobenzenesulfonamide

| | |
|---|---|
| MS (M + H)$^+$ Calcd. | 505 |
| MS (M + H)$^+$ Observ. | 505 |
| Retention Time | 1.38 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 8.09 (s, 1H), 7.78 (t, J=7.3 Hz, 1H), 7.69 (d, J=5.2 Hz, 1H), 7.56 (d, J=8.9 Hz, 1H), 7.49-7.27 (m, 2H), 7.23-6.99 (m, 6H), 6.96-6.80 (m, 3H), 6.71 (d, J=7.3 Hz, 2H), 4.71 (d, J=7.0 Hz, 1H), 3.03-2.77 (m, 2H).

Example 79

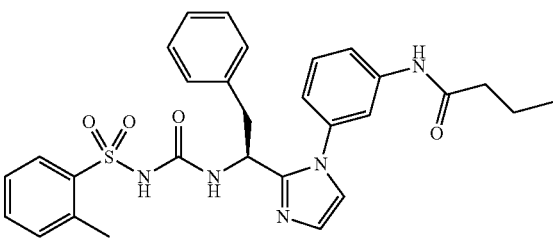 [SMILES: CCCC(=O)Nc1cccc(-n2ccnc2[C@H](Cc2ccccc2)NC(=O)NS(=O)(=O)c2ccccc2C)c1]

(S)-N-(3-(2-(2-phenyl-1-(3-(o-tolylsulfonyl)ureido)ethyl)-1H-imidazol-1-yl)phenyl)butyramide

| | |
|---|---|
| MS (M + H)$^+$ Calcd. | 546 |
| MS (M + H)$^+$ Observ. | 546 |
| Retention Time | 1.70 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 10.14 (s, 1H), 7.81 (d, J=7.7 Hz, 1H), 7.61-7.29 (m, 8H), 7.15-7.09 (m, 3H), 6.82-6.72 (m, 3H), 4.83 (d, J=7.3 Hz, 1H), 3.05-2.85 (m, 2H), 2.51 (s, 3H), 2.31 (t, J=7.3 Hz, 2H), 1.68-1.56 (m, 2H), 0.93 (t, J=7.3 Hz, 3H).

Example 80

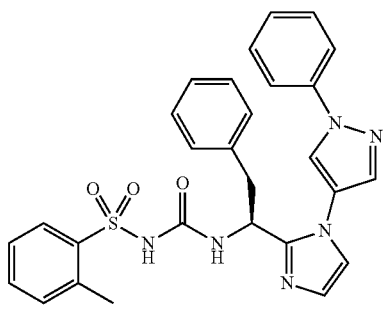 [SMILES: Cc1ccccc1S(=O)(=O)NC(=O)N[C@@H](Cc1ccccc1)c1nccn1-c1cnn(-c2ccccc2)c1]

(S)-2-methyl-N-((2-phenyl-1-(1-(1-phenyl-1H-pyrazol-4-yl)-1H-imidazol-2-yl)ethyl)carbamoyl)benzenesulfonamide

| | |
|---|---|
| MS (M + H)$^+$ Calcd. | 527 |
| MS (M + H)$^+$ Observ. | 527 |
| Retention Time | 1.78 min |
| LC Condition | |
| Solvent A | 5% acetonitrile:95% Water:10 mM Ammonium Acetate |

(S)-2-methyl-N-((2-phenyl-1-(1-(1-phenyl-1H-pyrazol-4-yl)-1H-imidazol-2-yl)ethyl)carbamoyl)benzenesulfonamide

| Solvent B | 95% acetonitrile:5% Water:10 mM Ammonium Acetate |
| --- | --- |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 8.38 (s, 1H), 7.84 (d, J=8.1 Hz, 1H), 7.75 (d, J=8.1 Hz, 2H), 7.60-7.49 (m, 4H), 7.46-7.27 (m, 5H), 7.26-7.01 (m, 5H), 6.84 (d, J=6.6 Hz, 2H), 4.89 (q, J=7.2 Hz, 1H), 3.12-2.93 (m, 2H), 2.52 (s, 3H).

Example 81

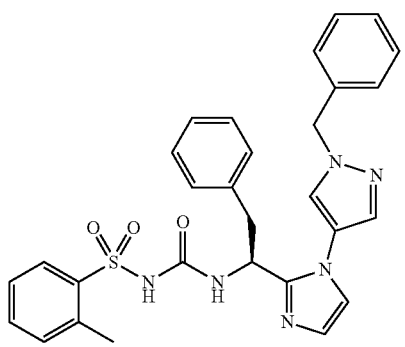 [SMILES: Cc1ccccc1S(=O)(=O)NC(=O)N[C@@H](Cc1ccccc1)c1nccn1-c1cnn(Cc2ccccc2)c1]

(S)-N-((1-(1-(1-benzyl-1H-pyrazol-4-yl)-1H-imidazol-2-yl)-2-phenylethyl)carbamoyl)-2-methylbenzenesulfonamide

| MS (M + H)$^+$ Calcd. | 541 |
| --- | --- |
| MS (M + H)$^+$ Observ. | 541 |
| Retention Time | 1.91 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 7.82 (d, J=7.3 Hz, 1H), 7.66 (br. s., 1H), 7.48 (br. s., 1H), 7.40-7.28 (m, 5H), 7.27-7.17 (m, 3H), 7.16-6.96 (m, 5H), 6.81 (br. s., 1H), 6.71 (d, J=7.3 Hz, 2H), 5.27 (s, 2H), 4.76 (d, J=6.2 Hz, 1H), 3.01-2.77 (m, 2H), 2.51 (s, 3H).

Example 82

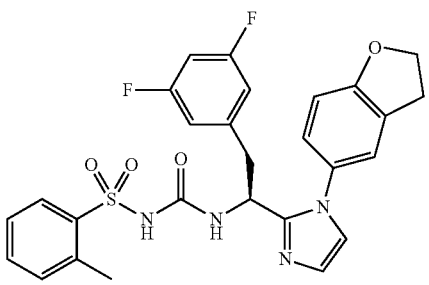 [SMILES: Cc1ccccc1S(=O)(=O)NC(=O)N[C@@H](Cc1cc(F)cc(F)c1)c1nccn1-c1ccc2c(c1)CCO2]

(S)-N-((2-(3,5-difluorophenyl)-1-(1-(2,3-dihydrobenzofuran-5-yl)-1H-imidazol-2-yl)ethyl)carbamoyl)-2-methylbenzenesulfonamide

| MS (M + H)$^+$ Calcd. | 539 |
| --- | --- |
| MS (M + H)$^+$ Observ. | 539 |
| Retention Time | 1.55 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 7.79 (d, J=7.7 Hz, 1H), 7.56-7.48 (m, 1H), 7.40-7.30 (m, 2H), 7.12 (s, 1H), 7.02 (s, 1H), 6.96 (t, J=9.2 Hz, 1H), 6.90 (d, J=7.7 Hz, 1H), 6.80-6.66 (m, 3H), 6.43 (d, J=7.3 Hz, 2H), 4.73 (d, J=7.3 Hz, 1H), 4.56 (t, J=8.6 Hz, 2H), 3.11 (t, J=8.6 Hz, 2H), 3.01-2.85 (m, 2H), 2.50 (s, 3H).

Example 83

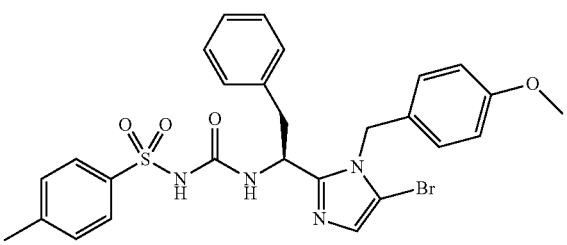

(S)-N-((1-(5-bromo-1-(4-methoxybenzyl)-1H-imidazol-2-yl)-2-phenylethyl)carbamoyl)-4-methylbenzenesulfonamide A solution of (S)-tert-butyl (1-(5-bromo-1-(4-methoxybenzyl)-1H-imidazol-2-yl)-2-phenylethyl)carbamate (24.3 mg, 50 μmol) in 1:1 TFA/DCM (1 mL) was stirred for 2 h. The solvent was evaporated to afford 1-(5-bromo-1-(4-methoxybenzyl)-1H-imidazol-2-yl)-2-phenylethanamine, TFA salt. It was used for next step without further purification. To a solution of 1-(5-bromo-1-(4-methoxybenzyl)-1H-imidazol-2-yl)-2-phenylethanamine, TFA salt in dichloromethane (1 mL) was added diisopropylethylamine (0.044 mL, 0.25 mmol) followed by 4-methylbenzenesulfonyl isocyanate (11 mg, 0.060 mmol) in dichloromethane (1 mL). The reaction mixture was stirred at r.t. for 1 hr. The solvent was evaporated and the residue was purified by prepHPLC to afford (18.6 mg, 65%) of the title compound.

$^1$H NMR (500 MHz, DMSO-$d_6$) δ 7.69 (d, J=7.9 Hz, 2H), 7.36 (d, J=7.9 Hz, 2H), 7.16 (d, J=7.6 Hz, 4H), 7.03-6.92 (m, 5H), 6.81 (d, J=8.5 Hz, 2H), 4.98 (d, J=7.6 Hz, 1H), 3.73 (s, 3H), 2.93 (d, J=7.3 Hz, 2H), 2.51 (br. s., 3H).

| | |
|---|---|
| MS (M + H)$^+$ Calcd. | 569 |
| MS (M + H)$^+$ Observ. | 569, 571 |
| Retention Time | 1.58 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

Example 84

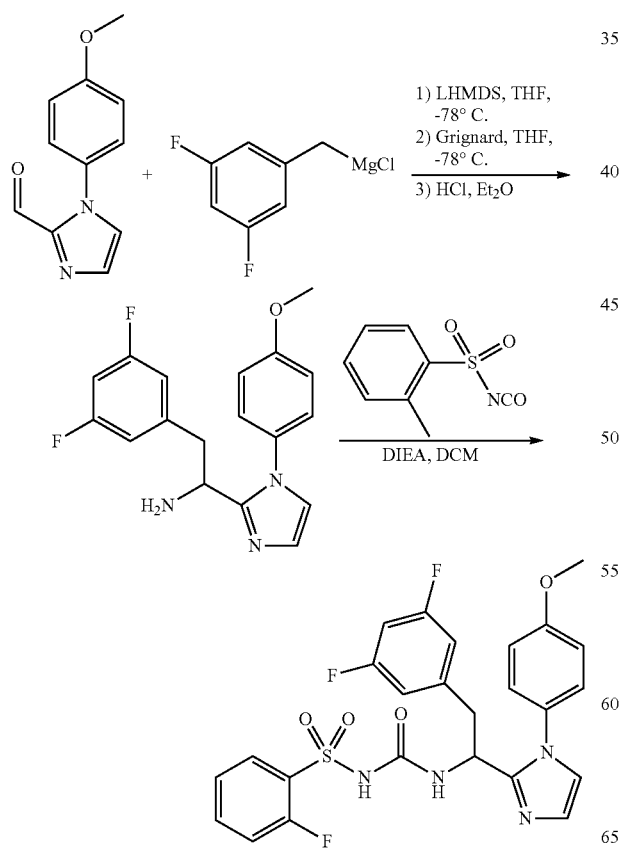

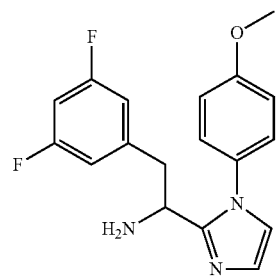 [SMILES: COc1ccc(-n2ccnc2C(N)Cc2cc(F)cc(F)c2)cc1]

2-(3,5-difluorophenyl)-1-(1-(4-methoxyphenyl)-1H-imidazol-2-yl)ethanamine

A solution of 1M lithium bis(trimethylsilyl)amide (0.47 mL, 0.47 mmol) in THF was added to a stirred solution of 1-(4-methoxyphenyl)-1H-imidazole-2-carbaldehyde (0.079 g, 0.391 mmol) in THF (1.5 mL) at −78° C. and then the reaction mixture was stirred for 15 min and at −78° C. and treated with (3,5-difluorobenzyl)magnesium chloride (1.875 mL, 0.469 mmol) in THF and stirred for 3 h at −78° C. The reaction was quenched with NH$_4$Cl (aq) (~10 mL) and then extracted with EtOAc (15 mL). The organic component was washed with water (~10 mL) and brine (~10 mL), dried (MgSO$_4$), filtered and conc to a yellow oil. Used as is in the next step.

| | |
|---|---|
| MS (M + H)$^+$ Calcd. | 330 |
| MS (M + H)$^+$ Observ. | 330 |
| Retention Time | 1.21 min |
| | LC Condition |
| Solvent A | 5% acetonitrile:95% Water:0.1% TFA |
| Solvent B | 95% acetonitrile:5% Water:0.1% TFA |
| Start % B | 0 |
| Final % B | 100 |
| Gradient Time | 2 min |
| Flow Rate | 1 mL/min |
| Wavelength | 220 |
| Column | Phenomenex Luna C18 30 × 2.0 mm 2 U |

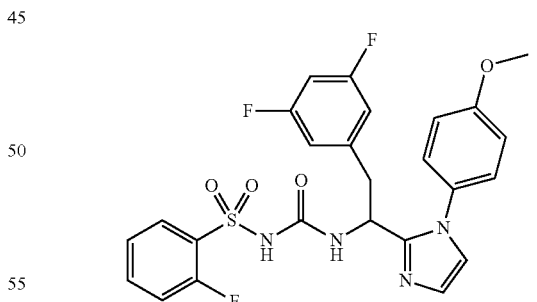

(rac)-N-((2-(3,5-difluorophenyl)-1-(1-(4-methoxyphenyl)-1H-imidazol-2-yl)ethyl)carbamoyl)-2-fluorobenzenesulfonamide 2-Fluorobenzenesulfonyl isocyanate (30 mg, 0.149 mmol) was added to a stirred solution of 1-(1-(4-methoxyphenyl)-1H-imidazol-2-yl)ethanamine (49 mg, 0.149 mmol) in methylene chloride (2 mL) and DIPEA (0.25 mL, 1.46 mmol) and the resulting reaction mixture was stirred at rt for 2 h. The reaction mixture was concentrated, dissolved into EtOAc (~2 mL), washed with 1M HCl (~1.5 mL), water (~1.5 mL), and brine (~1.5 mL). The solvent was evaporated and the residue was purified by prepHPLC to afford (5 mg) of the title compound.

$^1$H NMR (500 MHz, DMSO-$d_6$) δ 7.69 (br. s., 1H), 7.58 (br. s., 1H), 7.35-7.14 (m, 4H), 7.08-6.89 (m, 4H), 6.42 (d, J=6.2 Hz, 3H), 4.28 (br. s., 1H), 3.78 (s, 3H), 2.78-2.54 (m, 2H).

| N-((2-(3,5-difluorophenyl)-1-(1-(4-methoxyphenyl)-1H-imidazol-2-yl)ethyl)carbamoyl)-2-fluorobenzenesulfonamide | |
|---|---|
| MS (M + H)$^+$ Calcd. | 530 |
| MS (M + H)$^+$ Observ. | 530 |
| Retention Time | 1.57 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

Example 85

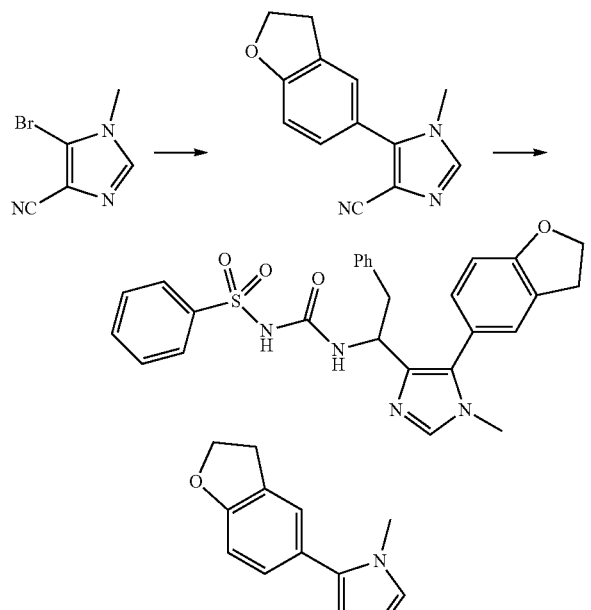

5-(2,3-dihydrobenzofuran-5-yl)-1-methyl-1H-imidazole-4-carbonitrile

Nitrogen was bubbled through a stirred clear colorless solution of 5-bromo-1-methyl-1H-imidazole-4-carbonitrile (500 mg, 2.69 mmol), triphenylphosphine (11 mg, 0.040 mmol) and sodium carbonate (513 mg, 4.84 mmol) in iPrOH (7 mL) and H$_2$O (4 mL) for 10 min. Palladium (II) acetate (6.03 mg, 0.027 mmol) was added to the reaction mixture, the reaction was flushed with nitrogen and then the reaction vessel was sealed and heated at 100° C. for 3 h. The reaction was cooled to rt, diluted with water (~30 mL) and DCM (~40 mL) and the layers were separated. The organic component was washed with sat. NH$_4$Cl (aq) (25 mL), and brine (25 mL), dried (MgSO$_4$) and concentrated. The crude residue was purified with a Biotage Horizon (40 g SiO$_2$, 75-100% EtOAc/hexanes, loading with DCM) to yield the title compound (536 mg) as an off-white solid.

$^1$H NMR (400 MHz, CHLOROFORM-d) δ 7.53 (s, 1H), 7.31 (s, 1H), 7.19 (dd, J=8.3, 1.8 Hz, 1H), 6.92 (d, J=8.3 Hz, 1H), 4.68 (t, J=8.8 Hz, 2H), 3.66 (s, 3H), 3.31 (t, J=8.8 Hz, 2H). LCMS:

| 5-(2,3-dihydrobenzofuran-5-yl)-1-methyl-1H-imidazole-4-carbonitrile | |
|---|---|
| MS (M + H)$^+$ Calcd. | 226 |
| MS (M + H)$^+$ Observ. | 226 |
| Retention Time | 1.23 min |
| | LC Condition |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 2 min |
| Flow Rate | 1 mL/min |
| Wavelength | 220 |
| Column | Phenomenex Luna 30 × 2.0 mm 3 u |

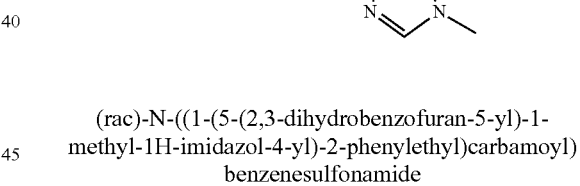

(rac)-N-((1-(5-(2,3-dihydrobenzofuran-5-yl)-1-methyl-1H-imidazol-4-yl)-2-phenylethyl)carbamoyl)benzenesulfonamide In a 5 mL microwave vessel, 5-(2,3-dihydrobenzofuran-5-yl)-1-methyl-1H-imidazole-4-carbonitrile (100 mg, 0.44 mmol) was slurried into THF (2 mL) and then treated with 2 M benzylmagnesium chloride (0.44 mL, 0.89 mmol) in THF. The reaction mixture was flushed with nitrogen (5 min) and then sealed and heated at 100° C. for 10 min with microwave irradiation. The crude reaction mixture was then treated with 3-methylbenzenesulfonyl isocyanate (210 mg, 1.07 mmol) in THF (1 mL) and stirred ON. NaBH$_4$ (50 mg, 1.3 mmol) was added to the reaction mixture and stirred at rt for 3 h, then additional NaBH$_4$ (40 mg) was added and the reaction mixture was and at rt for 1.5 h. The reaction was quenched with water (~20 mL), diluted with EtOAc (~20 mL) and stirred ON. The layers were separated and the organic component was washed with brine, dried (MgSO$_4$), filtered and concentrated. The crude material was dissolved into DMF, filtered and purified via preparative HPLC to yield racemic N-((1-(5-(2,3-dihydrobenzofuran-5-yl)-1-methyl-1H-imidazol-4-yl)-2-phenylethyl)carbamoyl)benzene-sulfonamide (18.8 mg).

Preparative HPLC Purification Conditions:
Column: XBridge C18, 19×200 mm, 5-μm particles;
Mobile Phase A: 5:95 acetonitrile:water with 0.1% trifluoroacetic acid;
Mobile Phase B: 95:5 acetonitrile:water with 0.1% trifluoroacetic acid;
Gradient: 20-80% B over 30 minutes, then a 5-minute hold at 100% B;
Flow: 20 mL/min.

Example 86

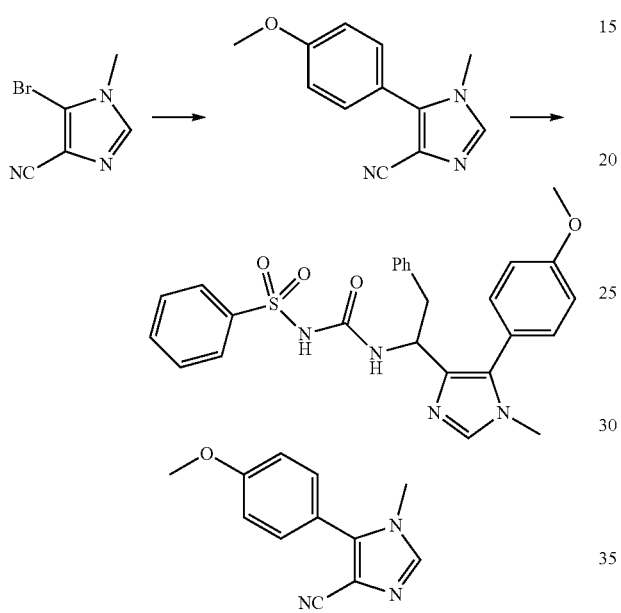

5-(4-methoxyphenyl)-1-methyl-1H-imidazole-4-carbonitrile

Nitrogen was bubbled through a stirred solution of 5-bromo-1-methyl-1H-imidazole-4-carbonitrile (500 mg, 2.69 mmol), (4-methoxyphenyl)boronic acid (613 mg, 4.03 mmol), triphenylphosphine (10.6 mg, 0.040 mmol) and sodium carbonate (513 mg, 4.84 mmol) in iPrOH (7 mL) and $H_2O$ (4 mL) for 10 min. Then palladium(II) acetate (6.03 mg, 0.027 mmol) was added, the reaction was flushed with nitrogen and the reaction vessel was sealed and heated at 100° C. for 3 h. The reaction was cooled to rt, diluted with water (~30 mL) and DCM (~40 mL) and the layers were separated. The organic component was washed with sat. $NH_4Cl$ (aq) (25 mL), and brine (25 mL), dried ($MgSO_4$) and concentrated to a brown oil. The crude residue was purified with a Biotage Horizon (40 g $SiO_2$, 80-100% EtOAc/hexanes) to yield the title compound (536 mg) as an off-white solid. $^1$H NMR (400 MHz, CHLOROFORM-d) δ 7.54 (s, 1H), 7.44-7.38 (m, 2H), 7.09-7.03 (m, 2H), 3.89 (s, 3H), 3.67 (s, 3H). LCMS:

| 5-(4-methoxyphenyl)-1-methyl-1H-imidazole-4-carbonitrile | |
|---|---|
| MS (M + H)$^+$ Calcd. | 214 |
| MS (M + H)$^+$ Observ. | 214 |
| Retention Time | 1.24 min |

| 5-(4-methoxyphenyl)-1-methyl-1H-imidazole-4-carbonitrile | |
|---|---|
| LC Condition | |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 2 min |
| Flow Rate | 1 mL/min |
| Wavelength | 220 |
| Column | Phenomenex Luna 30 × 2.0 mm 3 u |

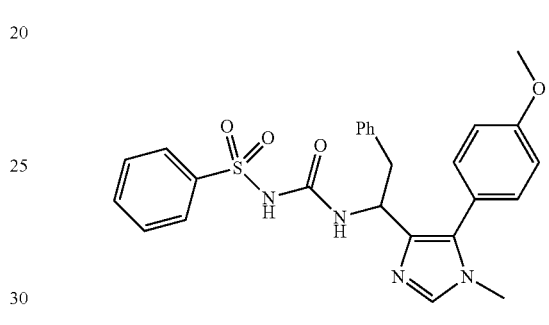

(rac)-N-((1-(5-(4-methoxyphenyl)-1-methyl-1H-imidazol-4-yl)-2-phenylethyl)carbamoyl)benzenesulfonamide A solution of 2M benzylmagnesium chloride (0.50 mL, 1.0 mmol) in THF was added to a solution of 5-(4-methoxyphenyl)-1-methyl-1H-imidazole-4-carbonitrile (110 mg, 0.516 mmol) in THF (2 mL) and the reaction solution was flushed with nitrogen, sealed and heated with microwave irradiation at 100° C. for 10 min. Then the reaction mixture was cooled to rt, treated with a solution of 3-methylbenzenesulfonyl isocyanate (203 mg, 1.03 mmol) in THF (1 mL) and stirred at rt for 3 h. Then $NaBH_4$ (60 mg, 1.5 mmol) was added and the reaction mixture was stirred at rt for an additional 3 h. The reaction was added to water (~20 mL) and EtOAc (~20 mL) and stirred. The layers were separated and the organic component was washed with brine (~20 mL) and concentrated. The crude material was dissolved into DMF, filtered and 50% was purified via preparative HPLC to yield racemic title compound (11.8 mg).

Preparative HPLC Purification Conditions:
Column: XBridge C18, 19×200 mm, 5-μm particles;
Mobile Phase A: 5:95 acetonitrile:water with 0.1% trifluoroacetic acid;
Mobile Phase B: 95:5 acetonitrile:water with 0.1% trifluoroacetic acid;
Gradient: 20-80% B over 30 minutes, then a 5-minute hold at 100% B;
Flow: 20 mL/min.

Example 87

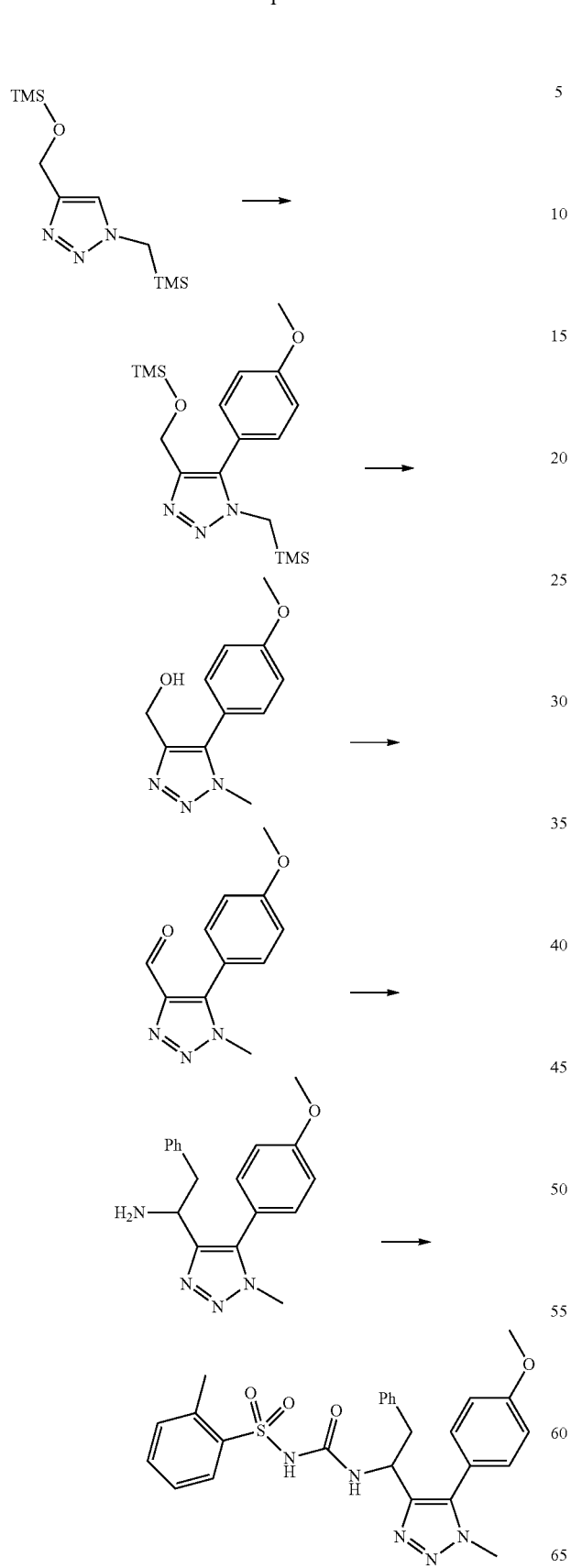

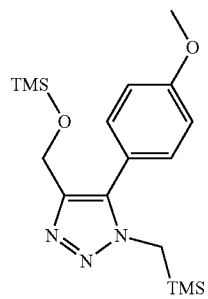 [SMILES: COc1ccc(-c2c(CO[Si](C)(C)C)nnn2C[Si](C)(C)C)cc1]

5-(4-methoxyphenyl)-1-(((trimethylsilyl)methyl)-4-((((trimethylsilyl)oxy)methyl)-1H-1,2,3-triazole A 2.5M solution of n-BuLi (0.70 mL, 1.8 mmol) in hexanes was added dropwise to a stirred solution of 4-(((tert-butyldimethylsilyl)oxy)methyl)-1-((trimethylsilyl)methyl)-1H-1,2,3-triazole (505 mg, 1.69 mmol) in THF (5.6 mL) at −78° C. and the reaction mixture was then stirred at −78° C. for 1 h. ZnCl$_2$ (276 mg, 2.02 mmol) was quickly added to the reaction under a blanket of nitrogen and the reaction mixture was stirred at −78° C. for 1 h, warm to rt and stirred 30 min. The reaction solution was then treated with 1-bromo-4-methoxybenzene (315 mg, 1.69 mmol), Pd$_2$(dba)$_3$ (31 mg, 0.034 mmol) and 2-dicyclohexylphosphino-2',6'-di-isopropoxy-1,1'-biphenyl (63 mg, 0.14 mmol), flushed with nitrogen, sealed and heated at 70° C. for 18 h. The reaction mixture was cooled to rt, diluted with EtOAc (~30 mL), washed with water (~15 mL) and brine (~10 mL), dried (MgSO$_4$), filtered and concentrated. The crude residue was purified with a Biotage Horizon (40 g SiO$_2$, 10-30% EtOAc/hexanes) to yield a 2:1 mixture of the title compound and the starting material 1-((trimethylsilyl)methyl)-4-((((trimethylsilyl)oxy)methyl)-1H-1,2,3-triazole (335 mg) as a yellow oil. The mixture of material was used in the subsequent step without further purification. LCMS:

| 5-(4-methoxyphenyl)-1-methyl-1H-imidazole-4-carbonitrile | |
|---|---|
| MS (M + H)$^+$ Calcd. | 406 |
| MS (M + H)$^+$ Observ. | 406 |
| Retention Time | 3.84 min |
| LC Condition | |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 0.8 min |
| Flow Rate | 1 mL/min |
| Wavelength | 220 |
| Column | Phenomenex Luna 50 × 2.0 mm 3 u |

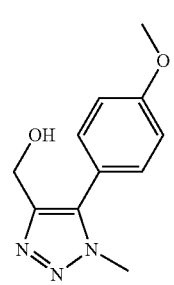 [SMILES: COc1ccc(-c2c(CO)nnn2C)cc1]

(5-(4-methoxyphenyl)-1-methyl-1H-1,2,3-triazol-4-yl)methanol

A solution of 1M TBAF (2.66 mL, 2.66 mmol) in THF was added to a stirred solution of a 2:1 mixture of 5-(4-methoxyphenyl)-1-(((trimethylsilyl)methyl)-4-(((trimethylsilyl)oxy)methyl)-1H-1,2,3-triazole (240 mg, 0.592 mmol) and 1-((trimethylsilyl)methyl)-4-(((trimethylsilyl)oxy)methyl)-1H-1,2,3-triazole (89 mg, 0.296 mmol) in THF (7 mL) and H$_2$O (0.032 mL, 1.8 mmol) at 0° C. The reaction mixture was allowed to warm to rt over 3 h and then quenched with ½ sat. NH$_4$Cl (aq) (~40 mL) and diluted with EtOAc (~20 mL). The layers were separated and the organic component was washed with brine (20 mL), dried (MgSO$_4$), filtered and concentrated. The crude residue was purified with a Biotage Horizon (12 g SiO$_2$, 60-100% EtOAc/hexanes) to yield the title compound (114 mg) as a white solid.

$^1$H NMR (400 MHz, CHLOROFORM-d) δ 7.38 (d, J=8.8 Hz, 2H), 7.06 (d, J=8.8 Hz, 2H), 4.70 (s, 2H), 4.01 (s, 3H), 3.89 (s, 3H), 2.27 (br. s., 1H). LCMS:

| (5-(4-methoxyphenyl)-1-methyl-1H-1,2,3-triazol-4-yl)methanol | |
|---|---|
| MS (M + H)$^+$ Calcd. | 220 |
| MS (M + H)$^+$ Observ. | 220 |
| Retention Time | 1.49 min |
| | LC Condition |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 4 min |
| Flow Rate | 0.8 mL/min |
| Wavelength | 220 |
| Column | Phenomenex Luna 50 × 2.0 mm 3 u |

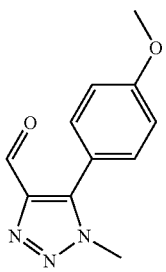 [SMILES: COc1ccc(-c2c(C=O)nnn2C)cc1]

5-(4-methoxyphenyl)-1-methyl-1H-1,2,3-triazole-4-carbaldehyde

Dess-Martin periodinane (225 mg, 0.532 mmol) was added to a stirred solution of (5-(4-methoxyphenyl)-1-methyl-1H-1,2,3-triazol-4-yl)methanol (111 mg, 0.506 mmol) in DCM (5 mL) and the reaction was stirred under nitrogen at rt for 4 h. The reaction mixture was diluted with Et$_2$O (~20 mL), treated with 1N Na$_2$S$_2$O$_3$ (aq.) (~20 mL) and stirred until both layers were clear. The layers were separated and the organic component was washed with sat. aq. NaHCO$_3$ (~15 mL) and brine (~10 mL), filtered and concentrated to dryness. The crude material was purified with a Biotage Horizon (12 g SiO$_2$, 40-100% EtOAc/hexanes) to yield the title compound (88 mg) as a white solid.

$^1$H NMR (400 MHz, CHLOROFORM-d) δ 10.16 (s, 1H), 7.42 (d, J=8.8 Hz, 2H), 7.08 (d, J=8.8 Hz, 2H), 4.05 (s, 3H), 3.90 (s, 3H). LCMS:

| 5-(4-methoxyphenyl)-1-methyl-1H-1,2,3-triazole-4-carbaldehyde | |
|---|---|
| MS (M + H)$^+$ Calcd. | 218 |
| MS (M + H)$^+$ Observ. | 218 |
| Retention Time | 1.83 min |
| | LC Condition |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 4 min |
| Flow Rate | 0.8 mL/min |
| Wavelength | 220 |
| Column | Phenomenex Luna 50 × 2.0 mm 3 u |

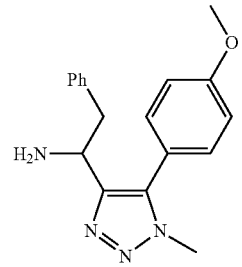

1-(5-(4-methoxyphenyl)-1-methyl-1H-1,2,3-triazol-4-yl)-2-phenylethanamine

A solution of 1M lithium bis(trimethylsilyl)amide (0.47 mL, 0.47 mmol) in THF was added to a stirred solution of 5-(4-methoxyphenyl)-1-methyl-1H-1,2,3-triazole-4-carbaldehyde (85 mg, 0.39 mmol) in THF (1.5 mL) at 0° C. and then the reaction mixture was allowed to warm to rt and stirred for 1.5 h. The reaction mixture was cooled to 0° C. and treated with 2M benzylmagnesium chloride (0.24 mL, 0.47 mmol) in THF and allowed to slowly warm to rt and stirred ON. The reaction was quenched with NH$_4$Cl (aq) (~10 mL) and then extracted with EtOAc (15 mL). The organic component was washed with water (~10 mL) and brine (~10 mL), dried (MgSO$_4$), filtered and conc. to a yellow oil. The crude oil was dissolved into DCM and then treated with 2M HCl in ether until pH<2. The crude solution was concentrated, treated with EtOAc (~3 mL) and stirred ON. The free flowing yellow solid was collected by filtration to yield a hydrochloride salt of the title compound (66 mg) as a yellow solid.

$^1$H NMR (400 MHz, METHANOL-d$_4$) δ 7.28-7.20 (m, 3H), 6.98-6.91 (m, 4H), 6.70-6.64 (m, 2H), 4.32 (dd, J=9.0, 6.5 Hz, 1H), 3.86 (s, 3H), 3.83 (s, 3H), 3.38-3.32 (m, 2H)(partially hidden under MeOH peak). LCMS:

| 1-(5-(4-methoxyphenyl)-1-methyl-1H-1,2,3-triazol-4-yl)-2-phenylethanamine | |
|---|---|
| MS (M + H)$^+$ Calcd. | 309 |
| MS (M + H)$^+$ and (2M + H)$^+$ Observ. | 309 and 617 |
| Retention Time | 0.88 min |

1-(5-(4-methoxyphenyl)-1-methyl-1H-1,2,3-triazol-4-yl)-2-phenylethanamine

LC Condition

| | |
|---|---|
| Solvent A | 100% Water: 0.05% TFA |
| Solvent B | 100% acetonitrile 0.05% TFA |
| Start % B | 0 |
| Final % B | 100 |
| Gradient Time | 1.5 min |
| Flow Rate | 0.8 mL/min |
| Wavelength | 220 |
| Column | Waters Aquity BEH C18 2.1 × 50 mm 1.7 U |

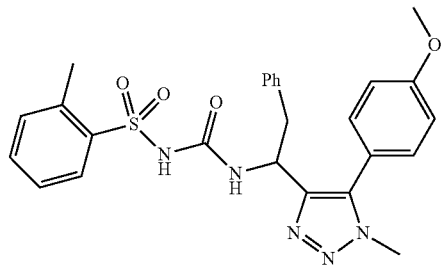 [SMILES: COc1ccc(-c2c(C(Cc3ccccc3)NC(=O)NS(=O)(=O)c3ccccc3C)nnn2C)cc1]

(rac)-N-((1-(5-(4-methoxyphenyl)-1-methyl-1H-1,2,3-triazol-4-yl)-2-phenylethyl)carbamoyl)-2-methyl-benzenesulfonamide 2-Methylbenzenesulfonyl isocyanate (24 mg, 0.12 mmol) was added to a stirred solution of 1-(5-(4-methoxyphenyl)-1-methyl-1H-1,2,3-triazol-4-yl)-2-phenylethanamine hydrochloride (21 mg, 0.061 mmol) in acetonitrile (1 mL) and DIPEA (0.04 mL, 0.2 mmol) and the resulting reaction mixture was stirred at rt for 3 h. The reaction mixture was concentrated, dissolved into EtOAc (~2 mL), washed with 1M HCl (~1.5 mL), water (~1.5 mL), and brine (~1.5 mL) and then concentrated. The crude amber oil was dissolved into MeOH, filtered and purified via preparative HPLC to yield the title compound (13 mg).

Preparative HPLC Purification Conditions:
Column: XBridge C18, 19×200 mm, 5-μm particles;
Mobile Phase A: 5:95 acetonitrile:water with 10-mM ammonium acetate;
Mobile Phase B: 95:5 acetonitrile:water with 10-mM ammonium acetate;
Gradient: 20-65% B over 30 minutes, then a 5-minute hold at 100% B;
Flow: 20 mL/min
LCMS:

(rac)-N-((1-(5-(4-methoxyphenyl)-1-methyl-1H-1,2,3-triazol-4-yl)-2-phenylethyl)carbamoyl)-2-methylbenzenesulfonamide

| | |
|---|---|
| MS (M + H)+ Calcd. | 506 |
| MS (M + H)+ Observ. | 506 |
| Retention Time | 1.79 min |
| LC Condition | |
| Solvent A | 100% Water: 0.05% TFA |
| Solvent B | 100% acetonitrile 0.05% TFA |
| Start % B | 0 |
| Final % B | 100 |
| Gradient Time | 1.5 min |
| Flow Rate | 0.8 mL/min |
| Wavelength | 220 |
| Column | Waters Aquity BEH C18 2.1 × 50 mm 1.7 U |

Example 88

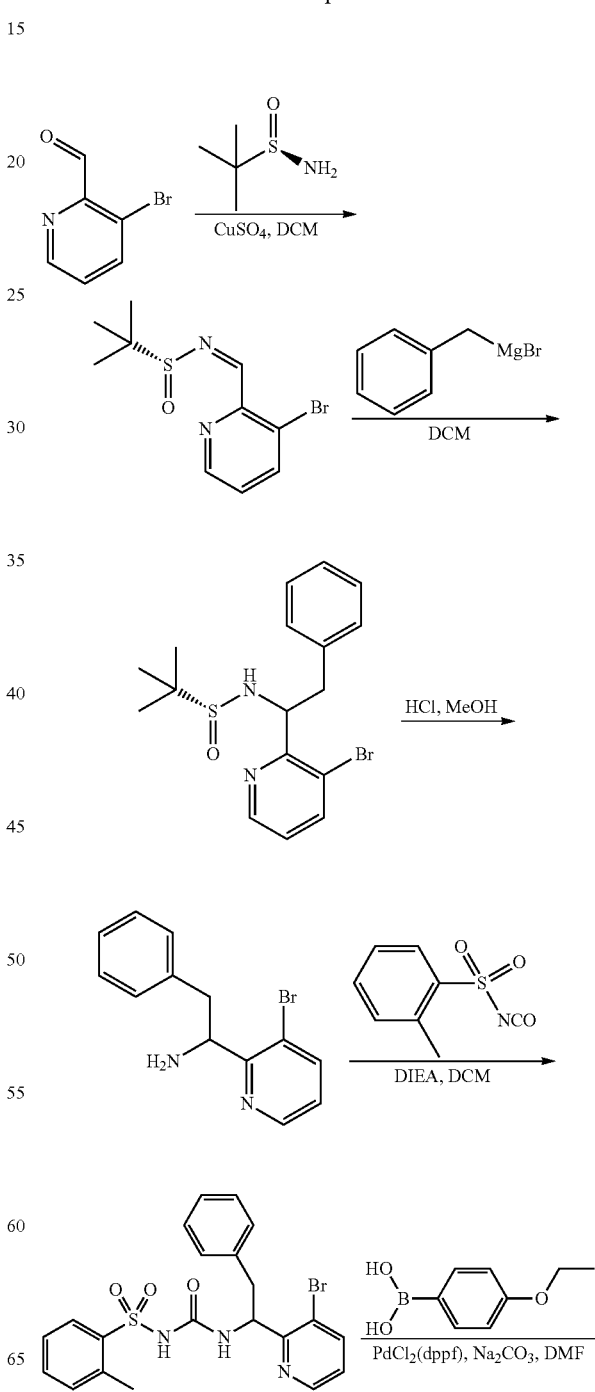

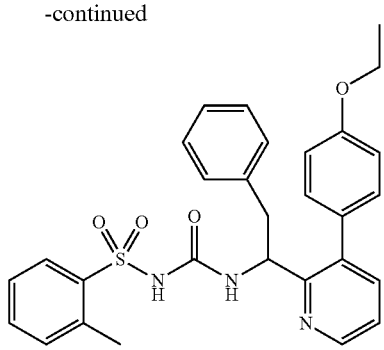

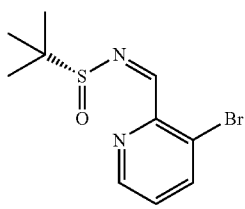

(R,Z)-N-((3-bromopyridin-2-yl)methylene)-2-methylpropane-2-sulfinamide

To the solution of 3-bromopicolinaldehyde (3.2 g, 17.20 mmol) and (R)-2-methylpropane-2-sulfinamide (2.279 g, 18.80 mmol) in dichloromethane (40 mL) stirred at RT was added cupric sulfate (5.49 g, 34.4 mmol). The resulted was stirred at RT for 5 h. The reaction mixture was filtered and then conc. and purified by Biotage (15-50% EtOAc/hexanes, 80 g $SiO_2$, Rf 0.26 with 30% EtOAc/Hexanes) to afford (3.40 g, 68.3% yield) of the title compound.

$^1$H NMR (400 MHz, CHLOROFORM-d) δ 9.05 (s, 1H), 8.74 (dd, J=4.5, 1.0 Hz, 1H), 8.01 (dd, J=8.0, 1.3 Hz, 1H), 7.29 (dd, J=8.0, 4.5 Hz, 1H), 1.32 (s, 9H).

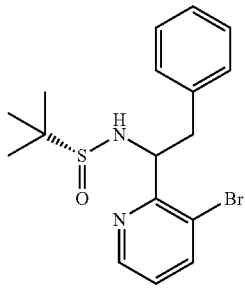 [SMILES: CC(C)(C)[S@@](=O)NC(Cc1ccccc1)c1ncccc1Br]

(R)-N-(1-(3-bromopyridin-2-yl)-2-phenylethyl)-2-methylpropane-2-sulfinamide

Benzylmagnesium bromide (8.02 ml, 7.22 mmol) was added dropwise over 30 min to a solution of (R,Z)-N-((3-bromopyridin-2-yl)methylene)-2-methylpropane-2-sulfinamide (1.74 g, 6.02 mmol) in dichloromethane (128 ml) in a 500-mL round bottom flask at −78° C. The reaction mixture was stirred at −78° C. for 3 hours. Another 2 mL of 0.9 M benzylmagnesium bromide was added and the reaction mixture was stirred at −78° C. for another hour. $NH_4Cl$ (aqueous solution, 20 mL) was added to the reaction and the mixture was allowed to warm to RT. Layers were separated and the aqueous was extracted with EtOAc (2×40 mL). The combined organic solution was dried over $Na_2SO_4$, filtered and concentrated. The crude product was used in the next step without purification.

| | |
|---|---|
| MS (M + H)$^+$ Calcd. | 381 |
| MS (M + H)$^+$ Observ. | 381 |
| Retention Time | 2.19 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

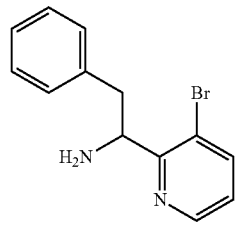 [SMILES: NC(Cc1ccccc1)c1ncccc1Br]

1-(3-bromopyridin-2-yl)-2-phenylethanamine

To the solution of (R)-N-(1-(3-bromopyridin-2-yl)-2-phenylethyl)-2-methylpropane-2-sulfinamide (0.270 g, 0.708 mmol) in MeOH (3 mL) was added 1.5 mL of HCl (6.00 mmol, 4.0 M in dioxane). The resulted was stirred at RT for 1 h. Solvent was evaporated in vacuo and the product was purified by preparative HPLC (0.1% TFA, MeOH/$H_2O$) to afford 0.181 g (82% yield) of the title compound.

$^1$H NMR (400 MHz, METHANOL-$d_4$) δ 8.66 (dd, J=4.6, 1.2 Hz, 1H), 8.03 (dd, J=8.2, 1.3 Hz, 1H), 7.35 (dd, J=8.1, 4.6 Hz, 1H), 7.31-7.25 (m, 3H), 7.12 (dd, J=7.1, 2.4 Hz, 2H), 5.09 (t, J=7.1 Hz, 1H), 3.36-3.26 (m, 1H), 3.21-3.13 (m, 1H).

| | |
|---|---|
| MS (M + H)$^+$ Calcd. | 277 |
| MS (M + H)$^+$ Observ. | 277 |
| Retention Time | 1.32 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 2 min |
| Flow Rate | 1 mL/min |
| Wavelength | 220 |
| Column | Phenomenex LUNA C18, 30 × 2, 3 u |

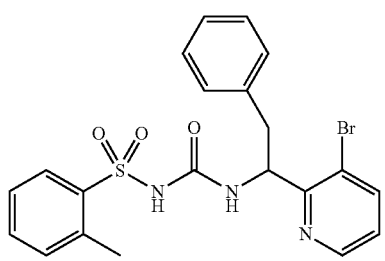 [SMILES: Cc1ccccc1S(=O)(=O)NC(=O)NC(Cc1ccccc1)c1ncccc1Br]

N-((1-(3-bromopyridin-2-yl)-2-phenylethyl)carbamoyl)-2-methylbenzenesulfonamide

The suspension of 1-(3-bromopyridin-2-yl)-2-phenylethanamine, TFA (126 mg, 0.322 mmol) in 5 mL of dichloromethane was added DIEA (0.225 mL, 1.288 mmol). A solution of 2-methylbenzenesulfonyl isocyanate (76 mg, 0.387 mmol) in 1 mL of dichloromethane was added dropwise. The resulted solution was stirred at RT for 1 h. Solvent was evaporated in vacuo. The product was purified by preparative HPLC (0.1% TFA, MeOH/H$_2$O) to afford 110 mg (55% yield) of the title compound.

$^1$H NMR (400 MHz, METHANOL-d$_4$) δ 8.55-8.47 (m, 1H), 8.00-7.91 (m, 2H), 7.58-7.49 (m, 1H), 7.43-7.29 (m, 2H), 7.22 (dd, J=8.1, 4.6 Hz, 1H), 7.17-7.05 (m, 3H), 6.95-6.82 (m, 2H), 5.51 (t, J=6.5 Hz, 1H), 3.10 (dd, J=13.6, 5.7 Hz, 1H), 2.91 (dd, J=13.4, 7.6 Hz, 1H), 2.62 (s, 3H).

| MS (M + H)$^+$ Calcd. | 474 |
|---|---|
| MS (M + H)$^+$ Observ. | 474 |
| Retention Time | 1.85 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

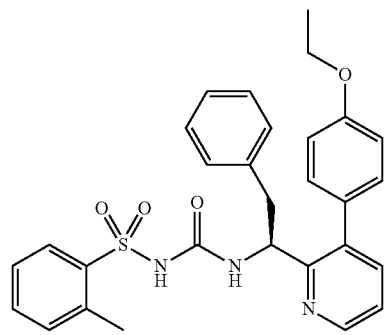 [SMILES: CCOc1ccc(-c2cccnc2[C@H](Cc2ccccc2)NC(=O)NS(=O)(=O)c2ccccc2C)cc1]

(S)-N-((1-(3-(4-ethoxyphenyl)pyridin-2-yl)-2-phenylethyl)carbamoyl)-2-methylbenzenesulfonamide To a mixture of N-((1-(3-bromopyridin-2-yl)-2-phenylethyl)carbamoyl)-2-methylbenzenesulfonamide (76 mg, 0.160 mmol), (4-ethoxyphenyl)boronic acid (31.9 mg, 0.192 mmol), sodium carbonate (0.3 mL, 0.900 mmol) and PdCl$_2$(dppf) (11.72 mg, 0.016 mmol) was added DMF (1 mL). The mixture was degassed and heated at 115° C. for 3 h. Water (20 mL) was added. The product was extracted with EtOAc (2×20 mL). Solvent was evaporated in vacuo. The product was purified by preparative HPLC (0.1% TFA, MeOH/H$_2$O) and the two enantiomers were separated by chiral preparative HPLC to afford 3.7 mg of the title compound and 4.8 mg of the R-enantiomer (Example 105).

$^1$H NMR (500 MHz, DMSO-d$_6$) δ 8.59 (d, J=4.4 Hz, 1H), 7.76 (d, J=8.1 Hz, 1H), 7.55-7.46 (m, 2H), 7.40-7.28 (m, 3H), 7.12-6.93 (m, 6H), 6.89 (d, J=8.4 Hz, 2H), 6.62 (d, J=6.6 Hz, 2H), 5.09-5.00 (m, 1H), 4.04 (q, J=7.0 Hz, 2H), 3.35 (br. s., 1H), 2.85 (dd, J=13.2, 6.2 Hz, 1H), 2.66 (dd, J=13.0, 7.5 Hz, 1H), 1.34 (t, J=7.0 Hz, 3H).

| MS (M + H)$^+$ Calcd. | 516 |
|---|---|
| MS (M + H)$^+$ Observ. | 516 |
| Retention Time | 1.83 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

Example 89

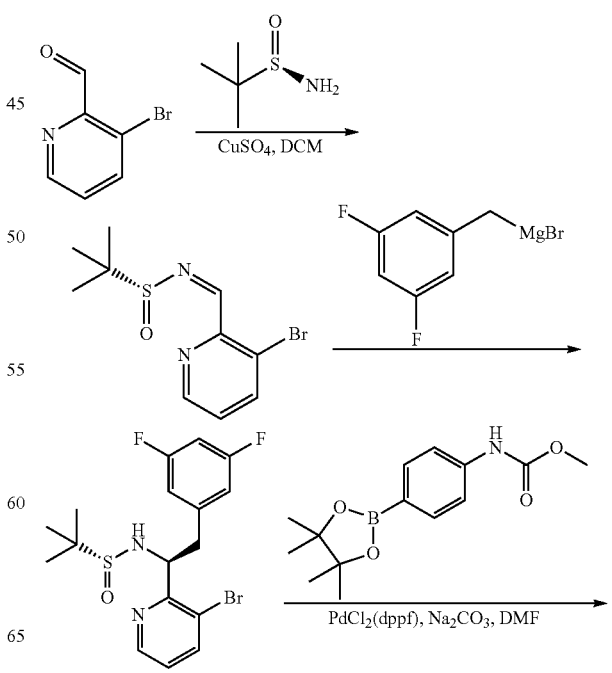

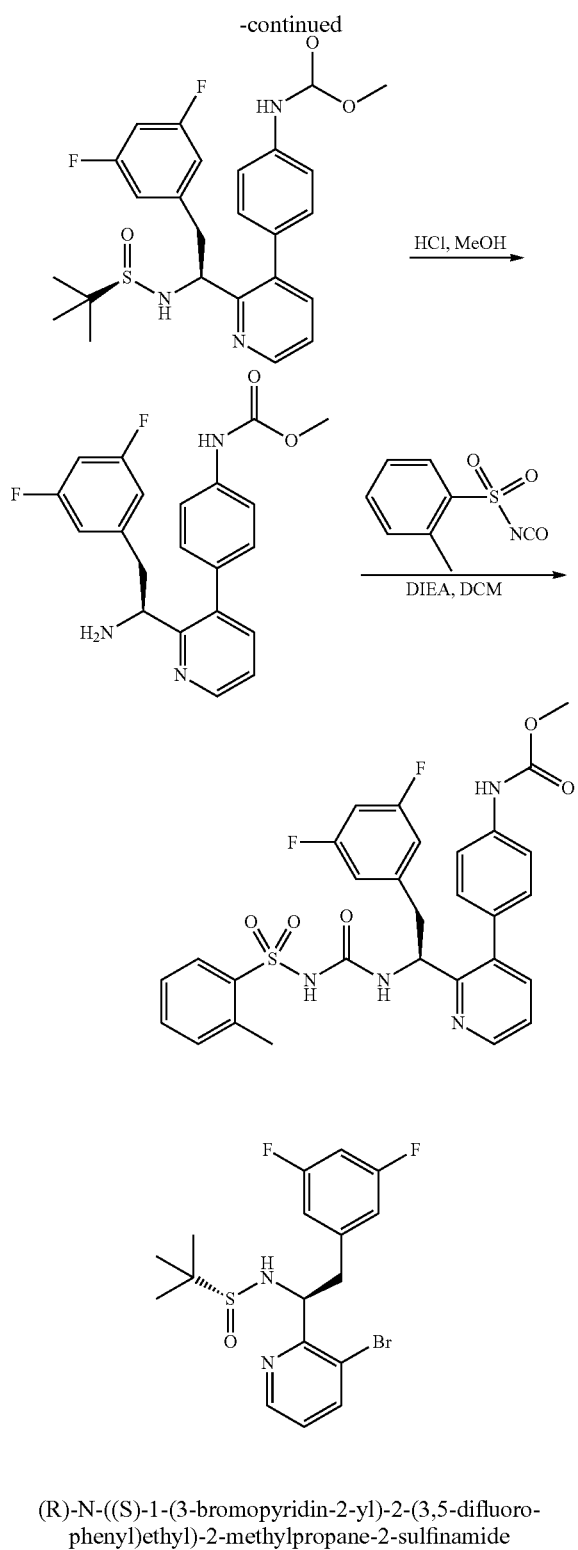

EtOAc (2×40 mL). The combined organic solution was dried over Na$_2$SO$_4$ overnight, filtered and concentrated. The crude product was purified by Biotage (Silica 80 gram flash column, EtOAc/hexanes gradient 20-55% EtOAc, Rf 0.36 with 50% EtOAc) to give 0.74 g (45.4% yield) of the title compound. $^1$H NMR (500 MHz, CHLOROFORM-d) δ 8.50 (dd, J=4.6, 1.4 Hz, 1H), 7.80 (dd, J=8.0, 1.6 Hz, 1H), 7.09 (dd, J=8.0, 4.6 Hz, 1H), 6.66-6.51 (m, 3H), 5.20 (dt, J=9.7, 6.8 Hz, 1H), 4.46 (d, J=9.8 Hz, 1H), 3.31 (d, J=6.9 Hz, 2H), 1.15 (s, 9H).

| | |
|---|---|
| MS (M + H)$^+$ Calcd. | 417 |
| MS (M + H)$^+$ Observ. | 417 |
| Retention Time | 2.15 min |
| | LC Condition |
| Solvent A | 10% acetonitrile: 90% Water: 0.1% TFA |
| Solvent B | 90% acetonitrile: 10% Water: 0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u | methyl (4-(2-((S)-2-(3,5-difluorophenyl)-1-((R)-1,1-dimethylethylsulfinamido)ethyl) pyridine-3-yl)phenyl)carbamate To a mixture of (R)-N-((S)-1-(3-bromopyridin-2-yl)-2-(3,5-difluorophenyl)ethyl)-2-methylpropane-2-sulfinamide (0.240 g, 0.575 mmol), methyl (4-(4,4,5,5-tetramethyl-1,3,2-dioxaborolan-2-yl)phenyl)carbamate (0.207 g, 0.748 mmol), 3.0 M sodium carbonate (1.150 mL, 3.45 mmol) and PdCl$_2$(dppf) (0.042 g, 0.058 mmol) was added DMF (5 mL). The mixture was degassed and heated at 110° C. for 2.5 h. Water (50 mL) was added to the reaction mixture. The product was extracted with EtOAc (2×40 mL). The combined extract was filtered through celite. The product was purified by preparative HPLC (0.1% TFA, MeOH/H$_2$O) to afford 60 mg (21% yield) of the title compound.

(R)-N-((S)-1-(3-bromopyridin-2-yl)-2-(3,5-difluorophenyl)ethyl)-2-methylpropane-2-sulfinamide 3,5-difluorobenzylmagnesium bromide (18.76 mL, 4.69 mmol) was added dropwise over 30 min to a solution of (R,Z)-N-((3-bromopyridin-2-yl)methylene)-2-methylpropane-2-sulfinamide (1.13 g, 3.91 mmol) in dichloromethane (90 mL) at −78° C. The reaction mixture was stirred at −78° C. for 3 hours. NH$_4$Cl (aqueous solution, 20 mL) was added to the reaction mixture and the mixture was allowed to warm to RT. Layers were separated and the aqueous was extracted with

| | |
|---|---|
| MS (M + H)$^+$ Calcd. | 488 |
| MS (M + H)$^+$ Observ. | 488 |
| Retention Time | 1.72 min |
| | LC Condition |
| Solvent A | 10% acetonitrile: 90% Water: 0.1% TFA |
| Solvent B | 90% acetonitrile: 10% Water: 0.1% TFA |
| Start % B | 0 |
| Final % B | 100 |

| | |
|---|---|
| Gradient Time | 3 min |
| Flow Rate | 1 mL/min |
| Wavelength | 220 |
| Column | Phenomenex LUNA C18, 30 × 2, 3 u |

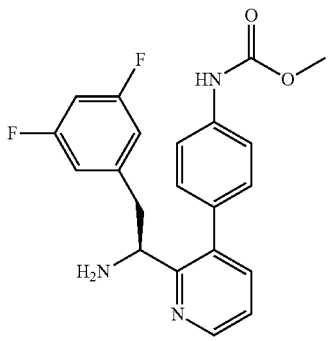 [SMILES: COC(=O)Nc1ccc(-c2cccnc2[C@@H](N)Cc2cc(F)cc(F)c2)cc1]

(S)-methyl (4-(2-(1-amino-2-(3,5-difluorophenyl)ethyl)pyridin-3-yl)phenyl)carbamate To the solution of methyl (4-(2-((S)-2-(3,5-difluorophenyl)-1-((R)-1, 1-dimethylethylsulfinamido)ethyl)pyridin-3-yl)phenyl)carbamate (60 mg, 0.123 mmol) in MeOH (2 mL) was added 4.0 M HCl in dioxane (1.11 mL, 4.43 mmol). The resulted was stirred at RT for 1 h. Solvent was evaporated in vacuo to afford the title compound, which was used in the next step without purification.

| | |
|---|---|
| MS (M + H)+ Calcd. | 384 |
| MS (M + H)+ Observ. | 384 |
| Retention Time | 1.42 min |
| | LC Condition |
| Solvent A | 10% acetonitrile: 90% Water: 0.1% TFA |
| Solvent B | 90% acetonitrile: 10% Water: 0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

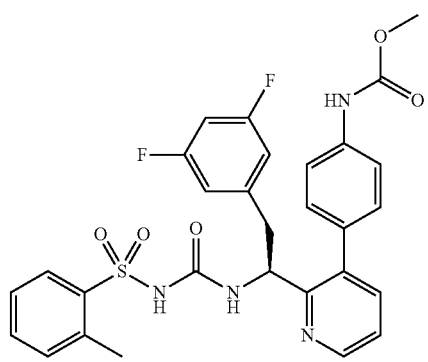 [SMILES: COC(=O)Nc1ccc(-c2cccnc2[C@H](Cc2cc(F)cc(F)c2)NC(=O)NS(=O)(=O)c2ccccc2C)cc1]

(S)-methyl (4-(2-(2-(3,5-difluorophenyl)-1-(3-(o-tolylsulfonyl)ureido)ethyl)pyridin-3-yl)phenyl)carbamate To the solution of (S)-methyl (4-(2-(1-amino-2-(3,5-difluorophenyl)ethyl)pyridin-3-yl)phenyl)carbamate (23.39 mg, 0.061 mmol) in 1 mL of dichloromethane in an 8-mL glass vial was added DIEA (0.043 mL, 0.244 mmol). The solution was stirred at RT while a solution of 2-methylbenzenesulfonyl isocyanate (14.4 mg, 0.073 mmol) in 1 mL of dichloromethane was added dropwise. The resulted was stirred at RT for 2 h. Solvent was evaporated in vacuo. The residue was dissolved in methanol and the product was purified by preparative HPLC (0.1% TFA, MeOH/H2O) to afford 11 mg (25% yield) of the title compound.

$^1$H NMR (400 MHz, METHANOL-$d_4$) δ 8.65 (dd, J=4.8, 1.5 Hz, 1H), 7.91 (d, J=7.8 Hz, 1H), 7.65 (dd, J=7.7, 1.6 Hz, 1H), 7.54-7.43 (m, 4H), 7.37 (d, J=7.5 Hz, 1H), 7.29 (t, J=7.7 Hz, 1H), 6.93 (d, J=8.5 Hz, 2H), 6.64 (tt, J=9.2, 2.2 Hz, 1H), 6.25-6.11 (m, 2H), 5.27 (t, J=7.2 Hz, 1H), 3.76 (s, 3H), 2.93-2.86 (m, 1H), 2.84-2.77 (m, 1H), 2.61 (s, 3H).

| | |
|---|---|
| MS (M + H)+ Calcd. | 581 |
| MS (M + H)+ Observ. | 581 |
| Retention Time | 2.02 min |
| | LC Condition |
| Solvent A | 10% acetonitrile: 90% Water: 0.1% TFA |
| Solvent B | 90% acetonitrile: 10% Water: 0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

Example 90

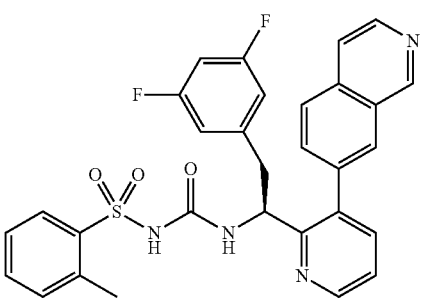 [SMILES: Cc1ccccc1S(=O)(=O)NC(=O)N[C@@H](Cc1cc(F)cc(F)c1)c1ncccc1-c1ccc2ccncc2c1]

(S)-N-((2-(3,5-difluorophenyl)-1-(3-(isoquinolin-7-yl)pyridin-2-yl)ethyl)carbamoyl)-2-methylbenzenesulfonamide The title compound was prepared with the procedures described in Example 89.

| | |
|---|---|
| MS (M + H)+ Calcd. | 559 |
| MS (M + H)+ Observ. | 559 |
| Retention Time | 1.56 min |

-continued

| | LC Condition |
|---|---|
| Solvent A | 10% acetonitrile: 90% Water : 0.1% TFA |
| Solvent B | 90% acetonitrile: 10% Water : 0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

1H NMR (400 MHz, DMSO-$d_6$) δ 10.67 (s, 1H), 9.59 (s, 1H), 8.76 (dd, J=4.8, 1.5 Hz, 1H), 8.68 (d, J=6.0 Hz, 1H), 8.32 (d, J=6.0 Hz, 1H), 8.24 (d, J=8.5 Hz, 1H), 8.06 (s, 1H), 7.89 (dd, J=8.5, 1.5 Hz, 1H), 7.82-7.73 (m, 2H), 7.58-7.46 (m, 2H), 7.39-7.27 (m, 2H), 7.18 (d, J=8.8 Hz, 1H), 6.98-6.87 (m, 1H), 6.33 (d, J=6.3 Hz, 2H), 4.99 (q, J=7.7 Hz, 1H), 2.98 (dd, J=13.3, 6.5 Hz, 1H), 2.91-2.79 (m, 1H), 2.48 (br. s., 3H).

Example 91

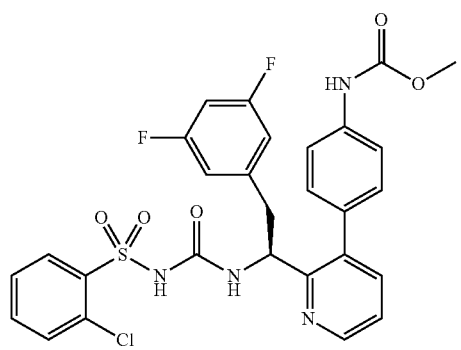 [SMILES: COC(=O)Nc1ccc(-c2cccnc2[C@H](Cc2cc(F)cc(F)c2)NC(=O)NS(=O)(=O)c2ccccc2Cl)cc1]

(S)-methyl (4-(2-(1-(3-((2-chlorophenyl)sulfonyl)ureido)-2-(3,5-difluorophenyl)ethyl)pyridin-3-yl)phenyl)carbamate, TFA The title compound was prepared with the procedures described in Example 89.

| MS (M + H)+ Calcd. | 601 |
|---|---|
| MS (M + H)+ Observ. | 601 |
| Retention Time | 2.01 min |
| | LC Condition |
| Solvent A | 10% acetonitrile: 90% Water: 0.1% TFA |
| Solvent B | 90% acetonitrile: 10% Water: 0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

$^1$H NMR (400 MHz, METHANOL-$d_4$) δ 8.64 (dd, J=4.9, 1.6 Hz, 1H), 8.08 (dd, J=7.9, 1.1 Hz, 1H), 7.69-7.56 (m, 3H), 7.52-7.40 (m, 4H), 6.95 (d, J=8.5 Hz, 2H), 6.64 (tt, J=9.2, 2.2 Hz, 1H), 6.20 (d, J=6.3 Hz, 2H), 5.28 (t, J=7.2 Hz, 1H), 3.76 (s, 3H), 2.95-2.87 (m, 1H), 2.86-2.78 (m, 1H)

Example 92

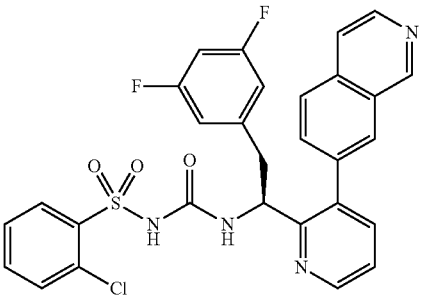

(S)-2-chloro-N-((2-(3,5-difluorophenyl)-1-(3-(isoquinolin-7-yl)pyridin-2-yl)ethyl)carbamoyl)benzenesulfonamide, 2 TFA The title compound was prepared with the procedures described in Example 89.

| MS (M + H)+ Calcd. | 579 |
|---|---|
| MS (M + H)+ Observ. | 579 |
| Retention Time | 1.55 min |
| | LC Condition |
| Solvent A | 10% acetonitrile: 90% Water: 0.1% TFA |
| Solvent B | 90% acetonitrile: 10% Water: 0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

$^1$H NMR (400 MHz, DMSO-$d_6$) δ 10.82 (br. s., 1H), 9.61 (s, 1H), 8.77 (dd, J=4.8, 1.5 Hz, 1H), 8.69 (d, J=6.3 Hz, 1H), 8.34 (d, J=6.0 Hz, 1H), 8.25 (d, J=8.5 Hz, 1H), 8.08 (s, 1H), 7.91 (d, J=7.8 Hz, 2H), 7.78 (dd, J=7.7, 1.6 Hz, 1H), 7.68-7.57 (m, 2H), 7.56-7.45 (m, 2H), 7.26 (d, J=8.8 Hz, 1H), 6.97-6.87 (m, 1H), 6.35 (d, J=6.5 Hz, 2H), 4.99 (q, J=7.8 Hz, 1H), 2.99 (dd, J=13.3, 6.3 Hz, 1H), 2.93-2.78 (m, 1H)

Example 93

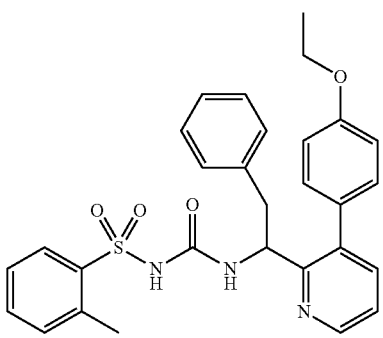

133

N-((1-(3-(4-ethoxyphenyl)pyridin-2-yl)-2-phenyl-ethyl)carbamoyl)-2-methylbenzenesulfonamide The title compound was prepared with the procedures described in Example 88.

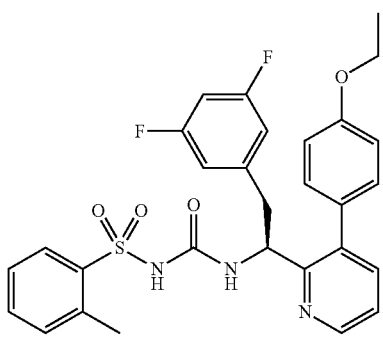

| | |
|---|---|
| MS (M + H)+ Calcd. | 516 |
| MS (M + H)+ Observ. | 516 |
| Retention Time | 1.89 min |
| | LC Condition |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

$^1$H NMR (500 MHz, DMSO-$d_6$) δ 10.68 (br. s., 1H), 8.59 (d, J=3.7 Hz, 1H), 7.77 (d, J=7.7 Hz, 1H), 7.56-7.48 (m, 2H), 7.40-7.28 (m, 5H), 7.21 (s, 2H), 7.15-7.10 (m, 2H), 7.08-7.02 (m, 3H), 7.00-6.94 (m, 2H), 6.89 (d, J=8.8 Hz, 2H), 6.62 (d, J=6.6 Hz, 2H), 5.04 (q, J=7.3 Hz, 1H), 2.85 (dd, J=13.4, 6.1 Hz, 1H), 2.66 (dd, J=13.2, 7.7 Hz, 1H), 1.34 (t, J=7.0 Hz, 3H).

Example 94

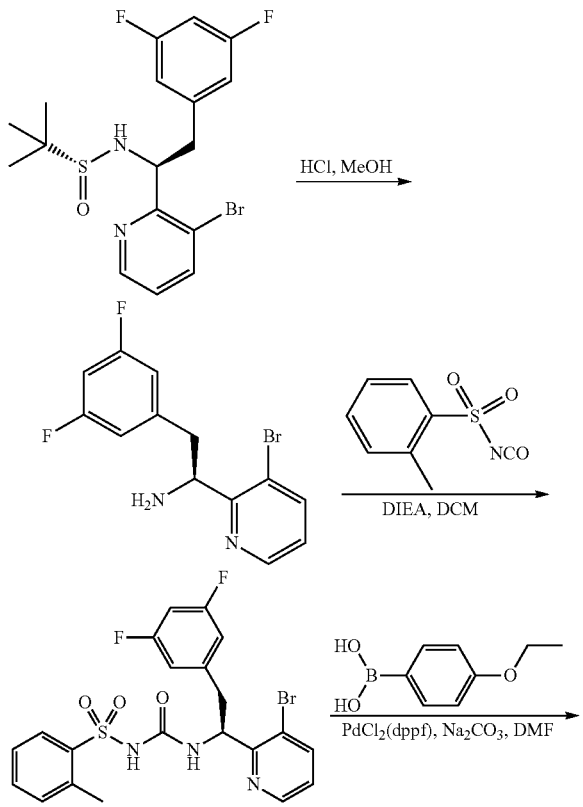

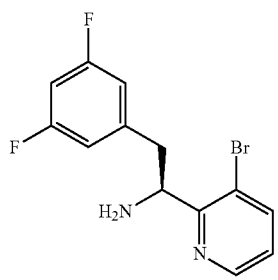 [SMILES: N[C@@H](Cc1cc(F)cc(F)c1)c1ncccc1Br]

(S)-1-(3-bromopyridin-2-yl)-2-(3,5-difluorophenyl)ethanamine

To the solution of (R)-N-((S)-1-(3-bromopyridin-2-yl)-2-(3,5-difluorophenyl)ethyl)-2-methylpropane-2-sulfinamide (0.692 g, 1.658 mmol) in MeOH (8 mL) stirred at RT was added 4.0 M HCl in dioxane (4 mL, 16.00 mmol). The resulted was stirred at RT for 1 h. Solvent was evaporated in vacuo to give the title compound.

$^1$H NMR (400 MHz, DMSO-$d_6$) δ 8.70 (dd, J=4.5, 1.3 Hz, 1H), 8.56 (br. s., 3H), 8.14 (dd, J=8.2, 1.3 Hz, 1H), 7.43 (dd, J=8.1, 4.6 Hz, 1H), 7.14 (tt, J=9.5, 2.2 Hz, 1H), 6.84-6.74 (m, 2H), 4.99 (t, J=6.8 Hz, 1H), 3.28-3.09 (m, 2H).

| | |
|---|---|
| MS (M + H)+ Calcd. | 313 |
| MS (M + H)+ Observ. | 313 |
| Retention Time | 1.27 min |
| | LC Condition |
| Solvent A | 10% acetonitrile: 90% Water: 0.1% TFA |
| Solvent B | 90% acetonitrile: 10% Water: 0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

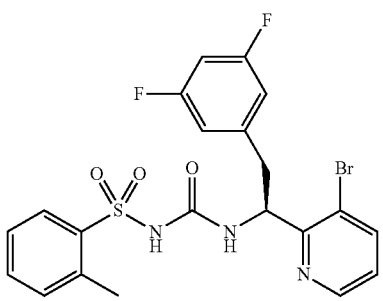 [SMILES: Cc1ccccc1S(=O)(=O)NC(=O)N[C@@H](Cc1cc(F)cc(F)c1)c1ncccc1Br]

(S)-N-((1-(3-bromopyridin-2-yl)-2-(3,5-difluorophenyl)ethyl)carbamoyl)-2-methylbenzenesulfonamide (S)-1-(3-bromopyridin-2-yl)-2-(3,5-difluorophenyl) ethanamine, HCl (0.580 g, 1.658 mmol) was dissolved in 10 mL of dichloromethane, followed by the addition of DIEA (1.448 mL, 8.29 mmol) and a solution of 2-methylbenzenesulfonyl isocyanate (0.343 g, 1.741 mmol) in 3 mL of dichloromethane dropwise. The resulted was stirred at RT for 1 h. Solvent was evaporated in vacuo. The residue was dissolved in dichloromethane (150 mL) and washed with aqueous NaHCO$_3$ (2×70 mL). 42 mg of the crude product was purified by preparative HPLC (0.1% TFA, MeOH/H$_2$O). The remaining was used in the next step without purification.

$^1$H NMR (400 MHz, METHANOL-d$_4$) δ 8.54 (d, J=4.8 Hz, 1H), 7.97 (t, J=7.2 Hz, 2H), 7.57-7.48 (m, 1H), 7.39-7.29 (m, 2H), 7.25 (dd, J=8.0, 4.5 Hz, 1H), 6.76-6.65 (m, 1H), 6.49 (d, J=6.3 Hz, 2H), 5.50 (dd, J=7.5, 5.8 Hz, 1H), 3.09 (dd, J=13.6, 5.8 Hz, 1H), 2.89 (dd, J=13.6, 7.8 Hz, 1H), 2.61 (s, 3H).

| MS (M + H)$^+$ Calcd. | 510 |
| MS (M + H)$^+$ Observ. | 510 |
| Retention Time | 2.23 min |
| LC Condition | |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

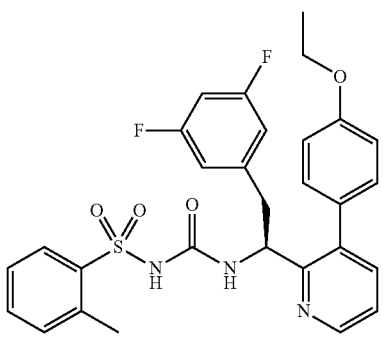 [SMILES: CCOc1ccc(-c2cccnc2[C@H](Cc2cc(F)cc(F)c2)NC(=O)NS(=O)(=O)c2ccccc2C)cc1]

(S)-N-((2-(3,5-difluorophenyl)-1-(3-(4-ethoxyphenyl)pyridin-2-yl)ethyl)carbamoyl)-2-methylbenzenesulfonamide, TFA To a mixture of (S)-N-((1-(3-bromopyridin-2-yl)-2-(3,5-difluorophenyl)ethyl)carbamoyl)-2-methylbenzenesulfonamide (50 mg, 0.098 mmol), (4-ethoxyphenyl)boronic acid (19.51 mg, 0.118 mmol), sodium carbonate 3.0 M aq. solution (0.25 mL, 0.750 mmol) and PdCl$_2$(dppf) (7.2 mg, 9.80 μmol) was added DMF (1 mL). The mixture was degassed and stirred at 115° C. for 16 h. The reaction mixture was filtered and acidified by addition of acetic acid. The product was purified by preparative HPLC (0.1% TFA, ACN/H$_2$O) to afford 8.2 mg (13% yield).

$^1$H NMR (500 MHz, DMSO-d$_6$) δ 8.61 (d, J=4.0 Hz, 1H), 7.79 (d, J=7.7 Hz, 1H), 7.57 (d, J=7.0 Hz, 1H), 7.53-7.48 (m, 1H), 7.39 (dd, J=7.7, 4.8 Hz, 1H), 7.36-7.30 (m, 2H), 7.18 (d, J=8.8 Hz, 1H), 7.07 (d, J=8.4 Hz, 2H), 6.99-6.84 (m, 3H), 6.29 (d, J=6.6 Hz, 2H), 5.14-5.03 (m, 1H), 4.05 (q, J=7.0 Hz, 2H), 3.90 (s, 1H), 3.41 (br. s., 1H), 3.17 (s, 1H), 2.92-2.81 (m, 1H), 2.79-2.67 (m, 1H), 1.34 (t, J=6.8 Hz, 3H).

| MS (M + H)$^+$ Calcd. | 552 |
| MS (M + H)$^+$ Observ. | 552 |
| Retention Time | 1.98 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

Example 95

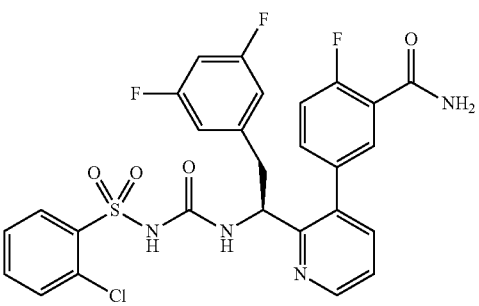 [SMILES: NC(=O)c1cc(-c2cccnc2[C@H](Cc2cc(F)cc(F)c2)NC(=O)NS(=O)(=O)c2ccccc2Cl)ccc1F]

(S)-5-(2-(1-(3-((2-chlorophenyl)sulfonyl)ureido)-2-(3,5-difluorophenyl)ethyl)pyridin-3-yl)-2-fluorobenzamide, TFA The title compound was prepared with the procedures described in Example 89.

| MS (M + H)$^+$ Calcd. | 589 |
| MS (M + H)$^+$ Observ. | 589 |
| Retention Time | 1.81 min |

-continued

| | LC Condition |
|---|---|
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

$^1$H NMR (400 MHz, METHANOL-$d_4$) δ 8.70 (dd, J=4.8, 1.5 Hz, 1H), 8.08 (d, J=8.0 Hz, 1H), 7.68-7.54 (m, 3H), 7.50-7.41 (m, 2H), 7.34 (d, J=6.0 Hz, 1H), 7.24-7.16 (m, 2H), 6.64 (t, J=9.3 Hz, 1H), 6.25 (d, J=6.3 Hz, 2H), 5.13 (t, J=7.4 Hz, 1H), 3.05-2.80 (m, 2H).

Example 96

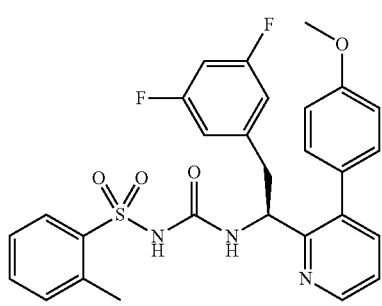 [SMILES: COc1ccc(-c2cccnc2[C@H](Cc2cc(F)cc(F)c2)NC(=O)NS(=O)(=O)c2ccccc2C)cc1]

(S)-N-((2-(3,5-difluorophenyl)-1-(3-(4-methoxyphenyl)pyridin-2-yl)ethyl)carbamoyl)-2-methylbenzenesulfonamide, TFA The title compound was prepared with the procedures described in Example 94.

| MS (M + H)$^+$ Calcd. | 538 |
|---|---|
| MS (M + H)$^+$ Observ. | 538 |
| Retention Time | 1.77 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

$^1$H NMR (500 MHz, DMSO-$d_6$) δ 8.62 (d, J=4.4 Hz, 1H), 7.79 (d, J=7.7 Hz, 1H), 7.58 (d, J=7.7 Hz, 1H), 7.55-7.51 (m, 1H), 7.41 (dd, J=7.7, 4.8 Hz, 1H), 7.38-7.32 (m, 2H), 7.25-7.01 (m, 4H), 6.98-6.89 (m, 3H), 6.29 (d, J=6.2 Hz, 2H), 5.17-4.99 (m, 1H), 3.79 (s, 3H), 2.91-2.82 (m, 1H), 2.78-2.69 (m, 1H), 2.51 (s, 3H).

Example 97

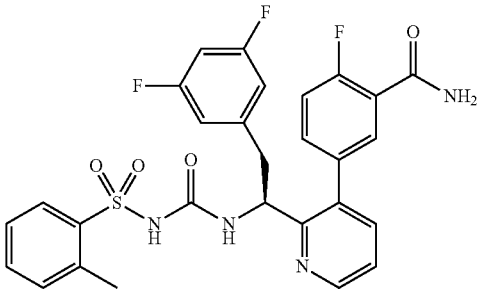 [SMILES: Cc1ccccc1S(=O)(=O)NC(=O)N[C@@H](Cc1cc(F)cc(F)c1)c1ncccc1-c1ccc(F)c(C(N)=O)c1]

(S)-5-(2-(2-(3,5-difluorophenyl)-1-(3-(o-tolylsulfonyl)ureido)ethyl)pyridin-3-yl)-2-fluorobenzamide, TFA The title compound was prepared with the procedures described in Example 89.

| MS (M + H)$^+$ Calcd. | 569 |
|---|---|
| MS (M + H)$^+$ Observ. | 569 |
| Retention Time | 1.85 min |
| | LC Condition |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

$^1$H NMR (500 MHz, METHANOL-$d_4$) δ 8.71 (dd, J=4.9, 1.7 Hz, 1H), 7.91 (dd, J=7.9, 1.3 Hz, 1H), 7.64 (dd, J=7.8, 1.7 Hz, 1H), 7.54-7.43 (m, 2H), 7.36 (d, J=7.6 Hz, 1H), 7.32 (dd, J=6.9, 2.4 Hz, 1H), 7.30-7.26 (m, 1H), 7.23-7.14 (m, 2H), 6.64 (tt, J=9.2, 2.3 Hz, 1H), 6.28-6.17 (m, 2H), 5.13 (t, J=7.3 Hz, 1H), 3.01-2.84 (m, 2H), 2.60 (s, 3H).

Example 98

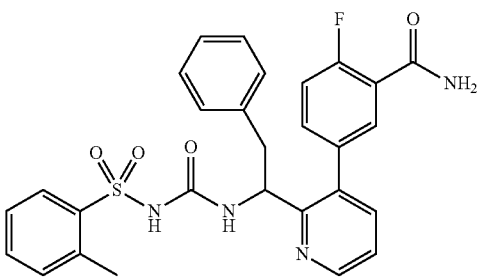 [SMILES: Cc1ccccc1S(=O)(=O)NC(=O)NC(Cc1ccccc1)c1ncccc1-c1ccc(F)c(C(N)=O)c1]

2-fluoro-5-(2-(2-phenyl-1-(3-(o-tolylsulfonyl)ureido)ethyl)pyridin-3-yl)benzamide, TFA The title compound was prepared with the procedures described in Example 88.

| | |
|---|---|
| MS (M + H)+ Calcd. | 533 |
| MS (M + H)+ Observ. | 533 |
| Retention Time | 2.32 min |
| | LC Condition |
| Solvent A | 10% Methanol:90% Water:0.1% TFA |
| Solvent B | 90% Methanol:10% Water:0.1% TFA |
| Start % B | 0 |
| Final % B | 100 |
| Gradient Time | 3 min |
| Flow Rate | 1 mL/min |
| Wavelength | 220 |
| Column | PHENOMENEX-LUNA 2.0 × 30 mm 3 um |

$^1$H NMR (400 MHz, METHANOL-$d_4$) δ 8.72 (dd, J=4.9, 1.5 Hz, 1H), 7.89 (dd, J=7.9, 1.1 Hz, 1H), 7.66 (dd, J=7.8, 1.7 Hz, 1H), 7.53-7.46 (m, 2H), 7.36 (d, J=7.3 Hz, 1H), 7.28 (t, J=7.6 Hz, 1H), 7.21-6.99 (m, 6H), 6.65-6.58 (m, 2H), 5.08 (dd, J=8.1, 6.8 Hz, 1H), 3.00-2.89 (m, 2H), 2.59 (s, 3H)

Example 99

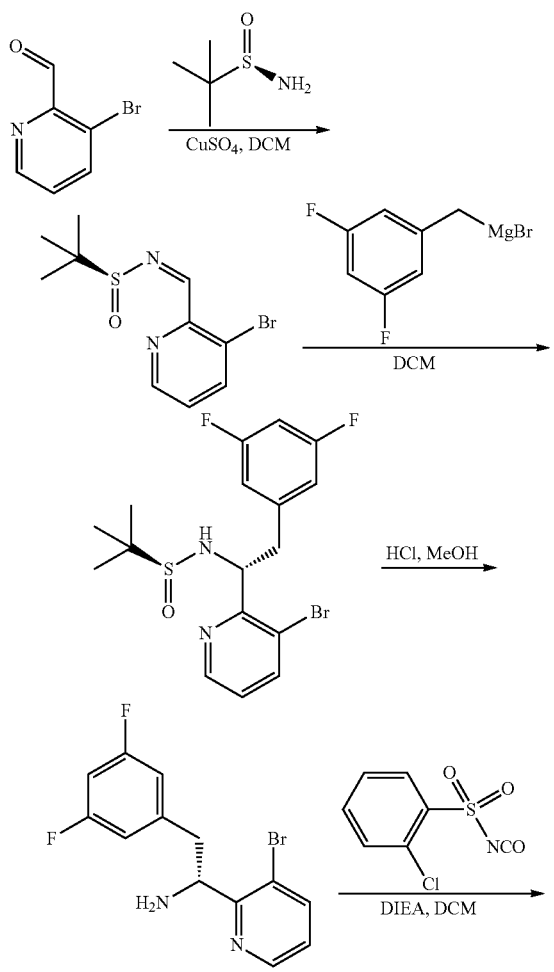

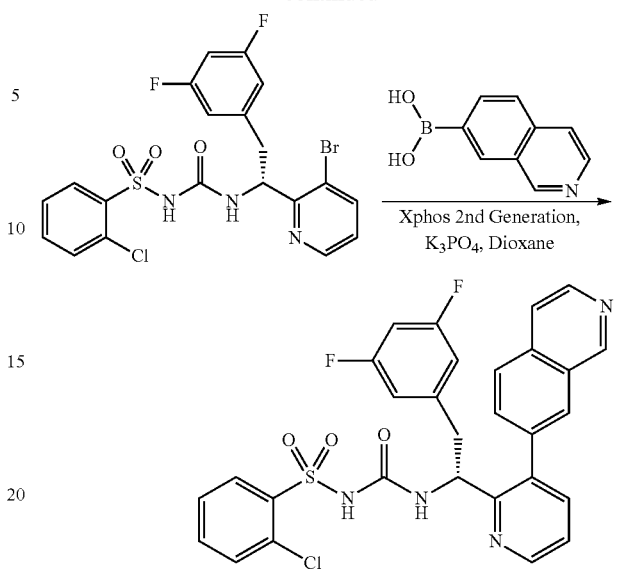

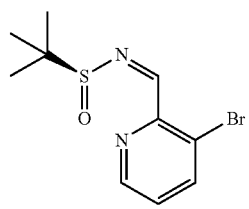

(S,Z)-N-((3-bromopyridin-2-yl)methylene)-2-methylpropane-2-sulfinamide

To the solution of 3-bromopicolinaldehyde (3.2 g, 17.20 mmol) and (S)-2-methylpropane-2-sulfinamide (2.279 g, 18.80 mmol) in dichloromethane (40 mL) stirred at RT was added cupric sulfate (5.49 g, 34.4 mmol). The resulted was stirred at RT overnight. The reaction mixture was filtered and then conc. and purified by Biotage (15-50% EtOAc/hexanes, 120 g SiO$_2$) to afford (3.40 g, 68.3% yield) of the title compound.

$^1$H NMR (500 MHz, CHLOROFORM-d) δ 9.05 (s, 1H), 8.76 (dd, J=4.5, 1.3 Hz, 1H), 8.04 (dd, J=8.2, 1.4 Hz, 1H), 7.31 (dd, J=8.2, 4.6 Hz, 1H), 1.33 (s, 9H).

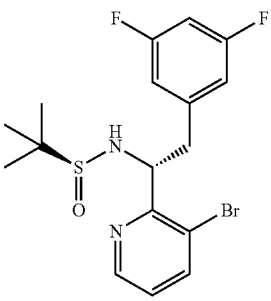 [SMILES: CC(C)(C)[S@](=O)N[C@H](Cc1cc(F)cc(F)c1)c1ncccc1Br]

(S)-N-((R)-1-(3-bromopyridin-2-yl)-2-(3,5-difluorophenyl)ethyl)-2-methylpropane-2-sulfinamide 3,5-difluorobenzylmagnesium bromide (10 mL, 2.500 mmol) was added dropwise to a solution of (S,Z)-N-((3-bromopyridin-2-yl)methylene)-2-methylpropane-2-sulfinamide (0.500 g, 1.729 mmol) in dichloromethane (40 mL) at −78° C. The reaction was stirred at −78° C. for 5 hours. NH$_4$Cl (aq., 10 mL) was added to the reaction and the mixture was allowed to warm to RT. Layers were separated and the aqueous was extracted with EtOAc (2×40 mL). The combined organic solution was dried over Na$_2$SO$_4$ overnight, filtered and concentrated. The crude product was purified by Biotage (Silica 24 gram flash column, EtOAc/hexanes gradient 20-55% EtOAc, Rf 0.36 with 50% EtOAc) to afford (0.242 g, 33.5% yield) of the title compound.

$^1$H NMR (400 MHz, CHLOROFORM-d) δ 8.50 (dd, J=4.6, 1.1 Hz, 1H), 7.80 (dd, J=8.2, 1.4 Hz, 1H), 7.09 (dd, J=8.2, 4.6 Hz, 1H), 6.65-6.51 (m, 3H), 5.20 (dt, J=9.5, 6.8 Hz, 1H), 4.51-4.43 (m, 1H), 3.31 (d, J=6.8 Hz, 2H), 1.15 (s, 9H).

| | |
|---|---|
| MS (M + H)$^+$ Calcd. | 417 |
| MS (M + H)$^+$ Observ. | 417 |
| Retention Time | 2.11 min |
| LC Condition | |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

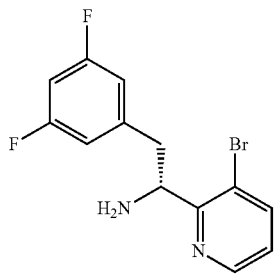 [SMILES: N[C@H](Cc1cc(F)cc(F)c1)c1ncccc1Br]

(R)-1-(3-bromopyridin-2-yl)-2-(3,5-difluorophenyl)ethanamine

To the solution of (S)-N-((R)-1-(3-bromopyridin-2-yl)-2-(3,5-difluorophenyl)ethyl)-2-methylpropane-2-sulfinamide (0.300 g, 0.719 mmol) in MeOH (3 mL) stirred at RT was added 4.0 M HCl in dioxane (1.5 mL, 6.00 mmol). The resulted was stirred at RT for 1 h. Solvent was evaporated in vacuo to give 0.251 g (100% yield) of the title compound.

$^1$H NMR (400 MHz, DMSO-d$_6$) δ 8.70 (dd, J=4.6, 1.2 Hz, 1H), 8.58 (br. s., 3H), 8.14 (dd, J=8.1, 1.5 Hz, 1H), 7.43 (dd, J=8.3, 4.6 Hz, 1H), 7.13 (tt, J=9.4, 2.3 Hz, 1H), 6.83-6.73 (m, 2H), 4.99 (br. s., 1H), 3.18 (qd, J=13.5, 7.1 Hz, 2H).

| | |
|---|---|
| MS (M + H)$^+$ Calcd. | 313 |
| MS (M + H)$^+$ Observ. | 313 |
| Retention Time | 1.25 min |
| LC Condition | |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

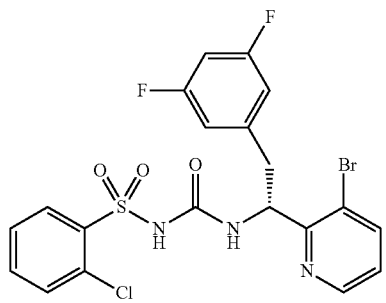 [SMILES: O=C(N[C@H](Cc1cc(F)cc(F)c1)c1ncccc1Br)NS(=O)(=O)c1ccccc1Cl]

(R)-N-((1-(3-bromopyridin-2-yl)-2-(3,5-difluorophenyl)ethyl)carbamoyl)-2-chlorobenzenesulfonamide (R)-1-(3-bromopyridin-2-yl)-2-(3,5-difluorophenyl)ethanamine, HCl (0.251 g, 0.719 mmol) was dissolved in 7 mL of dichloromethane, followed by the addition of DIEA (0.63 mL, 3.60 mmol) and a solution of 2-chlorobenzenesulfonyl isocyanate (0.219 g, 1.01 mmol) in 2.5 mL of dichloromethane dropwise. The resulted was stirred at RT for 1 h. Solvent was evaporated in vacuo. The product was purified by Biotage (24 g, EtOAc/DCM, 10-75%) to afford (0.253 g, 66.3% yield) of the title compound.

$^1$H NMR (400 MHz, METHANOL-d$_4$) δ 8.58-8.49 (m, 1H), 8.17-8.07 (m, 1H), 7.97 (dd, J=8.0, 1.3 Hz, 1H), 7.65-7.55 (m, 2H), 7.52-7.40 (m, 1H), 7.24 (dd, J=8.2, 4.6 Hz, 1H), 6.69 (tt, J=9.3, 2.2 Hz, 1H), 6.59-6.47 (m, 2H), 5.50 (dd, J=7.4, 5.9 Hz, 1H), 3.09 (dd, J=13.6, 5.5 Hz, 1H), 2.91 (dd, J=13.6, 7.8 Hz, 1H).

| | |
|---|---|
| MS (M + H)$^+$ Calcd. | 530 |
| MS (M + H)$^+$ Observ. | 530 |
| Retention Time | 2.19 min |
| LC Condition | |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

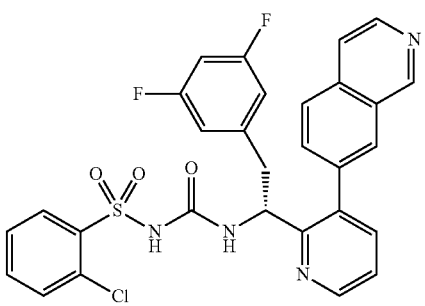 [SMILES: O=C(N[C@H](Cc1cc(F)cc(F)c1)c1ncccc1-c1ccc2ccncc2c1)NS(=O)(=O)c1ccccc1Cl]

(R)-2-chloro-N-((2-(3,5-difluorophenyl)-1-(3-(iso-quinolin-7-yl)pyridin-2-yl)ethyl)carbamoyl)benzenesulfonamide, 2 TFA To a mixture of (R)-N-((1-(3-bromopyridin-2-yl)-2-(3,5-difluorophenyl)ethyl)carbamoyl)-2-chlorobenzenesulfonamide (25 mg, 0.047 mmol), isoquinolin-7-ylboronic acid (10.6 mg, 0.061 mmol), tripotassium phosphate (0.071 mL, 0.141 mmol) and 2nd generation Xphos precatalyst (1.9 mg, 2.36 μmol) was added dioxane (1 mL) and water (0.200 mL). The mixture was degassed and stirred at 90° C. overnight. The product was purified by preparative HPLC (0.1% TFA, MeOH/H₂O) to afford (2.0 mg, 4.84% yield) of the title compound.

$^1$H NMR (400 MHz, METHANOL-$d_4$) δ 9.68 (s, 1H), 8.80 (dd, J=4.8, 1.5 Hz, 1H), 8.62 (d, J=6.5 Hz, 1H), 8.50 (d, J=6.5 Hz, 1H), 8.28 (d, J=8.5 Hz, 1H), 8.09 (d, J=9.3 Hz, 2H), 7.84 (d, J=7.0 Hz, 1H), 7.73 (dd, J=7.8, 1.5 Hz, 1H), 7.65-7.55 (m, 2H), 7.53-7.44 (m, 2H), 6.73-6.57 (m, 1H), 6.18 (d, J=6.3 Hz, 2H), 5.17 (t, J=7.4 Hz, 1H), 3.04-2.82 (m, 2H).

| | |
|---|---|
| MS (M + H)⁺ Calcd. | 579 |
| MS (M + H)⁺ Observ. | 579 |
| Retention Time | 1.56 min |
| | LC Condition |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

Example 100

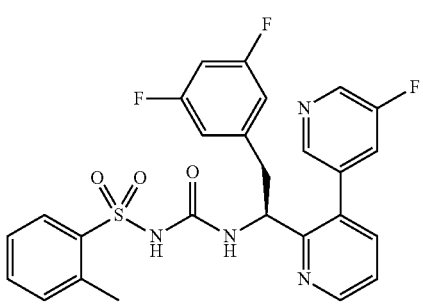 [SMILES: Cc1ccccc1S(=O)(=O)NC(=O)N[C@@H](Cc1cc(F)cc(F)c1)c1ncccc1-c1cncc(F)c1]

(S)-N-((2-(3,5-difluorophenyl)-1-(5'-fluoro-[3,3'-bipyridin]-2-yl)ethyl)carbamoyl)-2-methylbenzenesulfonamide, 2 TFA The title compound was prepared with the procedures described in Example 94.

| | |
|---|---|
| MS (M + H)⁺ Calcd. | 527 |
| MS (M + H)⁺ Observ. | 527 |
| Retention Time | 2.04 min |
| | LC Condition |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

$^1$H NMR (400 MHz, METHANOL-$d_4$) δ 8.77 (dd, J=4.8, 1.3 Hz, 1H), 8.49 (d, J=2.3 Hz, 1H), 8.04-7.89 (m, 2H), 7.61 (dd, J=7.7, 1.4 Hz, 1H), 7.53-7.43 (m, 2H), 7.36 (d, J=7.5 Hz, 1H), 7.32-7.23 (m, 2H), 6.69 (t, J=9.2 Hz, 1H), 6.22 (d, J=6.3 Hz, 2H), 5.06 (t, J=7.4 Hz, 1H), 2.94 (d, J=7.3 Hz, 2H), 2.61 (s, 3H)

Example 101

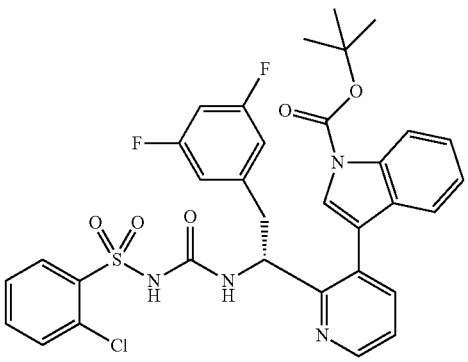 [SMILES: CC(C)(C)OC(=O)n1cc(-c2cccnc2[C@@H](Cc2cc(F)cc(F)c2)NC(=O)NS(=O)(=O)c2ccccc2Cl)c2ccccc21]

(R)-tert-butyl 3-(2-(1-(3-((2-chlorophenyl)sulfonyl)ureido)-2-(3,5-difluorophenyl)ethyl)pyridin-3-yl)-1H-indole-1-carboxylate, TFA The title compound was prepared with the procedures described in Example 99.

| | |
|---|---|
| MS (M + H)⁺ Calcd. | 667 |
| MS (M + H)⁺ Observ. | 667 |
| Retention Time | 2.70 min |
| | LC Condition |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

¹H NMR (400 MHz, CHLOROFORM-d) δ 8.76 (d, J=5.3 Hz, 1H), 8.61 (d, J=7.8 Hz, 1H), 8.26-8.11 (m, 2H), 7.96 (d, J=7.8 Hz, 1H), 7.72 (s, 1H), 7.63 (dd, J=7.8, 5.3 Hz, 1H), 7.57-7.48 (m, 2H), 7.42-7.33 (m, 2H), 7.32-7.20 (m, 1H), 7.16 (t, J=7.7 Hz, 1H), 6.91 (d, J=8.0 Hz, 1H), 6.39 (t, J=8.9 Hz, 1H), 6.11 (d, J=6.0 Hz, 2H), 5.63-5.50 (m, 1H), 3.08-2.99 (m, 1H), 2.97-2.87 (m, 1H), 1.68 (s, 9H)

Example 102

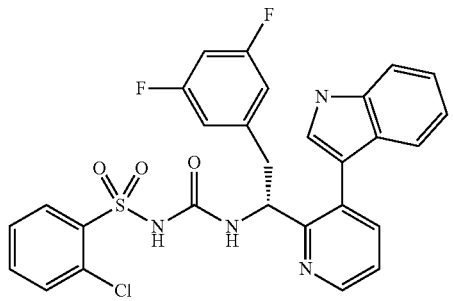 [SMILES: O=C(N[C@H](Cc1cc(F)cc(F)c1)c1ncccc1-c1c[nH]c2ccccc12)NS(=O)(=O)c1ccccc1Cl]

(R)-N-((1-(3-(1H-indol-3-yl)pyridin-2-yl)-2-(3,5-difluorophenyl)ethyl)carbamoyl)-2-chlorobenzene-sulfonamide, 2 TFA The title compound was prepared by removing the Boc protecting group of the compound in Example 101 with TFA.

| | |
|---|---|
| MS (M + H)⁺ Calcd. | 567 |
| MS (M + H)⁺ Observ. | 567 |
| Retention Time | 2.02 min |
| | LC Condition |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

¹H NMR (400 MHz, METHANOL-d₄) δ 8.65 (dd, J=5.0, 1.3 Hz, 1H), 8.07 (d, J=7.8 Hz, 1H), 8.01-7.95 (m, 1H), 7.65-7.56 (m, 3H), 7.50-7.40 (m, 2H), 7.20 (s, 1H), 7.15 (d, J=8.5 Hz, 1H), 7.00-6.90 (m, 1H), 6.57-6.42 (m, 1H), 6.08 (d, J=6.3 Hz, 2H), 5.51 (t, J=7.0 Hz, 1H), 3.09 (dd, J=13.7, 5.6 Hz, 1H), 2.94-2.77 (m, 2H)

Example 103

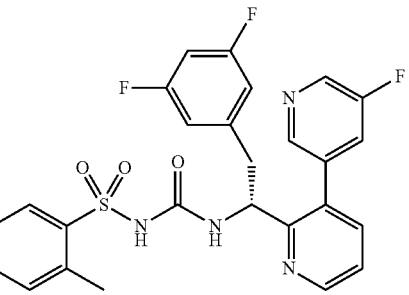

(R)-N-((2-(3,5-difluorophenyl)-1-(5'-fluoro-[3,3'-bipyridin]-2-yl)ethyl)carbamoyl)-2-methylbenzene-sulfonamide, 2 TFA The title compound was prepared with the procedures described in Example 99.

| | |
|---|---|
| MS (M + H)⁺ Calcd. | 527 |
| MS (M + H)⁺ Observ. | 527 |
| Retention Time | 2.03 min |
| | LC Condition |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

¹H NMR (400 MHz, METHANOL-d₄) δ 8.78 (dd, J=4.6, 1.4 Hz, 1H), 8.49 (d, J=2.5 Hz, 1H), 8.03-7.91 (m, 2H), 7.62 (dd, J=7.8, 1.5 Hz, 1H), 7.55-7.43 (m, 2H), 7.37 (d, J=7.5 Hz, 1H), 7.33-7.23 (m, 2H), 6.77-6.64 (m, 1H), 6.23 (d, J=6.3 Hz, 2H), 5.07 (t, J=7.4 Hz, 1H), 2.94 (d, J=7.3 Hz, 2H), 2.63 (s, 3H)

Example 104

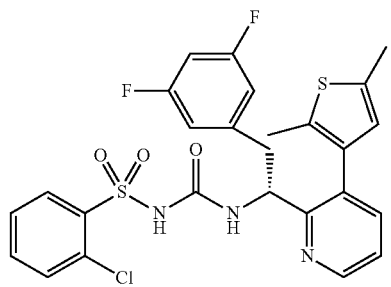 [SMILES: Cc1cc(-c2cccnc2[C@@H](Cc2cc(F)cc(F)c2)NC(=O)NS(=O)(=O)c2ccccc2Cl)c(C)s1]

(R)-2-chloro-N-((2-(3,5-difluorophenyl)-1-(3-(2,5-dimethylthiophen-3-yl)pyridin-2-yl)ethyl)carbamoyl)benzenesulfonamide, TFA The title compound was prepared with the procedures described in Example 99.

| MS (M + H)+ Calcd. | 562 |
|---|---|
| MS (M + H)+ Observ. | 562 |
| Retention Time | 2.41 min |
| LC Condition | |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

¹H NMR (400 MHz, METHANOL-d₄) δ 8.72-8.60 (m, 1H), 8.14-8.04 (m, 1H), 7.65-7.54 (m, 3H), 7.49-7.40 (m, 2H), 6.67 (t, J=9.3 Hz, 1H), 6.26 (d, J=6.3 Hz, 2H), 6.10 (br. s., 1H), 5.07 (br. s., 1H), 2.95-2.77 (m, 2H), 2.35 (s, 3H), 1.89 (s, 3H)

Example 105

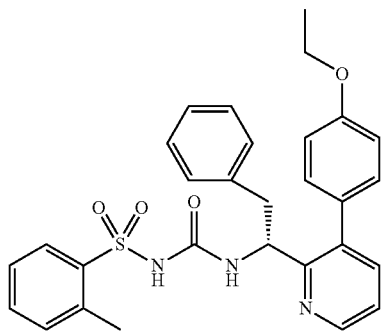 [SMILES: CCOc1ccc(-c2cccnc2[C@@H](Cc2ccccc2)NC(=O)NS(=O)(=O)c2ccccc2C)cc1]

(R)-N-((1-(3-(4-ethoxyphenyl)pyridin-2-yl)-2-phenylethyl)carbamoyl)-2-methylbenzenesulfonamide, TFA The title compound was prepared with the procedures described in Example 88.

| MS (M + H)+ Calcd. | 516 |
|---|---|
| MS (M + H)+ Observ. | 516 |
| Retention Time | 1.82 min |
| LC Condition | |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

¹H NMR (500 MHz, DMSO-d₆) δ 8.59 (d, J=3.7 Hz, 1H), 7.77 (d, J=8.1 Hz, 1H), 7.55-7.46 (m, 2H), 7.39-7.29 (m, 3H), 7.12-6.93 (m, 6H), 6.89 (d, J=8.4 Hz, 2H), 6.62 (d, J=7.0 Hz, 2H), 5.04 (q, J=7.7 Hz, 1H), 4.04 (q, J=7.0 Hz, 2H), 3.90 (s, 1H), 3.35 (br. s., 1H), 2.89 (s, 1H), 2.85 (dd, J=13.4, 6.1 Hz, 1H), 2.73 (s, 1H), 2.66 (dd, J=13.4, 7.5 Hz, 1H), 1.34 (t, J=7.0 Hz, 3H).

Example 106

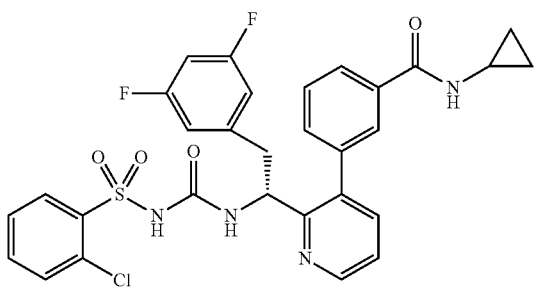 [SMILES: O=C(N[C@H](Cc1cc(F)cc(F)c1)c1ncccc1-c1cccc(C(=O)NC2CC2)c1)NS(=O)(=O)c1ccccc1Cl]

(R)-3-(2-(1-(3-((2-chlorophenyl)sulfonyl)ureido)-2-(3,5-difluorophenyl)ethyl)pyridin-3-yl)-N-cyclopropylbenzamide, TFA The title compound was prepared with the procedures described in Example 99.

| MS (M + H)+ Calcd. | 611 |
|---|---|
| MS (M + H)+ Observ. | 611 |
| Retention Time | 1.98 min |
| LC Condition | |
| Solvent A | 10% acetonitrile: 90% Water: 0.1% TFA |
| Solvent B | 90% acetonitrile: 10% Water: 0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

¹H NMR (400 MHz, METHANOL-d₄) δ 8.70 (dd, J=4.8, 1.3 Hz, 1H), 8.10 (d, J=7.8 Hz, 1H), 7.82 (d, J=7.8 Hz, 1H), 7.68-7.54 (m, 3H), 7.50-7.40 (m, 4H), 7.16 (d, J=7.5 Hz, 1H), 6.62 (t, J=9.2 Hz, 1H), 6.17 (d, J=6.0 Hz, 2H), 5.21 (t, J=7.3 Hz, 1H), 3.01-2.75 (m, 3H), 0.90-0.75 (m, 2H), 0.71-0.63 (m, 2H).

Example 107

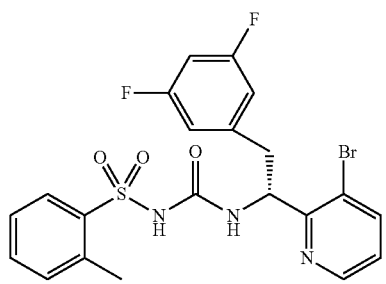 [SMILES: Cc1ccccc1S(=O)(=O)NC(=O)N[C@H](Cc1cc(F)cc(F)c1)c1ncccc1Br]

(R)-N-((1-(3-bromopyridin-2-yl)-2-(3,5-difluorophe-nyl)ethyl)carbamoyl)-2-methylbenzenesulfonamide, TFA The title compound was prepared with the procedures described in Example 99.

| MS (M + H)+ Calcd. | 510 |
| MS (M + H)+ Observ. | 510 |
| Retention Time | 2.25 min |
| LC Condition | |
| Solvent A | 10% acetonitrile: 90% Water: 0.1% TFA |
| Solvent B | 90% acetonitrile: 10% Water: 0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

$^1$H NMR (400 MHz, METHANOL-d$_4$) δ 8.54 (dd, J=4.5, 1.3 Hz, 1H), 8.02-7.93 (m, 2H), 7.56-7.47 (m, 1H), 7.41-7.29 (m, 2H), 7.25 (dd, J=8.2, 4.6 Hz, 1H), 6.70 (tt, J=9.2, 2.3 Hz, 1H), 6.49 (d, J=6.3 Hz, 2H), 5.50 (dd, J=7.5, 5.8 Hz, 1H), 3.09 (dd, J=13.6, 5.8 Hz, 1H), 2.89 (dd, J=13.4, 7.7 Hz, 1H), 2.61 (s, 3H)

Example 108

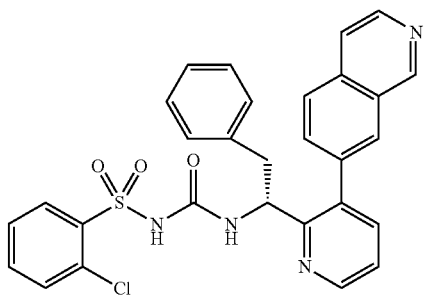 [SMILES: O=C(N[C@H](Cc1ccccc1)c1ncccc1-c1ccc2ccncc2c1)NS(=O)(=O)c1ccccc1Cl]

(S)-2-chloro-N-((1-(3-(isoquinolin-7-yl)pyridin-2-yl)-2-phenylethyl)carbamoyl)benzenesulfonamide, 2 TFA The title compound was prepared with the procedures described in Example 88.

| MS (M + H)+ Calcd. | 543 |
| MS (M + H)+ Observ. | 543 |
| Retention Time | 1.46 min |
| LC Condition | |
| Solvent A | 10% acetonitrile: 90% Water: 0.1% TFA |
| Solvent B | 90% acetonitrile: 10% Water: 0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

$^1$H NMR (400 MHz, DMSO-d$_6$) δ 10.80 (s, 1H), 9.48 (s, 1H), 8.76 (dd, J=4.6, 1.6 Hz, 1H), 8.66 (d, J=6.0 Hz, 1H), 8.25 (d, J=6.0 Hz, 1H), 8.15 (d, J=8.5 Hz, 1H), 7.92 (d, J=7.8 Hz, 1H), 7.83 (s, 1H), 7.74-7.63 (m, 4H), 7.55-7.46 (m, 2H), 7.23 (d, J=8.5 Hz, 1H), 7.11-6.97 (m, 3H), 6.62 (d, J=7.3 Hz, 2H), 5.00-4.84 (m, 1H), 2.96 (dd, J=13.2, 6.9 Hz, 1H), 2.77 (dd, J=13.2, 6.9 Hz, 1H).

Example 109

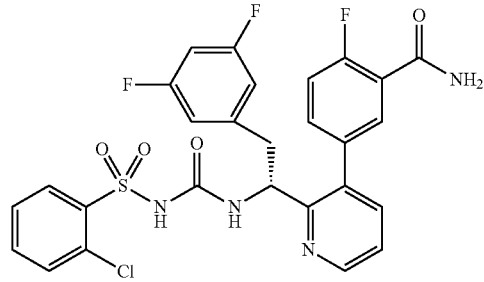 [SMILES: NC(=O)c1cc(-c2cccnc2[C@@H](Cc2cc(F)cc(F)c2)NC(=O)NS(=O)(=O)c2ccccc2Cl)ccc1F]

(R)-5-(2-(1-(3-((2-chlorophenyl)sulfonyl)ureido)-2-(3,5-difluorophenyl)ethyl)pyridin-3-yl)-2-fluoroben-zamide, TFA The title compound was prepared with the procedures described in Example 99.

| MS (M + H)+ Calcd. | 589 |
| MS (M + H)+ Observ. | 589 |
| Retention Time | 1.44 min |
| LC Condition | |
| Solvent A | 10% acetonitrile: 90% Water: 0.1% TFA |
| Solvent B | 90% acetonitrile: 10% Water: 0.1% TFA |
| Start % B | 0 |
| Final % B | 100 |
| Gradient Time | 2 min |
| Flow Rate | 1 mL/min |
| Wavelength | 220 |
| Column | Phenomenex LUNA C18, 30 × 2, 3 u |

$^1$H NMR (400 MHz, METHANOL-d$_4$) δ 8.70 (dd, J=4.8, 1.5 Hz, 1H), 8.12-8.05 (m, 1H), 7.65-7.54 (m, 3H), 7.50-7.39 (m, 2H), 7.36-7.30 (m, 1H), 7.23-7.15 (m, 2H), 6.63 (t, J=9.3 Hz, 1H), 6.24 (d, J=6.3 Hz, 2H), 5.13 (t, J=7.4 Hz, 1H), 2.92 (qd, J=13.3, 7.4 Hz, 2H)

Example 110

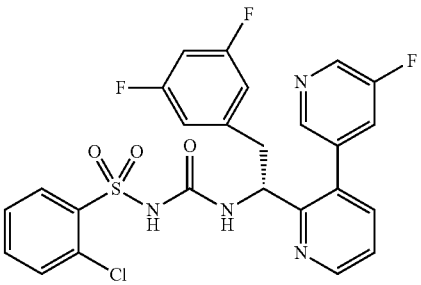 [SMILES: O=C(N[C@H](Cc1cc(F)cc(F)c1)c1ncccc1-c1cncc(F)c1)NS(=O)(=O)c1ccccc1Cl]

(R)-2-chloro-N-((2-(3,5-difluorophenyl)-1-(5'-fluoro-[3,3'-bipyridin]-2-yl)ethyl)carbamoyl)benzenesulfonamide, TFA The title compound was prepared with the procedures described in Example 99.

| | |
|---|---|
| MS (M + H)+ Calcd. | 547 |
| MS (M + H)+ Observ. | 547 |
| Retention Time | 1.45 min |
| LC Condition | |
| Solvent A | 10% Methanol: 90% Water: 0.1% TFA |
| Solvent B | 90% Methanol: 10% Water: 0.1% TFA |
| Start % B | 2 |
| Final % B | 98 |
| Gradient Time | 1.5 min |
| Flow Rate | 0.8 mL/min |
| Wavelength | 220 |
| Column | Waters Aquity BEH C18 2.1 X 50 mm 1.7 U |

$^1$H NMR (400 MHz, METHANOL-d$_4$) δ 8.76 (dd, J=4.8, 1.5 Hz, 1H), 8.47 (d, J=2.5 Hz, 1H), 8.10 (d, J=7.8 Hz, 1H), 7.99 (s, 1H), 7.66-7.54 (m, 3H), 7.50-7.41 (m, 2H), 7.27 (d, J=9.3 Hz, 1H), 6.74-6.63 (m, 1H), 6.24 (d, J=6.3 Hz, 2H), 5.07 (t, J=7.4 Hz, 1H), 2.95 (d, J=7.3 Hz, 2H)

Example 111

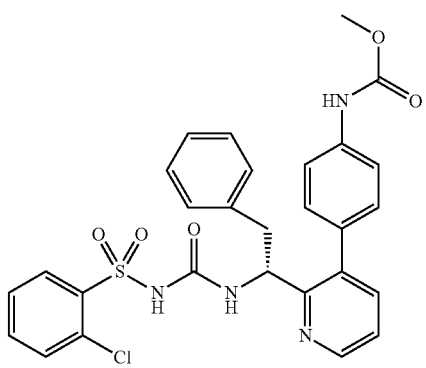 [SMILES: COC(=O)Nc1ccc(-c2cccnc2[C@@H](Cc2ccccc2)NC(=O)NS(=O)(=O)c2ccccc2Cl)cc1]

(R)-methyl (4-(2-(1-(3-((2-chlorophenyl)sulfonyl)ureido)-2-phenylethyl)pyridin-3-yl)phenyl)carbamate, TFA The title compound was prepared with the procedures described in Example 88.

| | |
|---|---|
| MS (M + H)+ Calcd. | 565 |
| MS (M + H)+ Observ. | 565 |
| Retention Time | 1.81 min |
| LC Condition | |
| Solvent A | 10% acetonitrile: 90% Water: 0.1% TFA |
| Solvent B | 90% acetonitrile: 10% Water: 0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

$^1$H NMR (400 MHz, DMSO-d$_6$) δ 10.75 (s, 1H), 9.77 (s, 1H), 8.61 (dd, J=4.5, 1.5 Hz, 1H), 7.93 (d, J=7.8 Hz, 1H), 7.66 (d, J=4.0 Hz, 2H), 7.58-7.49 (m, 2H), 7.47-7.36 (m, 3H), 7.14 (d, J=8.8 Hz, 1H), 7.10-7.01 (m, 3H), 6.94 (d, J=8.3 Hz, 2H), 6.68-6.58 (m, 2H), 5.01 (q, J=7.3 Hz, 1H), 3.68 (s, 3H), 2.89 (dd, J=13.4, 6.4 Hz, 1H), 2.75-2.62 (m, 1H).

Example 112

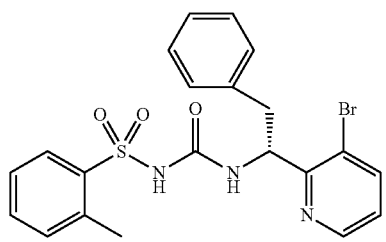 [SMILES: Cc1ccccc1S(=O)(=O)NC(=O)N[C@H](Cc1ccccc1)c1ncccc1Br]

(R)-N-((1-(3-bromopyridin-2-yl)-2-phenylethyl)carbamoyl)-2-methylbenzenesulfonamide, TFA The title compound was prepared with the procedures described in Example 99.

| | |
|---|---|
| MS (M + H)+ Calcd. | 474 |
| MS (M + H)+ Observ. | 474 |
| Retention Time | 2.13 min |
| LC Condition | |
| Solvent A | 10% acetonitrile: 90% Water: 0.1% TFA |
| Solvent B | 90% acetonitrile: 10% Water: 0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

$^1$H NMR (400 MHz, DMSO-d$_6$) δ 10.68 (s, 1H), 8.55 (d, J=4.6 Hz, 1H), 8.04 (d, J=8.1 Hz, 1H), 7.81 (d, J=7.8 Hz, 1H), 7.59-7.47 (m, 1H), 7.41-7.32 (m, 2H), 7.29 (dd, J=8.1, 4.6 Hz, 1H), 7.18-7.05 (m, 4H), 6.93-6.84 (m, 2H), 5.37-5.22 (m, 1H), 2.97 (dd, J=13.6, 5.5 Hz, 1H), 2.81 (dd, J=13.4, 7.8 Hz, 1H), 2.52 (s, 3H)

Example 113

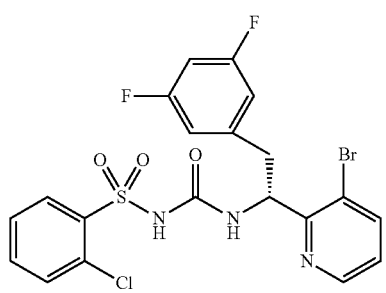 [SMILES: O=C(N[C@H](Cc1cc(F)cc(F)c1)c1ncccc1Br)NS(=O)(=O)c1ccccc1Cl]

(S)-N-((1-(3-bromopyridin-2-yl)-2-(3,5-difluorophenyl)ethyl)carbamoyl)-2-chlorobenzenesulfonamide, TFA The title compound was prepared with the procedures described in Example 99.

| MS (M + H)+ Calcd. | 530 |
| MS (M + H)+ Observ. | 530 |
| Retention Time | 2.21 min |
| LC Condition | |
| Solvent A | 10% acetonitrile: 90% Water: 0.1% TFA |
| Solvent B | 90% acetonitrile: 10% Water: 0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

$^1$H NMR (400 MHz, METHANOL-$d_4$) δ 8.58-8.49 (m, 1H), 8.10 (dd, J=8.2, 1.1 Hz, 1H), 7.97 (dd, J=8.0, 1.3 Hz, 1H), 7.67-7.55 (m, 2H), 7.51-7.42 (m, 1H), 7.24 (dd, J=8.0, 4.8 Hz, 1H), 6.69 (tt, J=9.3, 2.2 Hz, 1H), 6.53 (d, J=6.0 Hz, 2H), 5.50 (dd, J=7.5, 5.8 Hz, 1H), 3.09 (dd, J=13.6, 5.5 Hz, 1H), 2.91 (dd, J=13.6, 7.8 Hz, 1H).

Example 114

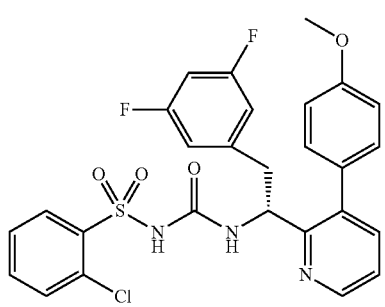 [SMILES: COc1ccc(-c2cccnc2[C@@H](Cc2cc(F)cc(F)c2)NC(=O)NS(=O)(=O)c2ccccc2Cl)cc1]

(S)-2-chloro-N-((2-(3,5-difluorophenyl)-1-(3-(4-methoxyphenyl)pyridin-2-yl)ethyl)carbamoyl)benzenesulfonamide, TFA The title compound was prepared with the procedures described in Example 99.

| MS (M + H)+ Calcd. | 558 |
| MS (M + H)+ Observ. | 558 |
| Retention Time | 2.17 min |
| LC Condition | |
| Solvent A | 10% acetonitrile: 90% Water: 0.1% TFA |
| Solvent B | 90% acetonitrile: 10% Water: 0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

$^1$H NMR (400 MHz, METHANOL-$d_4$) δ 8.62 (dd, J=4.9, 1.4 Hz, 1H), 8.09 (d, J=7.8 Hz, 1H), 7.69-7.56 (m, 3H), 7.52-7.38 (m, 2H), 7.02-6.86 (m, 4H), 6.64 (t, J=9.3 Hz, 1H), 6.19 (d, J=6.0 Hz, 2H), 5.28 (t, J=7.2 Hz, 1H), 3.82 (s, 3H), 2.94-2.85 (m, 1H), 2.84-2.75 (m, 1H)

Example 115

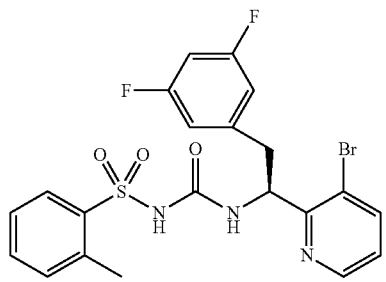 [SMILES: Cc1ccccc1S(=O)(=O)NC(=O)N[C@@H](Cc1cc(F)cc(F)c1)c1ncccc1Br]

(S)-2-chloro-N-((2-(3,5-difluorophenyl)-1-(3-(4-methoxyphenyl)pyridin-2-yl)ethyl)carbamoyl)benzenesulfonamide, TFA The title compound was prepared with the procedures described in Example 94.

| MS (M + H)+ Calcd. | 510 |
| MS (M + H)+ Observ. | 510 |
| Retention Time | 2.23 min |
| LC Condition | |
| Solvent A | 10% acetonitrile: 90% Water: 0.1% TFA |
| Solvent B | 90% acetonitrile: 10% Water: 0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

$^1$H NMR (400 MHz, METHANOL-$d_4$) δ 8.54 (d, J=4.8 Hz, 1H), 7.97 (t, J=7.2 Hz, 2H), 7.57-7.48 (m, 1H), 7.39-7.29 (m, 2H), 7.25 (dd, J=8.0, 4.5 Hz, 1H), 6.76-6.65 (m, 1H), 6.49 (d, J=6.3 Hz, 2H), 5.50 (dd, J=7.5, 5.8 Hz, 1H), 3.09 (dd, J=13.6, 5.8 Hz, 1H), 2.89 (dd, J=13.6, 7.8 Hz, 1H), 2.61 (s, 3H)

Example 116

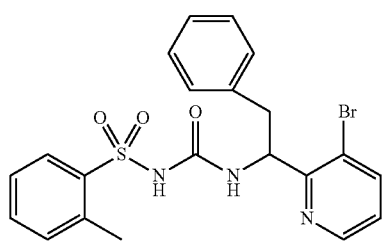 [SMILES: Cc1ccccc1S(=O)(=O)NC(=O)NC(Cc1ccccc1)c1ncccc1Br]

N-((1-(3-bromopyridin-2-yl)-2-phenylethyl)carbamoyl)-2-methylbenzenesulfonamide, TFA The title compound was prepared with the procedures described in Example 88.

| | |
|---|---|
| MS (M + H)+ Calcd. | 474 |
| MS (M + H)+ Observ. | 474 |
| Retention Time | 1.85 min |
| LC Condition | |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

$^1$H NMR (400 MHz, METHANOL-d$_4$) δ 8.55-8.47 (m, 1H), 8.00-7.91 (m, 2H), 7.58-7.49 (m, 1H), 7.43-7.29 (m, 2H), 7.22 (dd, J=8.1, 4.6 Hz, 1H), 7.17-7.05 (m, 3H), 6.95-6.82 (m, 2H), 5.51 (t, J=6.5 Hz, 1H), 3.10 (dd, J=13.6, 5.7 Hz, 1H), 2.91 (dd, J=13.4, 7.6 Hz, 1H), 2.62 (s, 3H)

Example 117

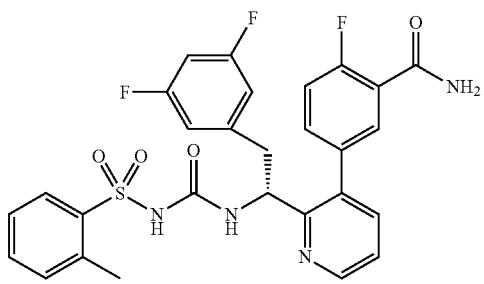 [SMILES: Cc1ccccc1S(=O)(=O)NC(=O)N[C@H](Cc1cc(F)cc(F)c1)c1ncccc1-c1ccc(F)c(C(N)=O)c1]

(R)-5-(2-(2-(3,5-difluorophenyl)-1-(3-(o-tolylsulfonyl)ureido)ethyl)pyridin-3-yl)-2-fluorobenzamide, TFA The title compound was prepared with the procedures described in Example 99.

| | |
|---|---|
| MS (M + H)+ Calcd. | 569 |
| MS (M + H)+ Observ. | 569 |
| Retention Time | 1.84 min |
| LC Condition | |
| Solvent A | 10% acetonitrile: 90% Water: 0.1% TFA |
| Solvent B | 90% acetonitrile: 10% Water: 0.1% TFA |
| Start % B | 0 |
| Final % B | 100 |
| Gradient Time | 3 min |
| Flow Rate | 1 mL/min |
| Wavelength | 220 |
| Column | Phenomenex LUNA C18, 30 × 2, 3 u |

$^1$H NMR (400 MHz, METHANOL-d$_4$) δ 8.71 (dd, J=4.8, 1.5 Hz, 1H), 7.91 (d, J=8.0 Hz, 1H), 7.63 (dd, J=7.7, 1.4 Hz, 1H), 7.53-7.42 (m, 2H), 7.39-7.12 (m, 5H), 6.69-6.59 (m, 1H), 6.23 (d, J=6.3 Hz, 2H), 5.13 (t, J=7.4 Hz, 1H), 3.02-2.82 (m, 2H), 2.60 (s, 3H).

Example 118

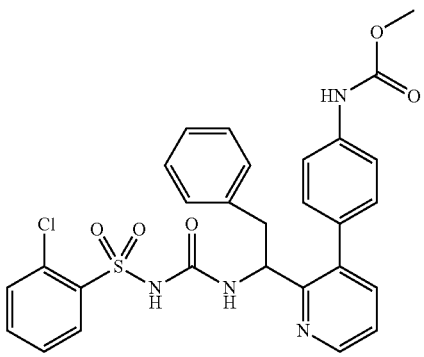 [SMILES: COC(=O)Nc1ccc(-c2cccnc2C(Cc2ccccc2)NC(=O)NS(=O)(=O)c2ccccc2Cl)cc1]

methyl (4-(2-(1-(3-((2-chlorophenyl)sulfonyl)ureido)-2-phenylethyl)pyridin-3-yl)phenyl)carbamate, TFA The title compound was prepared with the procedures described in Example 88.

| | |
|---|---|
| MS (M + H)+ Calcd. | 565 |
| MS (M + H)+ Observ. | 565 |
| Retention Time | 1.51 min |
| LC Condition | |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 9.77 (s, 1H), 8.61 (d, J=3.7 Hz, 1H), 7.99-7.88 (m, 4H), 7.73-7.62 (m, 3H), 7.56-7.49 (m, 2H), 7.43 (d, J=8.1 Hz, 2H), 7.05 (d, J=7.3 Hz, 3H), 6.94 (d, J=8.4 Hz, 2H), 6.64 (d, J=6.2 Hz, 2H), 5.07-4.93 (m, 1H), 3.68 (s, 3H), 2.68 (dd, J=13.4, 7.5 Hz, 1H).

Example 119

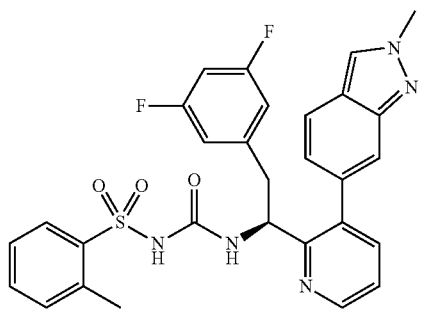 [SMILES: Cc1ccccc1S(=O)(=O)NC(=O)N[C@@H](Cc1cc(F)cc(F)c1)c1ncccc1-c1ccc2cn(C)nc2c1]

(S)-N-((2-(3,5-difluorophenyl)-1-(3-(2-methyl-2H-indazol-6-yl)pyridin-2-yl)ethyl)carbamoyl)-2-methylbenzenesulfonamide, TFA The title compound was prepared with the procedures described in Example 94.

| MS (M + H)⁺ Calcd. | 562 |
|---|---|
| MS (M + H)⁺ Observ. | 562 |
| Retention Time | 1.67 min |
| LC Condition | |
| Solvent A | 5% acetonitrile: 95% Water: 10 mM Ammonium Acetate |
| Solvent B | 95% acetonitrile: 5% Water: 10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

¹H NMR (500 MHz, DMSO-d₆) δ 8.68-8.65 (m, 1H), 8.40 (s, 1H), 7.79-7.68 (m, 3H), 7.54-7.49 (m, 1H), 7.46 (dd, J=7.3, 4.8 Hz, 1H), 7.40 (s, 1H), 7.37-7.29 (m, 2H), 7.22 (s, 1H), 7.16-7.10 (m, 1H), 6.91 (t, J=9.5 Hz, 1H), 6.81 (d, J=8.4 Hz, 1H), 6.27 (d, J=6.6 Hz, 2H), 5.21-5.07 (m, 1H), 4.20 (s, 3H), 2.98-2.87 (m, 1H), 2.74 (dd, J=13.0, 8.6 Hz, 1H), 2.51 (br. s., 3H).

Example 120

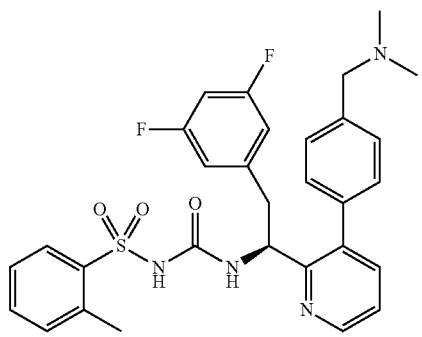 [SMILES: Cc1ccccc1S(=O)(=O)NC(=O)N[C@@H](Cc1cc(F)cc(F)c1)c1ncccc1-c1ccc(CN(C)C)cc1]

(S)-N-((2-(3,5-difluorophenyl)-1-(3-(4-((dimethylamino)methyl)phenyl)pyridin-2-yl)ethyl)carbamoyl)-2-methylbenzenesulfonamide, TFA The title compound was prepared with the procedures described in Example 94.

| MS (M + H)⁺ Calcd. | 565 |
|---|---|
| MS (M + H)⁺ Observ. | 565 |
| Retention Time | 1.42 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

¹H NMR (500 MHz, DMSO-d₆) δ 8.63 (br. s., 1H), 7.74 (d, J=7.3 Hz, 2H), 7.56 (d, J=7.3 Hz, 2H), 7.39 (br. s., 3H), 7.31 (d, J=7.7 Hz, 3H), 7.28-7.19 (m, 3H), 7.11 (d, J=6.6 Hz, 2H), 6.90 (t, J=9.4 Hz, 1H), 6.79 (br. s., 1H), 6.23 (d, J=7.3 Hz, 2H), 5.09 (d, J=7.0 Hz, 1H), 2.20 (s, 3H), 1.92 (s, 6H)

Example 121

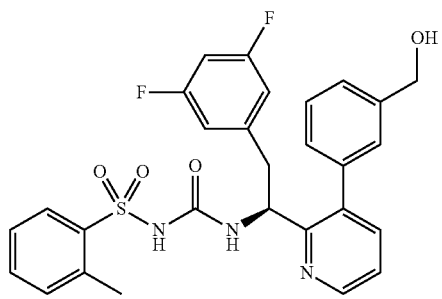 [SMILES: Cc1ccccc1S(=O)(=O)NC(=O)N[C@@H](Cc1cc(F)cc(F)c1)c1ncccc1-c1cccc(CO)c1]

(S)-N-((2-(3,5-difluorophenyl)-1-(3-(3-(hydroxymethyl)phenyl)pyridin-2-yl)ethyl)carbamoyl)-2-methylbenzenesulfonamide, TFA The title compound was prepared with the procedures described in Example 94.

| MS (M + H)⁺ Calcd. | 538 |
|---|---|
| MS (M + H)⁺ Observ. | 538 |
| Retention Time | 1.42 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

¹H NMR (500 MHz, DMSO-d₆) δ 10.66 (br. s., 1H), 8.66 (d, J=4.4 Hz, 1H), 7.96 (s, 1H), 7.77 (d, J=7.7 Hz, 1H), 7.61 (d, J=7.7 Hz, 1H), 7.52 (t, J=7.5 Hz, 1H), 7.44 (dd, J=7.7, 4.8 Hz, 1H), 7.40-7.29 (m, 4H), 7.13 (d, J=8.8 Hz, 1H), 7.09-7.02 (m, 2H), 6.93 (t, J=9.2 Hz, 1H), 6.33 (d, J=6.6 Hz, 2H), 5.11-4.94 (m, 1H), 4.50 (d, J=3.7 Hz, 2H), 2.98-2.91 (m, 2H), 2.80-2.75 (m, 1H), 1.17 (t, J=7.3 Hz, 2H).

Example 122

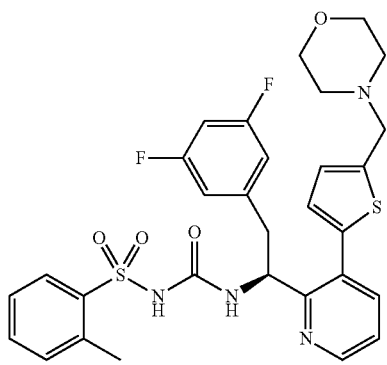 [SMILES: Cc1ccccc1S(=O)(=O)NC(=O)N[C@@H](Cc1cc(F)cc(F)c1)c1ncccc1-c1ccc(CN2CCOCC2)s1]

(S)-N-((2-(3,5-difluorophenyl)-1-(3-(5-(morpholinomethyl)thiophen-2-yl)pyridin-2-yl)ethyl)carbamoyl)-2-methylbenzenesulfonamide, 2 TFA The title compound was prepared with the procedures described in Example 94.

| | |
|---|---|
| MS (M + H)+ Calcd. | 613 |
| MS (M + H)+ Observ. | 613 |
| Retention Time | 1.82 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 8.69 (d, J=3.7 Hz, 1H), 7.76 (dd, J=15.6, 7.2 Hz, 2H), 7.56-7.49 (m, 1H), 7.45 (dd, J=7.7, 4.8 Hz, 1H), 7.38-7.27 (m, 3H), 7.26-7.18 (m, 1H), 7.15-7.08 (m, 1H), 7.04 (s, 1H), 6.95 (t, J=9.5 Hz, 1H), 6.44 (d, J=6.6 Hz, 2H), 5.42-5.24 (m, 1H), 4.55 (br. s., 2H), 4.05-3.42 (m, 6H), 3.30-2.98 (m, 2H), 2.94 (dd, J=13.6, 5.9 Hz, 1H), 2.88-2.78 (m, 1H), 2.48 (s, 3H)

Example 123

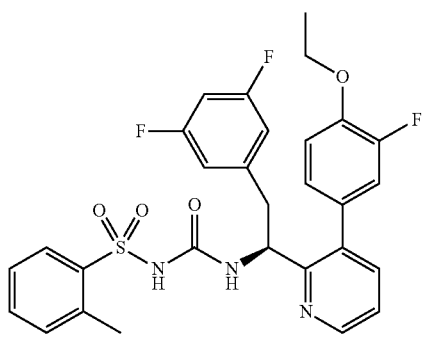 [SMILES: CCOc1ccc(-c2cccnc2[C@H](Cc2cc(F)cc(F)c2)NC(=O)NS(=O)(=O)c2ccccc2C)cc1F]

(S)-N-((2-(3,5-difluorophenyl)-1-(3-(4-ethoxy-3-fluorophenyl)pyridin-2-yl)ethyl)carbamoyl)-2-methylbenzenesulfonamide, TFA The title compound was prepared with the procedures described in Example 94.

| | |
|---|---|
| MS (M + H)+ Calcd. | 570 |
| MS (M + H)+ Observ. | 570 |
| Retention Time | 1.98 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-d$_6$) δ 10.67 (br. s., 1H), 8.64 (d, J=4.8 Hz, 1H), 7.79 (d, J=8.1 Hz, 1H), 7.59 (d, J=7.7 Hz, 1H), 7.55-7.50 (m, 1H), 7.40 (dd, J=7.7, 4.8 Hz, 1H), 7.37-7.31 (m, 2H), 7.19-7.09 (m, 2H), 6.99-6.85 (m, 3H), 6.31 (d, J=7.0 Hz, 2H), 5.06 (q, J=7.6 Hz, 1H), 4.14 (q, J=7.1 Hz, 2H), 2.96-2.84 (m, 1H), 2.77 (dd, J=13.2, 7.7 Hz, 1H), 2.73 (s, 3H), 1.36 (t, J=7.0 Hz, 3H).

Example 124

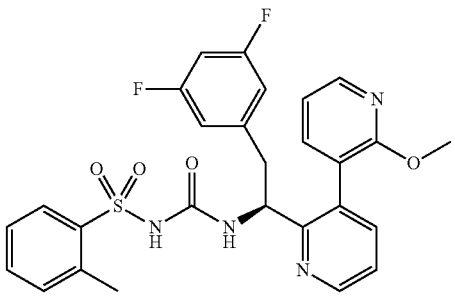 [SMILES: COc1ncccc1-c1cccnc1[C@H](Cc1cc(F)cc(F)c1)NC(=O)NS(=O)(=O)c1ccccc1C]

(S)-N-((2-(3,5-difluorophenyl)-1-(2'-methoxy-[3,3'-bipyridin]-2-yl)ethyl)carbamoyl)-2-methylbenzenesulfonamide, TFA The title compound was prepared with the procedures described in Example 94.

| | |
|---|---|
| MS (M + H)+ Calcd. | 539 |
| MS (M + H)+ Observ. | 539 |
| Retention Time | 1.74 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |

| | |
|---|---|
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

Example 125

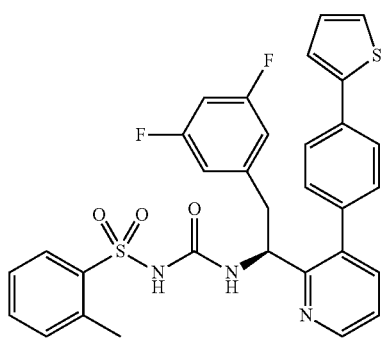 [SMILES: Cc1ccccc1S(=O)(=O)NC(=O)N[C@@H](Cc1cc(F)cc(F)c1)c1ncccc1-c1ccc(-c2cccs2)cc1]

(S)-N-((2-(3,5-difluorophenyl)-1-(3-(4-(thiophen-2-yl)phenyl)pyridin-2-yl)ethyl)carbamoyl)-2-methyl-benzenesulfonamide, TFA The title compound was prepared with the procedures described in Example 94.

| | |
|---|---|
| MS (M + H)⁺ Calcd. | 590 |
| MS (M + H)⁺ Observ. | 590 |
| Retention Time | 2.14 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 10.66 (s, 1H), 8.69-8.62 (m, 1H), 7.79 (d, J=7.7 Hz, 1H), 7.69-7.62 (m, 3H), 7.60-7.56 (m, 2H), 7.55-7.50 (m, 1H), 7.44 (dd, J=7.7, 4.8 Hz, 1H), 7.37-7.31 (m, 2H), 7.20-7.12 (m, 4H), 6.92 (t, J=9.4 Hz, 1H), 6.29 (d, J=6.2 Hz, 2H), 5.10 (q, J=7.6 Hz, 1H), 2.92-2.84 (m, 1H), 2.81-2.73 (m, 1H), 2.50 (s, 3H).

Example 126

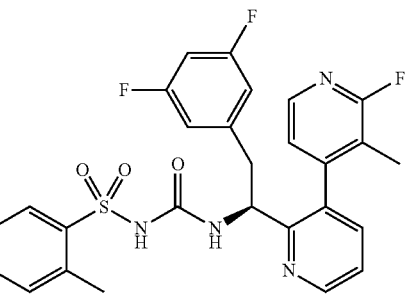

(S)-N-((2-(3,5-difluorophenyl)-1-(2'-fluoro-3'-methyl-[3,4'-bipyridin]-2-yl)ethyl)carbamoyl)-2-methylbenzenesulfonamide, TFA The title compound was prepared with the procedures described in Example 94.

| | |
|---|---|
| MS (M + H)⁺ Calcd. | 541 |
| MS (M + H)⁺ Observ. | 541 |
| Retention Time | 1.66 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

Example 127

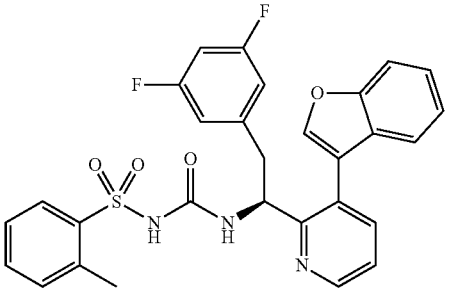 [SMILES: Cc1ccccc1S(=O)(=O)NC(=O)N[C@@H](Cc1cc(F)cc(F)c1)c1ncccc1-c1coc2ccccc12]

(S)-N-((1-(3-(benzofuran-3-yl)pyridin-2-yl)-2-(3,5-difluorophenyl)ethyl)carbamoyl)-2-methylbenzene-sulfonamide, TFA The title compound was prepared with the procedures described in Example 94.

| | |
|---|---|
| MS (M + H)⁺ Calcd. | 548 |
| MS (M + H)⁺ Observ. | 548 |
| Retention Time | 1.94 min |

-continued

| LC Condition | |
|---|---|
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 10.67 (s, 1H), 8.71 (d, J=4.8 Hz, 1H), 7.99 (s, 1H), 7.78 (t, J=7.9 Hz, 2H), 7.66 (d, J=8.4 Hz, 1H), 7.56-7.46 (m, 2H), 7.41-7.28 (m, 3H), 7.23-7.13 (m, 3H), 6.83 (t, J=9.5 Hz, 1H), 6.28 (d, J=6.2 Hz, 2H), 5.12 (q, J=7.5 Hz, 1H), 2.95-2.87 (m, 1H), 2.85-2.76 (m, 1H).

Example 128

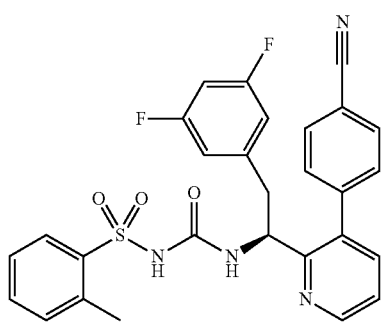 [SMILES: Cc1ccccc1S(=O)(=O)NC(=O)N[C@@H](Cc1cc(F)cc(F)c1)c1ncccc1-c1ccc(C#N)cc1]

(S)-N-((1-(3-(4-cyanophenyl)pyridin-2-yl)-2-(3,5-difluorophenyl)ethyl)carbamoyl)-2-methylbenzenesulfonamide, TFA The title compound was prepared with the procedures described in Example 94.

| MS (M + H)$^+$ Calcd. | 533 |
|---|---|
| MS (M + H)$^+$ Observ. | 533 |
| Retention Time | 1.56 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 8.71 (d, J=4.8 Hz, 1H), 7.86 (d, J=8.1 Hz, 2H), 7.79 (d, J=8.1 Hz, 1H), 7.64 (d, J=7.7 Hz, 1H), 7.56-7.50 (m, 1H), 7.46 (dd, J=7.7, 4.8 Hz, 1H), 7.39-7.31 (m, 4H), 7.16 (d, J=8.4 Hz, 1H), 6.94 (t, J=9.5 Hz, 1H), 6.31 (d, J=6.6 Hz, 2H), 4.96 (q, J=7.5 Hz, 1H), 2.88-2.83 (m, 1H), 2.83-2.77 (m, 1H), 2.73 (s, 1H).

Example 129

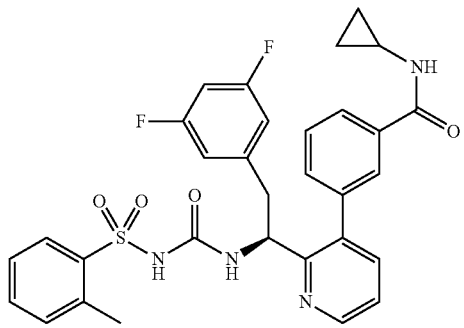 [SMILES: Cc1ccccc1S(=O)(=O)NC(=O)N[C@@H](Cc1cc(F)cc(F)c1)c1ncccc1-c1cccc(C(=O)NC2CC2)c1]

(S)-N-((2-(3,5-difluorophenyl)-1-(3-(2-methyl-2H-indazol-6-yl)pyridin-2-yl)ethyl)carbamoyl)-2-methylbenzenesulfonamide, TFA The title compound was prepared with the procedures described in Example 94.

| MS (M + H)$^+$ Calcd. | 591 |
|---|---|
| MS (M + H)$^+$ Observ. | 591 |
| Retention Time | 1.61 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

Example 130

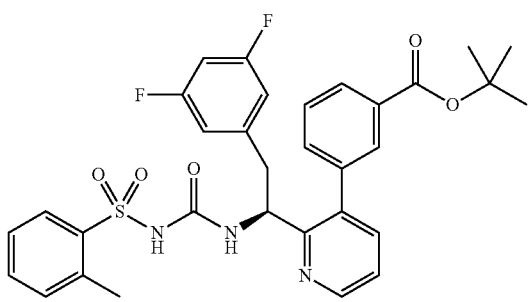 [SMILES: Cc1ccccc1S(=O)(=O)NC(=O)N[C@@H](Cc1cc(F)cc(F)c1)c1ncccc1-c1cccc(C(=O)OC(C)(C)C)c1]

(S)-tert-butyl 3-(2-(2-(3,5-difluorophenyl)-1-(3-(o-tolylsulfonyl)ureido)ethyl)pyridin-3-yl)benzoate, TFA The title compound was prepared with the procedures described in Example 94.

| MS (M + H)+ Calcd. | 608 |
|---|---|
| MS (M + H)+ Observ. | 608 |
| Retention Time | 2.07 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 10.65 (s, 1H), 8.72 (d, J=4.0 Hz, 1H), 7.98-7.89 (m, 1H), 7.78 (d, J=7.7 Hz, 1H), 7.65 (d, J=6.6 Hz, 1H), 7.58 (s, 1H), 7.56-7.49 (m, 2H), 7.48-7.40 (m, 2H), 7.37-7.30 (m, 2H), 7.18-7.11 (m, 1H), 6.88 (t, J=9.5 Hz, 1H), 6.33 (d, J=6.2 Hz, 2H), 4.99 (q, J=7.9 Hz, 1H), 2.96-2.91 (m, 1H), 2.87-2.81 (m, 1H), 2.51 (br. s., 3H), 1.54 (s, 9H)

Example 131

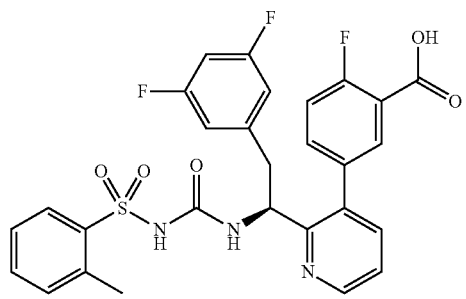 [SMILES: Cc1ccccc1S(=O)(=O)NC(=O)N[C@@H](Cc1cc(F)cc(F)c1)c1ncccc1-c1ccc(F)c(C(=O)O)c1]

(S)-5-(2-(2-(3,5-difluorophenyl)-1-(3-(o-tolylsulfonyl)ureido)ethyl)pyridin-3-yl)-2-fluorobenzoic Acid, TFA The title compound was prepared with the procedures described in Example 94.

| MS (M + H)+ Calcd. | 570 |
|---|---|
| MS (M + H)+ Observ. | 570 |
| Retention Time | 1.05 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 8.70 (d, J=4.4 Hz, 1H), 7.77 (d, J=8.1 Hz, 1H), 7.64 (d, J=7.7 Hz, 1H), 7.55-7.41 (m, 4H), 7.38-7.30 (m, 3H), 7.14 (d, J=8.8 Hz, 1H), 6.87 (t, J=9.5 Hz, 1H), 6.36 (d, J=7.0 Hz, 2H), 4.96 (q, J=7.5 Hz, 1H), 3.37 (br. s., 1H), 2.96-2.90 (m, 1H), 2.87-2.80 (m, 1H), 2.51 (br. s., 3H).

Example 132

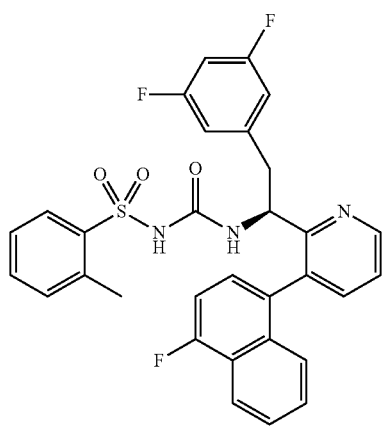 [SMILES: Cc1ccccc1S(=O)(=O)NC(=O)N[C@@H](Cc1cc(F)cc(F)c1)c1ncccc1-c1ccc(F)c2ccccc12]

(S)-N-((2-(3,5-difluorophenyl)-1-(3-(4-fluoronaphthalen-1-yl)pyridin-2-yl)ethyl)carbamoyl)-2-methylbenzenesulfonamide, TFA The title compound was prepared with the procedures described in Example 94.

| MS (M + H)+ Calcd. | 576 |
|---|---|
| MS (M + H)+ Observ. | 576 |
| Retention Time | 2.07 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 8.78 (d, J=4.8 Hz, 1H), 8.16-8.05 (m, 1H), 7.74 (d, J=7.3 Hz, 1H), 7.71-7.59 (m, 2H), 7.58-7.42 (m, 4H), 7.40-7.06 (m, 4H), 7.03-6.91 (m, 2H), 6.90-6.83 (m, 1H), 6.74 (t, J=9.2 Hz, 1H), 6.17 (d, J=7.3 Hz, 1H), 5.98 (d, J=6.2 Hz, 1H), 4.68 (d, J=7.3 Hz, 1H), 4.44-4.27 (m, 1H).

Example 133

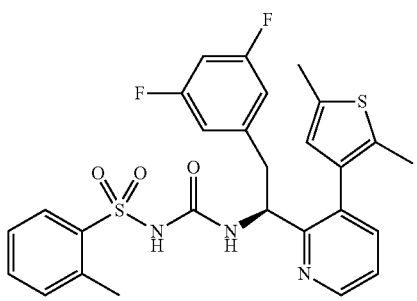 [SMILES: Cc1cc(-c2cccnc2[C@H](Cc2cc(F)cc(F)c2)NC(=O)NS(=O)(=O)c2ccccc2C)c(C)s1]

(S)-N-((2-(3,5-difluorophenyl)-1-(3-(2,5-dimethylthiophen-3-yl)pyridin-2-yl)ethyl)carbamoyl)-2-methylbenzenesulfonamide, TFA The title compound was prepared with the procedures described in Example 94.

| | |
|---|---|
| MS (M + H)+ Calcd. | 542 |
| MS (M + H)+ Observ. | 542 |
| Retention Time | 2.14 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 3 min |
| Flow Rate | 1 mL/min |
| Wavelength | 220 |
| Column | Waters BEH C18, 2.0 × 50 mm, 1.7-μm particles |

$^1$H NMR (500 MHz, DMSO-$d_6$) δ 8.63 (d, J=4.8 Hz, 1H), 7.80 (d, J=7.7 Hz, 1H), 7.55-7.49 (m, 2H), 7.39 (dd, J=7.3, 4.8 Hz, 1H), 7.36-7.30 (m, 2H), 7.20 (s, 1H), 7.16-7.08 (m, 1H), 7.01-6.92 (m, 1H), 6.26 (d, J=6.6 Hz, 3H), 4.87 (br. s., 1H), 2.85-2.77 (m, 1H), 2.75-2.66 (m, 1H), 2.33 (s, 3H), 1.85 (s, 3H).

Biological Methods

HIV cell culture assay—MT-2 cells, 293T cells and the proviral DNA clone of $NL_{4-3}$ virus were obtained from the NIH AIDS Research and Reference Reagent Program. MT-2 cells were propagated in RPMI 1640 media supplemented with 10% heat inactivated fetal bovine serum (FBS), 100 ug/ml penicillin G and up to 100 units/ml streptomycin. The 293T cells were propagated in DMEM media supplemented with 10% heat inactivated FBS, 100 ug/ml penicillin G and 100 ug/ml streptomycin. A recombinant $NL_{4-3}$ proviral clone, in which a section of the nef gene was replaced with the *Renilla luciferase* gene, was used to make the reference virus used in these studies.

The recombinant virus was prepared through transfection of the recombinant $NL_{4-3}$ proviral clone into 293T cells using Transit-293 Transfection Reagent from Mirus Bio LLC (Madison, Wis.). Supernatent was harvested after 2-3 days and the amount of virus present was titered in MT-2 cells using luciferase enzyme activity as a marker by measuring luciferase enzyme activity. Luciferase was quantitated using the EnduRen Live Cell Substrate from Promega (Madison, Wis.). Antiviral activities of compounds toward the recombinant virus were quantified by measuring luciferase activity in MT-2 cells infected for 4-5 days with the recombinant virus in the presence of serial dilutions of the compound.

The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assay. In Techniques in HIV Research. ed. Aldovini A, Walker B D. 71-76. New York: Stockton Press. 1990).

Compound cytotoxicity and the corresponding $CC_{50}$ values were determined using the same protocol as described in the antiviral assay except that uninfected cells were used. Cytotoxicity was assessed on day 4 in uninfected MT2 cells by using a XTT (2,3-bis[2-Methoxy-4-nitro-5-sulfophenyl]-2H-tetrazolium-5-carboxyanilide inner salt)-based colorimetric assay (Sigma-Aldrich, St Louis, Mo.).

Compounds demonstrate antiviral activity as depicted in Table 1 below. Activity equal to A refers to a compound having an $EC_{50} \leq 100$ nM, while B and C denote compounds having an $EC_{50}$ between 100 nM and 1 uM (B) or >1 uM (C).

TABLE 1

| Example | Structure | Activity | $EC_{50}$ (μM) | $CC_{50}$ (μM) |
|---|---|---|---|---|
| 1 | 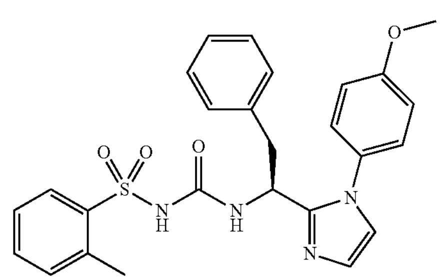 [SMILES: COc1ccc(-n2ccnc2[C@H](Cc2ccccc2)NC(=O)NS(=O)(=O)c2ccccc2C)cc1] | A | — | >100 |

TABLE 1-continued

| Example | Structure | Activity | EC$_{50}$ (μM) | CC$_{50}$ (μM) |
|---|---|---|---|---|
| 2 | 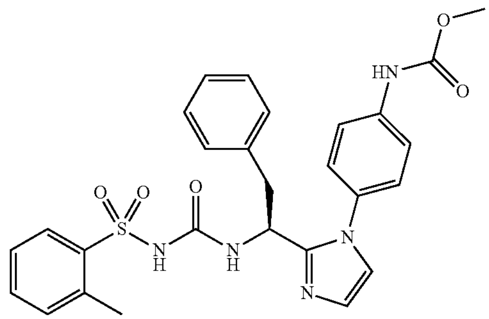 [SMILES: COC(=O)Nc1ccc(-n2ccnc2[C@H](Cc2ccccc2)NC(=O)NS(=O)(=O)c2ccccc2C)cc1] | A | — | >100 |
| 3 | 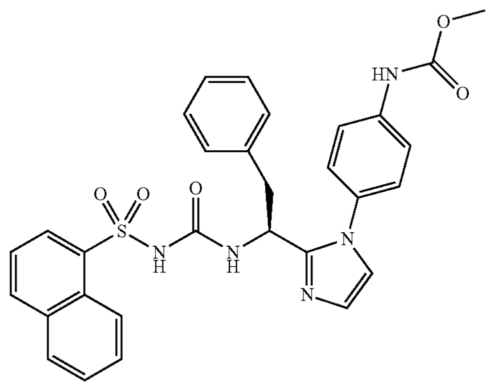 [SMILES: COC(=O)Nc1ccc(-n2ccnc2[C@H](Cc2ccccc2)NC(=O)NS(=O)(=O)c2cccc3ccccc23)cc1] | B | 0.1 | >100 |
| 4 | 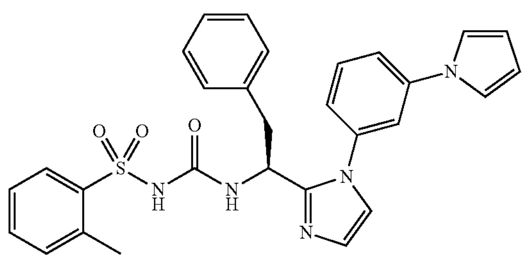 [SMILES: Cc1ccccc1S(=O)(=O)NC(=O)N[C@@H](Cc1ccccc1)c1nccn1-c1cccc(-n2cccc2)c1] | C | — | >100 |
| 5 | 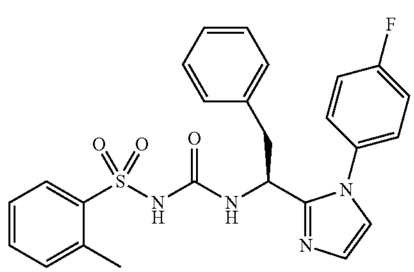 | B | — | >100 |
| 6 | 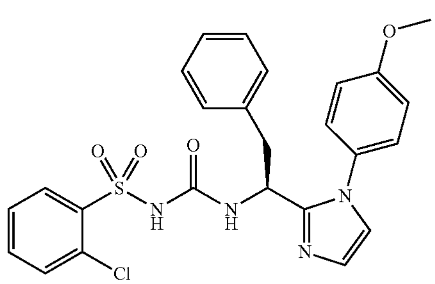 [SMILES: COc1ccc(-n2ccnc2[C@H](Cc2ccccc2)NC(=O)NS(=O)(=O)c2ccccc2Cl)cc1] | A | 0.05 | >100 |

TABLE 1-continued

| Example | Structure | Activity | EC$_{50}$ (μM) | CC$_{50}$ (μM) |
|---|---|---|---|---|
| 7 | 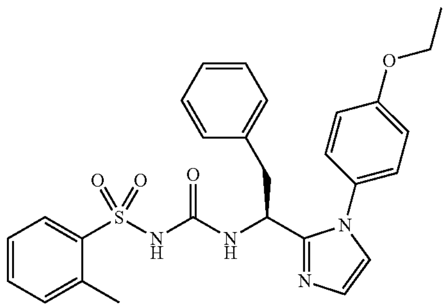 [SMILES: CCOc1ccc(-n2ccnc2[C@H](Cc2ccccc2)NC(=O)NS(=O)(=O)c2ccccc2C)cc1] | A | — | >100 |
| 8 | 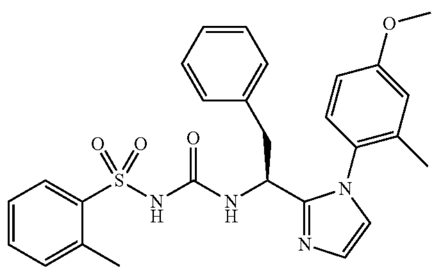 [SMILES: COc1ccc(-n2ccnc2[C@H](Cc2ccccc2)NC(=O)NS(=O)(=O)c2ccccc2C)c(C)c1] | B | — | >100 |
| 9 | 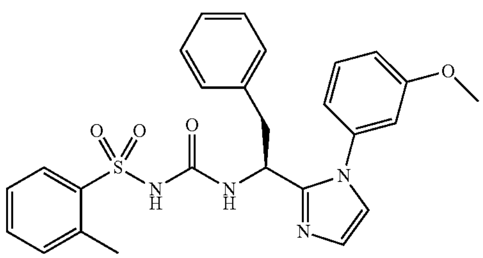 [SMILES: COc1cccc(-n2ccnc2[C@H](Cc2ccccc2)NC(=O)NS(=O)(=O)c2ccccc2C)c1] | A | 0.05 | >100 |
| 10 | 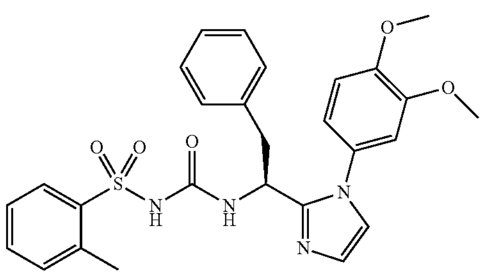 [SMILES: COc1ccc(-n2ccnc2[C@H](Cc2ccccc2)NC(=O)NS(=O)(=O)c2ccccc2C)cc1OC] | A | — | >100 |
| 11 | 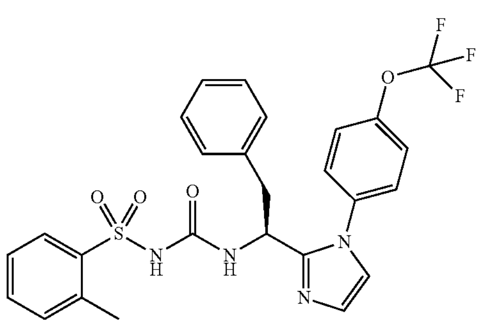 [SMILES: Cc1ccccc1S(=O)(=O)NC(=O)N[C@@H](Cc1ccccc1)c1nccn1-c1ccc(OC(F)(F)F)cc1] | A | — | 59 |

TABLE 1-continued

| Example | Structure | Activity | EC$_{50}$ (μM) | CC$_{50}$ (μM) |
|---------|-----------|----------|----------------|----------------|
| 12 | 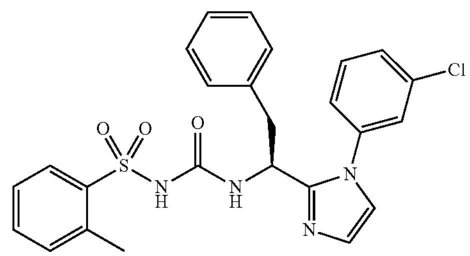 [SMILES: Cc1ccccc1S(=O)(=O)NC(=O)N[C@@H](Cc1ccccc1)c1nccn1-c1cccc(Cl)c1] | A | 0.05 | >100 |
| 13 | 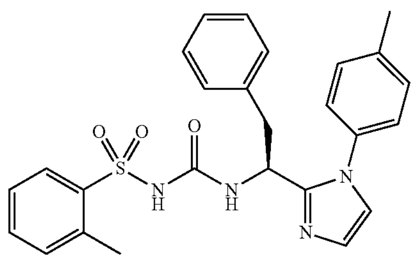 [SMILES: Cc1ccc(-n2ccnc2[C@H](Cc2ccccc2)NC(=O)NS(=O)(=O)c2ccccc2C)cc1] | A | — | >100 |
| 14 | 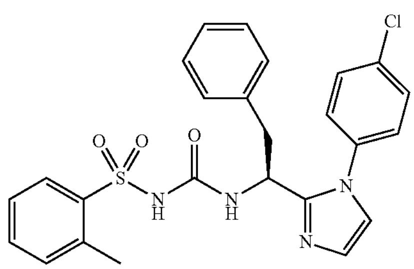 | B | — | >100 |
| 15 | 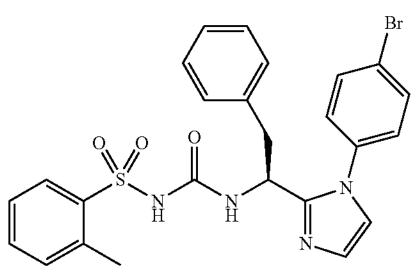 [SMILES: Cc1ccccc1S(=O)(=O)NC(=O)N[C@@H](Cc1ccccc1)c1nccn1-c1ccc(Cl)cc1] | B | 0.19 | >100 |
| 16 | 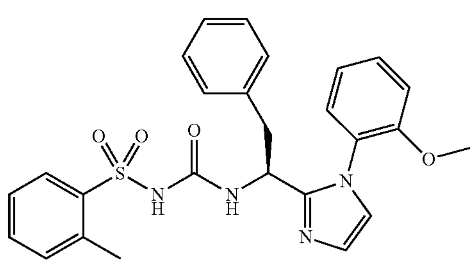 [SMILES: COc1ccccc1-n1ccnc1[C@H](Cc1ccccc1)NC(=O)NS(=O)(=O)c1ccccc1C] | C | — | >100 |
| 17 | 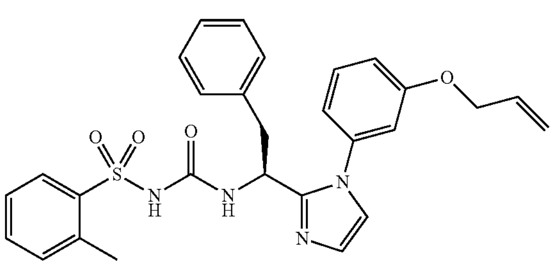 [SMILES: C=CCOc1cccc(-n2ccnc2[C@H](Cc2ccccc2)NC(=O)NS(=O)(=O)c2ccccc2C)c1] | B | — | >33 |

TABLE 1-continued

| Example | Structure | Activity | EC$_{50}$ (μM) | CC$_{50}$ (μM) |
|---------|-----------|----------|----------------|----------------|
| 18 | 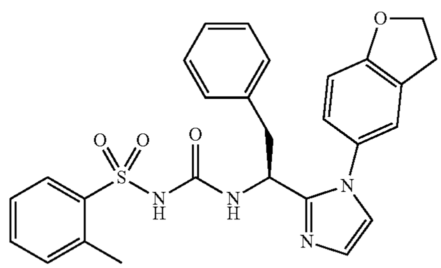 [SMILES: Cc1ccccc1S(=O)(=O)NC(=O)N[C@@H](Cc1ccccc1)c1nccn1-c1ccc2c(c1)CCO2] | A | 0.01 | >100 |
| 19 | 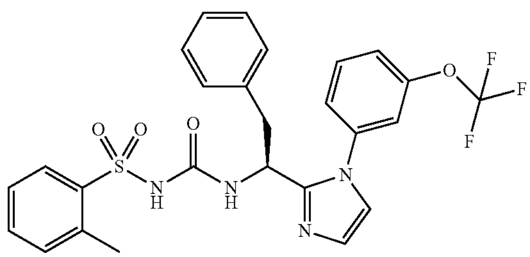 [SMILES: Cc1ccccc1S(=O)(=O)NC(=O)N[C@@H](Cc1ccccc1)c1nccn1-c1cccc(OC(F)(F)F)c1] | B | — | >33 |
| 20 | 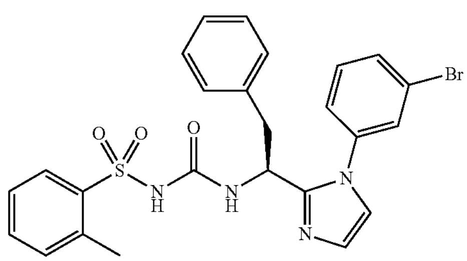 [SMILES: Cc1ccccc1S(=O)(=O)NC(=O)N[C@@H](Cc1ccccc1)c1nccn1-c1cccc(Br)c1] | A | — | >33 |
| 21 | 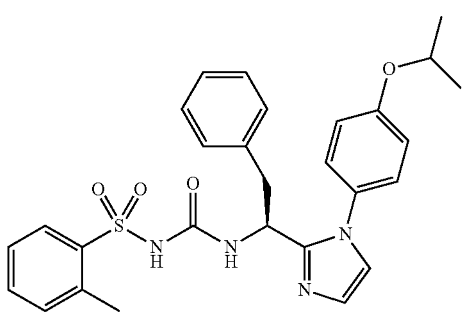 [SMILES: Cc1ccccc1S(=O)(=O)NC(=O)N[C@@H](Cc1ccccc1)c1nccn1-c1ccc(OC(C)C)cc1] | A | 0.05 | >100 |
| 22 | 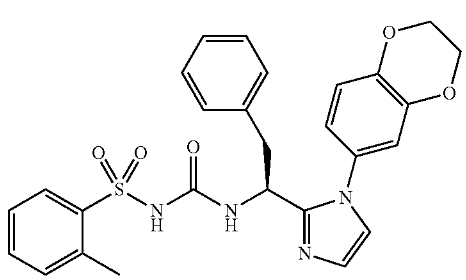 [SMILES: Cc1ccccc1S(=O)(=O)NC(=O)N[C@@H](Cc1ccccc1)c1nccn1-c1ccc2c(c1)OCCO2] | B | — | >100 |

TABLE 1-continued
| Example | Structure | Activity | EC₅₀ (μM) | CC₅₀ (μM) |
|---|---|---|---|---|
| 23 | 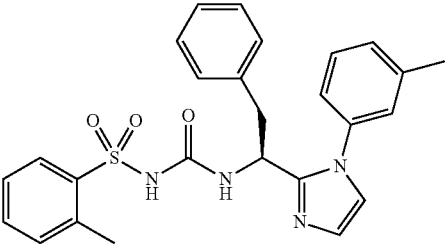 [SMILES: Cc1cccc(-n2ccnc2[C@H](Cc2ccccc2)NC(=O)NS(=O)(=O)c2ccccc2C)c1] | A | — | >100 |
| 24 | 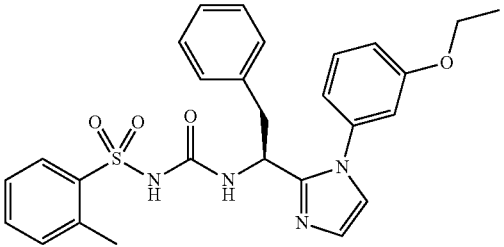 [SMILES: CCOc1cccc(-n2ccnc2[C@H](Cc2ccccc2)NC(=O)NS(=O)(=O)c2ccccc2C)c1] | B | 0.60 | >100 |
| 25 | 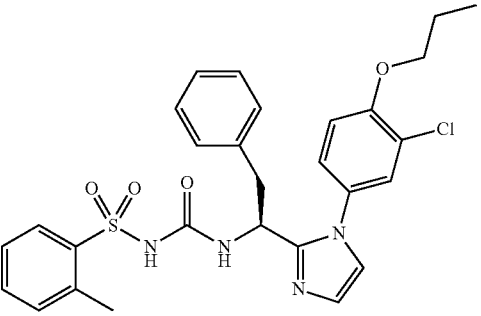 [SMILES: CCCOc1ccc(-n2ccnc2[C@H](Cc2ccccc2)NC(=O)NS(=O)(=O)c2ccccc2C)cc1Cl] | A | — | 50 |
| 26 | 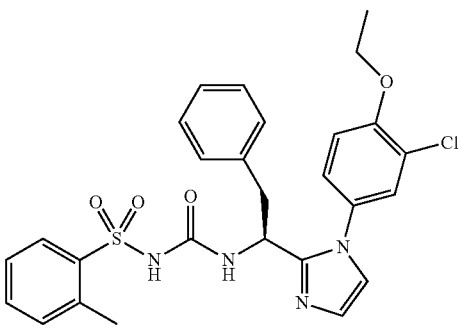 [SMILES: CCOc1ccc(-n2ccnc2[C@H](Cc2ccccc2)NC(=O)NS(=O)(=O)c2ccccc2C)cc1Cl] | A | — | >100 |
| 27 | 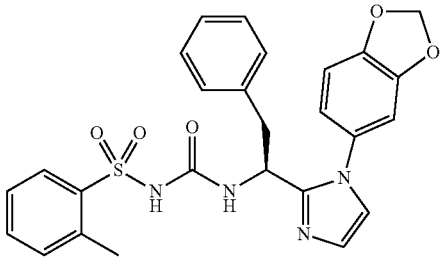 [SMILES: Cc1ccccc1S(=O)(=O)NC(=O)N[C@@H](Cc1ccccc1)c1nccn1-c1ccc2c(c1)OCO2] | A | 0.07 | >100 |

TABLE 1-continued

| Example | Structure | Activity | EC$_{50}$ (μM) | CC$_{50}$ (μM) |
|---------|-----------|----------|----------------|----------------|
| 28 | 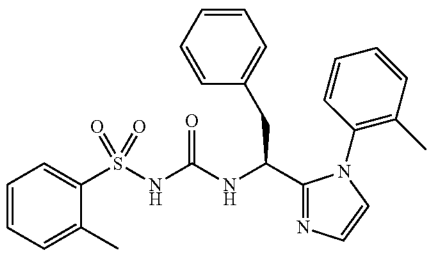 [SMILES: Cc1ccccc1-n1ccnc1[C@H](Cc1ccccc1)NC(=O)NS(=O)(=O)c1ccccc1C] | C | — | >100 |
| 29 | 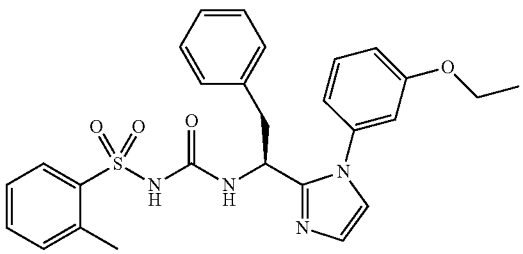 [SMILES: CCOc1cccc(-n2ccnc2[C@H](Cc2ccccc2)NC(=O)NS(=O)(=O)c2ccccc2C)c1] | C | — | >100 |
| 30 | 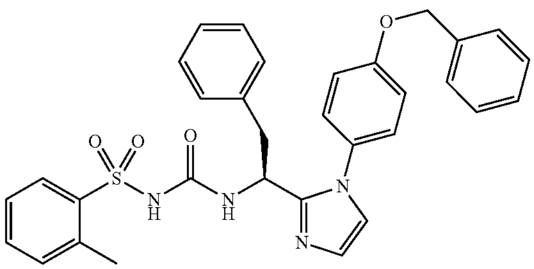 [SMILES: Cc1ccccc1S(=O)(=O)NC(=O)N[C@@H](Cc1ccccc1)c1nccn1-c1ccc(OCc2ccccc2)cc1] | B | 0.28 | >100 |
| 31 | 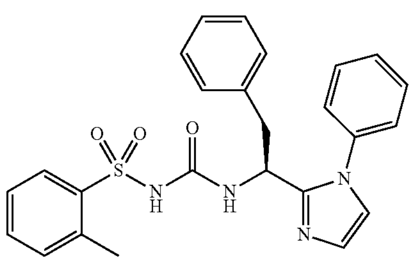 [SMILES: Cc1ccccc1S(=O)(=O)NC(=O)N[C@@H](Cc1ccccc1)c1nccn1-c1ccccc1] | B | — | >100 |
| 32 | 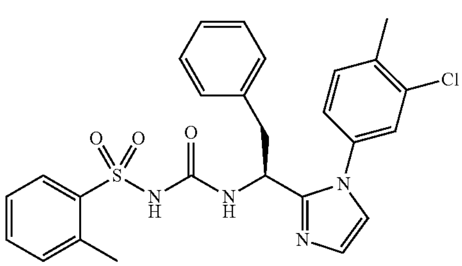 [SMILES: Cc1ccc(-n2ccnc2[C@H](Cc2ccccc2)NC(=O)NS(=O)(=O)c2ccccc2C)cc1Cl] | A | — | >100 |

TABLE 1-continued

| Example | Structure | Activity | EC$_{50}$ (μM) | CC$_{50}$ (μM) |
|---------|-----------|----------|----------------|----------------|
| 33 | 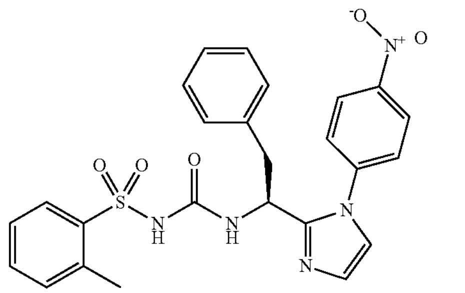 | B | 0.19 | >100 |
| 34 | 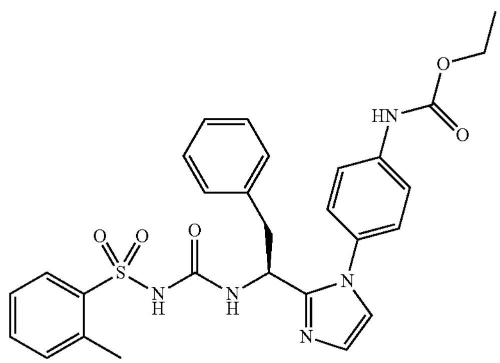 [SMILES: CCOC(=O)Nc1ccc(-n2ccnc2[C@H](Cc2ccccc2)NC(=O)NS(=O)(=O)c2ccccc2C)cc1] | A | — | >100 |
| 35 | 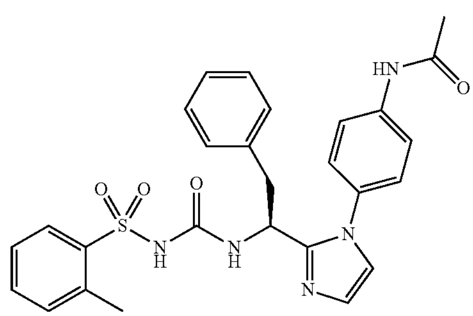 [SMILES: CC(=O)Nc1ccc(-n2ccnc2[C@H](Cc2ccccc2)NC(=O)NS(=O)(=O)c2ccccc2C)cc1] | B | — | >33 |
| 36 | 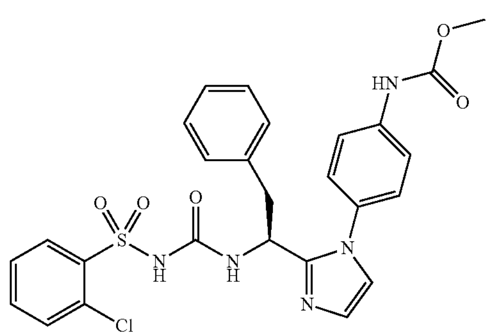 [SMILES: COC(=O)Nc1ccc(-n2ccnc2[C@H](Cc2ccccc2)NC(=O)NS(=O)(=O)c2ccccc2Cl)cc1] | A | 0.06 | >100 |

TABLE 1-continued

| Example | Structure | Activity | EC$_{50}$ (μM) | CC$_{50}$ (μM) |
|---------|-----------|----------|----------------|----------------|
| 37 | 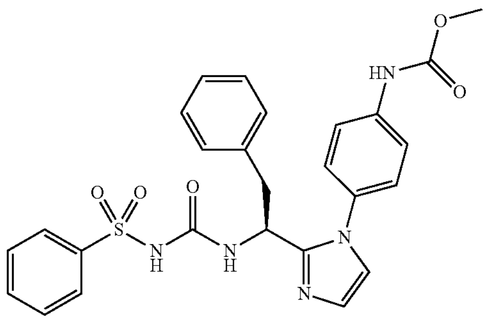 [SMILES: COC(=O)Nc1ccc(-n2ccnc2[C@H](Cc2ccccc2)NC(=O)NS(=O)(=O)c2ccccc2)cc1] | B | — | >33 |
| 38 | 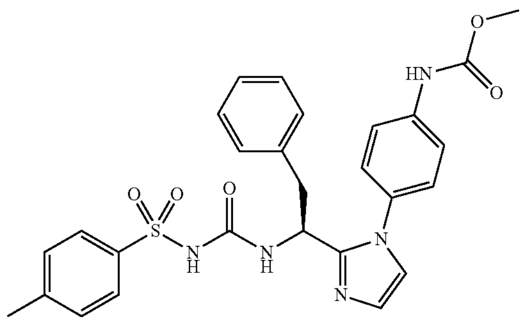 | B | — | >100 |
| 39 | 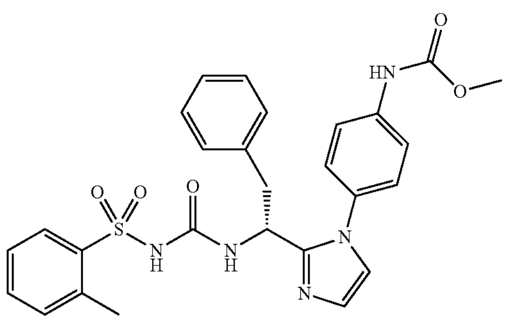 [SMILES: COC(=O)Nc1ccc(-n2ccnc2[C@@H](Cc2ccccc2)NC(=O)NS(=O)(=O)c2ccccc2C)cc1] | C | 1.42 | >11 |
| 40 | 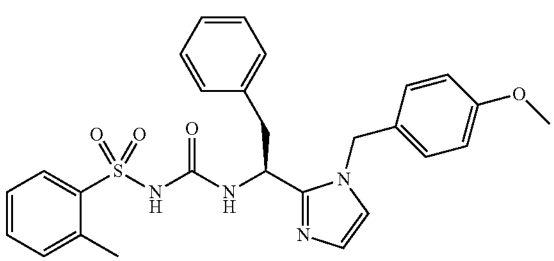 [SMILES: COc1ccc(Cn2ccnc2[C@H](Cc2ccccc2)NC(=O)NS(=O)(=O)c2ccccc2C)cc1] | B | — | >33 |
| 41 | 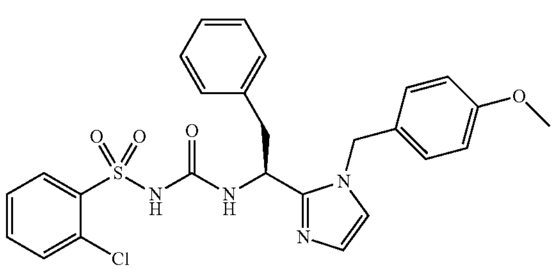 [SMILES: COc1ccc(Cn2ccnc2[C@H](Cc2ccccc2)NC(=O)NS(=O)(=O)c2ccccc2Cl)cc1] | B | — | >33 |

TABLE 1-continued

| Example | Structure | Activity | EC$_{50}$ (μM) | CC$_{50}$ (μM) |
|---|---|---|---|---|
| 42 | 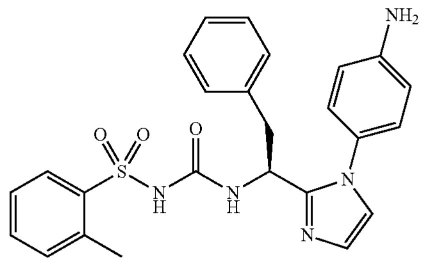 [SMILES: Cc1ccccc1S(=O)(=O)NC(=O)N[C@@H](Cc1ccccc1)c1nccn1-c1ccc(N)cc1] | A | 0.04 | >100 |
| 43 | 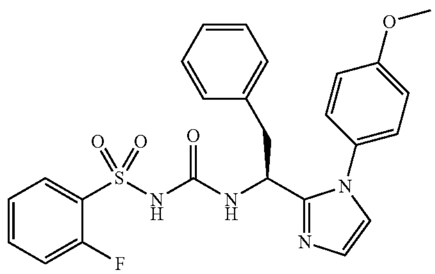 | A | — | >100 |
| 44 | 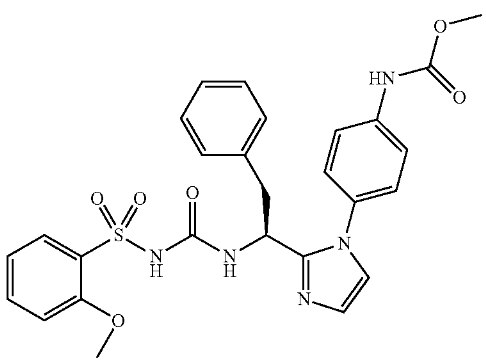 [SMILES: COC(=O)Nc1ccc(-n2ccnc2[C@H](Cc2ccccc2)NC(=O)NS(=O)(=O)c2ccccc2OC)cc1] | A | — | >100 |
| 45 | 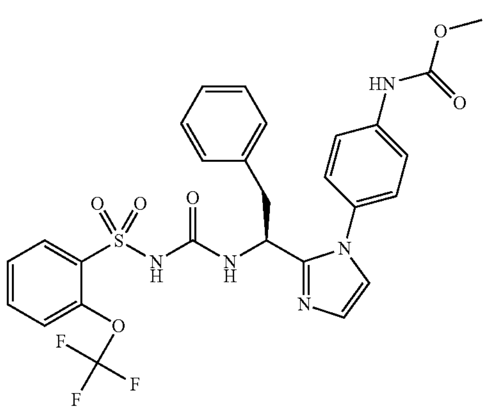 [SMILES: COC(=O)Nc1ccc(-n2ccnc2[C@H](Cc2ccccc2)NC(=O)NS(=O)(=O)c2ccccc2OC(F)(F)F)cc1] | A | 0.06 | >100 |

TABLE 1-continued

| Example | Structure | Activity | EC$_{50}$ (μM) | CC$_{50}$ (μM) |
|---|---|---|---|---|
| 46 | 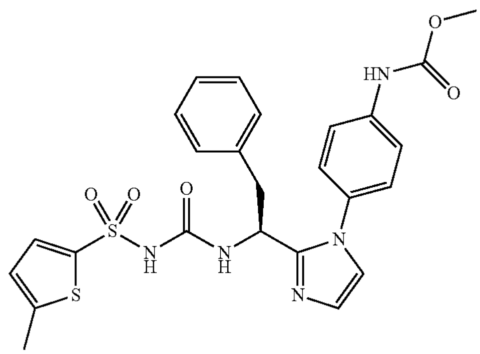 [SMILES: COC(=O)Nc1ccc(-n2ccnc2[C@H](Cc2ccccc2)NC(=O)NS(=O)(=O)c2ccc(C)s2)cc1] | B | — | >100 |
| 47 | 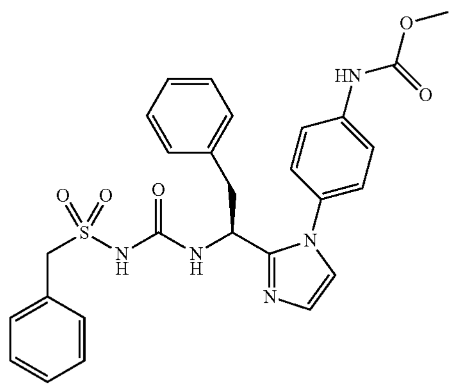 [SMILES: COC(=O)Nc1ccc(-n2ccnc2[C@H](Cc2ccccc2)NC(=O)NS(=O)(=O)Cc2ccccc2)cc1] | B | — | >33 |
| 48 | 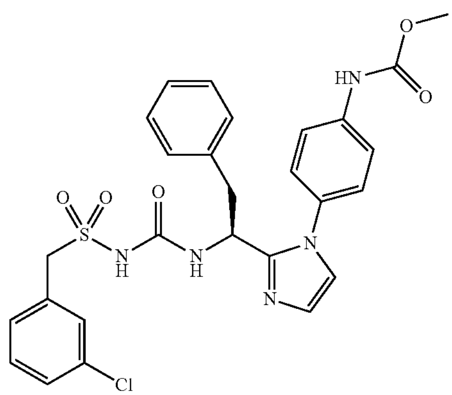 [SMILES: COC(=O)Nc1ccc(-n2ccnc2[C@H](Cc2ccccc2)NC(=O)NS(=O)(=O)Cc2cccc(Cl)c2)cc1] | A | 0.07 | >100 |
| 49 | 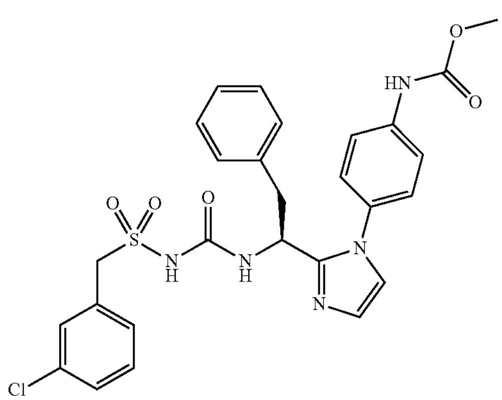 [SMILES: COC(=O)Nc1ccc(-n2ccnc2[C@H](Cc2ccccc2)NC(=O)NS(=O)(=O)Cc2cccc(Cl)c2)cc1] | B | — | >100 |

TABLE 1-continued

| Example | Structure | Activity | EC$_{50}$ (μM) | CC$_{50}$ (μM) |
|---------|-----------|----------|----------------|----------------|
| 50 | 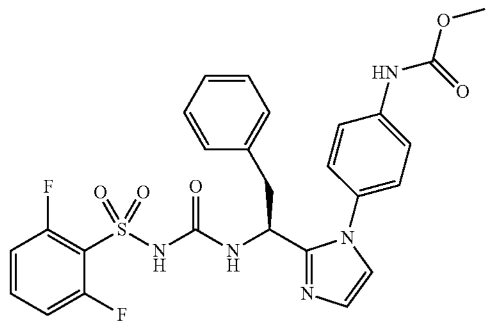 [SMILES: COC(=O)Nc1ccc(-n2ccnc2[C@H](Cc2ccccc2)NC(=O)NS(=O)(=O)c2c(F)cccc2F)cc1] | B | — | >100 |
| 51 | 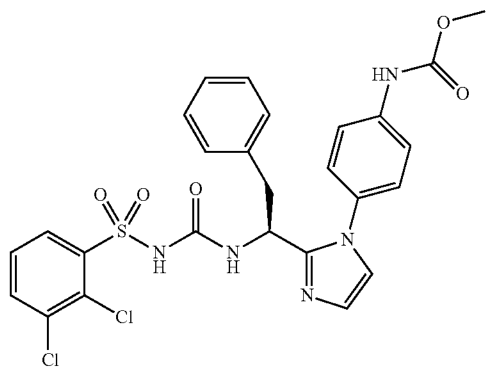 [SMILES: COC(=O)Nc1ccc(-n2ccnc2[C@H](Cc2ccccc2)NC(=O)NS(=O)(=O)c2cccc(Cl)c2Cl)cc1] | B | 0.16 | >100 |
| 52 | 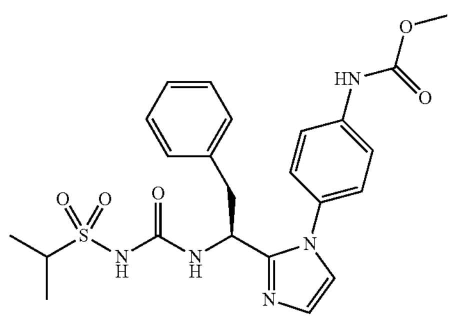 [SMILES: COC(=O)Nc1ccc(-n2ccnc2[C@H](Cc2ccccc2)NC(=O)NS(=O)(=O)C(C)C)cc1] | B | — | >100 |
| 53 | 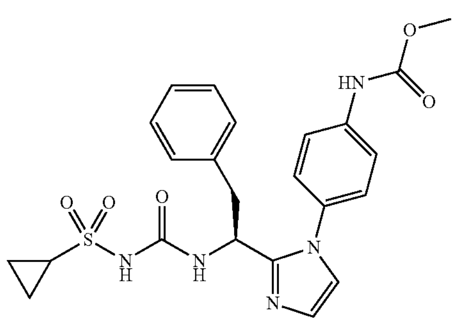 [SMILES: COC(=O)Nc1ccc(-n2ccnc2[C@H](Cc2ccccc2)NC(=O)NS(=O)(=O)C2CC2)cc1] | B | — | >100 |

TABLE 1-continued

| Example | Structure | Activity | EC$_{50}$ (μM) | CC$_{50}$ (μM) |
|---------|-----------|----------|----------------|----------------|
| 54 | 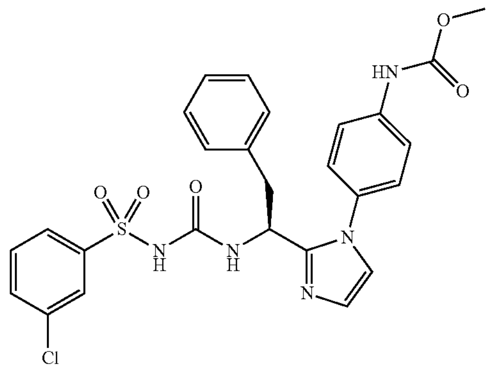 [SMILES: COC(=O)Nc1ccc(-n2ccnc2[C@H](Cc2ccccc2)NC(=O)NS(=O)(=O)c2cccc(Cl)c2)cc1] | B | 0.15 | >100 |
| 55 | 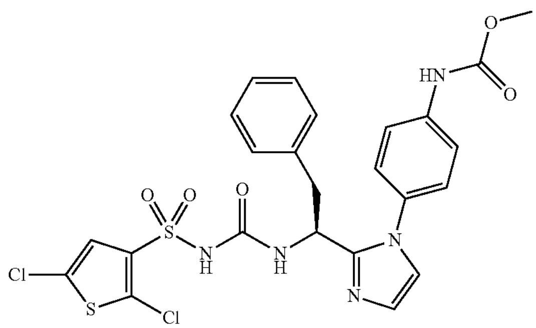 [SMILES: COC(=O)Nc1ccc(-n2ccnc2[C@H](Cc2ccccc2)NC(=O)NS(=O)(=O)c2cc(Cl)sc2Cl)cc1] | A | — | >100 |
| 56 | 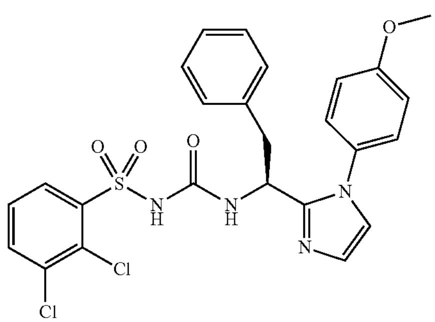 [SMILES: COc1ccc(-n2ccnc2[C@H](Cc2ccccc2)NC(=O)NS(=O)(=O)c2cccc(Cl)c2Cl)cc1] | A | — | >100 |
| 57 | 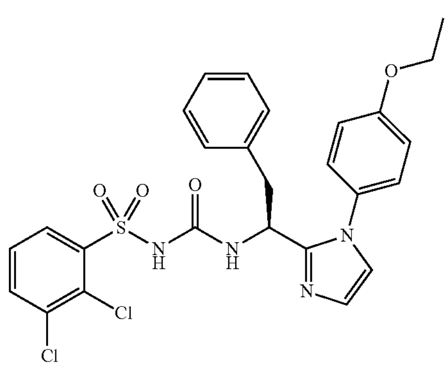 [SMILES: CCOc1ccc(-n2ccnc2[C@H](Cc2ccccc2)NC(=O)NS(=O)(=O)c2cccc(Cl)c2Cl)cc1] | A | 0.03 | >100 |

TABLE 1-continued

| Example | Structure | Activity | EC$_{50}$ (μM) | CC$_{50}$ (μM) |
|---------|-----------|----------|----------------|----------------|
| 58 | 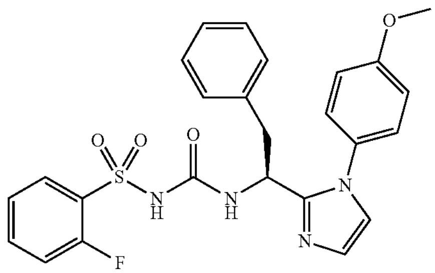 [SMILES: COc1ccc(-n2ccnc2[C@H](Cc2ccccc2)NC(=O)NS(=O)(=O)c2ccccc2F)cc1] | A | — | >33 |
| 59 | 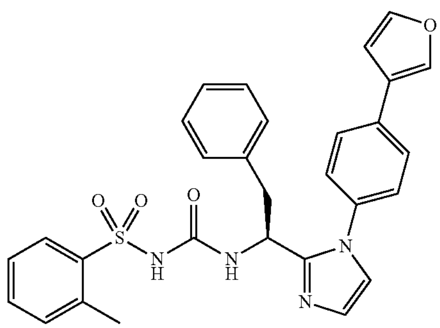 [SMILES: Cc1ccccc1S(=O)(=O)NC(=O)N[C@@H](Cc1ccccc1)c1nccn1-c1ccc(-c2ccoc2)cc1] | A | — | >33 |
| 60 | 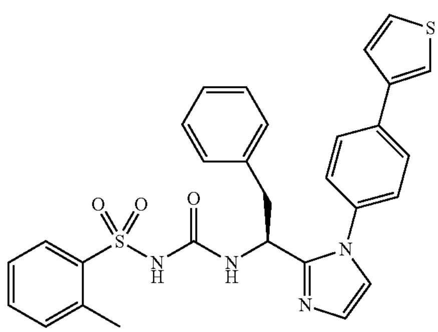 [SMILES: Cc1ccccc1S(=O)(=O)NC(=O)N[C@@H](Cc1ccccc1)c1nccn1-c1ccc(-c2ccsc2)cc1] | A | 0.03 | >100 |
| 61 | 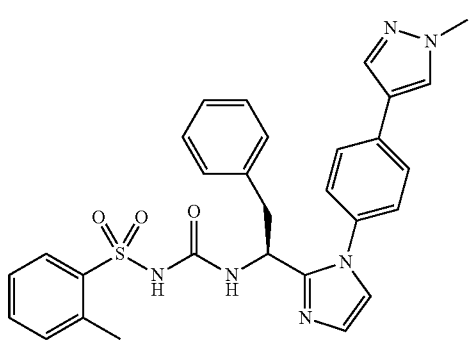 [SMILES: Cc1ccccc1S(=O)(=O)NC(=O)N[C@@H](Cc1ccccc1)c1nccn1-c1ccc(-c2cnn(C)c2)cc1] | A | — | >33 |

TABLE 1-continued
| Example | Structure | Activity | EC$_{50}$ (μM) | CC$_{50}$ (μM) |
|---------|-----------|----------|----------------|----------------|
| 62 | 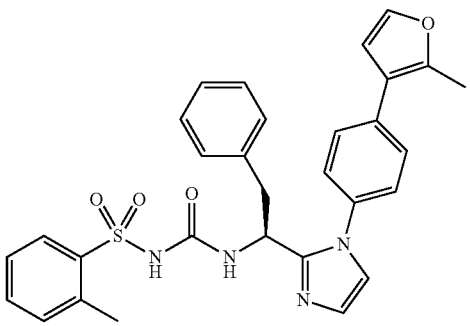 [SMILES: Cc1ccccc1S(=O)(=O)NC(=O)N[C@@H](Cc1ccccc1)c1nccn1-c1ccc(-c2ccoc2C)cc1] | A | — | >100 |
| 63 | 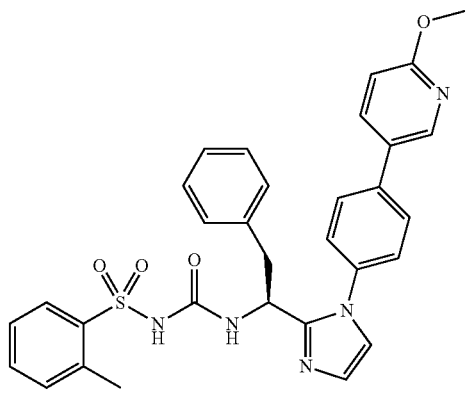 [SMILES: COc1ccc(-c2ccc(-n3ccnc3[C@H](Cc3ccccc3)NC(=O)NS(=O)(=O)c3ccccc3C)cc2)cn1] | B | 0.1 | >100 |
| 64 | 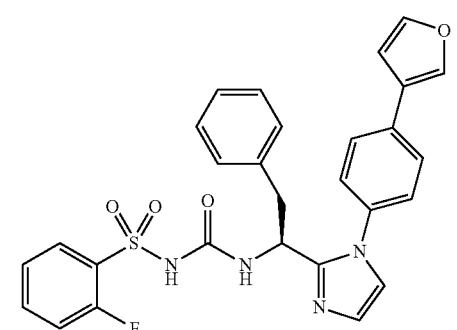 | A | — | >100 |
| 65 | 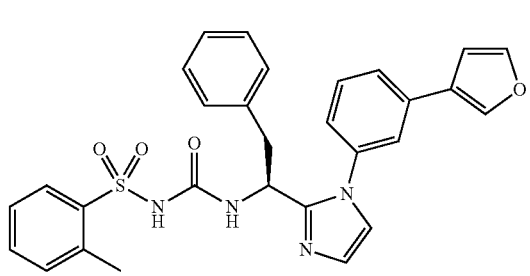 [SMILES: Cc1ccccc1S(=O)(=O)NC(=O)N[C@@H](Cc1ccccc1)c1nccn1-c1cccc(-c2ccoc2)c1] | B | — | >100 |

TABLE 1-continued

| Example | Structure | Activity | EC$_{50}$ (μM) | CC$_{50}$ (μM) |
|---------|-----------|----------|----------------|----------------|
| 66 | 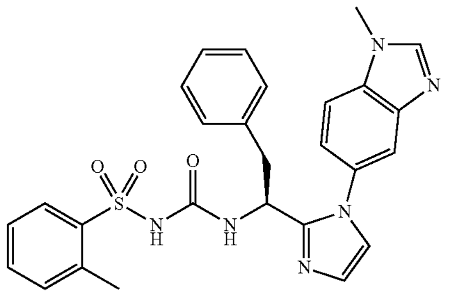 [SMILES: Cc1ccccc1S(=O)(=O)NC(=O)N[C@@H](Cc1ccccc1)c1nccn1-c1ccc2c(c1)ncn2C] | B | 0.34 | >100 |
| 67 | 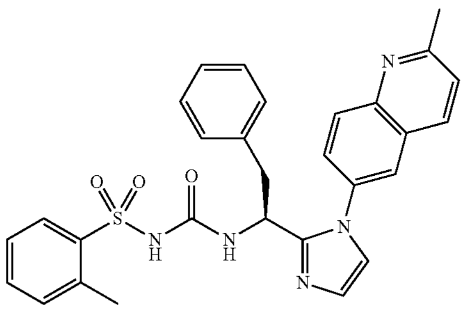 [SMILES: Cc1ccc2cc(-n3ccnc3[C@H](Cc3ccccc3)NC(=O)NS(=O)(=O)c3ccccc3C)ccc2n1] | A | — | >100 |
| 68 | 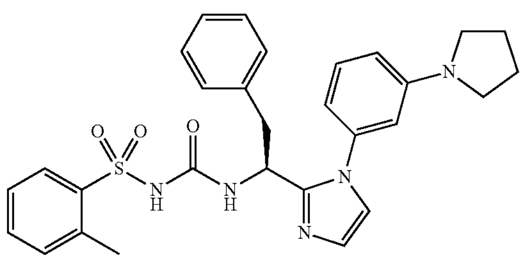 [SMILES: Cc1ccccc1S(=O)(=O)NC(=O)N[C@@H](Cc1ccccc1)c1nccn1-c1cccc(N2CCCC2)c1] | B | — | >100 |
| 69 | 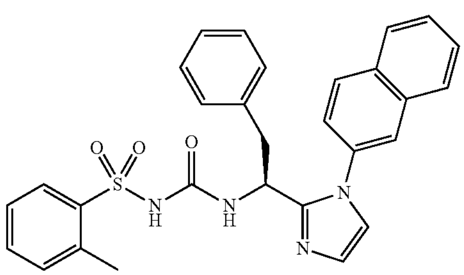 [SMILES: Cc1ccccc1S(=O)(=O)NC(=O)N[C@@H](Cc1ccccc1)c1nccn1-c1ccc2ccccc2c1] | A | 0.04 | >100 |
| 70 | 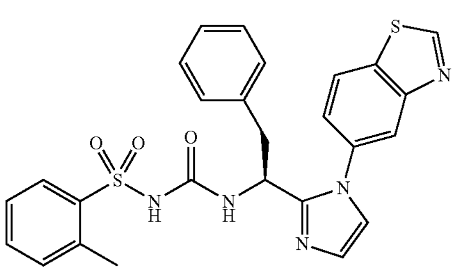 [SMILES: Cc1ccccc1S(=O)(=O)NC(=O)N[C@@H](Cc1ccccc1)c1nccn1-c1ccc2scnc2c1] | A | — | >100 |

TABLE 1-continued

| Example | Structure | Activity | EC$_{50}$ (μM) | CC$_{50}$ (μM) |
|---|---|---|---|---|
| 71 | 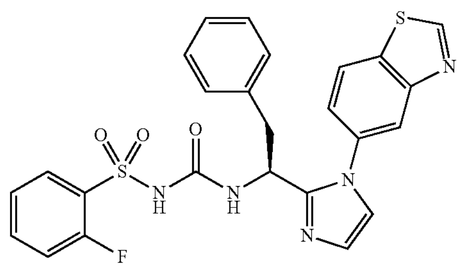 [SMILES: O=C(N[C@@H](Cc1ccccc1)c1nccn1-c1ccc2scnc2c1)NS(=O)(=O)c1ccccc1F] | B | — | >100 |
| 72 | 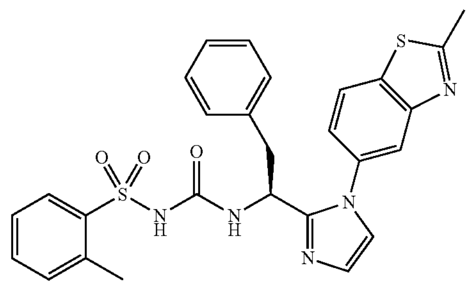 [SMILES: Cc1nc2cc(-n3ccnc3[C@H](Cc3ccccc3)NC(=O)NS(=O)(=O)c3ccccc3C)ccc2s1] | A | 0.05 | >100 |
| 73 | 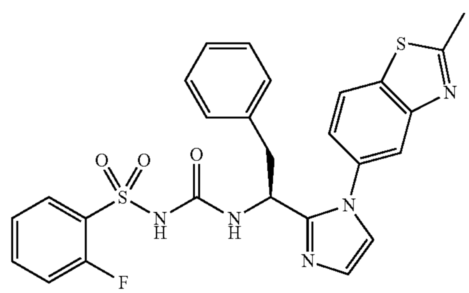 [SMILES: Cc1nc2cc(-n3ccnc3[C@H](Cc3ccccc3)NC(=O)NS(=O)(=O)c3ccccc3F)ccc2s1] | B | — | >100 |
| 74 | 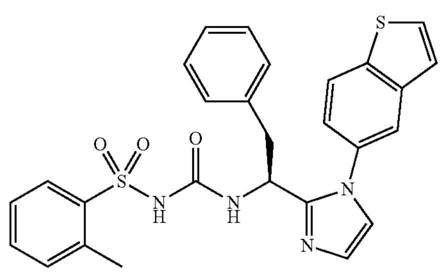 [SMILES: Cc1ccccc1S(=O)(=O)NC(=O)N[C@@H](Cc1ccccc1)c1nccn1-c1ccc2sccc2c1] | A | — | 39 |
| 75 | 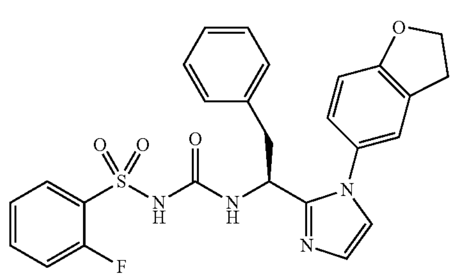 [SMILES: O=C(N[C@@H](Cc1ccccc1)c1nccn1-c1ccc2c(c1)CCO2)NS(=O)(=O)c1ccccc1F] | A | 0.02 | >100 |

TABLE 1-continued

| Example | Structure | Activity | EC$_{50}$ (μM) | CC$_{50}$ (μM) |
|---|---|---|---|---|
| 76 | 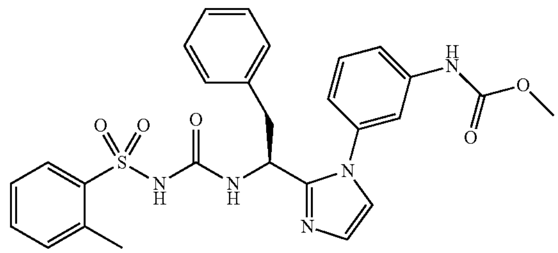 [SMILES: COC(=O)Nc1cccc(-n2ccnc2[C@H](Cc2ccccc2)NC(=O)NS(=O)(=O)c2ccccc2C)c1] | B | — | >100 |
| 77 | 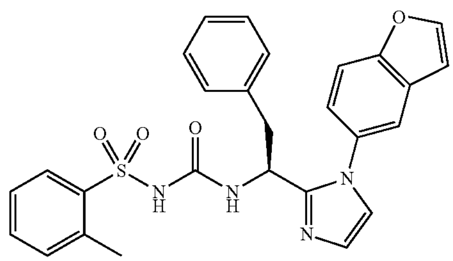 [SMILES: Cc1ccccc1S(=O)(=O)NC(=O)N[C@@H](Cc1ccccc1)c1nccn1-c1ccc2occc2c1] | A | — | >100 |
| 78 | 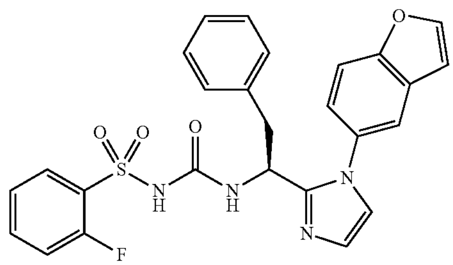 [SMILES: O=C(N[C@@H](Cc1ccccc1)c1nccn1-c1ccc2occc2c1)NS(=O)(=O)c1ccccc1F] | A | 0.02 | >100 |
| 79 | 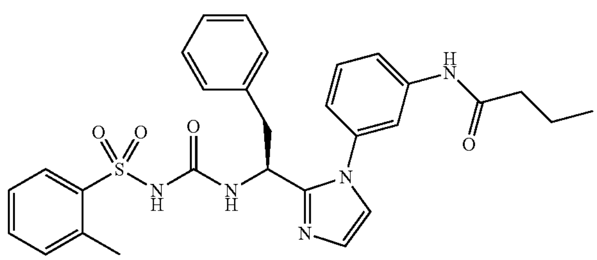 [SMILES: CCCC(=O)Nc1cccc(-n2ccnc2[C@H](Cc2ccccc2)NC(=O)NS(=O)(=O)c2ccccc2C)c1] | C | — | >100 |
| 80 | 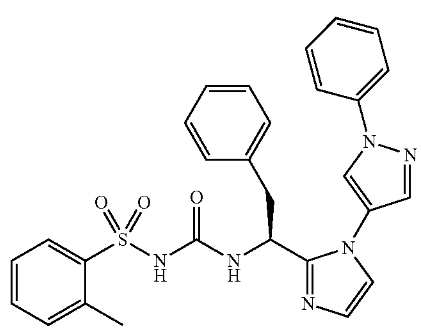 [SMILES: Cc1ccccc1S(=O)(=O)NC(=O)N[C@@H](Cc1ccccc1)c1nccn1-c1cnn(-c2ccccc2)c1] | A | — | >100 |

TABLE 1-continued

| Example | Structure | Activity | EC$_{50}$ (μM) | CC$_{50}$ (μM) |
|---------|-----------|----------|----------------|----------------|
| 81 | 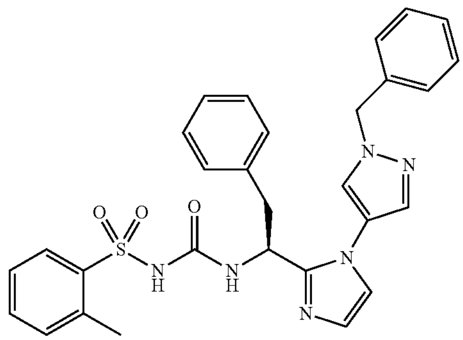 [SMILES: Cc1ccccc1S(=O)(=O)NC(=O)N[C@@H](Cc1ccccc1)c1nccn1-c1cnn(Cc2ccccc2)c1] | B | 0.55 | >100 |
| 82 | 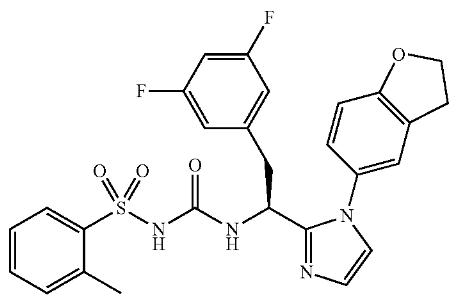 [SMILES: Cc1ccccc1S(=O)(=O)NC(=O)N[C@@H](Cc1cc(F)cc(F)c1)c1nccn1-c1ccc2c(c1)CCO2] | B | — | >100 |
| 83 | 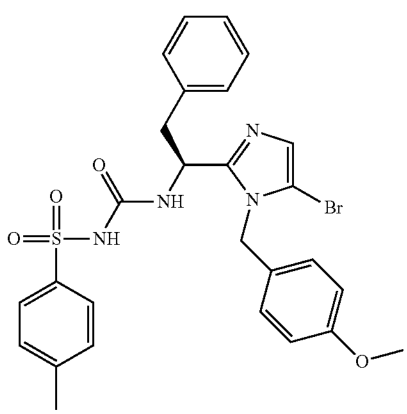 [SMILES: COc1ccc(Cn2c(Br)cnc2[C@H](Cc2ccccc2)NC(=O)NS(=O)(=O)c2ccc(C)cc2)cc1] | C | — | >33 |
| 84 | 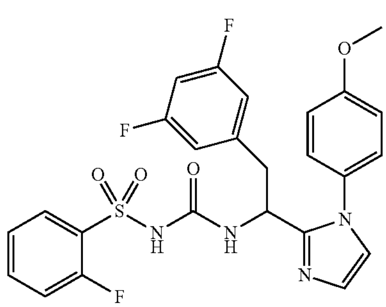 [SMILES: COc1ccc(-n2ccnc2C(Cc2cc(F)cc(F)c2)NC(=O)NS(=O)(=O)c2ccccc2F)cc1] | B | 0.69 | >100 |

TABLE 1-continued

| Example | Structure | Activity | EC$_{50}$ (μM) | CC$_{50}$ (μM) |
|---|---|---|---|---|
| 85 | 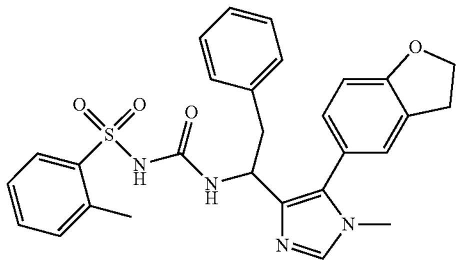 [SMILES: Cc1ccccc1S(=O)(=O)NC(=O)NC(Cc1ccccc1)c1ncn(C)c1-c1ccc2c(c1)CCO2] | B | — | >100 |
| 86 | 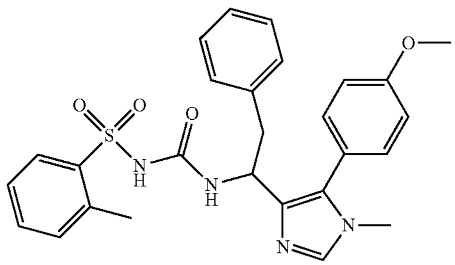 [SMILES: COc1ccc(-c2c(C(Cc3ccccc3)NC(=O)NS(=O)(=O)c3ccccc3C)ncn2C)cc1] | B | — | >100 |
| 87 | 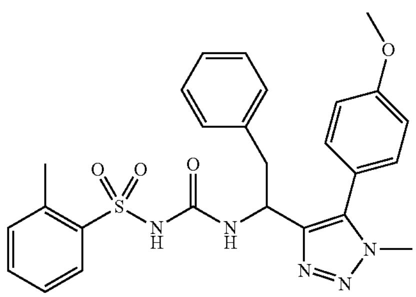 [SMILES: COc1ccc(-c2c(C(Cc3ccccc3)NC(=O)NS(=O)(=O)c3ccccc3C)nnn2C)cc1] | B | 0.22 | >100 |
| 88 | 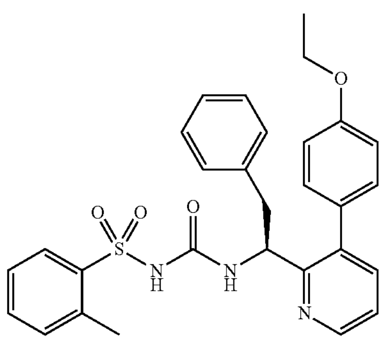 [SMILES: CCOc1ccc(-c2cccnc2[C@H](Cc2ccccc2)NC(=O)NS(=O)(=O)c2ccccc2C)cc1] | B | — | >100 |
| 89 | 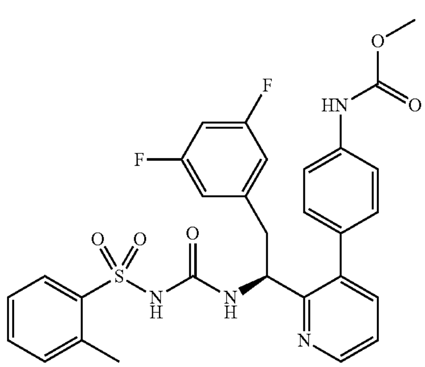 [SMILES: COC(=O)Nc1ccc(-c2cccnc2[C@H](Cc2cc(F)cc(F)c2)NC(=O)NS(=O)(=O)c2ccccc2C)cc1] | B | — | >100 |

TABLE 1-continued

| Example | Structure | Activity | EC$_{50}$ (μM) | CC$_{50}$ (μM) |
|---|---|---|---|---|
| 90 | 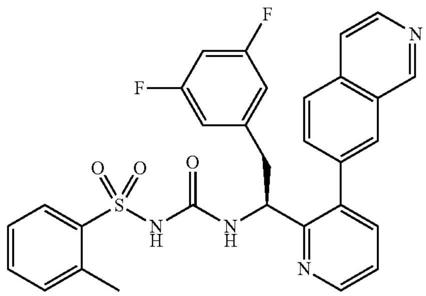 [SMILES: Cc1ccccc1S(=O)(=O)NC(=O)N[C@@H](Cc1cc(F)cc(F)c1)c1ncccc1-c1ccc2ccncc2c1] | B | 0.23 | >100 |
| 91 | 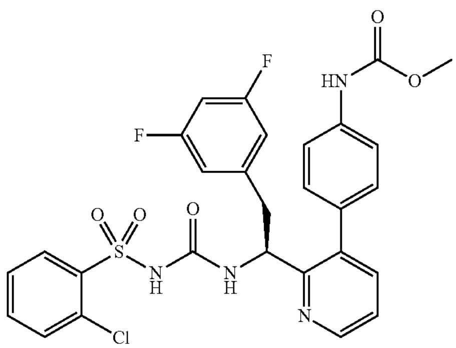 [SMILES: COC(=O)Nc1ccc(-c2cccnc2[C@H](Cc2cc(F)cc(F)c2)NC(=O)NS(=O)(=O)c2ccccc2Cl)cc1] | B | — | >100 |
| 92 | 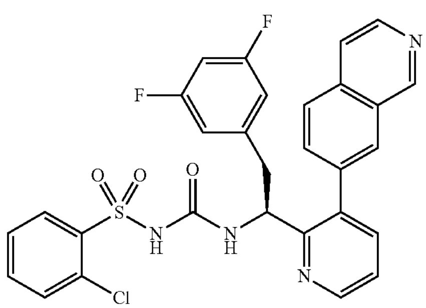 [SMILES: O=C(N[C@@H](Cc1cc(F)cc(F)c1)c1ncccc1-c1ccc2ccncc2c1)NS(=O)(=O)c1ccccc1Cl] | B | — | >100 |
| 93 | 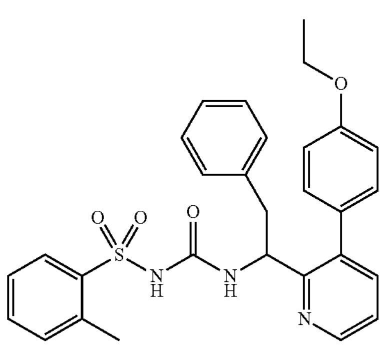 [SMILES: CCOc1ccc(-c2cccnc2C(Cc2ccccc2)NC(=O)NS(=O)(=O)c2ccccc2C)cc1] | B | 0.42 | >100 |

TABLE 1-continued

| Example | Structure | Activity | EC$_{50}$ (μM) | CC$_{50}$ (μM) |
|---------|-----------|----------|----------------|----------------|
| 94 | 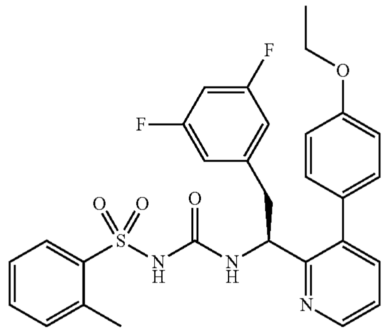 [SMILES: CCOc1ccc(-c2cccnc2[C@H](Cc2cc(F)cc(F)c2)NC(=O)NS(=O)(=O)c2ccccc2C)cc1] | B | — | >100 |
| 95 | 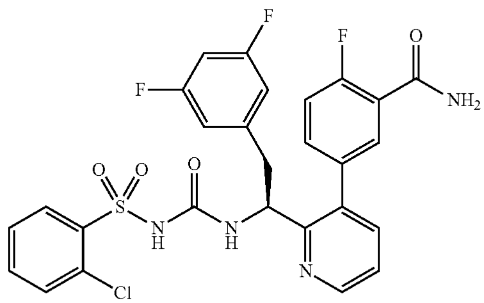 [SMILES: NC(=O)c1cc(-c2cccnc2[C@H](Cc2cc(F)cc(F)c2)NC(=O)NS(=O)(=O)c2ccccc2Cl)ccc1F] | B | — | >100 |
| 96 | 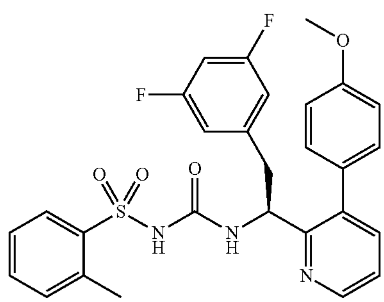 [SMILES: COc1ccc(-c2cccnc2[C@H](Cc2cc(F)cc(F)c2)NC(=O)NS(=O)(=O)c2ccccc2C)cc1] | B | 0.59 | >33 |
| 97 | 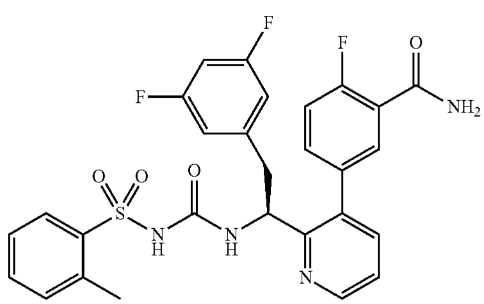 [SMILES: Cc1ccccc1S(=O)(=O)NC(=O)N[C@@H](Cc1cc(F)cc(F)c1)c1ncccc1-c1ccc(F)c(C(N)=O)c1] | B | — | >100 |
| 98 | 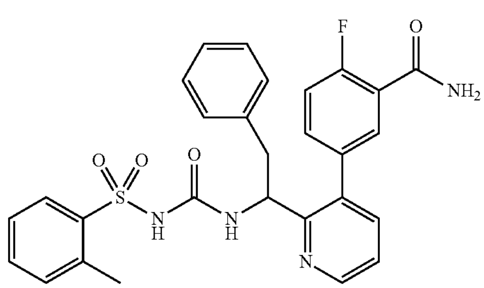 [SMILES: Cc1ccccc1S(=O)(=O)NC(=O)NC(Cc1ccccc1)c1ncccc1-c1ccc(F)c(C(N)=O)c1] | B | — | >33 |

TABLE 1-continued

| Example | Structure | Activity | EC$_{50}$ (μM) | CC$_{50}$ (μM) |
|---|---|---|---|---|
| 99 | 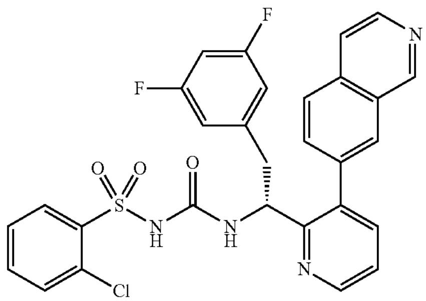 [SMILES: O=C(N[C@H](Cc1cc(F)cc(F)c1)c1ncccc1-c1ccc2ccncc2c1)NS(=O)(=O)c1ccccc1Cl] | C | 1.06 | >33 |
| 100 | 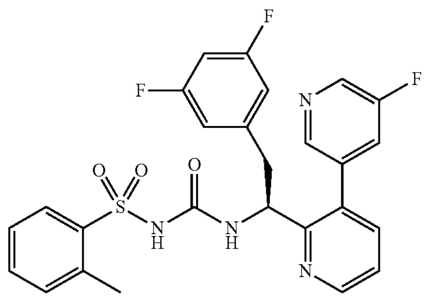 [SMILES: Cc1ccccc1S(=O)(=O)NC(=O)N[C@@H](Cc1cc(F)cc(F)c1)c1ncccc1-c1cncc(F)c1] | C | — | >100 |
| 101 | 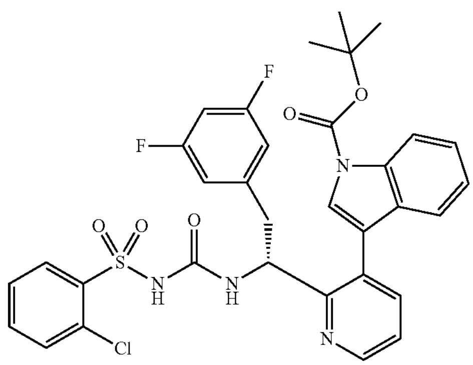 [SMILES: CC(C)(C)OC(=O)n1cc(-c2cccnc2[C@@H](Cc2cc(F)cc(F)c2)NC(=O)NS(=O)(=O)c2ccccc2Cl)c2ccccc21] | C | — | 36 |
| 102 | 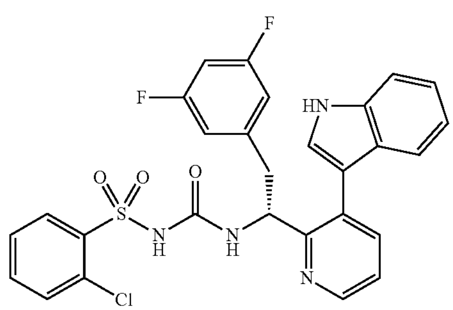 [SMILES: O=C(N[C@H](Cc1cc(F)cc(F)c1)c1ncccc1-c1c[nH]c2ccccc12)NS(=O)(=O)c1ccccc1Cl] | C | 11.46 | >33 |
| 103 | 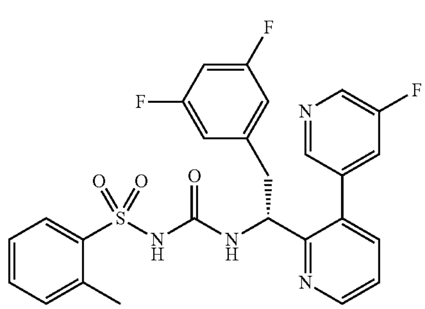 [SMILES: Cc1ccccc1S(=O)(=O)NC(=O)N[C@H](Cc1cc(F)cc(F)c1)c1ncccc1-c1cncc(F)c1] | C | — | >100 |

TABLE 1-continued

| Example | Structure | Activity | EC$_{50}$ (μM) | CC$_{50}$ (μM) |
|---|---|---|---|---|
| 104 | 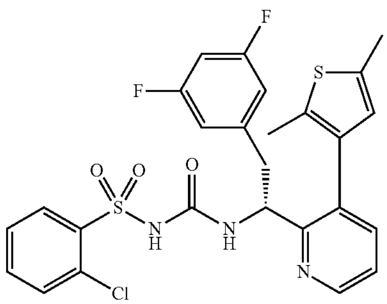 [SMILES: Cc1cc(-c2cccnc2[C@@H](Cc2cc(F)cc(F)c2)NC(=O)NS(=O)(=O)c2ccccc2Cl)c(C)s1] | C | — | >33 |
| 105 | 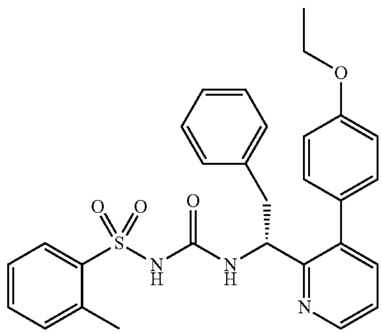 [SMILES: CCOc1ccc(-c2cccnc2[C@@H](Cc2ccccc2)NC(=O)NS(=O)(=O)c2ccccc2C)cc1] | C | 16.71 | 75 |
| 106 | 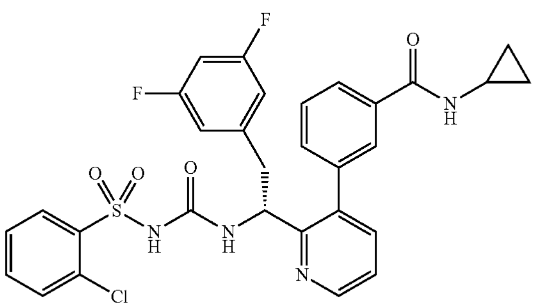 [SMILES: O=C(N[C@H](Cc1cc(F)cc(F)c1)c1ncccc1-c1cccc(C(=O)NC2CC2)c1)NS(=O)(=O)c1ccccc1Cl] | C | — | >100 |
| 107 | 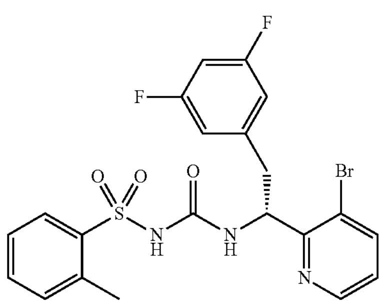 [SMILES: Cc1ccccc1S(=O)(=O)NC(=O)N[C@H](Cc1cc(F)cc(F)c1)c1ncccc1Br] | C | — | >33 |
| 108 | 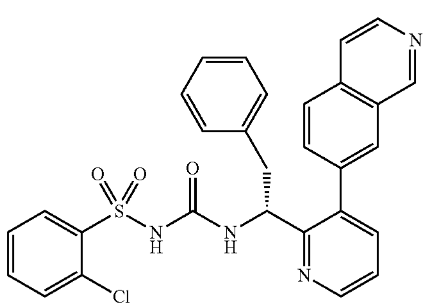 [SMILES: O=C(N[C@H](Cc1ccccc1)c1ncccc1-c1ccc2ccncc2c1)NS(=O)(=O)c1ccccc1Cl] | C | 19.99 | >100 |

TABLE 1-continued

| Example | Structure | Activity | EC$_{50}$ (μM) | CC$_{50}$ (μM) |
|---|---|---|---|---|
| 109 | 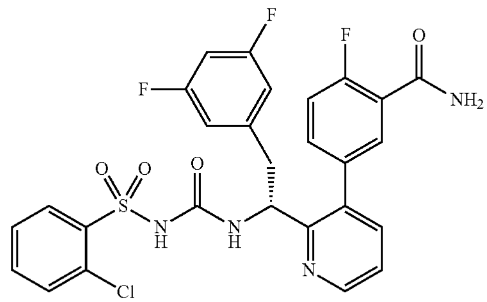 [SMILES: NC(=O)c1cc(-c2cccnc2[C@@H](Cc2cc(F)cc(F)c2)NC(=O)NS(=O)(=O)c2ccccc2Cl)ccc1F] | C | — | >100 |
| 110 | 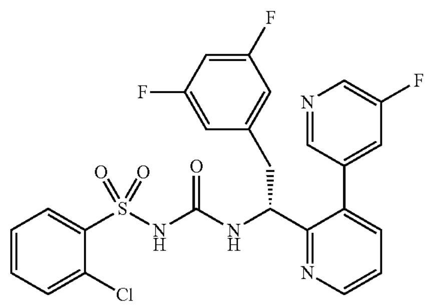 [SMILES: O=C(N[C@H](Cc1cc(F)cc(F)c1)c1ncccc1-c1cncc(F)c1)NS(=O)(=O)c1ccccc1Cl] | C | — | >33 |
| 111 | 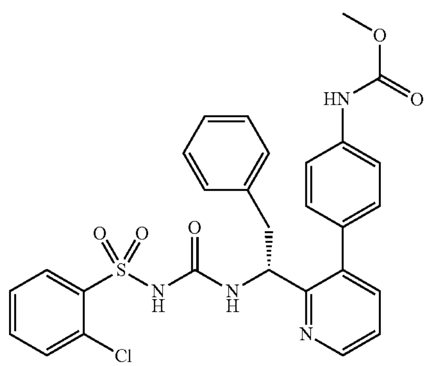 [SMILES: COC(=O)Nc1ccc(-c2cccnc2[C@@H](Cc2ccccc2)NC(=O)NS(=O)(=O)c2ccccc2Cl)cc1] | C | 30.40 | 82 |
| 112 | 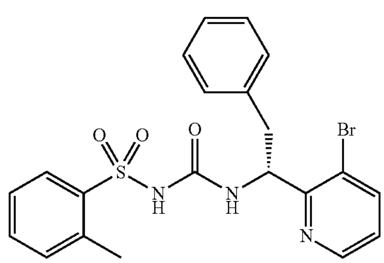 | C | — | >100 |
| 113 | 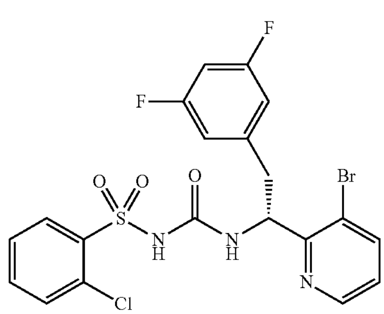 [SMILES: O=C(N[C@H](Cc1cc(F)cc(F)c1)c1ncccc1Br)NS(=O)(=O)c1ccccc1Cl] | C | — | >100 |

TABLE 1-continued

| Example | Structure | Activity | EC$_{50}$ (μM) | CC$_{50}$ (μM) |
|---------|-----------|----------|----------------|----------------|
| 114 | 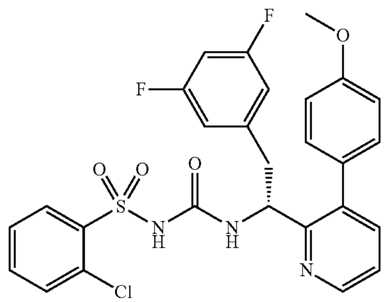 [SMILES: COc1ccc(-c2cccnc2[C@@H](Cc2cc(F)cc(F)c2)NC(=O)NS(=O)(=O)c2ccccc2Cl)cc1] | C | 34.44 | >100 |
| 115 | 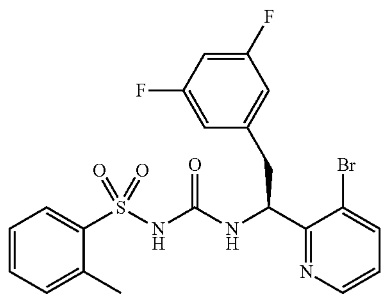 [SMILES: Cc1ccccc1S(=O)(=O)NC(=O)N[C@@H](Cc1cc(F)cc(F)c1)c1ncccc1Br] | C | — | >100 |
| 116 | 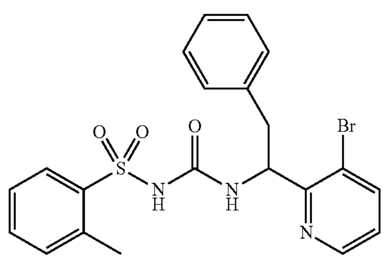 [SMILES: Cc1ccccc1S(=O)(=O)NC(=O)NC(Cc1ccccc1)c1ncccc1Br] | C | — | >100 |
| 117 | 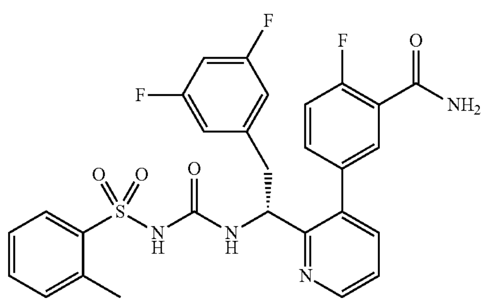 [SMILES: Cc1ccccc1S(=O)(=O)NC(=O)N[C@H](Cc1cc(F)cc(F)c1)c1ncccc1-c1ccc(F)c(C(N)=O)c1] | C | 8.34 | >100 |
| 118 | 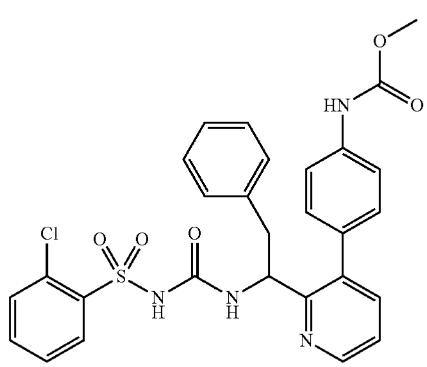 [SMILES: COC(=O)Nc1ccc(-c2cccnc2C(Cc2ccccc2)NC(=O)NS(=O)(=O)c2ccccc2Cl)cc1] | C | — | >100 |

TABLE 1-continued

| Example | Structure | Activity | EC$_{50}$ (μM) | CC$_{50}$ (μM) |
|---------|-----------|----------|----------------|----------------|
| 119 | 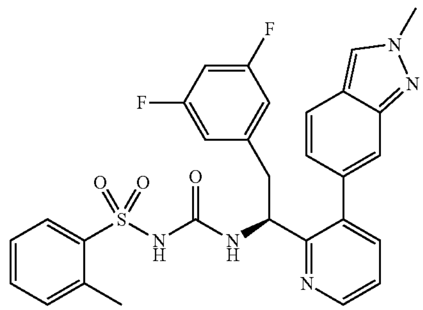 [SMILES: Cc1ccccc1S(=O)(=O)NC(=O)N[C@@H](Cc1cc(F)cc(F)c1)c1ncccc1-c1ccc2cn(C)nc2c1] | B | — | 58 |
| 120 | 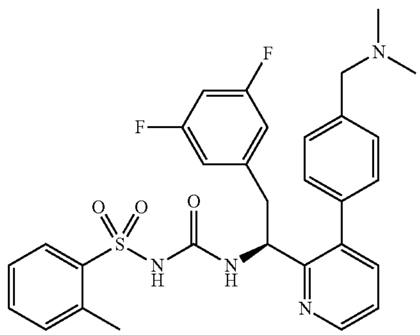 [SMILES: Cc1ccccc1S(=O)(=O)NC(=O)N[C@@H](Cc1cc(F)cc(F)c1)c1ncccc1-c1ccc(CN(C)C)cc1] | B | 0.36 | >100 |
| 121 | 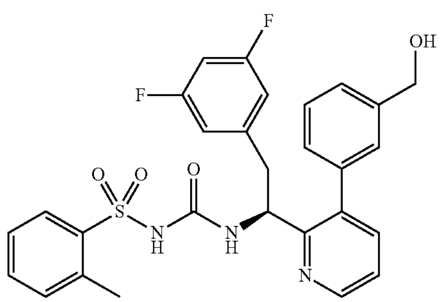 [SMILES: Cc1ccccc1S(=O)(=O)NC(=O)N[C@@H](Cc1cc(F)cc(F)c1)c1ncccc1-c1cccc(CO)c1] | B | — | >100 |
| 122 | 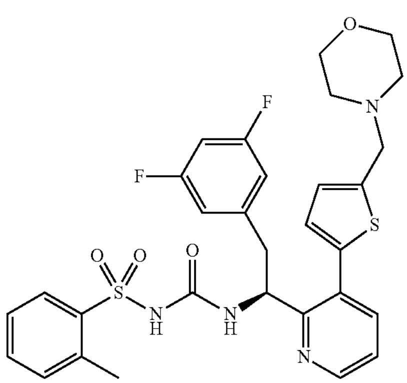 [SMILES: Cc1ccccc1S(=O)(=O)NC(=O)N[C@@H](Cc1cc(F)cc(F)c1)c1ncccc1-c1ccc(CN2CCOCC2)s1] | B | — | >100 |

TABLE 1-continued

| Example | Structure | Activity | EC$_{50}$ (µM) | CC$_{50}$ (µM) |
|---|---|---|---|---|
| 123 | 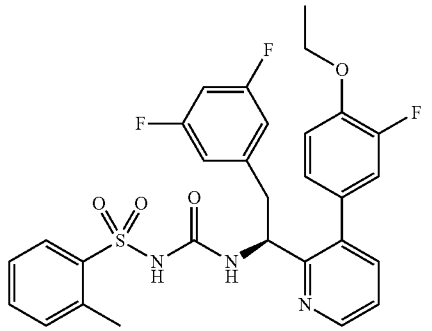 [SMILES: CCOc1ccc(-c2cccnc2[C@H](Cc2cc(F)cc(F)c2)NC(=O)NS(=O)(=O)c2ccccc2C)cc1F] | B | 0.6 | 55 |
| 124 | 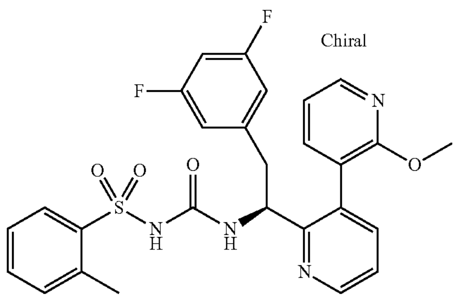 [SMILES: COc1ncccc1-c1cccnc1[C@H](Cc1cc(F)cc(F)c1)NC(=O)NS(=O)(=O)c1ccccc1C] | C | — | >100 |
| 125 | 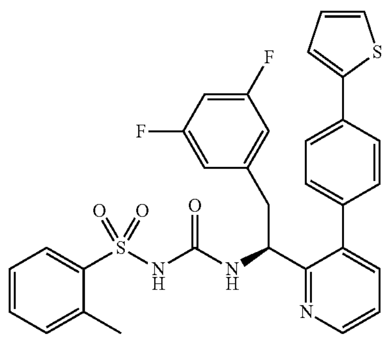 [SMILES: Cc1ccccc1S(=O)(=O)NC(=O)N[C@@H](Cc1cc(F)cc(F)c1)c1ncccc1-c1ccc(-c2cccs2)cc1] | C | — | 38 |
| 126 | 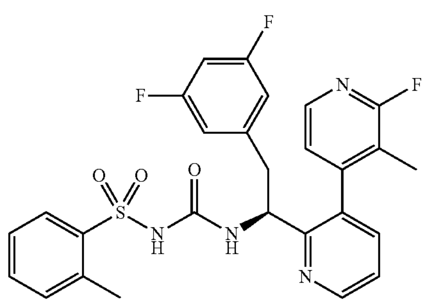 [SMILES: Cc1ccccc1S(=O)(=O)NC(=O)N[C@@H](Cc1cc(F)cc(F)c1)c1ncccc1-c1ccnc(F)c1C] | C | 1.52 | >33 |
| 127 | 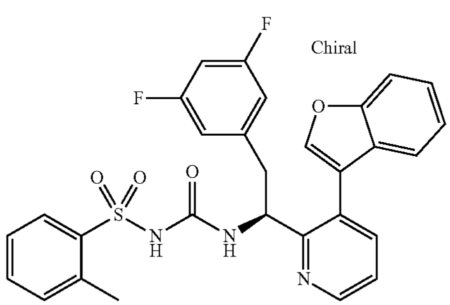 [SMILES: Cc1ccccc1S(=O)(=O)NC(=O)N[C@@H](Cc1cc(F)cc(F)c1)c1ncccc1-c1coc2ccccc12] | C | — | 72 |

TABLE 1-continued

| Example | Structure | Activity | EC$_{50}$ (μM) | CC$_{50}$ (μM) |
|---|---|---|---|---|
| 128 | 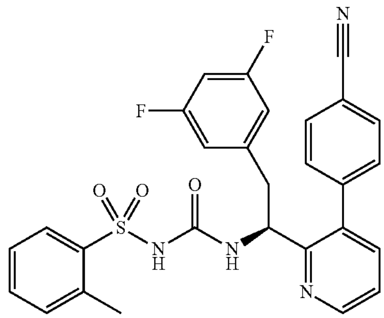 [SMILES: Cc1ccccc1S(=O)(=O)NC(=O)N[C@@H](Cc1cc(F)cc(F)c1)c1ncccc1-c1ccc(C#N)cc1] | C | — | 80 |
| 129 | 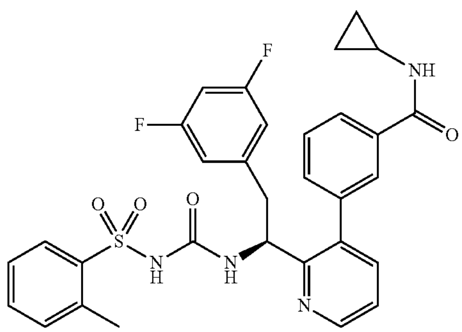 [SMILES: Cc1ccccc1S(=O)(=O)NC(=O)N[C@@H](Cc1cc(F)cc(F)c1)c1ncccc1-c1cccc(C(=O)NC2CC2)c1] | C | 1.83 | >100 |
| 130 | 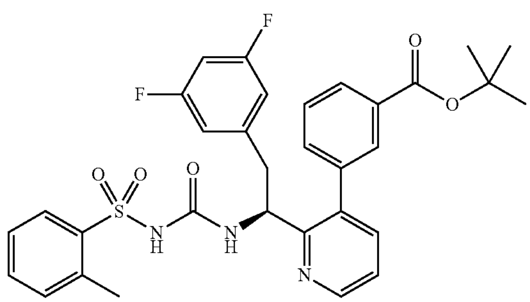 [SMILES: Cc1ccccc1S(=O)(=O)NC(=O)N[C@@H](Cc1cc(F)cc(F)c1)c1ncccc1-c1cccc(C(=O)OC(C)(C)C)c1] | C | — | 53 |
| 131 | 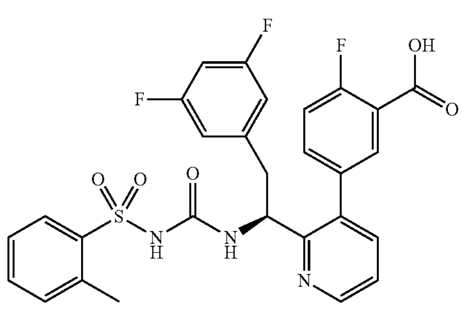 | C | — | >100 |

TABLE 1-continued
| Example | Structure | Activity | EC$_{50}$ (µM) | CC$_{50}$ (µM) |
|---------|-----------|----------|----------------|----------------|
| 132 | 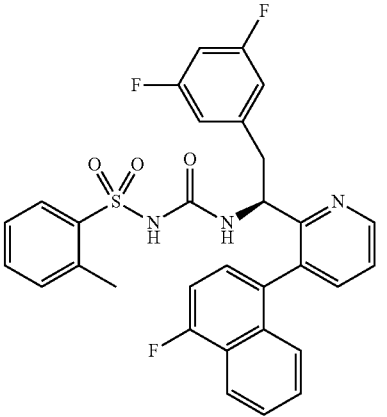 [SMILES: Cc1ccccc1S(=O)(=O)NC(=O)N[C@@H](Cc1cc(F)cc(F)c1)c1ncccc1-c1ccc(F)c2ccccc12] | C | 4.81 | 73 |
| 133 | 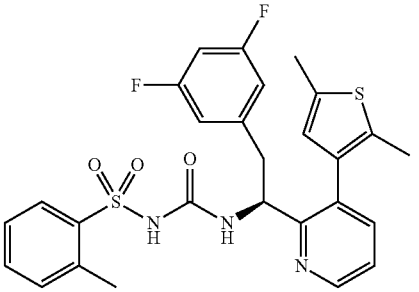 [SMILES: Cc1cc(-c2cccnc2[C@H](Cc2cc(F)cc(F)c2)NC(=O)NS(=O)(=O)c2ccccc2C)c(C)s1] | C | — | 71 |
| 134 | 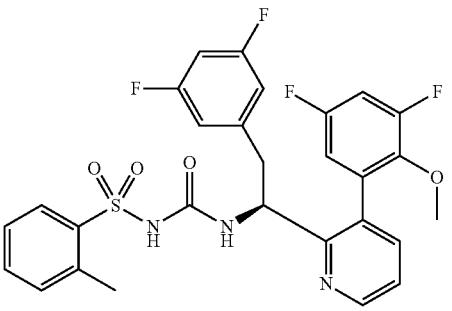 [SMILES: COc1c(F)cc(F)cc1-c1cccnc1[C@H](Cc1cc(F)cc(F)c1)NC(=O)NS(=O)(=O)c1ccccc1C] | C | — | >50 |

The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

What is claimed is:
1. A compound of Formula I or a pharmaceutically acceptable salt thereof:

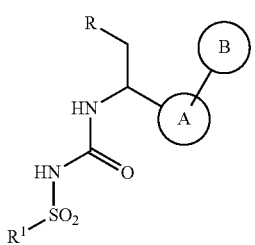

I wherein:
R is phenyl; and is substituted with 0-3 substituents selected from the group of alkyl, alkenyloxy, alkoxycarbonyl, alkylcarbonylamino, aminocarbonyl, aryl, benzyloxy, cyano, cycloalkoxy, cycloalkyl, halo, haloalkyl, haloalkoxy, hydroxy and (morpholinyl)sulfonyl $R^1$ is selected from the group of alkyl, cycloalkyl, (cycloalkyl)alkyl, aryl, and 5-6 member heteroaryl; and is substituted with 0-3 substituents selected from the group of alkyl, alkoxy, alkoxycarbonyl, aryl, cyano, cycloalkyl, halo, haloalkoxy, haloalkyl, 5-6 member heteroaryl, nitro, and N—$R^2R^3$, where $R^2$ and $R^3$ are each independently selected from H, alkyl, and cycloalkyl, or $R^2$ and $R^3$ together form heterocycles comprised of 1-3 rings;

A is a five or six-member heteroaryl ring optionally substituted with alkyl, alkenyl, alkynyl, alkoxy, cycloalkoxy, cycloalkyl, halo and haloalkyl; and B is selected from the group of alkyl, aryl, arylalkyl, $C_3$-$C_9$ cycloalkyl, and 5-6 member heteroaryl, and is substituted with 0-3 substituents selected from the group of alkyl, alkylsulphonyl, alkoxy, alkylaryl, allyloxy, arylalkoxy, cycloalkoxy, cycloalkyl, halo, haloalkoxy, heteroarylcycloalkyl amido, hydroxymethyl, nitro, —CN, —COOR$^2$, —NR$^2$R$^3$, —N(R$^2$) COOR$^3$, —CONR$^2$R$^3$, NH—CO-alkyl, and morpholinyl.

2. A compound or salt of claim 1, wherein $R^1$ is phenyl and is substituted with 0-3 substituents selected from the group of alkyl, alkoxy, alkoxycarbonyl, aryl, cyano, cycloalkyl, halo, haloalkoxy, haloalkyl, 5-6 member heteroaryl, nitro, and N—$R^2R^3$, where $R^2$ and $R^3$ are each independently selected from H, alkyl, and cycloalkyl, or $R^2$ and $R^3$ together form heterocycles comprised of 1-3 rings.

3. A compound or salt of claim 2, wherein said phenyl is substituted with one or more alkyl or halo groups.

4. A compound or salt of claim 1, wherein R is substituted with one or more halo groups.

5. A compound or salt of claim 4, wherein said halo group is fluoro.

6. A compound or salt of claim 2, wherein A is selected from the group consisting of imadazole-2-yl, imidazole-3-yl, triazolyl, oxazolyl, pyridyl, pyrimidinyl, and pyrazinyl groups.

7. A compound or salt of claim 6, wherein A is selected from the group consisting of imadazole-2-yl, imidazole-3-yl, triazolyl, and pyridyl groups.

8. A compound or salt of claim 1, wherein B is phenyl and is substituted with 0-3 substituents selected from the group of alkyl, alkylsulphonyl, alkoxy, alkylaryl, allyloxy, arylalkoxy, cycloalkoxy, cycloalkyl, halo, haloalkoxy, heteroarylcycloalkyl amido, hydroxymethyl, nitro, —CN, —COOR$^2$, —NR$^2$R$^3$, —N(R$^2$)COOR$^3$, —CONR$^2$R$^3$, NH—CO-alkyl, and morpholinyl.

9. A compound or salt of claim 8, wherein B is substituted with at least one member selected from the group of halo, $C_{1-6}$ alkyl, $C_{1-6}$ alkoxy, haloalkoxy, and —N(R$^2$)COOR$^3$.

10. A compound or salt, which is selected from the group consisting of:

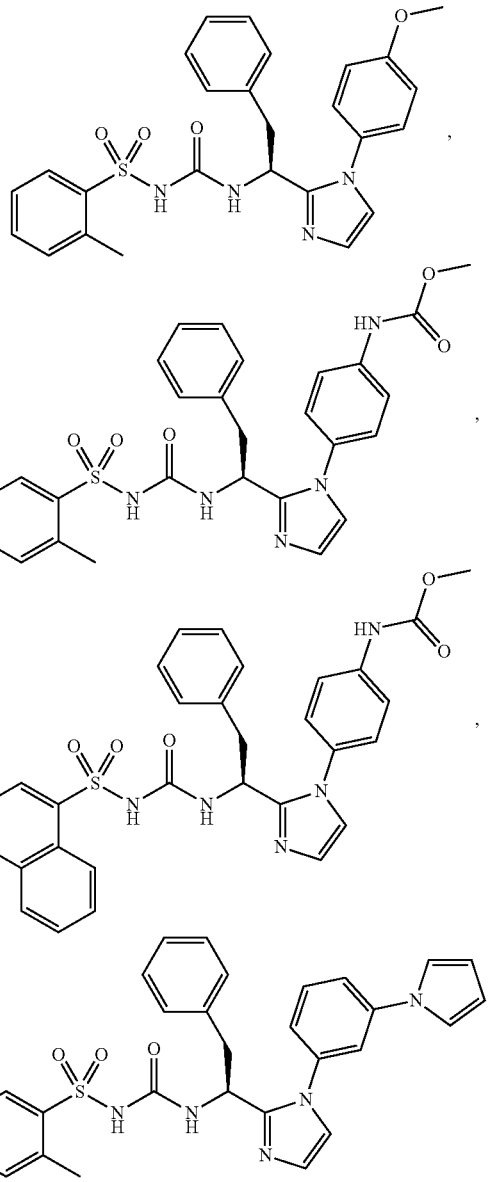

229
-continued
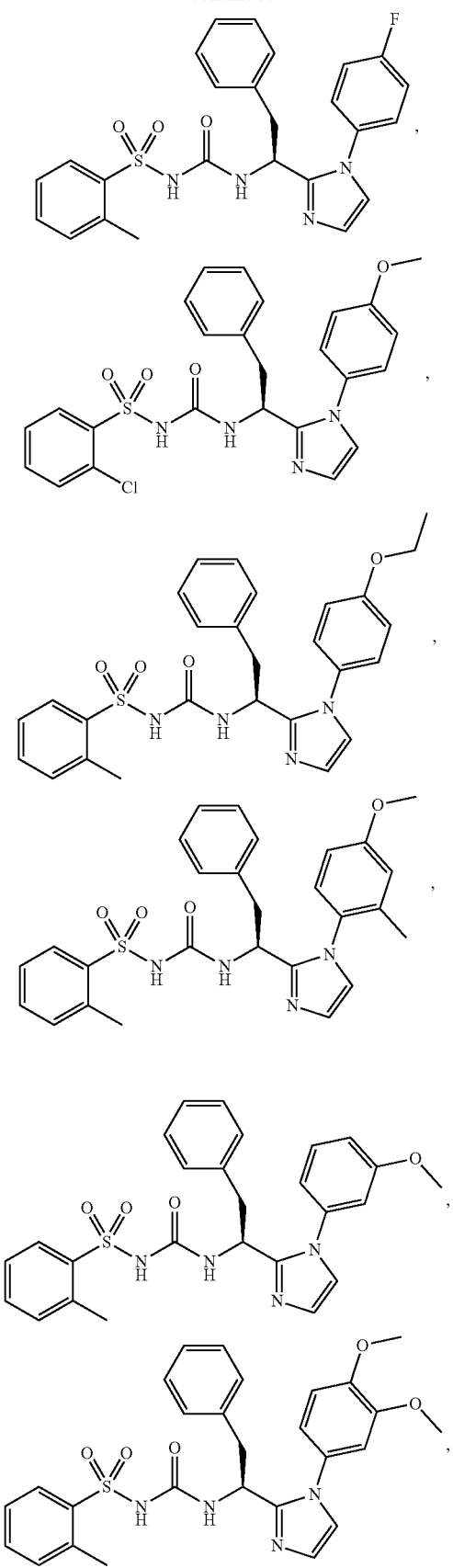
230
-continued
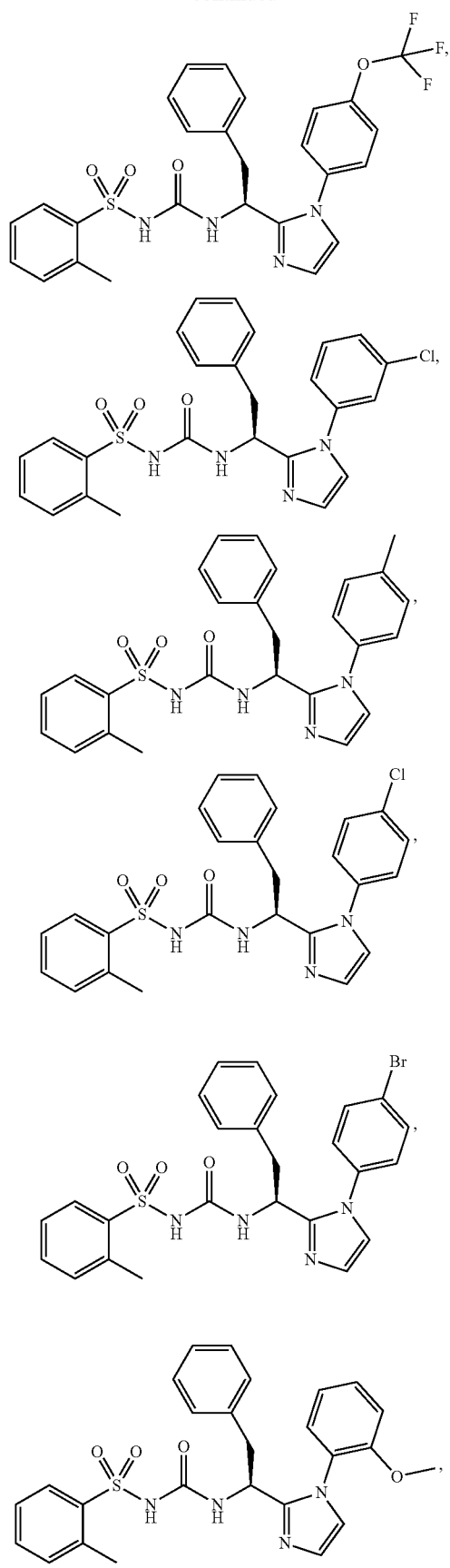

231
-continued
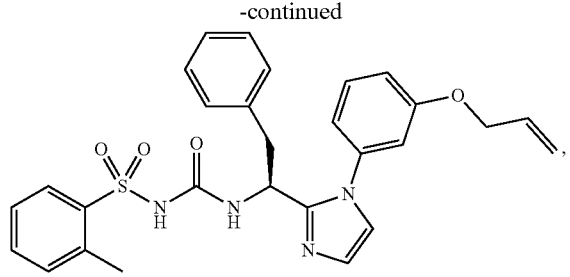
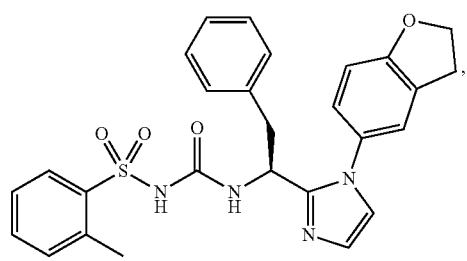
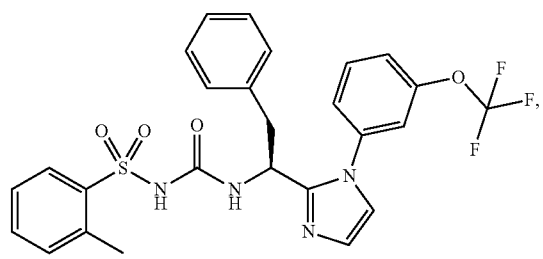
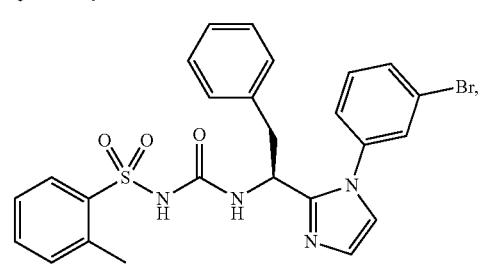
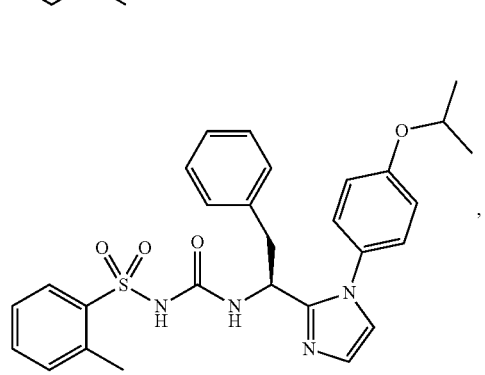
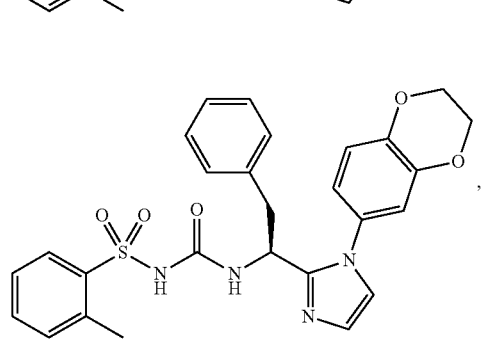
232
-continued
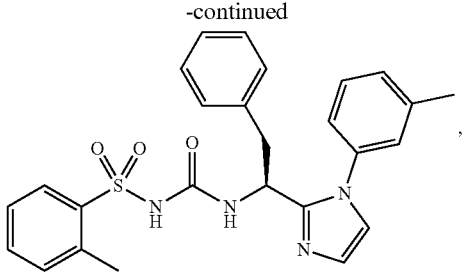
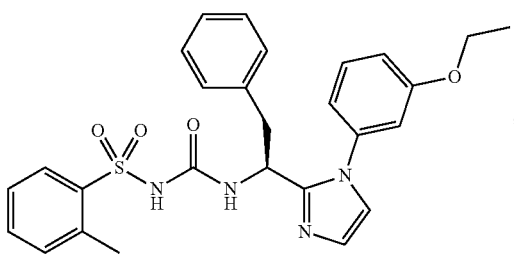
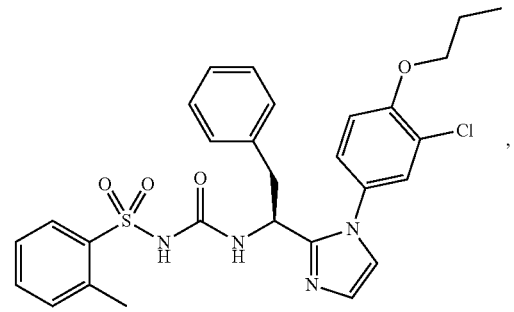
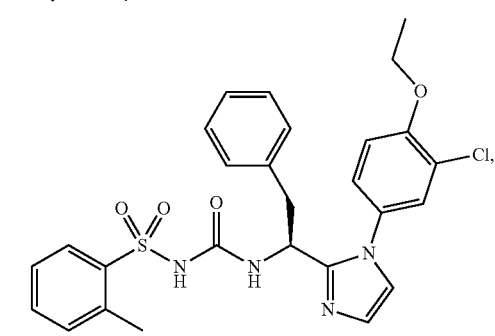
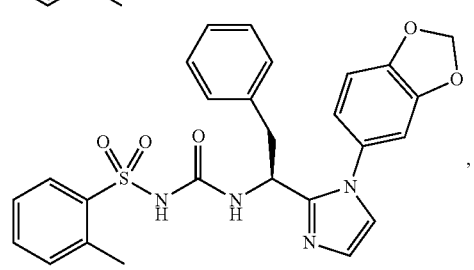
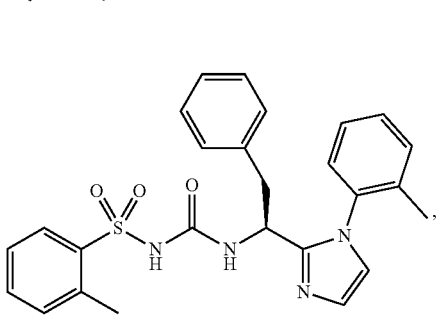

233
-continued
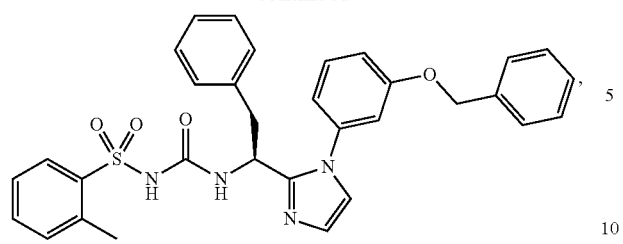
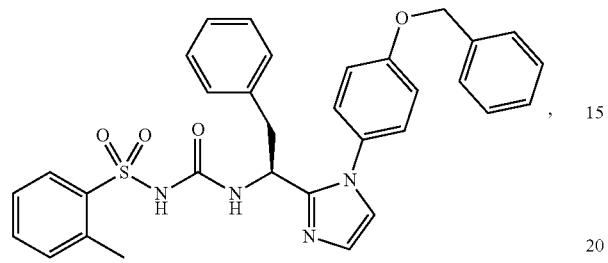
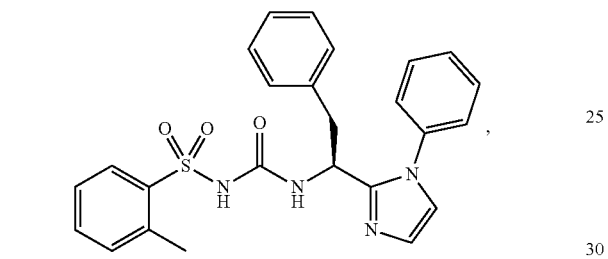
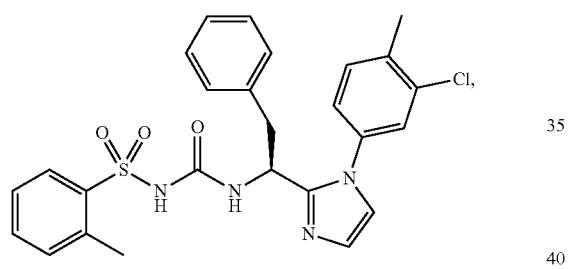
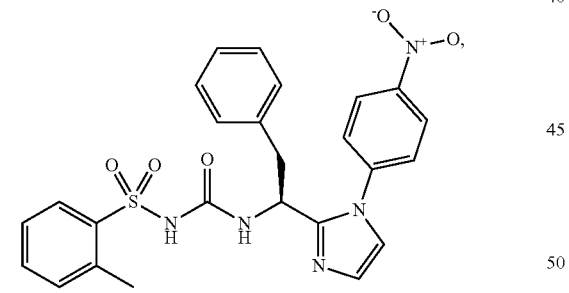
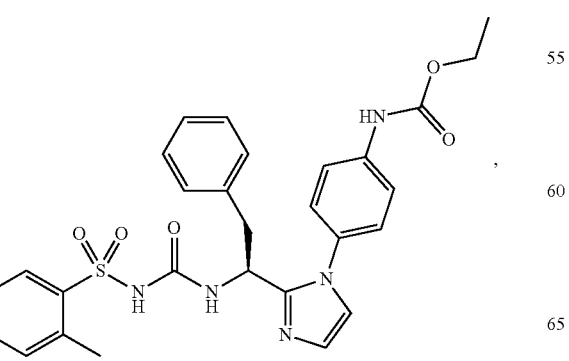
234
-continued
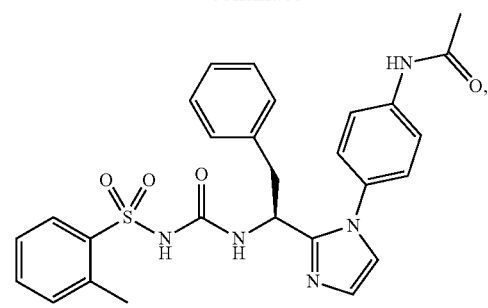
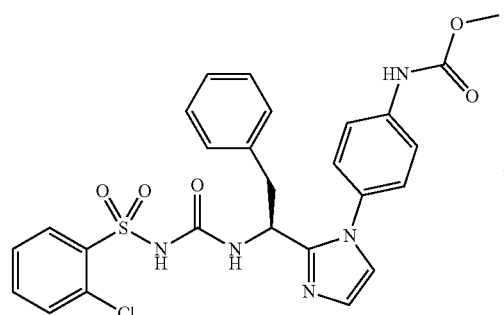
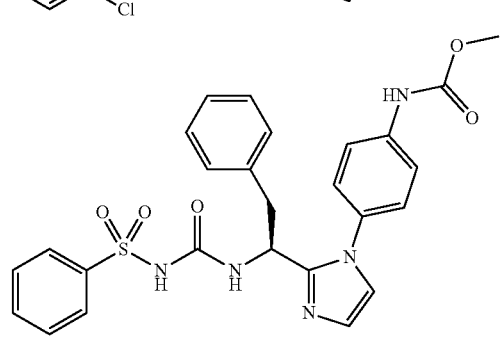
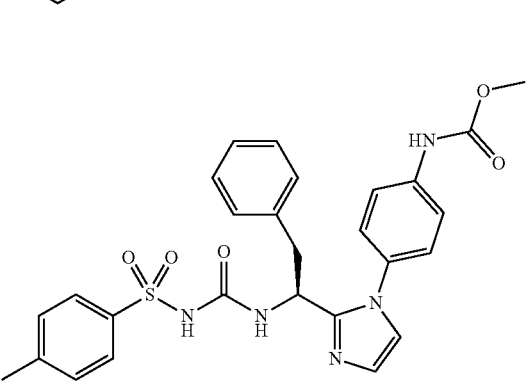
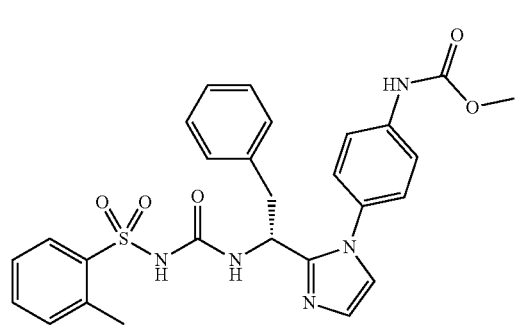

235
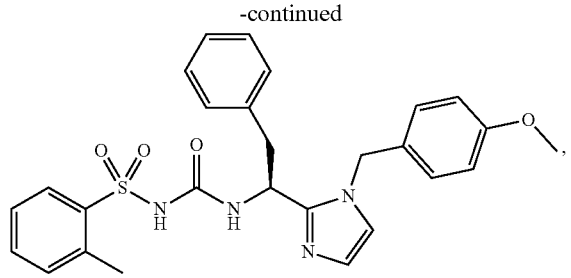
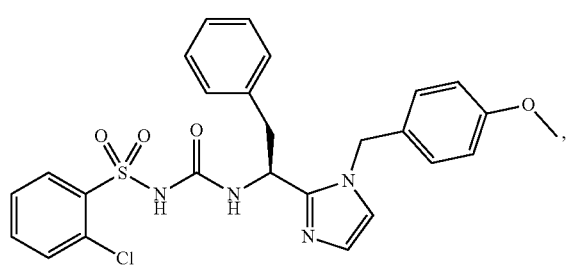
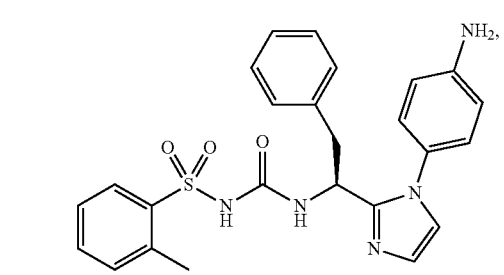
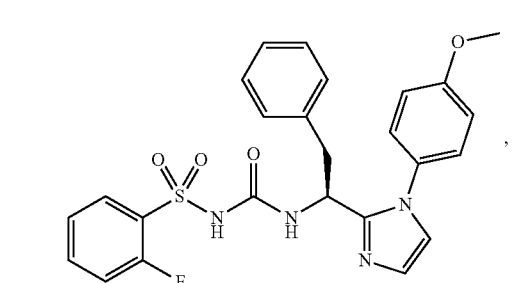
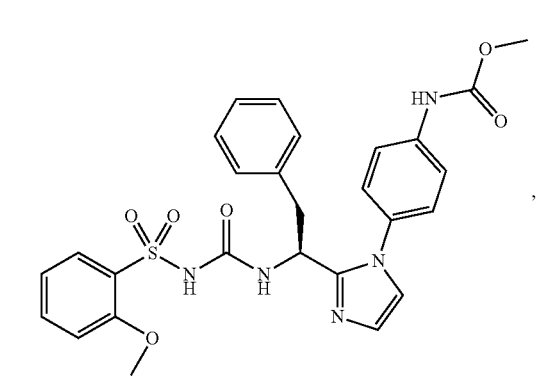
236
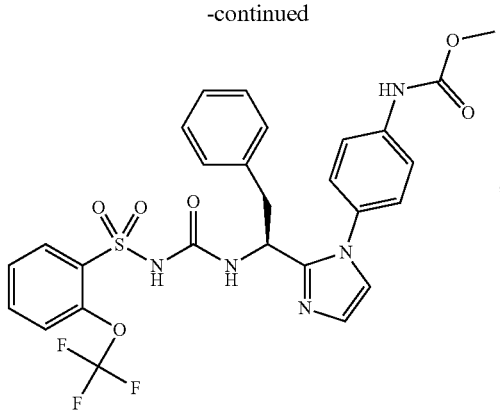
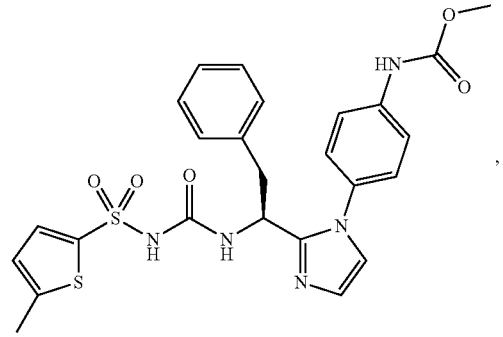
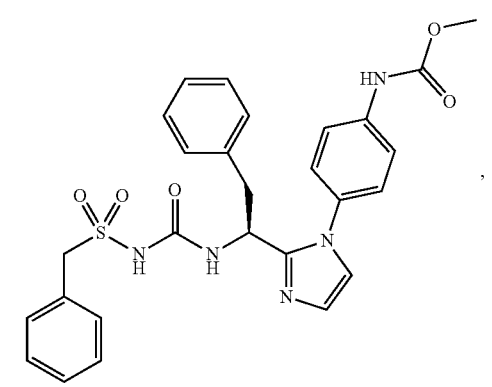
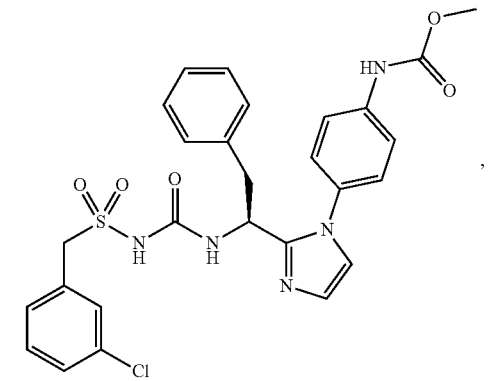

237
-continued
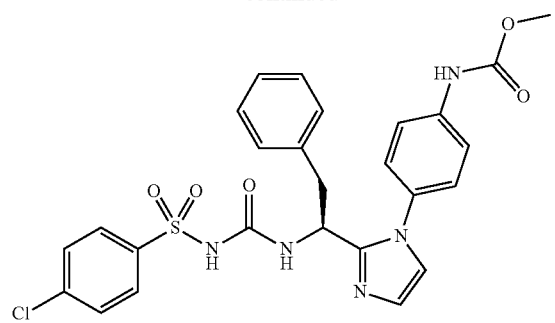,
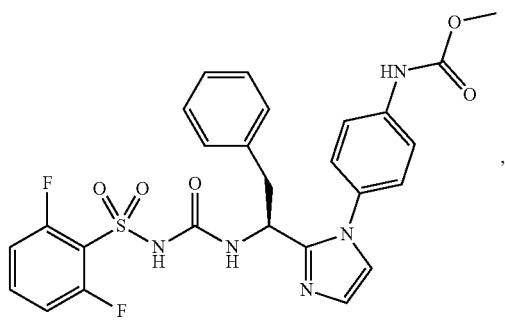,
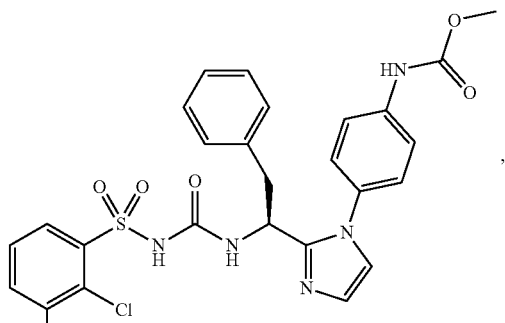,
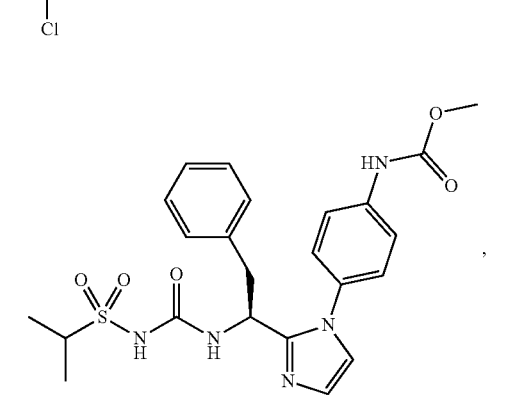,
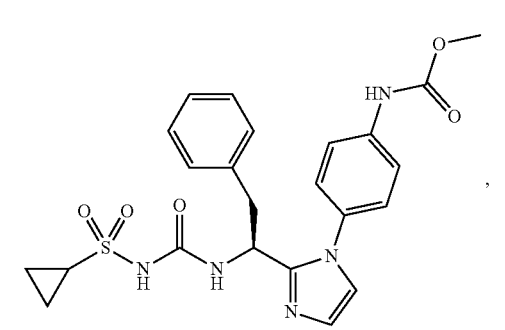,
238
-continued
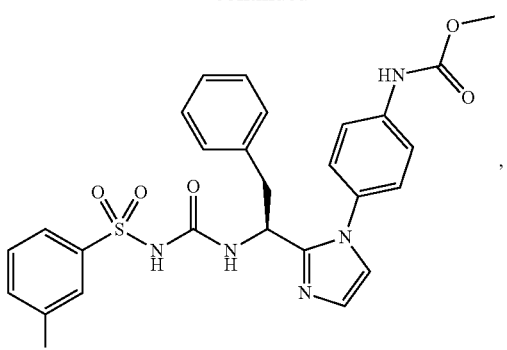,
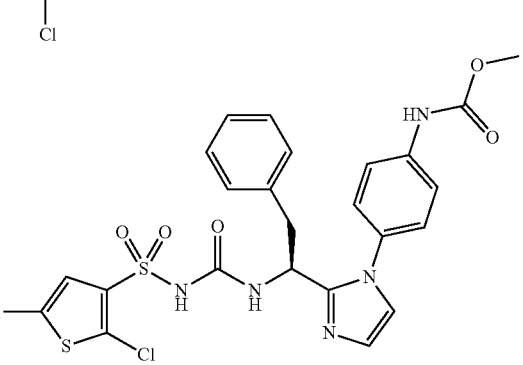,
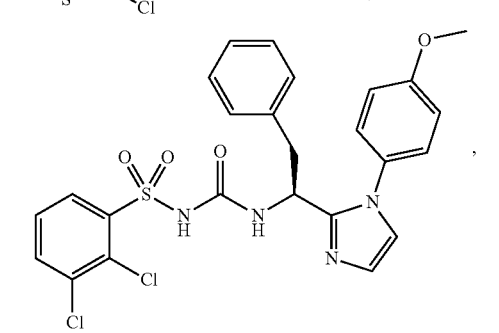,
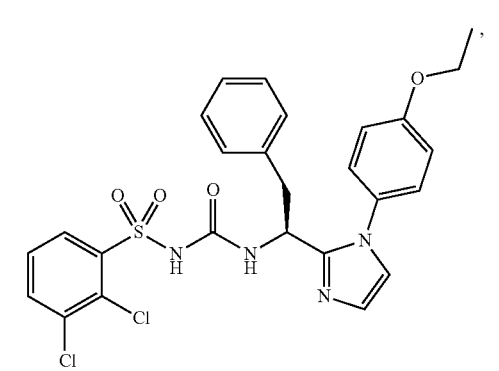,
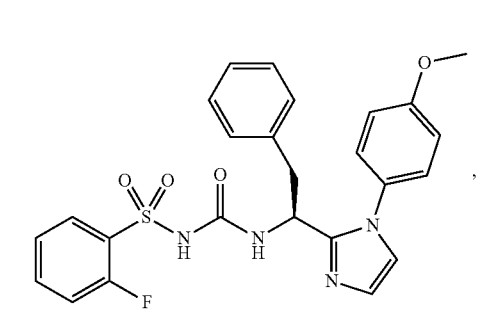, 239
-continued
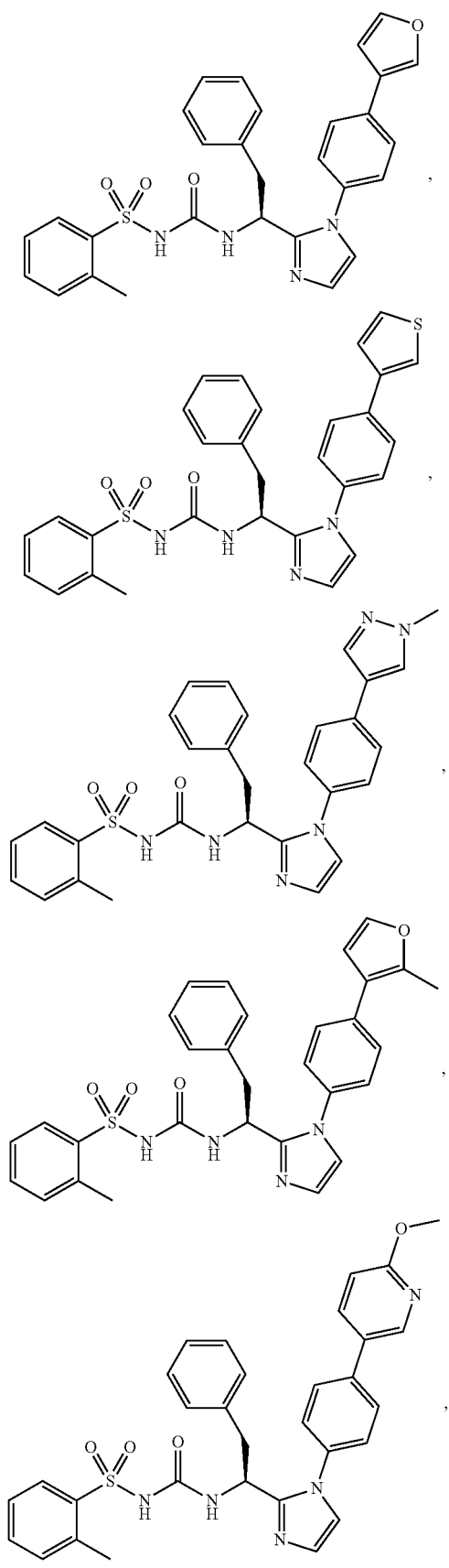
240
-continued
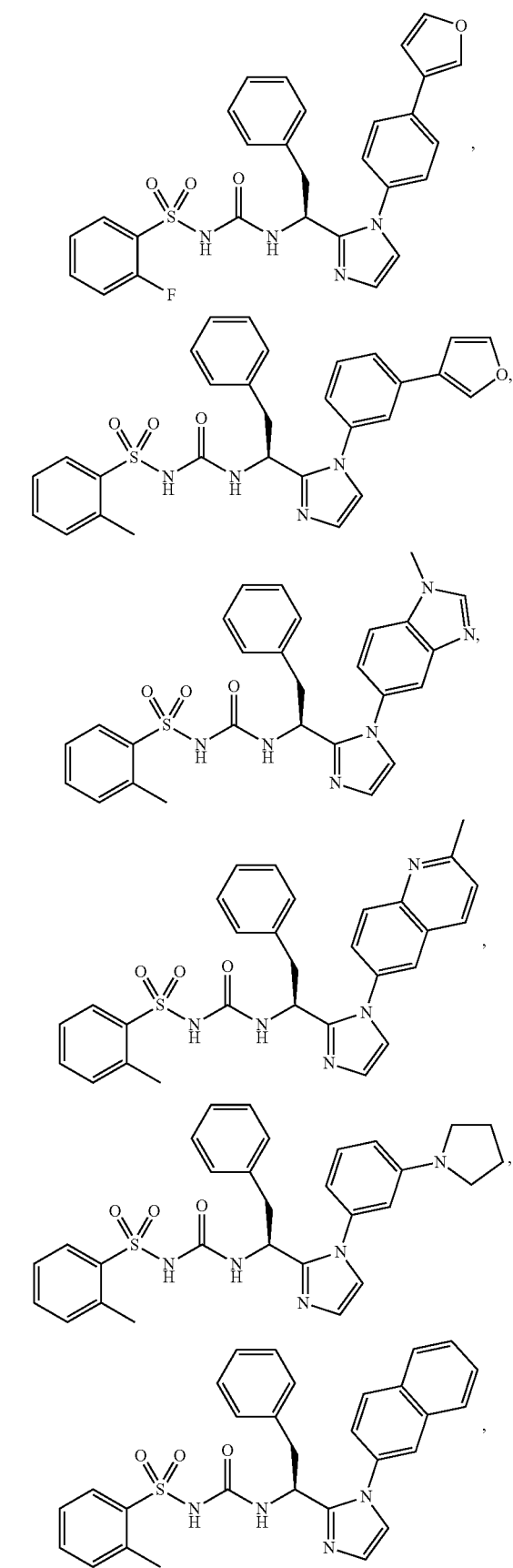

241
-continued
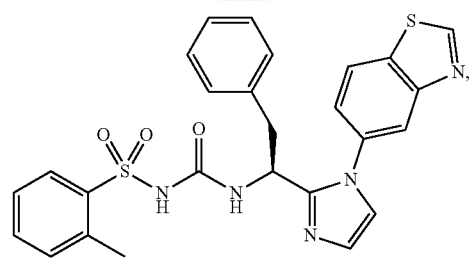
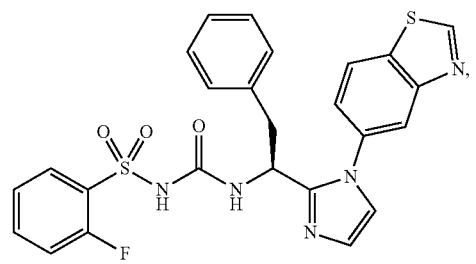
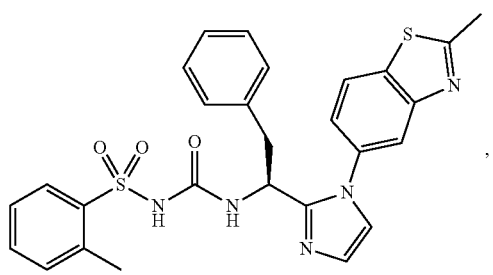
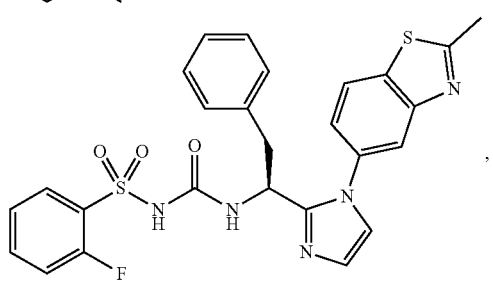
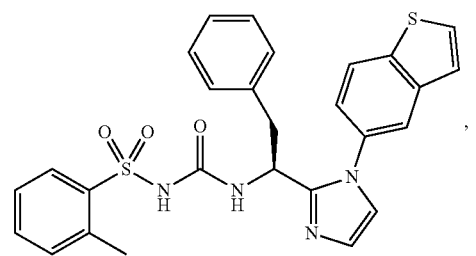
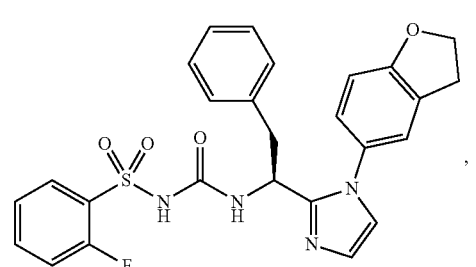
242
-continued
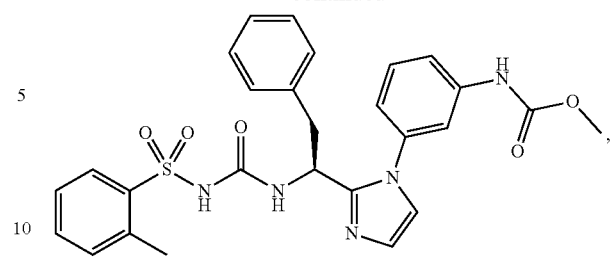
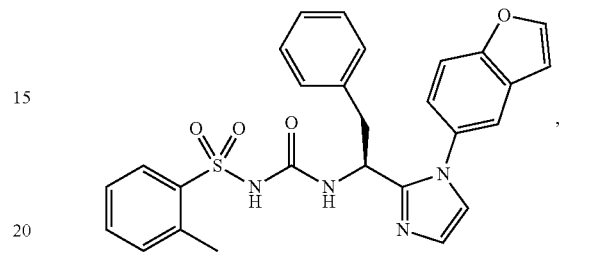
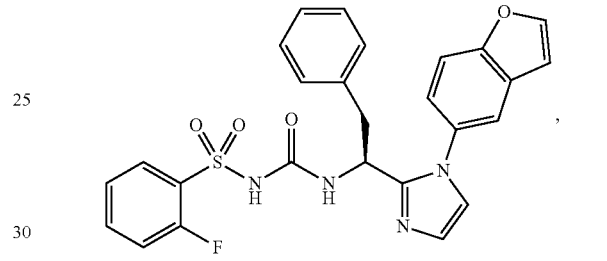
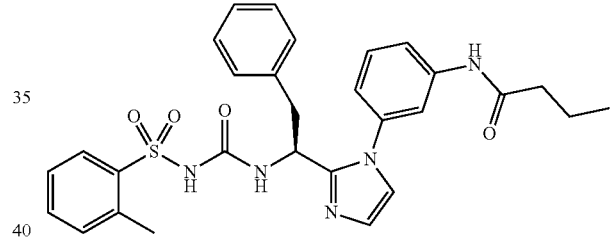
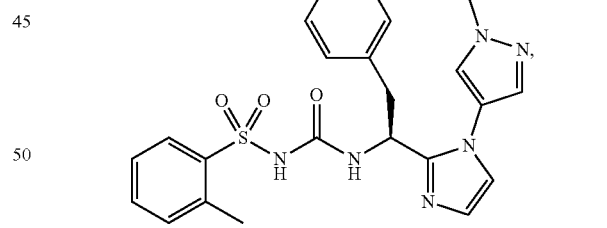
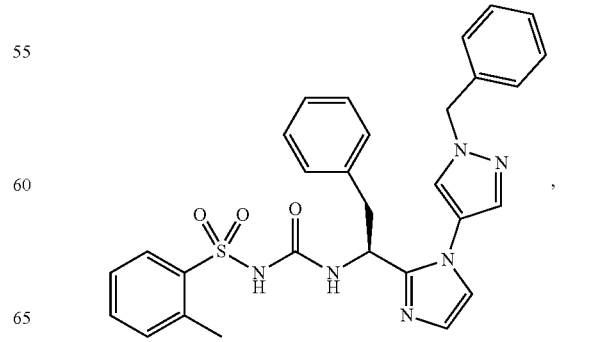

243
-continued
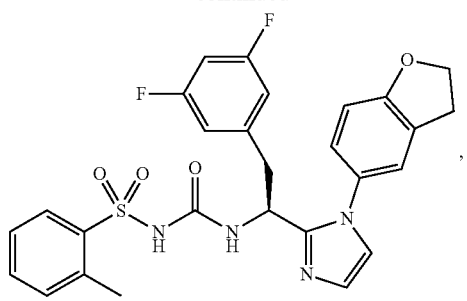
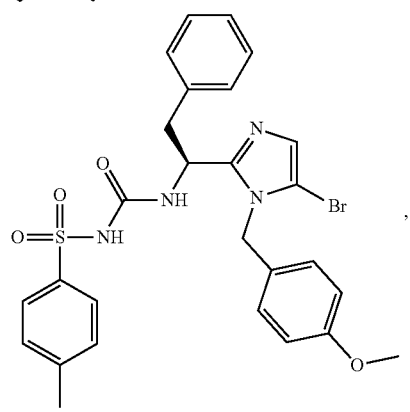
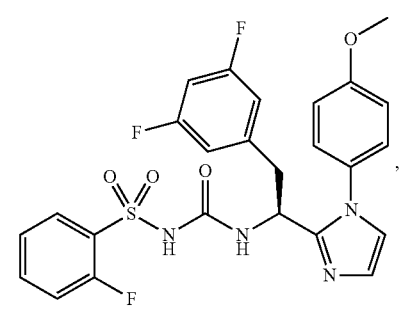
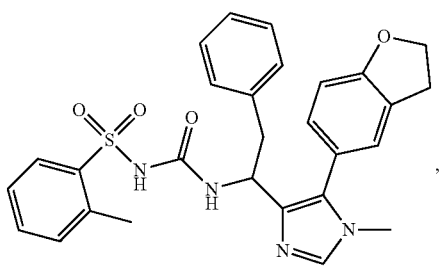
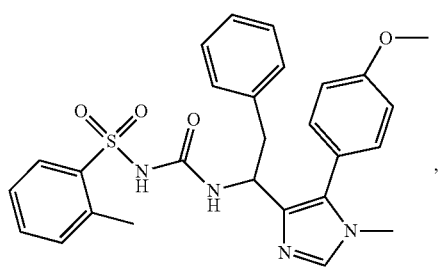
244
-continued
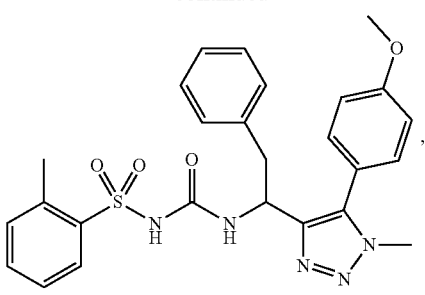
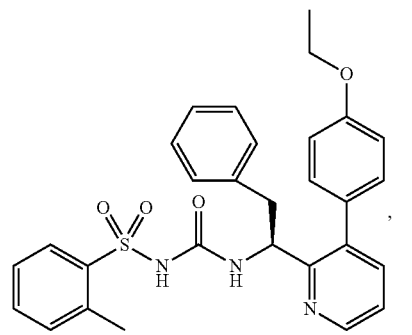
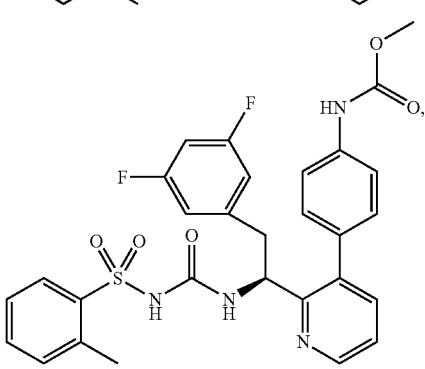
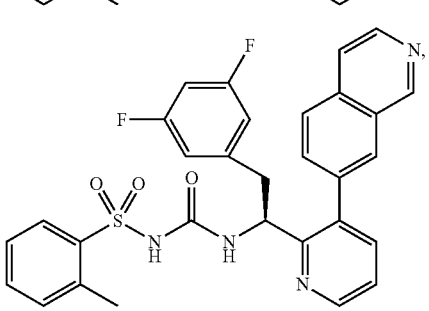
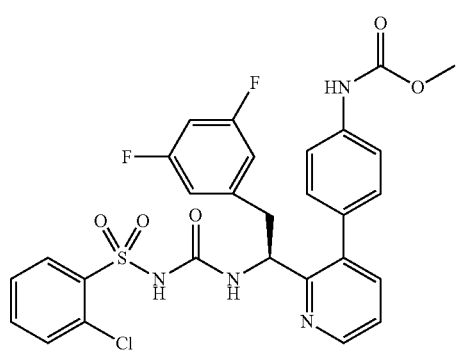

245
-continued
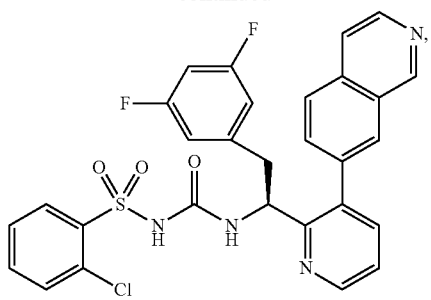
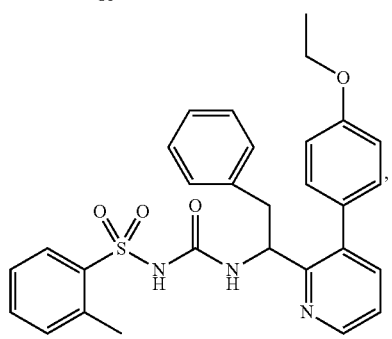
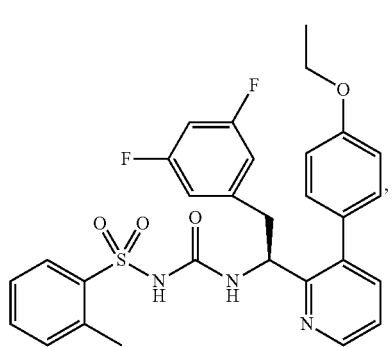
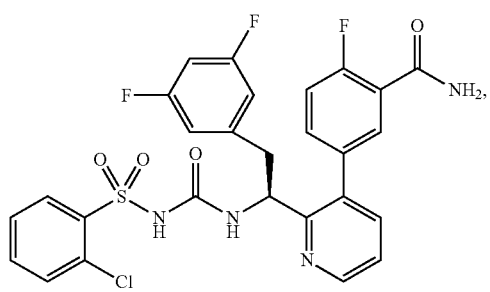
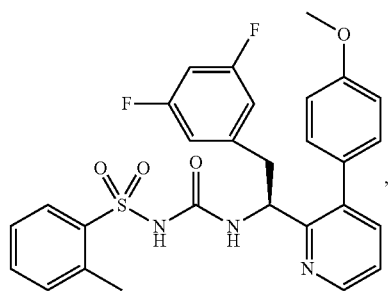
246
-continued
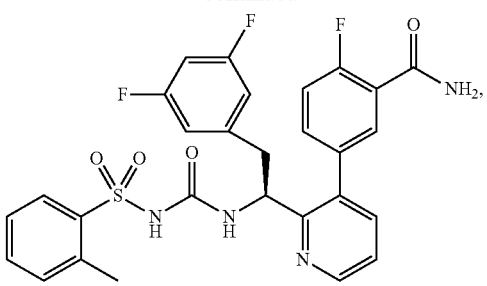
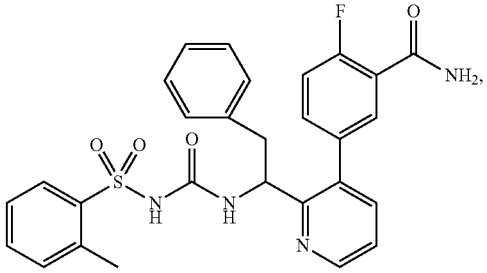
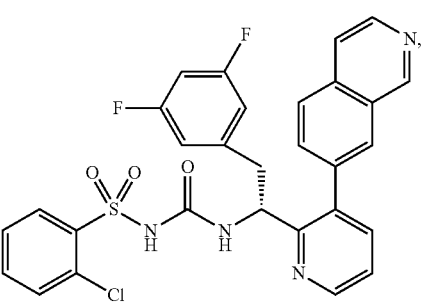
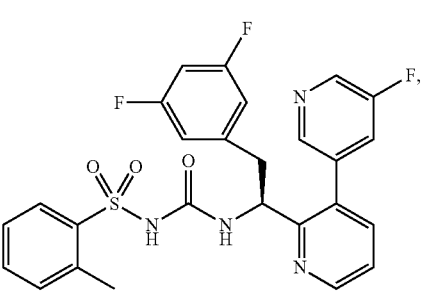
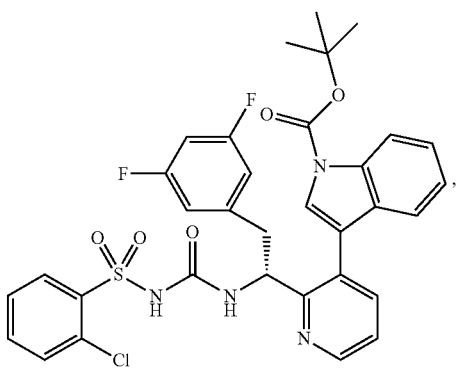

247
-continued
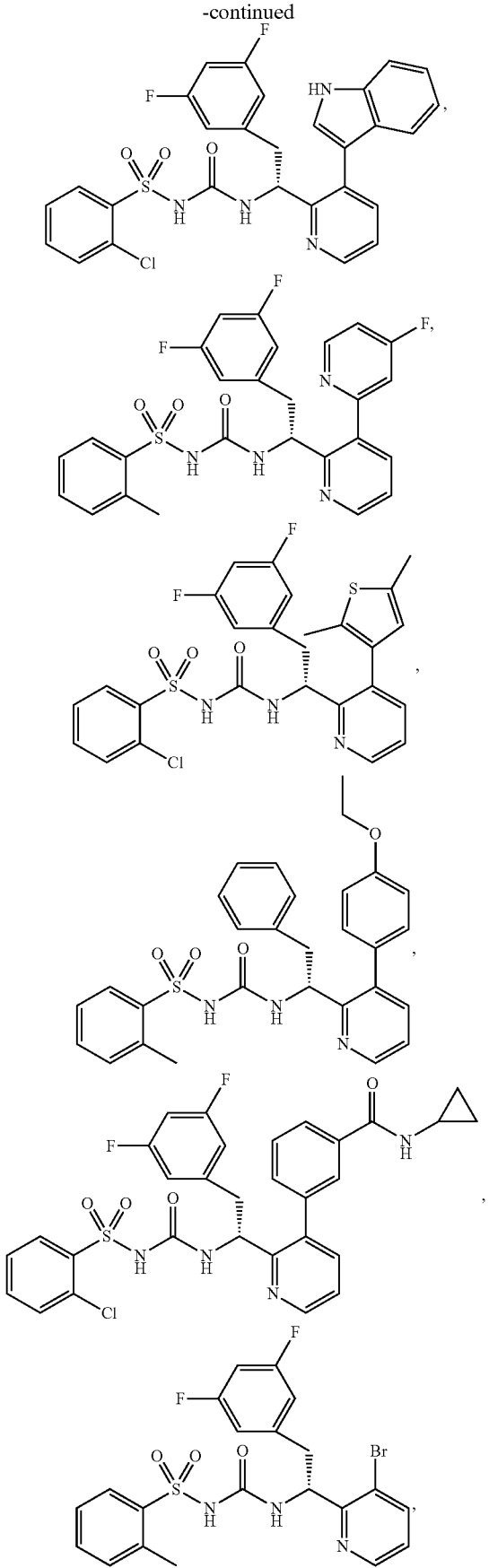
248
-continued
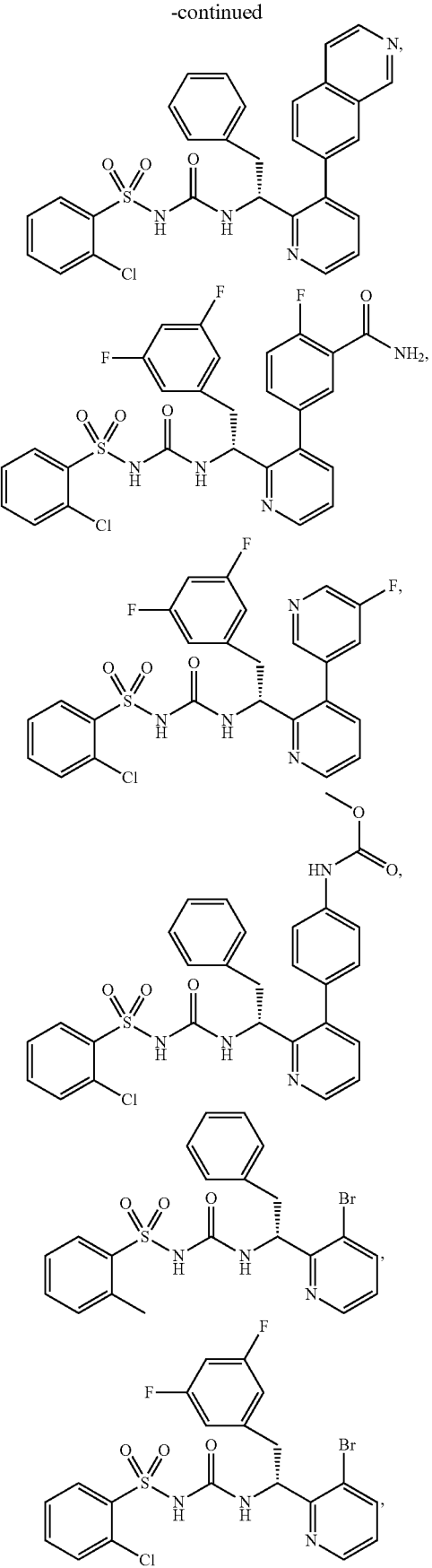

249
-continued
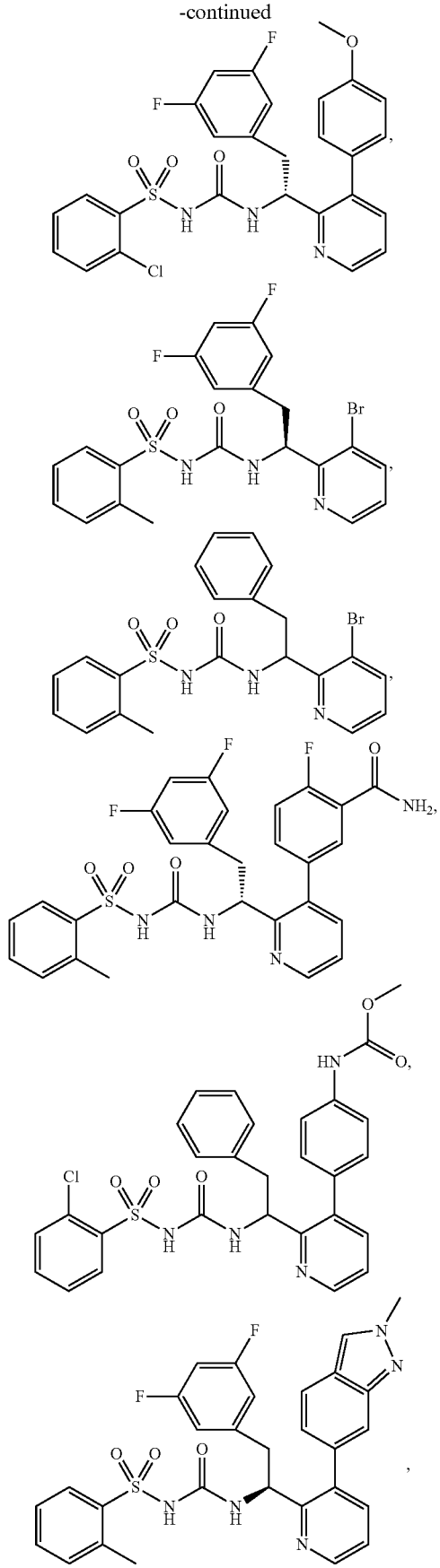
250
-continued
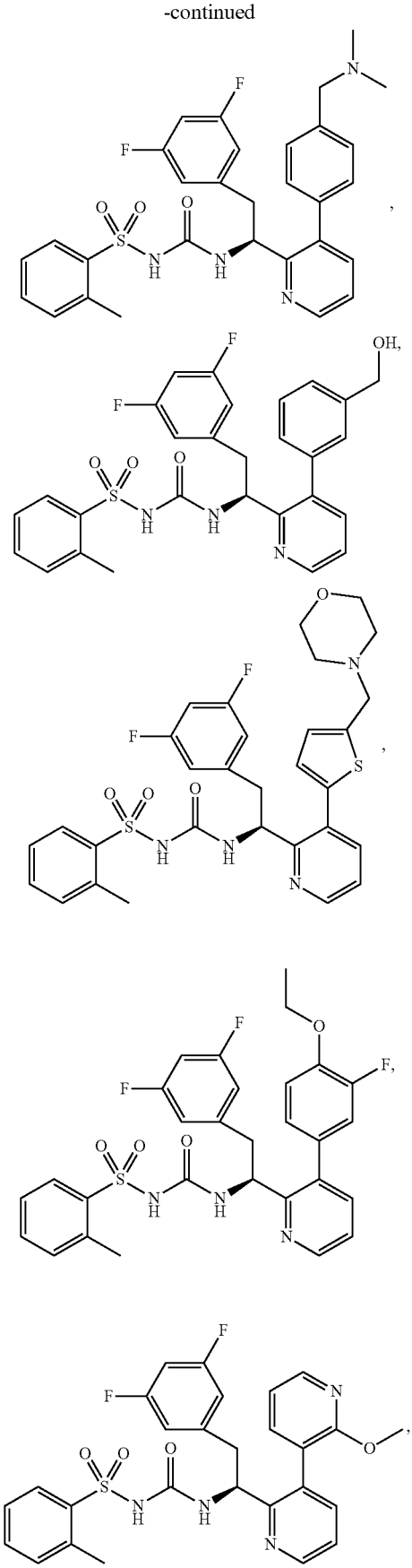

251
-continued
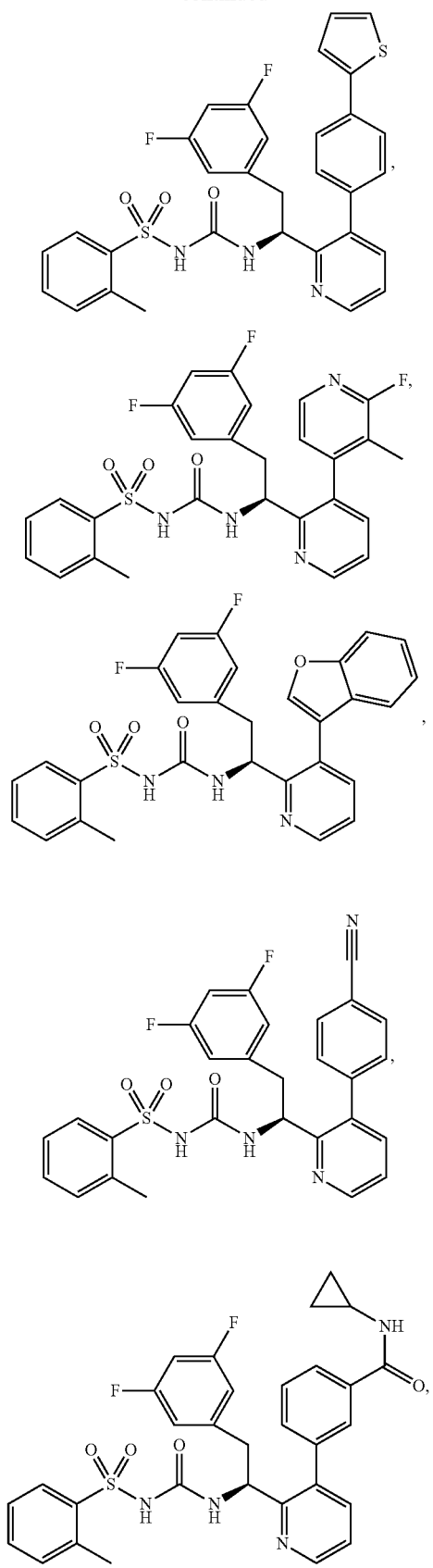
252
-continued
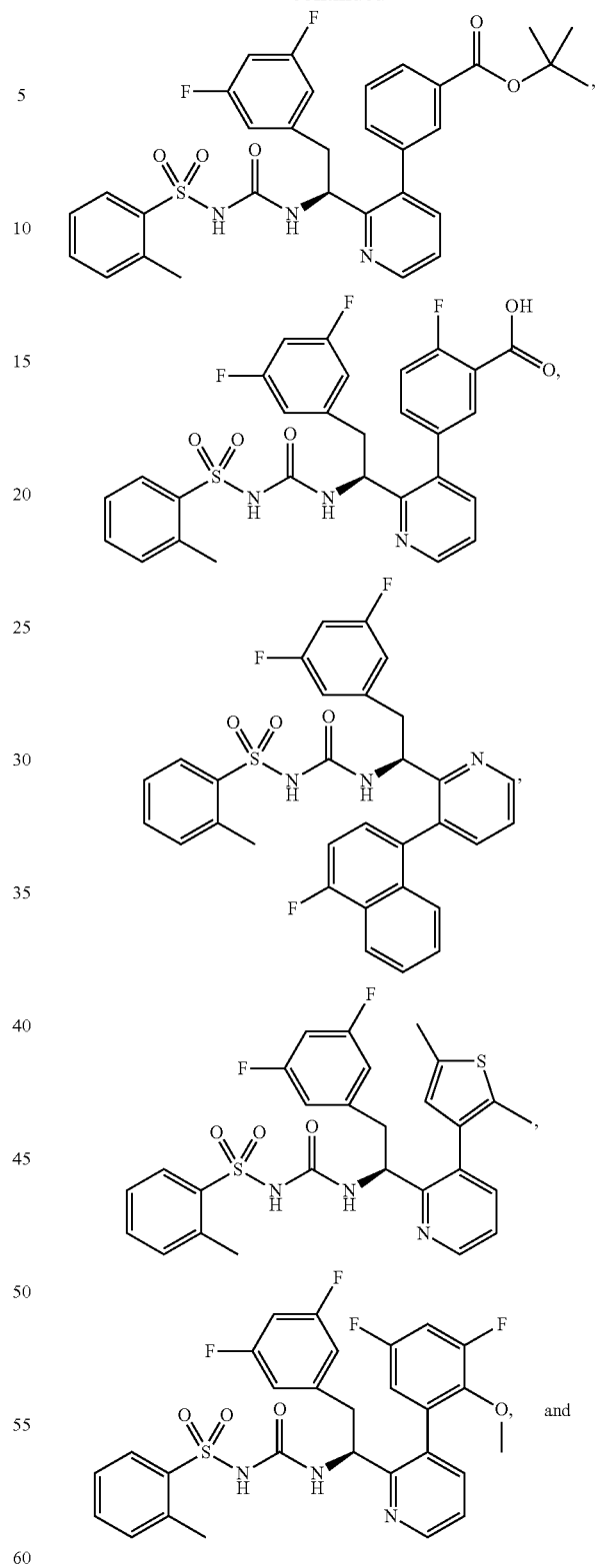
pharmaceutically acceptable salts thereof.
11. A compound or salt, which is selected from the group consisting of:

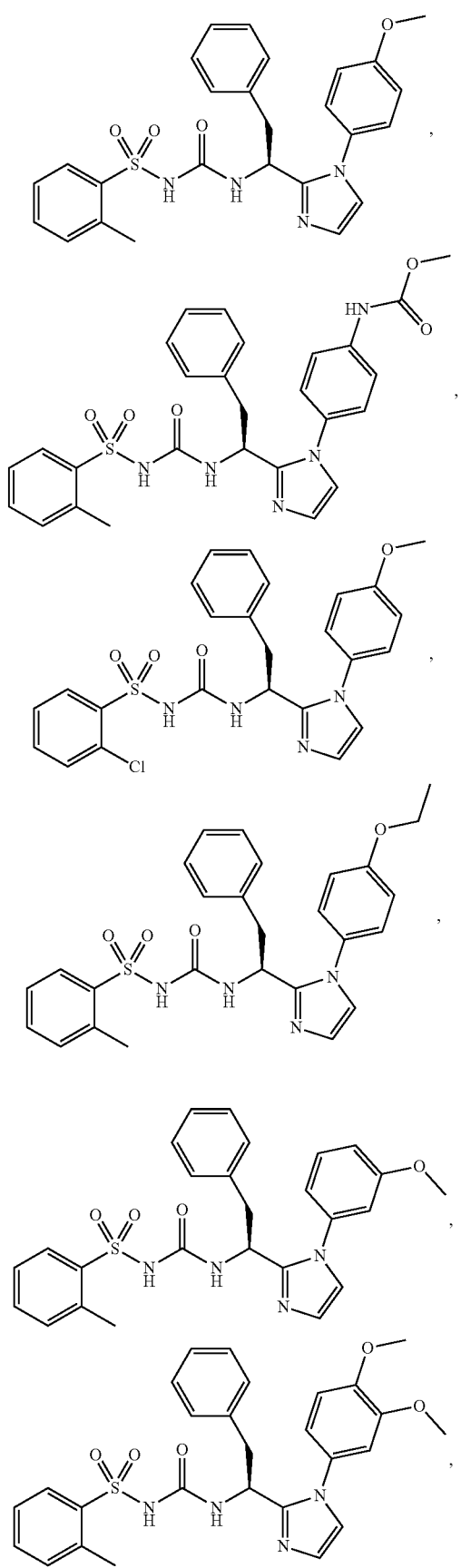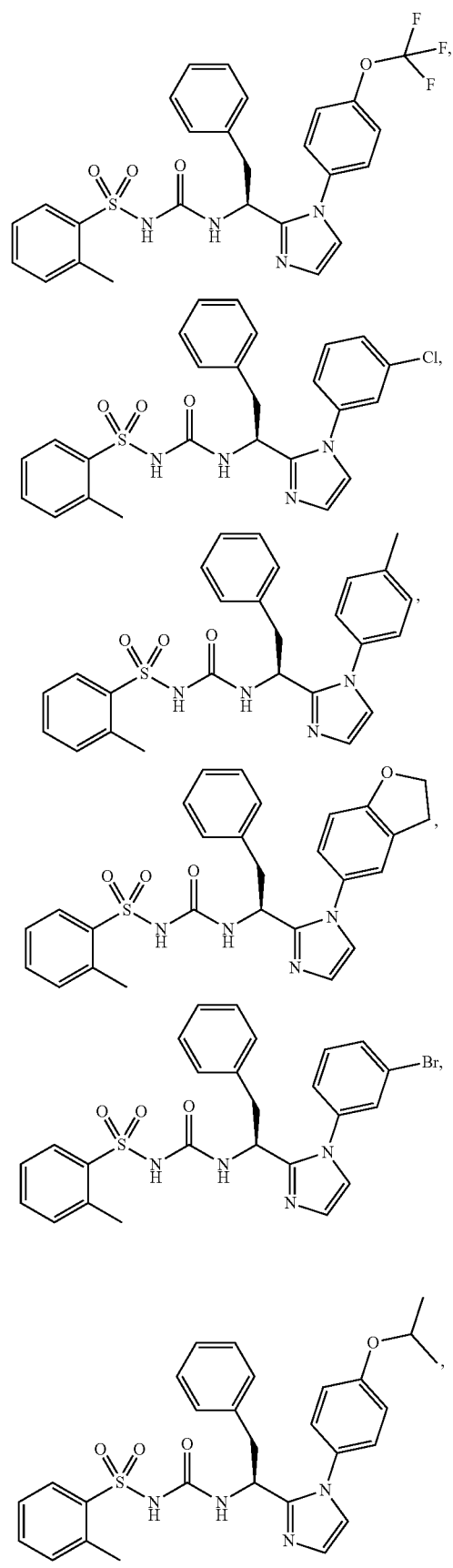

255
-continued
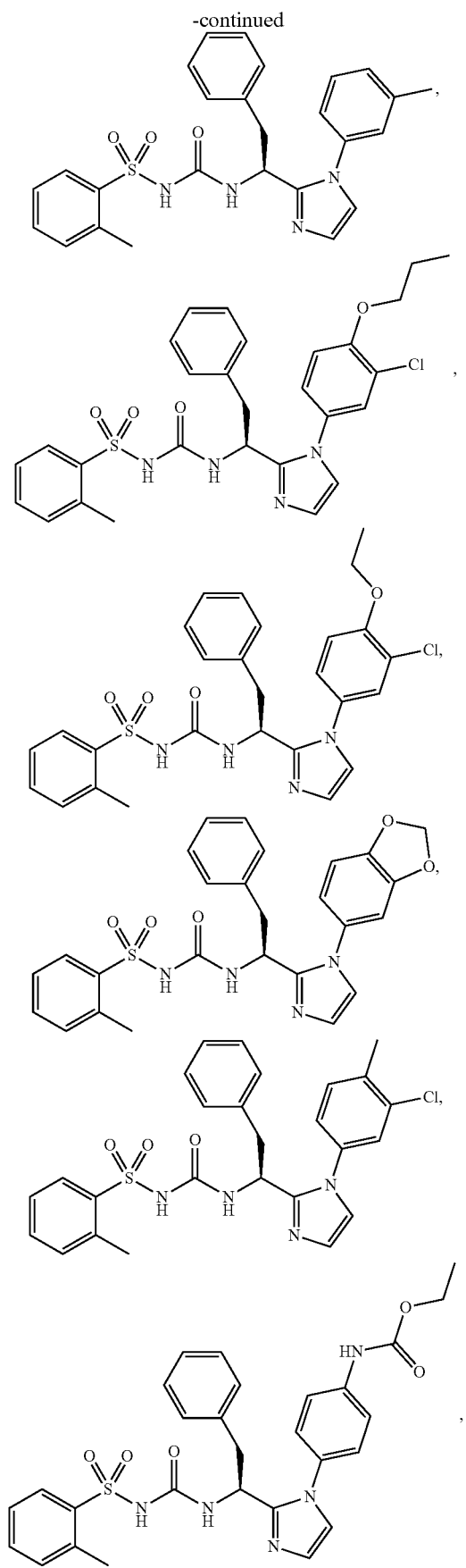
256
-continued
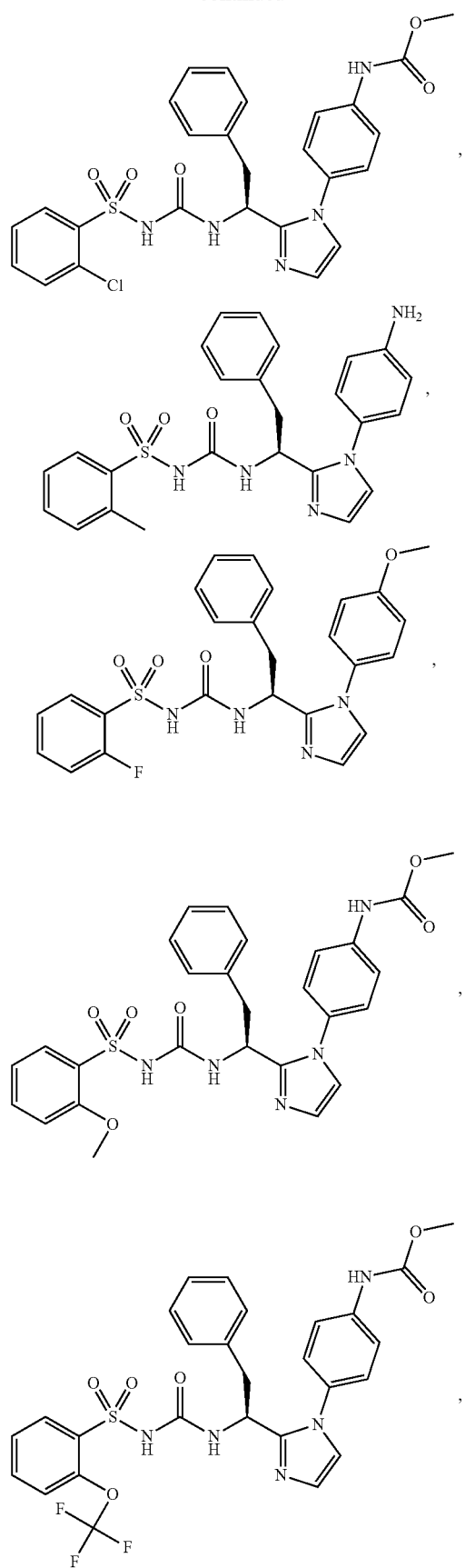

257
-continued
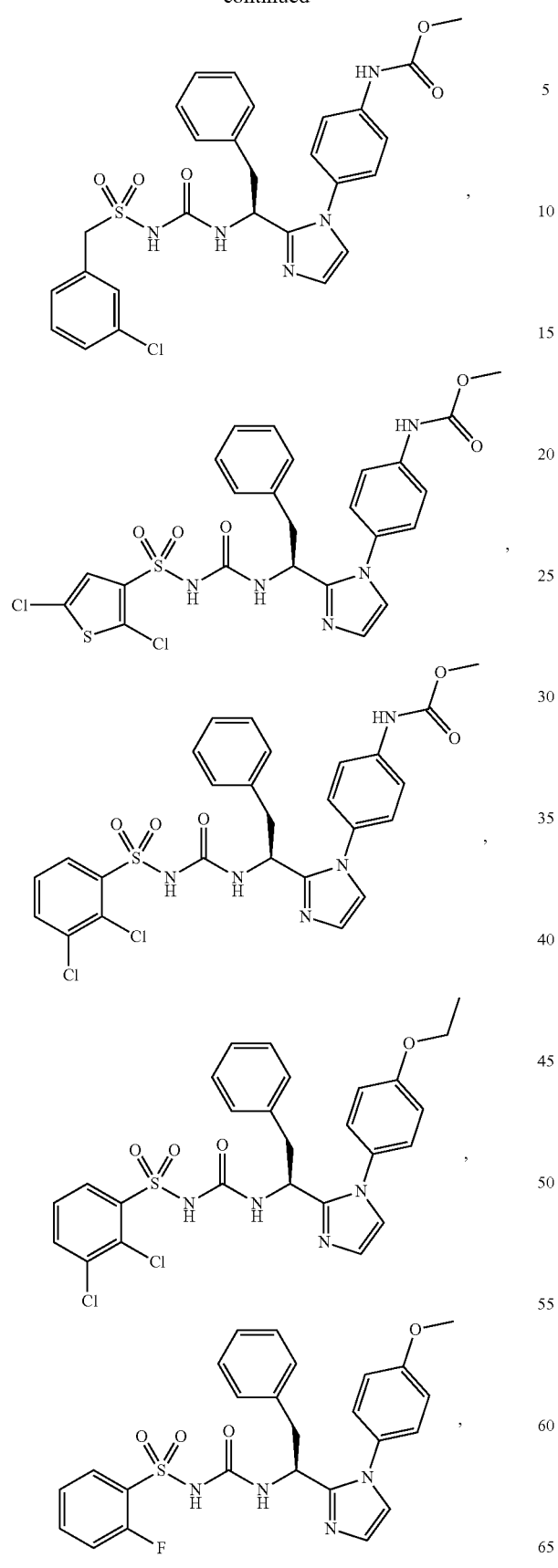
258
-continued
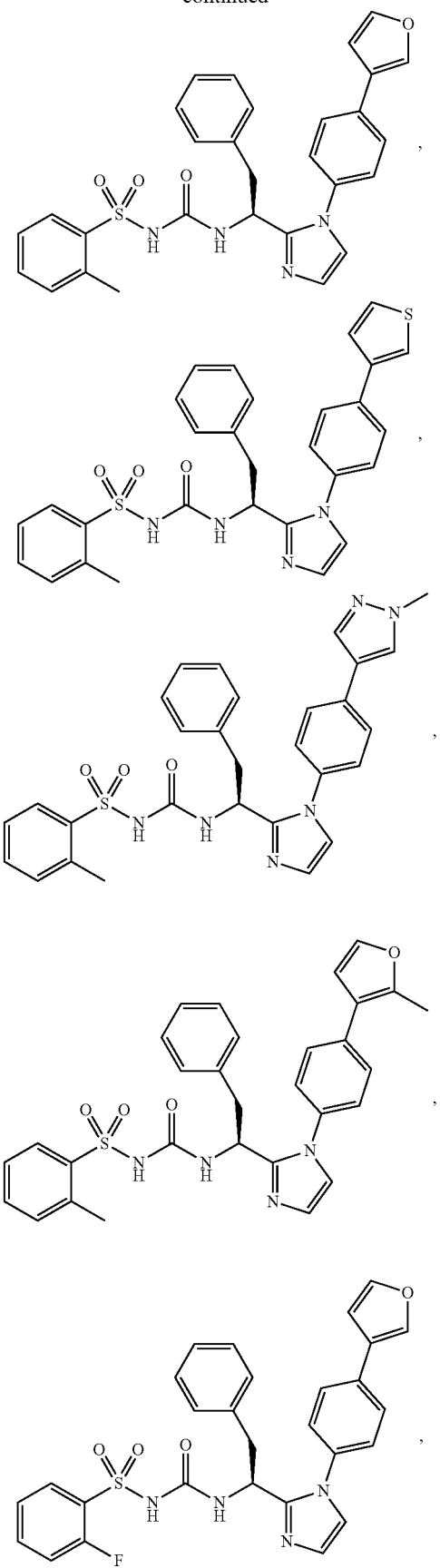

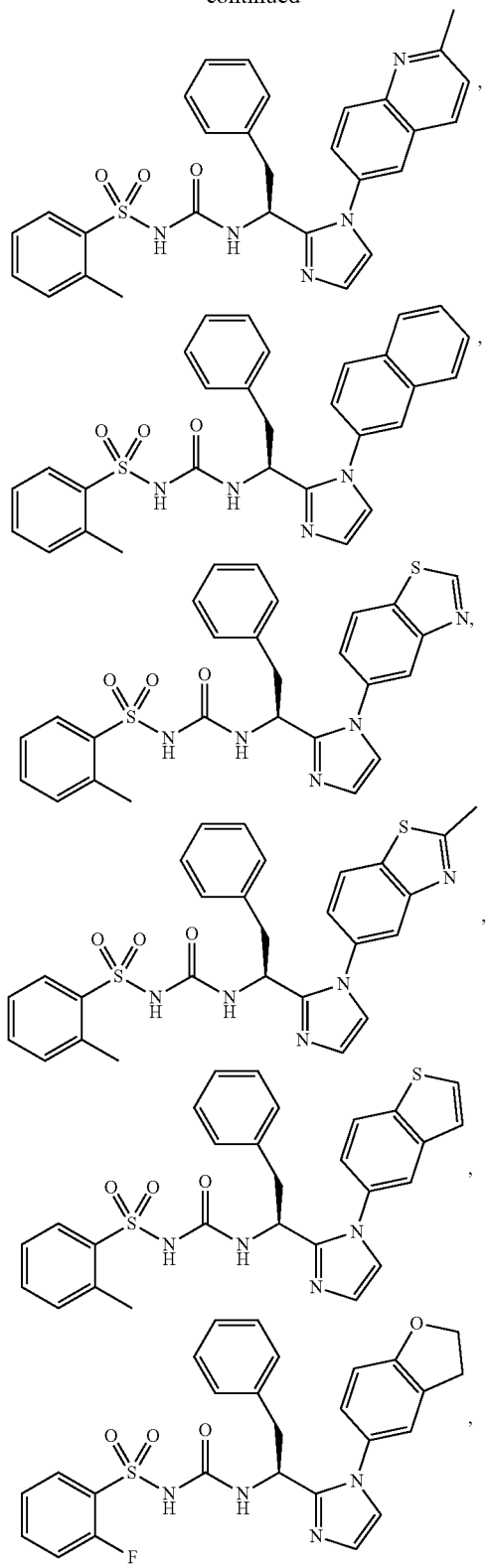

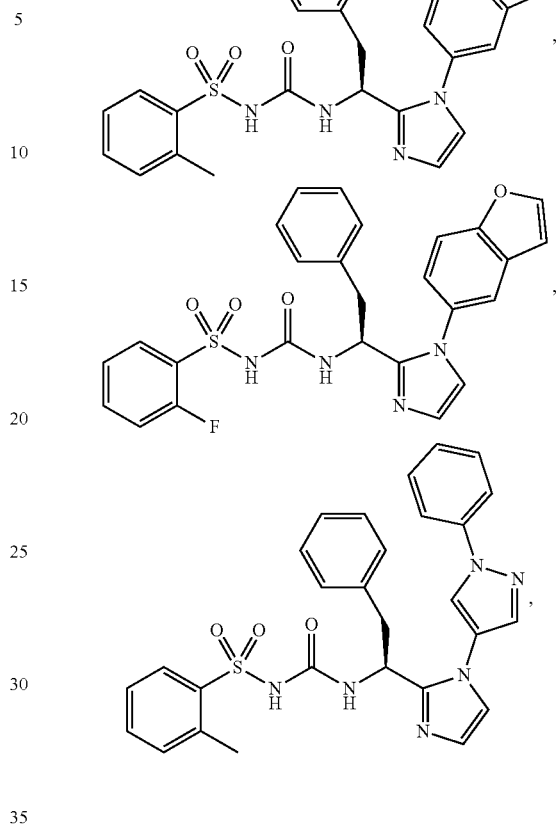

and pharmaceutically acceptable salts thereof.

12. A composition comprising a compound or salt of claim 1 and a pharmaceutically acceptable carrier, excipient and/or diluent.

13. A composition comprising a compound or salt of claim 2 and a pharmaceutically acceptable carrier, excipient and/or diluent.

14. A composition comprising a compound or salt of claim 6 and a pharmaceutically acceptable carrier, excipient and/or diluent.

15. A composition comprising a compound or salt of claim 10 and a pharmaceutically acceptable carrier, excipient and/or diluent.

16. A composition comprising a compound or salt of claim 11 and a pharmaceutically acceptable carrier, excipient and/or diluent.

17. A method of treating HIV infection comprising administering a therapeutically effective amount of a compound or salt of claim 1 to a patient.

18. A compound or salt of claim 7, wherein each of B, R and $R^1$ are phenyl groups.

* * * * *